US00RE39850E

(19) United States
(12) Reissued Patent
Delorme et al.

(10) Patent Number: US RE39,850 E
(45) Date of Reissued Patent: Sep. 18, 2007

(54) INHIBITORS OF HISTONE DEACETYLASE

(75) Inventors: Daniel Delorme, St-Lazare (CA); Rico Lavoie, Montreal (CA); Carl Thibault, Mascouche (CA); Elie Abou-Khalil, Laval (CA); Rejean Ruel, St- Lambert (CA)

(73) Assignee: Methylgene, Inc. (CA)

(21) Appl. No.: 10/880,444

(22) Filed: Jun. 29, 2004

Related U.S. Patent Documents

Reissue of:
(64) Patent No.: 6,541,661
Issued: Apr. 1, 2005
Appl. No.: 09/718,265
Filed: Nov. 22, 2000

U.S. Applications:
(60) Provisional application No. 60/167,035, filed on Nov. 23, 1999.

(51) Int. Cl.

| | |
|---|---|
| ***C07C 409/00*** | (2006.01) |
| ***C07C 251/00*** | (2006.01) |
| ***C07C 69/00*** | (2006.01) |
| ***C07C 229/00*** | (2006.01) |
| ***A01N 61/00*** | (2006.01) |

(52) U.S. Cl. ..... 560/318; 514/1; 560/4; 560/19; 560/24; 560/319

(58) Field of Classification Search ..... 560/4, 560/19, 24, 318, 319; 514/1
See application file for complete search history.

(56) References Cited

U.S. PATENT DOCUMENTS

| | | | | |
|---|---|---|---|---|
| 2,279,560 | A | 4/1942 | Dietrich | |
| 2,279,973 | A | 4/1942 | Dietrich | |
| 4,013,768 | A | 3/1977 | Fauran et al. | |
| 4,035,376 | A | 7/1977 | Janssen et al. | 260/295 |
| 4,173,577 | A | 11/1979 | Sallmann et al. | |
| 4,792,560 | A | 12/1988 | Huang | 541/311 |
| 4,977,188 | A | 12/1990 | Kneen et al. | 514/575 |
| 5,028,629 | A | 7/1991 | Hite et al. | 541/575 |
| 5,218,124 | A | 6/1993 | Failli et al. | 548/180 |
| 5,364,944 | A | 11/1994 | Failli et al. | 548/341.1 |
| 5,700,811 | A | 12/1997 | Breslow et al. | |
| 5,773,647 | A | 6/1998 | Leone-Bay et al. | 562/444 |
| 5,776,888 | A | 7/1998 | Leone-Bay et al. | 514/2 |
| 5,929,097 | A | 7/1999 | Levin et al. | 514/351 |
| 6,090,958 | A | 7/2000 | Leone-Bay et al. | |
| 6,653,309 | B1 | 11/2003 | Saunders et al. | |
| 2003/0232859 | A1 | 12/2003 | Kozlowski et al. | |

FOREIGN PATENT DOCUMENTS

| | | | |
|---|---|---|---|
| EP | 0196674 | | 10/1986 |
| EP | 0519831 | A1 | 6/1992 |
| EP | 0737671 | A2 | 10/1996 |
| EP | 0827742 | A1 | 3/1998 |
| EP | 0847992 | A1 | 6/1998 |
| GB | 0023986.3 | | 9/2000 |
| JP | A-56-0511441 | | 5/1981 |
| JP | 11-302173 | | 11/1999 |
| WO | WO 90/01929 | | 3/1990 |
| WO | WO 93/12075 | | 6/1993 |
| WO | WO93/12075 | A1 | 6/1993 |
| WO | WO 95/13264 | | 5/1995 |
| WO | WO-A-9506554 | | 9/1995 |
| WO | WO 96/30036 | | 10/1996 |
| WO | WO 97/11366 | | 3/1997 |
| WO | WO 97/36480 | | 10/1997 |
| WO | WO 97/43249 | | 11/1997 |
| WO | WO 98/16503 | | 4/1998 |
| WO | WO 98/34632 | | 8/1998 |
| WO | WO98/38859 | A1 | 11/1998 |
| WO | WO-98/55449 | | 12/1998 |
| WO | WO 99/31052 | | 6/1999 |
| WO | WO00/56704 | A1 | 9/2000 |
| WO | WO00/69819 | A1 | 11/2000 |
| WO | WO-A-0222577 | | 3/2002 |
| WO | WO 02/30879 | | 4/2002 |

OTHER PUBLICATIONS

Allais et al., "Derives de las serie des acides benzoylphenylacetiques anti–imflammatories et analgesiques", Eur. J. Med. Chem., 9(4):381–389 (1974).
Atsushi et al., Japanese Patent Office—Patent Abstracts of Japan, Pub. No. 07287412 A, Oct. 31, 1995.
Coker et al., "A Treatise on Photo–Elasticity" Cambridge at the University Press, 215–220 (1993).
Csordas, "On the Biological Role of Histone Acetylation" Biochem, J. 1990, vol. 265, pp 23–38.
Finnin et al., "Structures of a Histone Deacetylase Homologue Bound to the TSA and SAHA Inhibitors" Letters to Nature, 1999, vol. 401, pp 188–193.
Grozinger et al., "Three Proteins Define a Class of Human Histone Deacetylases Related to Yeast Hda 1p" Proc. Natl. Acad. Sci USA, 96, 1993, pp 4868–4873.
Janssen, "Suprofen (R 25 061), a New Potent Inhibitor of Prostaglandin Biosynthesis" Arzneim.–Porsch. (Drug Res.) 1975, 25, Nr. 10.
Jung et al., "Amide Analogues of Trichostatin A as Inhibitors of Histone Deacetylase and Inducers of Terminal Cell Differentiation" J. Med. Chem., 1999, vol. 42, pp. 4669–4679.
Kao et al., "Isolation of a Novel Histone Deacetylase Reveals That Class I and Class II Deacetylases Promote SMRT–Mediated Repression" Genes & Development, 2000, vol. 14, pp 55–66.
Kim et al., "Oxamflatin is a novel antitumor compound that inhibits mammalian histone deacetylase" Oncogene, 1999, vol. 18, pp. 2461–2470.
Makoto et al., Japanese Patent Office—Patent Abstracts of Japan, Pub. No. 59112963 A, Jun. 29, 1984.

(Continued)

*Primary Examiner*—Jane Zara
(74) *Attorney, Agent, or Firm*—Keown & Zucchero, LLP

(57) ABSTRACT

The invention relates to the inhibition of histone deactylase. The invention provides compounds and methods for inhibiting histone deacetylase enzymatic activity. The invention also provides compositions and methods for treating cell proliferative diseases and conditions.

157 Claims, No Drawings

OTHER PUBLICATIONS

Ohtani et al., "(2E)–5–[3–[(Phenylsulfonyl)amino]phenyl]–pent–2–en–4–ynohydroxamic Acid and its Derivatives as Novel and Potent Inhibitors of ras Transformation" J Med Chem., 1996, vol. 39, No. 15, pp 2871–2873.
Richon et al., "A Class of Hybrid Polar Inducers of Transformed Cell Differentiation Inhibits Histone Deacetylases" Proc. Natl. Acad Sci, 1998, vol. 95, pp 3003–3007.
Richon et al., "Second generation hybird polar compounds are potent inducers of transformed cell differentiation" Proc. Natl. Acad. Sci. U S A., 1996, vol. 93, No. 12, pp. 5705–5708.
Rovnyak et al., "Synthesis and Antiinflammatory Activities of ( α–Cyclopropl–p–tolyl)acetic Acid and Related Compounds" J Med Chem., 1973, vol. 16, No. 5, pp 487–490.
Saito et al., "A Synthetic Inhibitor of Histone Deacetylase, MS–27–275, with Marked in Vivo Antitumor Activity Against Human Tumors" Proc Natl Acad Sci U S A., 1999, vol. 96, No. 8, pp 4592–4597.
Sanchez del Pino et al., "Properties of the Yeast Nuclear Histone Deacetylase" Biochem J., 1994, vol. 303 ( Pt 3), pp 723–729.
Sonoda et al., "Oxamflatin: a novel compound which reverses malignant phenotype to normal one via induction of JunD" Oncogene, 1996, vol. 13, No. 1, pp 143–149.
Summers JB et al., "Hydroxamic acid inhibitors of 5–lipoxygenase: quantitative structure–activity relationships" J Med Chem., 1990, vol. 33, No. 3, pp. 992–998.
Suzuki et al., "Synthesis and Histone Deacetylase Inhibitory Activity of New Benzamide Derivatives" J Med Chem., 1999, vol. 42, No. 15, pp 3001–3003.
Taunton et al., "A Mammalian Histone Deacetylase Related to the Yeast Transcriptional Regulator Rpd3p" Science, 1996, vol. 272, pp 408–411.
Toyoki et al., Japanese Patent Office—Patent Abstracts of Japan, Pub. No. 10287634 A, Oct. 27, 1998.
Tsuji et al., "A new antifungal antibiotic, trichostatin" J Antibiot (Tokyo)., 1976, vol. 29, No. 1, pp 1–6.
Tsuneshi et al., Japanese Patent Office—Patent Abstracts of Japan, Pub. No. 10162583 A, Jul. 7, 1998.
Wyngaert et al., "Cloning and Characterization of Human Histone Deacetylase 8" FRBS, 2000, vol. 478, pp 77–83.
Yoshida et al., "Potent and Specific Inhibition of Mammalian Histone Deacetylase Both in Vivo and in Vitro by Trichostatin A" J Biol Chem., 1990, vol. 265, No. 28, pp 17174–17179.
Yoshida et al., "Effects of Trichostatins on Differentiation of Murine Eryothroleukemia Cells" Cancer Res., 1987, vol. 47, No. 14, pp 3688–3691.
Yoshida et al., "Reversible Arrest of Proliferation of Rat 3Y1 Fibroblasts in Both the G1 and G2 Phases by Trichostatin A" 1988, vol. 177, pp 122–131.
Database Beilstein; Beilstein Informationssysteme GmbH; XP002162157.
Database Beilstein; Beilstein Informationssysteme GmbH; XP002162158.
Database Beilstein; Beilstein Informationssysteme GmbH; XP002162159.
Database Beilstein; Beilstein Informationssysteme GmbH; XP002162160.
Database Beilstein; Beilstein Informationssysteme GmbH; XP002162161.
Hideo K. et al., "Substituted Acetohydroxamic Derivatives", Chem. Ab., 91(13):Abstract No. 107818 (1979).
Kim, Y.B. et al., "Oxamflatin is a Novel Antitumor Compounds that Inhibits Mammalian Histone Deacetylase", Chemical Abstracts, 181(8):Abstract No. 97120 (1999).
Glick, R.D. et al., "Hybrid Polar Histon Deacetylase Inhibitor Induces Apoptosis and CD95/CD95 Ligand Expression in Human Neuroblastoma", Chem. Ab., 131(24): Abstract No. 317417 (1999).
Hikaru, Sonoda et al., "Oxamflatin: A Novel Compound Which Reverses Malignant Phenotype to Normal One Via Induction of JunD", Oncogene, 13:143–149.
Young, Bae Kim et al., "Oxamflatin is a Novel Antitumor Compound that Inhibits Mammalian Histone Deacetylase", Oncogene, 18:2461–2470.
Mitsuake, Ohtani et al., Journal of Medicinal Chemistry, 39(15):2871–2873.
Tsuneji, Suzuki et al., "Synthesis and Histone Deacetylase Inhibitory Activity of New Benzamide Derivatives", Journal of Medicinal Chemistry, 42(15):3001–3003 (1999).
Manfred, Jung et al., "Amide Analogues of Trichostatin A as Inhibitors of Histone Deacetylase and Inducers of Terminal Cell Differentiation", J. Med. Chem., 42:4669–4679 (1999).

INHIBITORS OF HISTONE DEACETYLASE

Matter enclosed in heavy brackets [ ] appears in the original patent but forms no part of this reissue specification; matter printed in italics indicates the additions made by reissue.

CROSS-REFERENCE TO RELATED APPLICATIONS

This application claims priority from U.S. Provisional Patent Application Ser. No. 60/167,035, filed on Nov. 23, 1999.

BACKGROUND OF THE INVENTION

1. Field of the Invention

This invention relates to the inhibition of histone deacetylase. More particularly, the invention relates to compounds and methods for inhibiting histone deacetylase enzymatic activity.

2. Summary of the Related Art

In eukaryotic cells, nuclear DNA associates with histones to form a compact complex called chromatin. The histones constitute a family of basic proteins which are generally highly conserved across eukaryotic species. The core histones, termed H2A, H2B, H3, and H4, associate to form a protein core. DNA winds around this protein core, with the basic amino acids of the histones interacting with the negatively charged phosphate groups of the DNA. Approximately 146 base pairs of DNA wrap around a histone core to make up a nucleosome particle, the repeating structural motif of chromatin.

Csordas, Biochem. J., 286: 23–38 (1990) teaches that histones are subject to posttranslational acetylation of the ε-amino groups of N-terminal lysine residues, a reaction that is catalyzed by histone acetyl transferase (HAT1). Acetylation neutralizes the positive charge of the lysine side chain, and is thought to impact chromatin structure. Indeed, Taunton et al., Science, 272: 408–411 (1996), teaches that access of transcription factors to chromatin templates is enhanced by histone hyperacetylation. Taunton et al. further teaches that an enrichment in underacetylated histone H4 has been found in transcriptionally silent regions of the genome.

Histone acetylation is a reversible modification, with deacetylation being catalyzed by a family of enzymes termed histone deacetylases (HDACs). Grozinger et al., Proc. Natl. Acad. Sci. USA, 96: 4868–4873 (1999), teaches that HDACs may be divided into two classes, the first represented by yeast Rpd3-like proteins, and the second represented by yeast Hda1-like proteins. Grozinger et al. also teaches that the human HDAC1, HDAC2, and HDAC3 proteins are members of the first class of HDACs, and discloses new proteins, named HDAC4, HDAC5, and HDAC6, which are members of the second class of HDACs. Kao et al., Genes & Dev., 14: 55–66 (2000), discloses HDAC7, a new member of the second class of HDACs. Van den Wyngaert, FEBS, 478: 77–83 (2000) discloses HDAC8, a new member of the first class of HDACs.

Richon et al., Proc. Natl. Acad. Sci. USA, 95: 3003–3007 (1998), discloses that HDAC activity is inhibited by trichostatin A (TSA), a natural product isolated from Streptomyces hygroscopicus, and by a synthetic compound, suberoylanilide hydroxamic acid (SAHA). Yoshida and Beppu, Exper. Cell Res., 177: 122–131 (1988), teaches that TSA causes arrest of rat fibroblasts at the $G_1$ and $G_2$ phases of the cell cycle, implicating HDAC in cell cycle regulation. Indeed, Finnin et al., Nature, 401: 188–193 (1999), teaches that TSA and SAHA inhibit cell growth, induce terminal differentiation, and prevent the formation of tumors in mice.

These findings suggest that inhibition of HDAC activity represents a novel approach for intervening in cell cycle regulation and that HDAC inhibitors have great therapeutic potential in the treatment of cell proliferative diseases or conditions. To date, only a few inhibitors of histone deacetylase are known in the art. There is thus a need to identify additional HDAC inhibitors and to identify the structural features required for potent HDAC inhibitory activity.

BRIEF SUMMARY OF THE INVENTION

The invention provides compounds and methods for treating cell proliferative diseases. In particular, the invention provides new inhibitors of histone deacetylase enzymatic activity.

In a first aspect, therefore, the invention provides novel inhibitors of histone deacetylase. In one embodiment, the novel inhibitors of histone deacetylase are represented by formula (1):

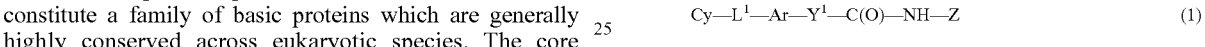

$$\text{Cy—L}^1\text{—Ar—Y}^1\text{—C(O)—NH—Z} \quad (1)$$

wherein

Cy is cycloalkyl, aryl, heteroaryl, or heterocyclyl, any of which may be optionally substituted;

$L^1$ is —$(CH_2)_m$—W—, where m is 0, 1, 2, 3, or 4, and W is selected from the group consisting of —C(O)NH—, —$S(O)_2$NH—, —NHC(O)—, —$NHS(O)_2$—, and —NH—C(O)—NH—;

Ar is arylene, wherein said arylene optionally may be additionally substituted and optionally may be fused to an aryl or heteroaryl ring, or to a saturated or partially unsaturated cycloalkyl or heterocyclic ring, any of which may be optionally substituted;

$Y^1$ is a chemical bond or a straight- or branched-chain saturated alkylene, wherein said alkylene may be optionally substituted; and Z is selected from the group consisting of anilinyl, pyridyl, thiadiazolyl, and —O—M, M being H or a pharmaceutically acceptable cation;

provided that when $L^1$ is —C(O)NH—, $Y^1$ is —$(CH_2)_n$—, n being 1, 2, or 3, and Z is —O—M, then Cy is not aminophenyl, dimethylaminophenyl, or hydroxyphenyl; and further provided that when $L^1$ is —C(O)NH— and Z is pyridyl, then Cy is not substituted indolinyl.

In a second embodiment, the novel inhibitors of histone deacetylase are represented by formula (2):

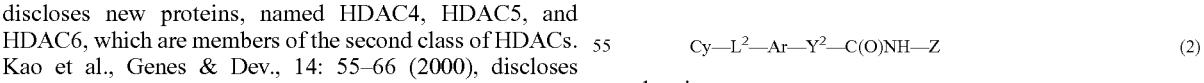

$$\text{Cy—L}^2\text{—Ar—Y}^2\text{—C(O)NH—Z} \quad (2)$$

wherein

Cy is cycloalkyl, aryl, heteroaryl, or heterocyclyl, any of which may be optionally substituted, provided that Cy is not a (spirocycloalkyl)heterocyclyl;

$L^2$ is $C_1$–$C_6$ saturated alkylene or $C_2$–$C_6$ alkenylene, wherein the alkylene or alkenylene optionally may be substituted, provided that $L^2$ is not —C(O)—, and wherein one of the carbon atoms of the alkylene optionally may be replaced by a heteroatom moiety selected from the group consisting of O; NR', R' being alkyl, acyl, or hydrogen; S; S(O); or $S(O)_2$;

Ar is arylene, wherein said arylene optionally may be additionally substituted and optionally may be fused to an aryl or heteroaryl ring, or to a saturated or partially unsaturated cycloalkyl or heterocyclic ring, any of which may be optionally substituted; and $Y^2$ is a chemical bond or a straight- or branched-chain saturated alkylene, which may be optionally substituted, provided that the alkylene is not substituted with a substituent of the formula —C(O)R wherein R comprises an α-amino acyl moiety; and Z is selected from the group consisting of anilinyl, pyridyl, thiadiazolyl, and —O—M, M being H or a pharmaceutically acceptable cation;

provided that when the carbon atom to which Cy is attached is oxo substituted, then Cy and Z are not both pyridyl.

In a third embodiment, the novel inhibitors of histone deacetylase are represented by formula (3):

$$Cy—L^3—Ar—Y^3—C(O)NH—Z \quad (3)$$

wherein

Cy is cycloalkyl, aryl, heteroaryl, or heterocyclyl, any of which may be optionally substituted, provided that Cy is not a (spirocycloalkyl)heterocyclyl;

$L^3$ is selected from the group consisting of (a) $—(CH_2)_m—W—$, where m is 0, 1, 2, 3, or 4, and W is selected from the group consisting of —C(O)NH—, $—S(O)_2NH—$, —NHC(O)—, $—NHS(O)_2—$, and —NH—C(O)—NH—; and (b) $C_1$–$C_6$ alkylene or $C_2$–$C_6$ alkenylene, wherein the alkylene or alkenylene optionally may be substituted, provided that $L^3$ is not —C(O)—, and wherein one of the carbon atoms of the alkylene optionally may be replaced by O; NR', R' being alkyl, acyl, or hydrogen; S; (S(O); or $S(O)_2$;

Ar is arylene, wherein said arylene optionally may be additionally substituted and optionally may be fused to an aryl or heteroaryl ring, or to a saturated or partially unsaturated cycloalkyl or heterocyclic ring, any of which may be optionally substituted; and $Y^3$ is $C_2$ alkenylene or $C_2$ alkynylene, wherein one or both carbon atoms of the alkenylene optionally may be substituted with alkyl, aryl, alkaryl, or aralkyl; and Z is selected from the group consisting of anilinyl, pyridyl, thiadiazolyl, and —O—M, M being H or a pharmaceutically acceptable cation;

provided that when Cy is unsubstituted phenyl, Ar is not phenyl wherein $L^3$ and $Y^3$ are oriented ortho or meta to each other.

In a fourth embodiment, the novel histone deacetylase inhibitor is selected from the group represented by formulae (4)–(6):

(4)

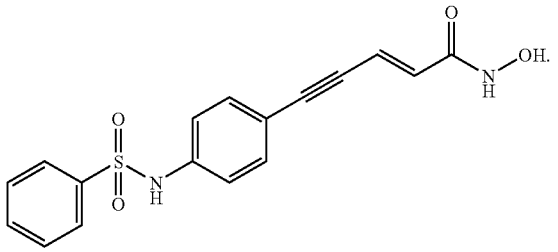

(5)

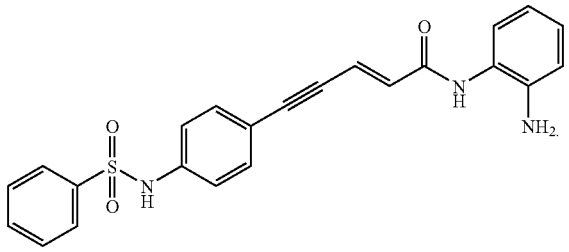

(6)

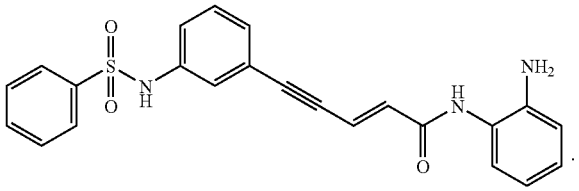

In a second aspect, the invention provides a pharmaceutical composition comprising an inhibitor of histone deacetylase represented by any one of formulae (1)–(6) and a pharmaceutically acceptable carrier, excipient, or diluent.

In a third aspect, the invention provides methods for inhibiting histone deacetylase in a cell, comprising contacting a cell in which inhibition of histone deacetylase is desired with an inhibitor of histone deacetylase. In a first embodiment according to this aspect of the invention, the inhibitor of histone deacetylase is represented by formula (1):

$$Cy—L^1—Ar—Y^1—C(O)—NH—Z \quad (1)$$

wherein

Cy is cycloalkyl, aryl, heteroaryl, or heterocyclyl, any of which may be optionally substituted;

$L^1$ is $—(CH_2)_m—W—$, where m is 0, 1, 2, 3, or 4, and W is selected from the group consisting of —C(O)NH—, $—S(O)_2NH—$, —NHC(O)—, $—NHS(O)_2—$, and —NH—C(O)—NH—;

Ar is arylene, wherein said arylene optionally may be additionally substituted and optionally may be fused to an aryl or heteroaryl ring, or to a saturated or partially unsaturated cycloalkyl or heterocyclic ring, any of which may be optionally substituted;

$Y^1$ is a chemical bond or a straight- or branched-chain saturated alkylene, wherein said alkylene may be optionally substituted; and Z is selected from the group consisting of anilinyl, pyridyl, 2-thioxo-1,3,4-thiadiazol-2-yl, and —O—M, M being H or a pharmaceutically acceptable cation;

provided that when $L^1$ is —C(O)NH—, Y is $—(CH_2)_n—$, n being 1, 2, or 3, and Z is —O—M, then Cy is not aminophenyl, dimethylaminophenyl, or hydroxyphenyl.

In a second embodiment according to this aspect of the invention, the inhibitor of histone deacetylase is represented by formula (2)

$$Cy—L^2—Ar—Y^2—C(O)NH—Z \quad (2)$$

wherein

Cy is cycloalkyl, aryl, heteroaryl, or heterocyclyl, any of which may be optionally substituted;

$L^2$ is $C_1$–$C_6$ saturated alkylene or $C_2$–$C_6$ alkenylene, either of which may be optionally substituted;

Ar is arylene, wherein said arylene optionally may be additionally substituted and optionally may be fused to an aryl or heteroaryl ring, or to a saturated or partially unsaturated cycloalkyl or heterocyclic ring, any of which may be optionally substituted; and $Y^2$ is a chemical bond or a straight- or branched-chain saturated alkylene, which may be optionally substituted, provided that the alkylene is not substituted with a substituent of the formula —C(O)R wherein R comprises an α-amino acyl moiety; and Z is selected from the group consisting of anilinyl, pyridyl, 2-thioxo-1,3,4-thiadiazol-2-yl, and —O—M, M being H or a pharmaceutically acceptable cation.

In a third embodiment according to this aspect of the invention, the inhibitor of histone deacetylase is represented by formula (3):

$$Cy—L^3—Ar—Y^3—C(O)NH—Z \quad (3)$$

wherein

Cy is cycloalkyl, aryl, heteroaryl, or heterocyclyl, any of which may be optionally substituted, provided that Cy is not a (spirocycloalkyl)heterocyclyl;

$L^3$ is selected from the group consisting of (a) $—(CH_2)_m—W—$, where m is 0, 1, 2, 3, or 4, and W is selected from the group consisting of —C(O)NH—, $—S(O)_2NH—$, —NHC(O)—, $—NHS(O)_2—$, and —NH—C(O)—NH—; and (b) $C_1$–$C_6$ alkylene or $C_2$–$C_6$ alkenylene, wherein the alkylene or alkenylene optionally may be substituted, provided that $L^3$ is not —C(O)—, and wherein one of the carbon atoms of the alkylene optionally may be replaced by O; NR', R' being alkyl, acyl, or hydrogen; S; S(O); or $S(O)_2$;

Ar is arylene, wherein said arylene optionally may be additionally substituted and optionally may be fused to an aryl or heteroaryl ring, or to a saturated or partially unsaturated cycloalkyl or heterocyclic ring, any of which may be optionally substituted; and $Y^3$ is $C_2$ alkenylene or $C_2$ alkynylene, wherein one or both carbon atoms of the alkenylene optionally may be substituted with alkyl, aryl, alkaryl, or aralkyl; and Z is selected from the group consisting of anilinyl, pyridyl, thiadiazolyl, and —O—M, M being H or a pharmaceutically acceptable cation;

provided that when Cy is unsubstituted phenyl, Ar is not phenyl wherein $L^3$ and $Y^3$ are oriented ortho or meta to each other.

In a fourth embodiment according to this aspect of the invention, the novel histone deacetylase inhibitor is selected from the group represented by formulae (4)–(6):

(4)

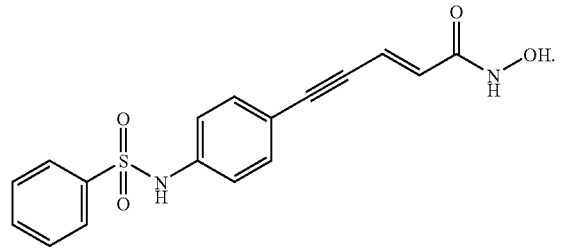

(5)

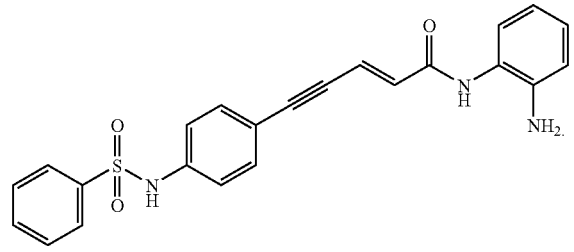

(6)

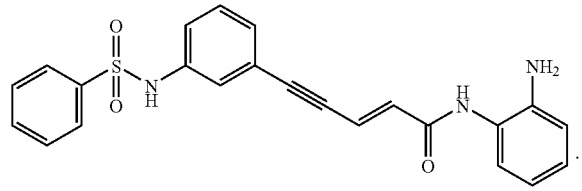

DETAILED DESCRIPTION OF THE PREFERRED EMBODIMENTS

The invention provides compounds and methods for inhibiting histone deacetylase enzymatic activity. The invention also provides compositions and methods for treating cell proliferative diseases and conditions. The patent and scientific literature referred to herein establishes knowledge that is available to those with skill in the art. The issued patents, applications, and references that are cited herein are hereby incorporated by reference to the same extent as if each was specifically and individually indicated to be incorporated by reference. In the case of inconsistencies, the present disclosure will prevail.

For purposes of the present invention, the following definitions will be used:

As used herein, the terms "histone deacetylase" and "HDAC" are intended to refer to any one of a family of enzymes that remove acetyl groups from the ϵ-amino groups of lysine residues at the N-terminus of a histone. Unless otherwise indicated by context, the term "histone" is meant to refer to any histone protein, including H1, H2A, H2B, H3, H4, and H5, from any species. Preferred histone deacetylases include class I and class II enzymes. Preferably the histone deacetylase is a human HDAC, including, but not limited to, HDAC-1, HDAC-2, HDAC-3, HDAC-4, HDAC-5, HDAC-6, HDAC-7, and HDAC-8. In some other preferred embodiments, the histone deacetylase is derived from a protozoal or fungal source.

The term "histone deacetylase inhibitor" or "inhibitor of histone deacetylase" is used to identify a compound having a structure as defined herein, which is capable of interacting with a histone deacetylase and inhibiting its enzymatic activity. Inhibiting histone deacetylase enzymatic activity means reducing the ability of a histone deacetylase to remove an acetyl group from a histone. In some preferred embodiments, such reduction of histone deacetylase activity is at least about 50%, more preferably at least about 75%, and still more preferably at least about 90%. In other preferred embodiments, histone deacetylase activity is reduced by at least 95% and more preferably by at least 99%.

Preferably, such inhibition is specific, i.e., the histone deacetylase inhibitor reduces the ability of a histone deacetylase to remove an acetyl group from a histone at a concentration that is lower than the concentration of the inhibitor that is required to produce another, unrelated biological effect. Preferably, the concentration of the inhibitor required for histone deacetylase inhibitory activity is at least 2-fold lower, more preferably at least 5-fold lower, even more preferably at least 10-fold lower, and most preferably at least 20-fold lower than the concentration required to produce an unrelated biological effect.

The term "alkyl" as employed herein refers to straight and branched chain aliphatic groups having from 1 to 12 carbon atoms, preferably 1–8 carbon atoms, and more preferably 1–6 carbon atoms, which may be optionally substituted with one, two or three substituents. Unless otherwise apparent from context, the term "alkyl" is meant to include saturated, unsaturated, and partially unsaturated aliphatic groups. When unsaturated groups are particularly intended, the terms "alkenyl" or "alkynyl" will be used. When only saturated groups are intended, the term "saturated alkyl" will be used. Preferred saturated alkyl groups include, without limitation, methyl, ethyl, propyl, isopropyl, butyl, isobutyl, sec-butyl, tert-butyl, pentyl, and hexyl.

An "alkylene" group is an alkyl group, as defined hereinabove, that is positioned between and serves to connect two other chemical groups. Preferred alkylene groups include, without limitation, methylene, ethylene, propylene, and butylene.

The term "cycloalkyl" as employed herein includes saturated and partially unsaturated cyclic hydrocarbon groups having 3 to 12 carbons, preferably 3 to 8 carbons, and more preferably 3 to 6 carbons, wherein the cycloalkyl group additionally may be optionally substituted. Preferred cycloalkyl groups include, without limitation, cyclopropyl, cyclobutyl, cyclopentyl, cyclopentenyl, cyclohexyl, cyclohexenyl, cycloheptyl, and cyclooctyl.

An "aryl" group is a $C_6$–$C_{14}$ aromatic moiety comprising one to three aromatic rings, which may be optionally substituted. Preferably, the aryl group is a $C_6$–$C_{10}$ aryl group. Preferred aryl groups include, without limitation, phenyl, naphthyl, anthracenyl, and fluorenyl. An "aralkyl" or "arylalkyl" group comprises an aryl group covalently linked to an alkyl group, either of which may independently be optionally substituted or unsubstituted. Preferably, the aralkyl group is ($C_1$–$C_6$)alk($C_6$–$C_{10}$)aryl, including, without limitation, benzyl, phenethyl, and naphthylmethyl. An "alkaryl" or "alkylaryl" group is an aryl group having one or more alkyl substituents. Examples of alkaryl groups include, without limitation, tolyl, xylyl, mesityl, ethylphenyl, tert-butylphenyl, and methylnaphthyl.

An "arylene" group is an aryl group, as defined hereinabove, that is positioned between and serves to connect two other chemical groups. Preferred arylene groups include, without limitation, phenylene and naphthylene. The term "arylene" is also meant to include heteroaryl bridging groups, including, but not limited to, benzothienyl, benzofuryl, quinolyl, isoquinolyl, and indolyl.

A "heterocyclyl" or "heterocyclic" group is a ring structure having from about 3 to about 8 atoms, wherein one or more atoms are selected from the group consisting of N, O, and S. The heterocyclic group may be optionally substituted on carbon at one or more positions. The heterocyclic group may also independently be substituted on nitrogen with alkyl, aryl, aralkyl, alkylcarbonyl, alkylsulfonyl, arylcarbonyl, arylsulfonyl, alkoxycarbonyl, aralkoxycarbonyl, or on sulfur with oxo or lower alkyl. Preferred heterocyclic groups include, without limitation, epoxy, aziridinyl, tetrahydrofuranyl, pyrrolidinyl, piperidinyl, piperazinyl, thiazolidinyl, oxazolidinyl, oxazolidinonyl, and morpholino. In certain preferred embodiments, the heterocyclic group is fused to an aryl or heteroaryl group. Examples of such fused heterocycles include, without limitation, tetrahydroquinoline and dihydrobenzofuran.

As used herein, the term "heteroaryl" refers to groups having 5 to 14 ring atoms, preferably 5, 6, 9, or 10 ring atoms; having 6, 10, or 14π electrons shared in a cyclic array; and having, in addition to carbon atoms, between one and about three heteroatoms selected from the group consisting of N, O, and S. Preferred heteroaryl groups include, without limitation, thienyl, benzothienyl, furyl, benzofuryl, dibenzofuryl, pyrrolyl, imidazolyl, pyrazolyl, pyridyl, pyrazinyl, pyrimidinyl, indolyl, quinolyl, isoquinolyl, quinoxalinyl, tetrazolyl, oxazolyl, thiazolyl, and isoxazolyl.

As employed herein, a "substituted" alkyl, cycloalkyl, aryl, heteroaryl, or heterocyclic group is one having between one and about four, preferably between one and about three, more preferably one or two, non-hydrogen substituents. Suitable substituents include, without limitation, halo, hydroxy, nitro, haloalkyl, alkyl, alkaryl, aryl, aralkyl, alkoxy, aryloxy, amino, acylamino, alkylcarbamoyl, arylcarbamoyl, aminoalkyl, alkoxycarbonyl, carboxy, hydroxyalkyl, alkanesulfonyl, arenesulfonyl, alkanesulfonamido, arenesulfonamido, aralkylsulfonamido, alkylcarbonyl, acyloxy, cyano, and ureido groups.

The term "halogen" or "halo" as employed herein refers to chlorine, bromine, fluorine, or iodine.

As herein employed, the term "acyl" refers to an alkylcarbonyl or arylcarbonyl substituent.

The term "acylamino" refers to an amide group attached at the nitrogen atom. The term "carbamoyl" refers to an amide group attached at the carbonyl carbon atom. The nitrogen atom of an acylamino or carbamoyl substituent may be additionally substituted. The term "sulfonamido" refers to a sulfonamide substituent attached by either the sulfur or the nitrogen atom. The term "amino" is meant to include $NH_2$, alkylamino, arylamino, and cyclic amino groups.

The term "ureido" as employed herein refers to a substituted or unsubstituted urea moiety.

Compounds

In a first aspect, the invention provides novel inhibitors of histone deacetylase. In a first embodiment, the novel inhibitors of histone deacetylase are represented by formula (1):

$$\text{Cy—L}^1\text{—Ar—Y—C(O)—NH—Z} \quad (1)$$

wherein

Cy is cycloalkyl, aryl, heteroaryl, or heterocyclyl, any of which may be optionally substituted;

$L^1$ is —$(CH_2)_m$—W—, where m is 0, 1, 2, 3, or 4, and W is selected from the group consisting of —C(O)NH—, —$S(O)_2$NH—, —NHC(O)—, —NHS$(O)_2$—, and —NH—C(O)—NH—;

Ar is arylene, wherein said arylene optionally may be additionally substituted and optionally may be fused to an aryl or heteroaryl ring, or to a saturated or partially unsaturated cycloalkyl or heterocyclic ring, any of which may be optionally substituted;

$Y^1$ is a chemical bond or a straight- or branched-chain saturated alkylene, wherein said alkylene may be optionally substituted; and Z is selected from the group consisting of anilinyl, pyridyl, thiadiazolyl, and —O—M, M being H or a pharmaceutically acceptable cation;

provided that when $L^1$ is —C(O)NH—, Y is —$(CH_2)_n$—, n being 1, 2, or 3, and Z is —O—M, then Cy is not aminophenyl, dimethylaminophenyl, or hydroxyphenyl; and further provided that when $L^1$ is —C(O)NH— and Z is pyridyl, then Cy is not substituted indolinyl.

In certain preferred embodiments, Cy is $C_6$–$C_{14}$ aryl, more preferably $C_6$–$C_{10}$ aryl, and most preferably phenyl or naphthyl, any of which may be optionally substituted. In certain other preferred embodiments, Cy is heteroaryl. In some preferred embodiments, the heteroaryl group is selected from the group consisting of thienyl, benzothienyl, furyl, benzofuryl, quinolyl, isoquinolyl, and thiazolyl, any of which may be optionally substituted. In certain particularly preferred embodiments, Cy is selected from the group consisting of phenyl, naphthyl, thienyl, benzothienyl, and quinolyl, any of which may be optionally substituted.

$L^1$ is —$(CH_2)_m$—W—, where m is 0, 1, 2, 3, or 4, and W is selected from the group consisting of —C(O)NH—, —$S(O)_2$NH—, —NHC(O)—, —NHS$(O)_2$—, and —NH—C(O)—NH—. Preferably, m is 0, 1, or 2, more preferably 0 or 1.

Preferably, Ar is $C_6$–$C_{14}$ arylene, more preferably $C_6$–$C_{10}$ arylene, any of which may be additionally substituted. In certain preferred embodiments, Ar is phenylene, preferably 4-phenylene. In some preferred embodiments, the phenylene is fused to an aryl or heteroaryl ring, or to a saturated or partially unsaturated cycloalkyl or heterocyclic ring, any of which groups also may be optionally substituted.

$Y^1$ is a chemical bond or is a straight- or branched-chain alkylene, which may be optionally substituted. In some preferred embodiments, $Y^1$ is a chemical bond, and the group —C(O)NH—Z is directly attached to Ar. In some other preferred embodiments, $Y^1$ is alkylene, preferably saturated alkylene. Preferably, the saturated alkylene is $C_1$–$C_8$ alkylene, more preferably $C_1$–$C_6$ alkylene, still more preferably $C_1$–$C_3$ alkylene, and yet still more preferably $C_1$–$C_2$ alkylene, any of which may be optionally substituted. In some particularly preferred embodiments, $Y^1$ is methylene.

Substituted alkyl, aryl, heterocyclyl, or heteroaryl groups have one or more, preferably between one and about three, more preferably one or two substituents, which are preferably selected from the group consisting of $C_1$–$C_6$ alkyl, preferably $C_1$–$C_4$ alkyl; halo, preferably Cl, Br, or F; haloalkyl, preferably $(halo)_{1\text{-}5}(C_1\text{–}C_6)$alkyl, more preferably $(halo)_{1\text{-}5}(C_1\text{–}C_3)$alkyl, and most preferably $CF_3$; $C_1$–$C_6$ alkoxy, preferably methoxy, ethoxy, or benzyloxy; $C_6$–$C_{10}$ aryloxy, preferably phenoxy; $C_1$–$C_6$ alkoxycarbonyl, preferably $C_1$–$C_3$ alkoxycarbonyl, most preferably carbomethoxy or carboethoxy; $C_6$–$C_{10}$ aryl, preferably phenyl; $(C_6\text{–}C_{10})$ar$(C_1\text{–}C_6)$alkyl, preferably $(C_6\text{–}C_{10})$ar$(C_1\text{–}C_3)$alkyl, more preferably benzyl, naphthylmethyl or phenethyl; hydroxy$(C_1\text{–}C_6)$alkyl, preferably hydroxy$(C_1\text{–}C_3)$alkyl, more preferably hydroxymethyl; amino$(C_1\text{–}C_6)$alkyl, preferably amino$(C_1\text{–}C_3)$alkyl, more preferably aminomethyl; $(C_1\text{–}C_6)$alkylamino, preferably methylamino, ethylamino, or propylamino; di-$(C_1\text{–}C_6)$alkylamino, preferably dimethylamino or diethylamino; $(C_1\text{–}C_6)$alkylcarbamoyl, preferably methylcarbamoyl, dimethylcarbamoyl, or benzylcarbamoyl; $(C_6\text{–}C_{10})$arylcarbamoyl, preferably phenylcarbamoyl; $(C_1\text{–}C_6)$alkaneacylamino, preferably acetylamino; $(C_6\text{–}C_{10})$ areneacylamino, preferably benzoylamino; $(C_1\text{–}C_6)$ alkanesulfonyl, preferably methanesulfonyl; $(C_1\text{–}C_6)$ alkanesulfonamido, preferably methanesulfonamido; $(C_6\text{–}C_{10})$arenesulfonyl, preferably benzenesulfonyl or toluenesulfonyl; $(C_6\text{–}C_{10})$arenesulfonamido, preferably benzenesulfonyl or toluenesulfonyl; $(C_6\text{–}C_{10})$ar$(C_1\text{–}C_6)$ alkylsulfonamido, preferably benzylsulfonamido; $C_1$–$C_6$ alkylcarbonyl, preferably $C_1$–$C_3$ alkylcarbonyl, more preferably acetyl; $(C_1\text{–}C_6)$acyloxy, preferably acetoxy; cyano; amino; carboxy; hydroxy; ureido; and nitro. One or more carbon atoms of an alkyl, cycloalkyl, or heterocyclyl group may also be optionally substituted with an oxo group.

In some particularly preferred embodiments, Cy is a phenyl, naphthyl, thienyl, benzothienyl, or quinolyl moiety which is unsubstituted or is substituted by one or two substituents independently selected from the group consisting of $C_1$–$C_4$ alkyl, $C_1$–$C_4$ haloalkyl, $C_6$–$C_{10}$ aryl, $(C_6\text{–}C_{10})$ ar$(C_1\text{–}C_6)$alkyl, halo, nitro, hydroxy, $C_1$–$C_6$ alkoxy, $C_1$–$C_6$ alkoxycarbonyl, carboxy, and amino.

In some preferred embodiments, Z is anilinyl or pyridyl, preferably 2-anilinyl or 2-pyridyl. In some other preferred embodiments, Z is thiadiazolyl, preferably 1,3,4-thiadiazol-2-yl, and more preferably a 5-substituted-1,3,4-thiadiazol2-yl. The thiadiazolyl is preferably substituted with a substituent selected from the group consisting of thiol, trifluoromethyl, amino, and sulfonamido.

In still other preferred embodiments, Z is —O—M, wherein M is hydrogen or any pharmaceutically acceptable cation. Examples of pharmaceutically acceptable cations include, without limitation, sodium, potassium, magnesium, and calcium.

In a second embodiment, the invention provides novel inhibitors of histone deacetylase represented by formula (2):

$$\text{Cy—L}^2\text{—Ar—Y}^2\text{—C(O)NH—Z} \quad (2)$$

wherein

Cy is cycloalkyl, aryl, heteroaryl, or heterocyclyl, any of which may be optionally substituted, provided that Cy is not a (spirocycloalkyl)heterocyclyl;

$L^2$ is $C_1$–$C_6$ saturated alkylene or $C_2$–$C_6$ alkenylene, wherein the alkylene or alkenylene optionally may be substituted, provided that $L^2$ is not —C(O)—, and wherein one of the carbon atoms of the alkylene optionally may be replaced by a heteroatom moiety selected from the group consisting of O; NR', R' being alkyl, acyl, or hydrogen; S; S(O); or $S(O)_2$;

Ar is arylene, wherein said arylene optionally may be additionally substituted and optionally may be fused to an aryl or heteroaryl ring, or to a saturated or partially unsaturated cycloalkyl or heterocyclic ring, any of which may be optionally substituted; and $Y^2$ is a chemical bond or a straight- or branched-chain saturated alkylene, which may be optionally substituted, provided that the alkylene is not substituted with a substituent of the formula —C(O)R wherein R comprises an α-amino acyl moiety; and Z is selected from the group consisting of anilinyl, pyridyl, thiadiazolyl, and —O—M, M being H or a pharmaceutically acceptable cation;

provided that when the carbon atom to which Cy is attached is oxo substituted, then Cy and Z are not both pyridyl.

Preferred substituents Cy, Ar, and Z according to this aspect of the invention are as defined above for the first embodiment. Preferred substituents $Y^2$ are as defined above for $Y^1$. In some preferred embodiments, $L^2$ is saturated $C_1$–$C_8$ alkylene, more preferably $C_1$–$C_6$ alkylene, still more preferably $C_1$–$C_4$ alkylene, any of which groups may be optionally substituted. In some other preferred embodiments, $L^2$ is $C_2$–$C_8$ alkenylene, more preferably $C_2$–$C_6$ alkenylene, and still more preferably $C_2$–$C_8$ alkenylene, any of which groups may be optionally substituted. The alkylene or alkenylene group may be substituted at one or more carbon positions with a substituent preferably selected from the list of preferred substituents recited above. More preferably, $L^2$ is substituted at one or two positions with a substituent independently selected from the group consisting of $C_1$–$C_6$ alkyl, $C_6$–$C_{10}$ aryl, amino, oxo, hydroxy, $C_1$–$C_4$ alkoxy, and $C_6$–$C_{10}$ aryloxy. In some particularly preferred embodiments, the alkylene or alkenylene group is substituted with one or two oxo or hydroxy groups. However, $L^2$ preferably is not —C(O)—, and when the carbon atom to which Cy is attached is oxo substituted, Cy and Z preferably are not both pyridyl.

In some preferred embodiments, $L^1$ is $C_1$–$C_6$ saturated alkylene, wherein on of the carbon atoms of the saturated alkylene is replaced by a heteroatom moiety selected from the group consisting of O; NR', R' being alkyl, acyl, or hydrogen; S; S(O); or $S(O)_2$. Preferably, the carbon atom adjacent to Cy is replaced by a heteroatom moiety. In some particularly preferred embodiments, $L^1$ is selected from the group consisting of $—S—(CH_2)_2—$, $—S(O)—(CH_2)_2—$, $—S(O)_2—(CH_2)_2—$, $—S—(CH_2)_3—$, $—S(O)—(CH_2)_3—$, and $—S(O)_2—(CH_2)_3—$.

In a third embodiment, the invention provides novel inhibitors of histone deacetylase represented by formula (3):

$$\text{Cy—L}^3\text{—Ar—Y}^3\text{—C(O)NH—Z} \quad (3)$$

wherein

Cy is cycloalkyl, aryl, heteroaryl, or heterocyclyl, any of which may be optionally substituted, provided that Cy is not a (spirocycloalkyl)heterocyclyl;

$L^3$ is selected from the group consisting of (a) $—(CH_2)_m—W—$, where m is 0, 1, 2, 3, or 4, and W is selected from the group consisting of C(O)NH—, $—S(O)_2NH—$, —NHC(O)—, $—NHS(O)_2—$, and —NH—C(O)—NH—; and (b) $C_1$–$C_6$ alkylene or $C_2$–$C_6$ alkenylene, wherein the alkylene or alkenylene optionally may be substituted, provided that $L^3$ is not —C(O)—, and wherein one of the carbon atoms of the alkylene optionally may be replaced by O; NR', R' being alkyl, acyl, or hydrogen; S; S(O); or $S(O)_2$;

Ar is arylene, wherein said arylene optionally may be additionally substituted and optionally may be fused to an aryl or heteroaryl ring, or to a saturated or partially unsaturated cycloalkyl or heterocyclic ring, any of which may be optionally substituted; and $Y^3$ is $C_2$ alkenylene or $C_2$ alkynylene, wherein one or both carbon atoms of the alkenylene optionally may be substituted with alkyl, aryl, alkaryl, or aralkyl; and Z is selected from the group consisting of anilinyl, pyridyl, thiadiazolyl, and —O—M, M being H or a pharmaceutically acceptable cation;

provided that when Cy is unsubstituted phenyl, Ar is not phenyl wherein $L^3$ and $Y^3$ are oriented ortho or meta to each other.

Preferred substituents Cy, Ar, and Z according to this aspect of the invention are as defined above for the first embodiment. Preferred substituents $L^3$ are as defined above for $L^1$ or $L^2$.

Preferably, $Y^3$ is $C_2$ alkenylene or $C_2$ alkynylene, wherein one or both carbon atoms of the alkenylene optionally may be substituted with $C_1$–$C_6$ alkyl, $C_6$–$C_{10}$ aryl, ($C_1$–$C_6$)alk ($C_6$–$C_{10}$)aryl, or ($C_6$–$C_{10}$)ar($C_1$–$C_6$)alkyl. More preferably, $Y^3$ is $C_2$ alkenylene or $C_2$ alkynylene, wherein one or both carbon atoms of the alkenylene optionally may be substituted with $C_1$–$C_4$ alkyl, $C_6$–$C_{14}$ aryl, ($C_1$–$C_4$)alk($C_6$–$C_{10}$) aryl, or ($C_6$–$C_{10}$)ar—($C_1$–$C_4$)alkyl. Still more preferably, $Y^3$ is selected from the group consisting of —C≡C—, —CH═CH—, —C($CH_3$)═CH—, and —CH═C($CH_3$)—.

Synthesis

Compounds of formula Cy—$L^1$—Ar—$Y^1$—C(O)—NH—O—M, wherein $L^1$ is —$S(O)_2NH$—, preferably may be prepared according to the synthetic routes depicted in Schemes 1–3. Accordingly, in certain preferred embodiments, compounds I are preferably prepared according to the general synthetic route depicted in Scheme 1. Thus, a sulfonyl chloride (II) is treated with an amine (III) in a solvent such as methylene chloride in the presence of an organic base such as triethylamine. Treatment of the crude product with a base such as sodium methoxide in an alcoholic solvent such as methanol effects cleavage of any dialkylated material and affords the sulfonamide (IV). Hydrolysis of the ester function in IV can be effected by treatment with a hydroxide base, such as lithium hydroxide, in a solvent mixture such as tetrahydrofuran and methanol to afford the corresponding acid (V).

In some embodiments, conversion of the acid V to the hydroxamic acid I may be accomplished by coupling V with a protected hydroxylamine, such as tetrahydropyranylhydroxylamine ($NH_2OTHP$), to afford the protected hydroxamate VI, followed by acidic hydrolysis of VI to provide the hydroxamic acid I. The coupling reaction is preferably accomplished with the coupling reagent dicyclohexylcarbodiimide (DCC) in a solvent such as methylene chloride (Method A) or with the coupling reagent 1-(3-dimethylaminopropyl)-3-ethylcarbodiimide in presence of N-hydroxy benzotriazole in an aprotic solvent such as dimethylformamide (Method D). Other coupling reagents are known in the art and may also be used for this reaction. Hydrolysis of VI is preferably effected by treatment with an organic acid such as camphorsulfonic acid in a protic solvent such as methanol.

Alternatively, in some other embodiments, acid V is converted to the corresponding acid chloride, preferably by treatment with oxalic chloride, followed by the addition of a protected hydroxylamine such as O-trimethylsilylhydroxylamine in a solvent such as methylene chloride, which then provides the hydroxylamine I upon workup (Method C).

Scheme 1

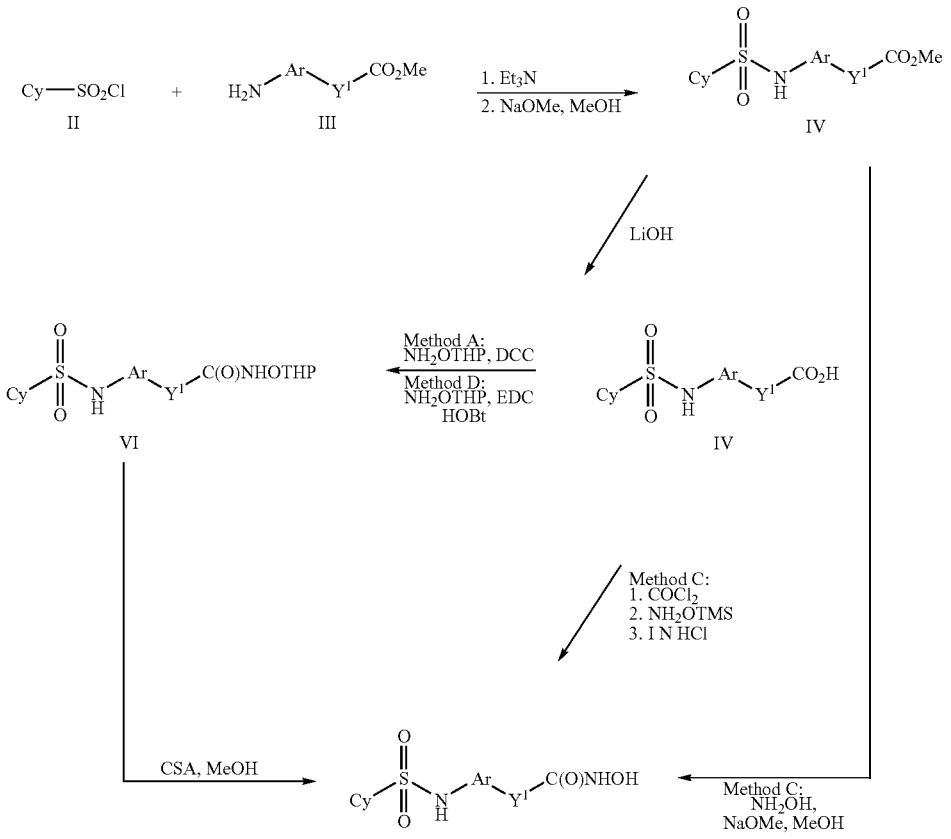

In still other embodiments, the ester IV is preferably treated with hydroxylamine in a solvent such as methanol in the presence of a base such as sodium methoxide to furnish the hydroxylamine I directly (Method B).
Scheme 2
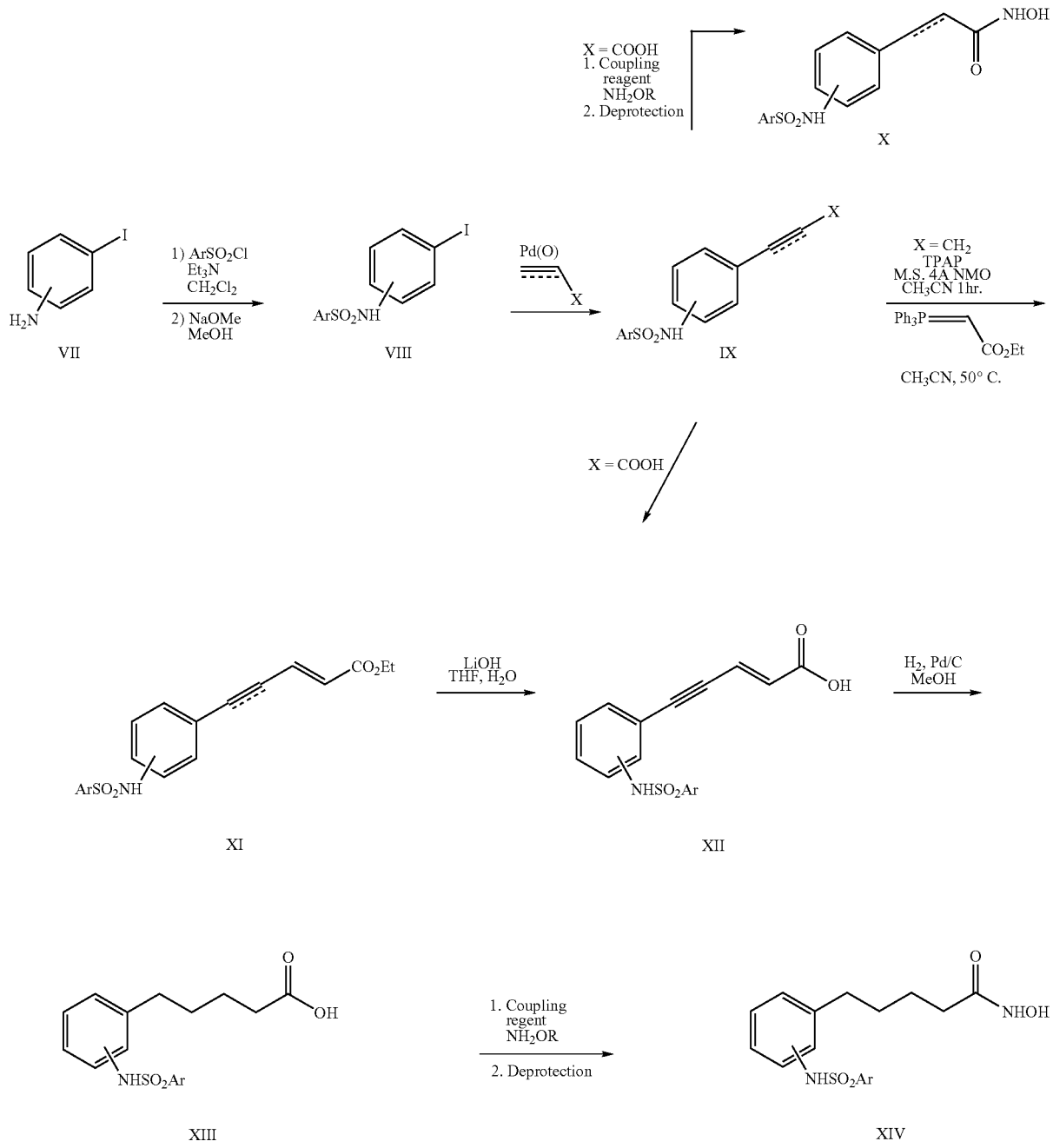

Compounds of formula X and XIV preferably are prepared according to the general procedure outlined in Scheme 2. Thus, an aminoaryl halide (VII) is treated with a sulfonyl chloride in presence of a base such as triethylamine, followed by treatment with an alkoxide base, to furnish the sulfonamide VIII. One of skill in the art will recognize that reverse sulfonamide analogs can be readily prepared by an analogous procedure, treating a haloarenesulfonyl halide with an arylamine.

Compound VIII is coupled with a terminal acetylene or olefinic compound in the presence of a palladium catalyst such as tetrakis(triphenylphosphine)palladium(0) in a solvent such as pyrrolidine to afford IX.

le;.5qOxidation of the compound of formula IX ($X=CH_2OH$), followed by homologation of the resulting aldehyde using a Wittig type reagent such as carbethoxymethylenetriphenylphosphorane in a solvent such as acetonitrile, gives the compound of formula XI. Basic hydrolysis of XI, such as by treatment with lithium hydroxide in a mixture of THF and water, provides the acid XII. Hydrogenation of XII may preferably be performed over a palladium catalyst such as Pd/C in a protic solvent such as methanol to afford the saturated acid XIII. Coupling of the acid XIII with an O-protected hydroxylamine such as O-tetrahydropyranylhydroxylamine is effected by treatment with a coupling reagent such as 1-(3-dimethylaminopropyl)-3-ethylcarbodiimide in the presence of N-hydroxybenzotriazole (HOBT), or N,N-dicyclohexylcarbodiimide (DCC), in a solvent such as DMF, followed by deprotection to furnish the compound of general formula XIV.

The acid IX, wherein X=COOH, may be coupled directly with an O-protected hydroxylamine such as O-tetrahydropyranylhydroxylamine, followed by deprotection of the hydroxy protecting group to furnish the hydroxamic acid X.

Compounds of formula $Cy—L^1—Ar—Y^1—C(O)—NH—O—M$, wherein $L^1$ is —C(O)NH—, preferably may be prepared according to the synthetic routes analogous to those depicted in Schemes 1–2, substituting acid chloride starting materials for the sulfonyl chloride starting materials in those Schemes.

Scheme 3

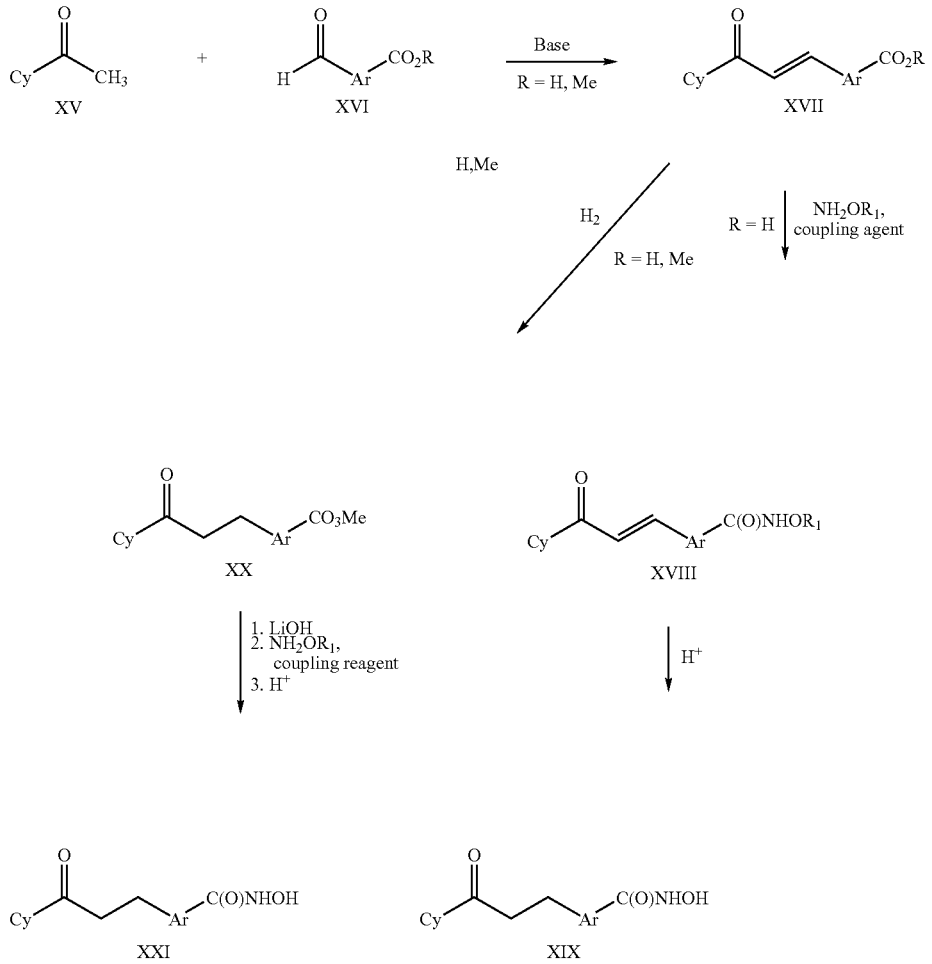

Compounds of the formula Cy—$L^2$—Ar—$Y^2$—C(O)—NH—O—M are preferably prepared according to the synthetic routes outlined in Schemes 3–5. Accordingly, in certain preferred embodiments, compounds of formulae XIX and XXI ($L^2$=—C(O)—CH═CH— or —C(O)$CH_2$CH—) preferably are prepared according to the route described in Scheme 3. Thus, a substituted aryl acetophenone (XV) is treated with an aryl aldehyde (XVI) in a protic solvent such as methanol in the presence of a base such as sodium methoxide to afford the enone XVII.

The acid substituent of XVII (R=H) is coupled with an O-protected hydroxylamine such as O-tetrahydropyranylhydroxylamine ($R_1$=tetrahydropyranyl) to afford the O-protected-N-hydroxybenzamide XVIII. The coupling reaction is preferably performed by treating the acid and hydroxylamine with dicyclohexylcarbodiimide in a solvent such as methylene chloride or with 1-(3-dimethylaminopropyl)-3-ethylcarbodiimide in the presence of N-hydroxybenzotriazole in a solvent such as dimethylformamide. Other coupling reagents are known in the art and may also be used in this reaction. O-Deprotection is accomplished by treatment of XVIII with an acid such as camphorsulfonic acid in a solvent such as methanol to afford the hydroxamic acid XIX ($L^2$=—C(O)—CH═CH—).

Saturated compounds of formula XXI ($L^2$=—C(O)—$CH_2CH_2$—) are preferably prepared by hydrogenation of XVII (R=Me) over a palladium catalyst, such as 10% Pd/C, in a solvent such as methanol-tetrahydrofuran. Basic hydrolysis of the resultant product XIX with lithium hydroxide, followed by N-hydroxy amide formation and acid hydrolysis as described above, then affords the hydroxamic acid XXI.

Scheme 4

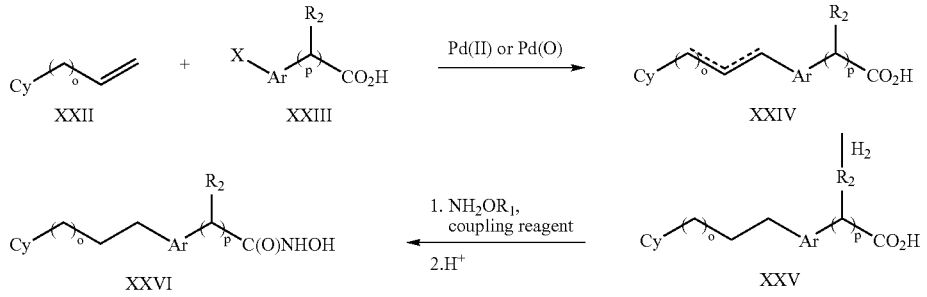

Compound of formula XXVI ($L^2$=$CH_2)_{o+2}$—) are preferably prepared by the general procedures described in Schemes 4 and 5. Thus, in some embodiments, a terminal olefin (XXII) is coupled with an aryl halide (XXIII) in the presence of a catalytic amount of a palladium source, such as palladium acetate or tris(dibenzylideneacetone) dipalladium(0), a phosphine, such as triphenylphosphine, and a base, such as triethylamine, in a solvent such as acetonitrile to afford the coupled product XXIV. Hydrogenation, followed by N-hydroxyamide formation and acid hydrolysis, as described above, affords the hydroxamic acid XXVI.

Scheme 5

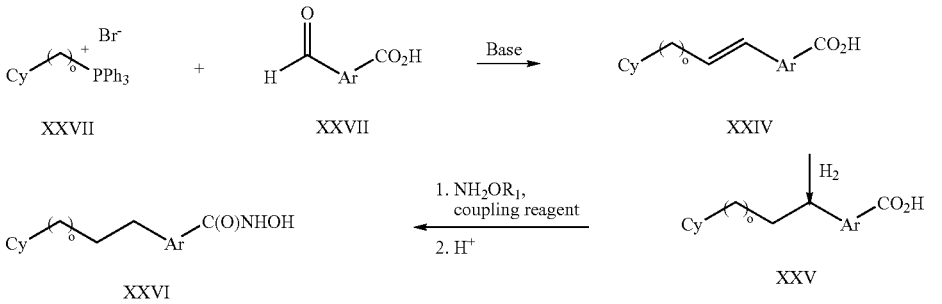

Alternatively, in some other embodiments, a phosphonium salt of formula XXVII is treated with an aryl aldehyde of formula XXVIII in the presence of base, such as lithium hexamethyldisilazide, in a solvent, such as tetrahydrofuran, to produce the compound XXIV. Hydrogenation, followed by N-hydroxyamide formation and acidic hydrolysis, then affords the compounds XXVI.

Scheme 6

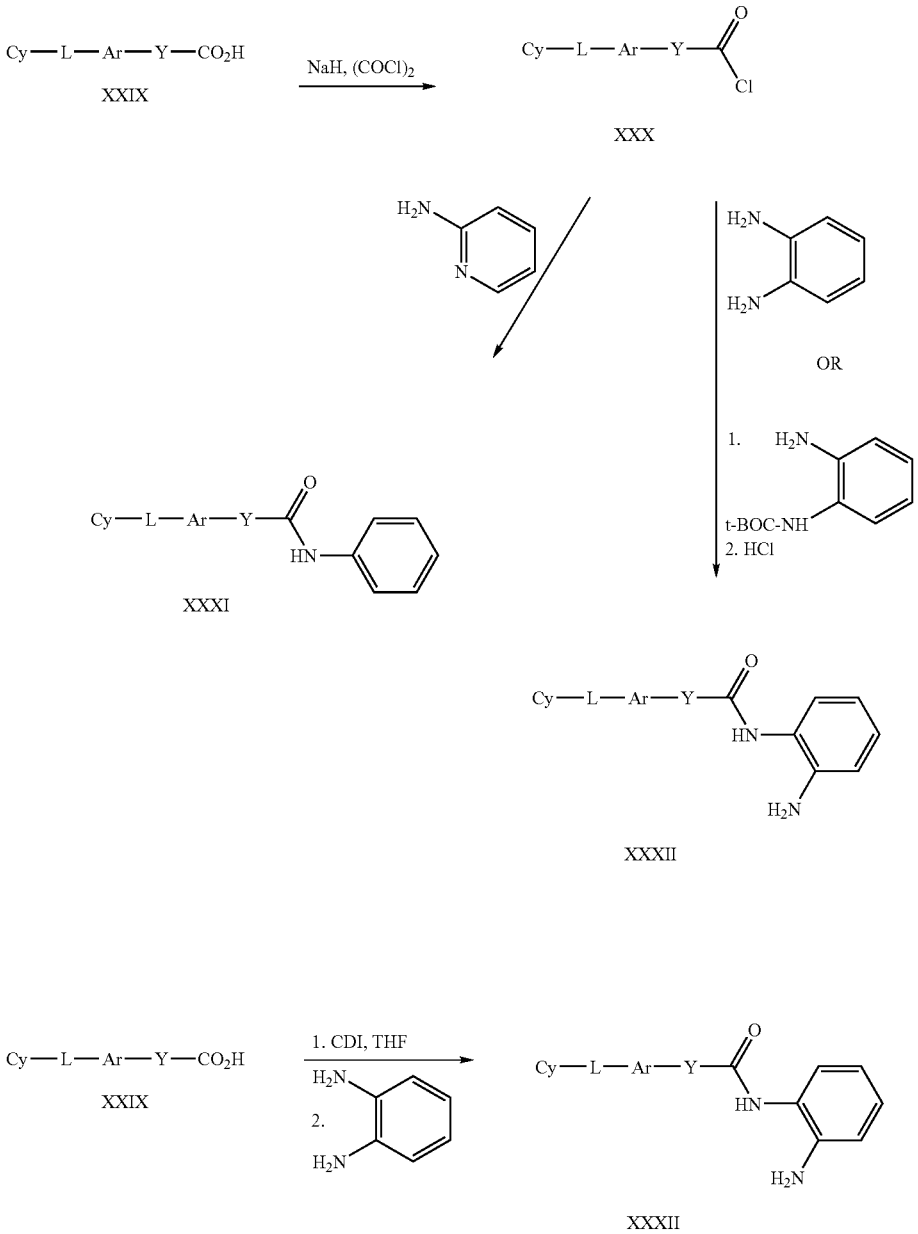

Compounds of formula Cy—L—Ar—Y—C(O)—NH—Z, wherein L is $L^1$ or $L^2$, Y is $Y^1$ or $Y^2$, and Z is anilinyl or pyridyl, are preferably prepared according to synthetic routes outlined in Scheme 6. An acid of formula Cy—L—Ar—Y—C(O)—OH (XXIX), prepared by one of the methods shown in Schemes 1–5, is converted to the corresponding acid chloride XXX according to standard methods, e.g., by treatment with sodium hydride and oxalyl chloride. Treatment of XXX with 2-aminopyridine and a tertiary base such as N-methylmorpholine, preferably in dichloromethane at reduced temperature, then affords the pyridyl amide XXXI. In a similar fashion, the acid chloride XXX may be treated with 1,2-phenylenediamine to afford the anilinyl amide XXXII. Alternatively, the acid chloride XXX may be treated with a mono-protected 1,2-phenylenediamine, such as 2-(t-BOC-amino)aniline, followed by deprotection, to afford XXXII.

In another alternative procedure, the acid XXIX may be activated by treatment with carbonyldiimidazole (CDI), followed by treatment with 1,2-phenylenediamine and trifluoroacetic acid to afford the anilinyl amide XXXII.

Scheme 7

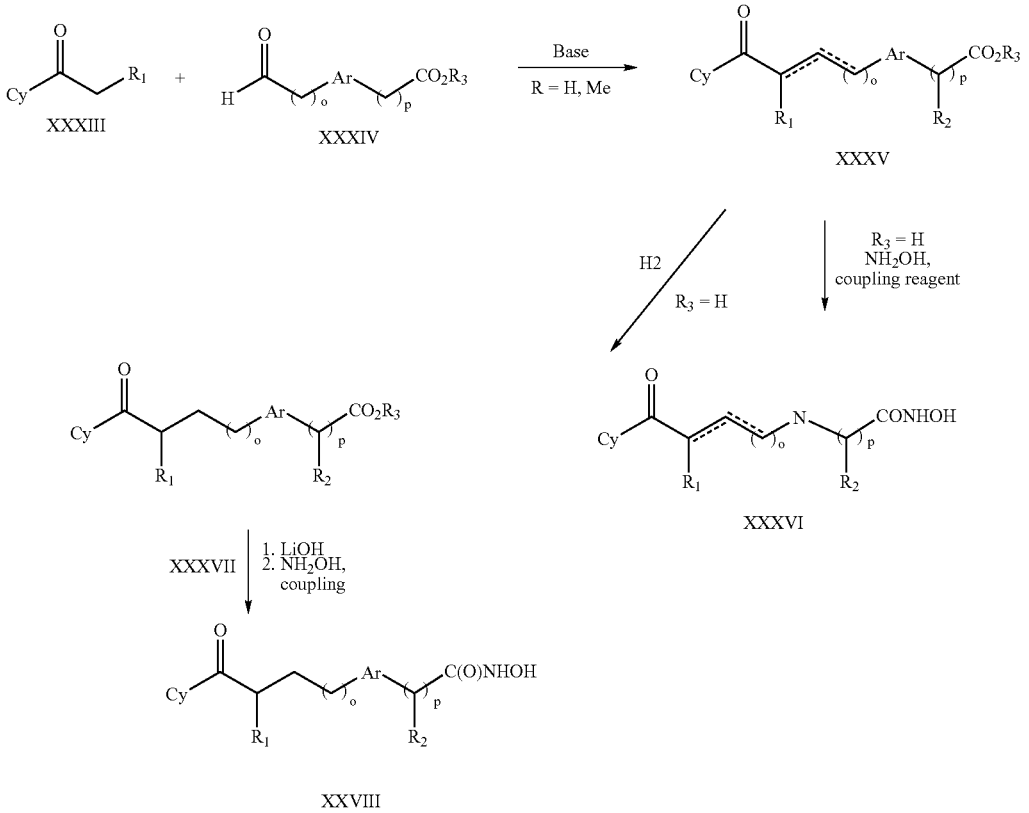

Compounds of formula XXXVIII ($L^2$=—C(O)-alkylene-) preferably are prepared according to the general procedure depicted in Scheme 7. Thus, Aldol condensation of ketone XXXIII ($R_1$=H or alkyl) with aldehyde XXXIV affords the adduct XXXV. The adduct XXXV may be directly converted to the corresponding hydroxamic acid XXXVI, or may first undergo hydrogenation to afford the saturated compound XXVII and then be converted to the hydroxamic acid XXXVIII.

Scheme 8

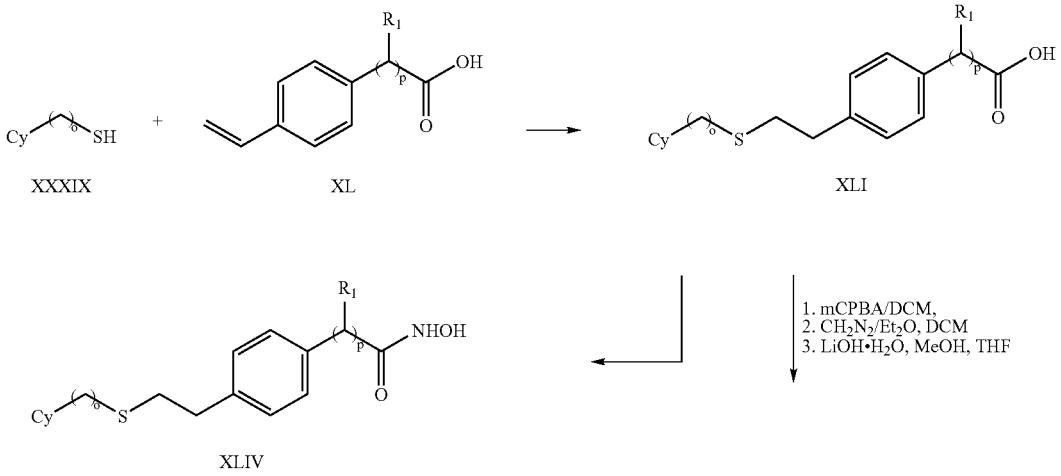

-continued

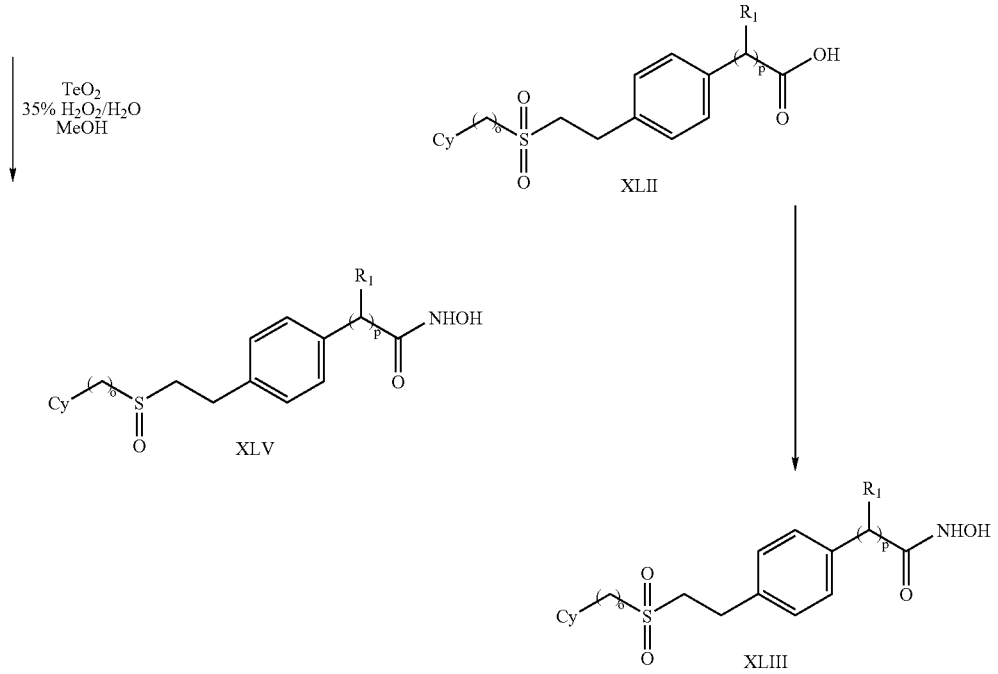

Compounds of formula (2), wherein one of the carbon atoms in $L^2$ is replaced with S, S(O), or $S(O)_2$ preferably are prepared according to the general procedure outlined in Scheme 8. Thus, thiol XXXIX is added to olefin XL to produce XLI. The reaction is preferably conducted in the presence of a radical initiator such as 2,2'-azobisisobutyronitrile (AIBN) or 1,1'-azobis (cyclohexanecarbonitrile) (VAZO™). Sulfide oxidation, preferably by treatment with m-chloroperbenzoic acid (mCPBA), affords the corresponding sulfone, which is conveniently isolated after conversion to the methyl ester by treatment with diazomethane. Ester hydrolysis then affords the acid XLII, which is converted to the hydroxamic acid XLIII according to any of the procedures described above. The sulfide XLI also may be converted directly to the corresponding hydroxamic acid XLIV, which then may be selectively oxidized to the sulfoxide XLV, for example, by treatment with hydrogen peroxide and tellurium dioxide.

Pharmaceutical Compositions

In a second aspect, the invention provides pharmaceutical compositions comprising an inhibitor of histone deacetylase represented by any one of formulae (1)–(6) and a pharmaceutically acceptable carrier, excipient, or diluent. Compounds of the invention may be formulated by any method well known in the art and may be prepared for administration by any route, including, without limitation, parenteral, oral, sublingual, transdermal, topical, intranasal, intratracheal, or intrarectal. In certain preferred embodiments, compounds of the invention are administered intravenously in a hospital setting. In certain other preferred embodiments, administration may preferably be by the oral route.

The characteristics of the carrier will depend on the route of administration. As used herein, the term "pharmaceutically acceptable" means a non-toxic material that is compatible with a biological system such as a cell, cell culture, tissue, or organism, and that does not interfere with the effectiveness of the biological activity of the active ingredient(s). Thus, compositions according to the invention may contain, in addition to the inhibitor, diluents, fillers, salts, buffers, stabilizers, solubilizers, and other materials well known in the art. The preparation of pharmaceutically acceptable formulations is described in, e.g., Remington's Pharmaceutical Sciences, 18th Edition, ed. A. Gennaro, Mack Publishing Co., Easton, Pa., 1990.

Inhibition of Histone Deacetylase

In a third aspect, the invention provides a method of inhibiting histone deacetylase in a cell, comprising contacting a cell in which inhibition of histone deacetylase is desired with an inhibitor of histone deacetylase according to the invention. In a first embodiment according to this aspect of the invention, the inhibitor of histone deacetylase is represented by the formula (1)

$$Cy—L^1—Ar—Y^1—C(O)—NH—Z \quad (1)$$

wherein

Cy is cycloalkyl, aryl, heteroaryl, or heterocyclyl, any of which may be optionally substituted;

$L^1$ is $—(CH_2)_n—W—$, where m is 0, 1, 2, 3, or 4, and W is selected from the group consisting of C(O)NH—, $—S(O)_2NH—$, —NHC(O)—, $—NHS(O)_2—$, and —NH—C(O)—NH—;

Ar is arylene, wherein said arylene optionally may be additionally substituted and optionally may be fused to an aryl or heteroaryl ring, or to a saturated or partially unsaturated cycloalkyl or heterocyclic ring, any of which may be optionally substituted;

$Y^1$ is a chemical bond or a straight- or branched-chain saturated alkylene, wherein said alkylene may be optionally substituted; and Z is selected from the group consisting of anilinyl, pyridyl, 2-thioxo-1,3,4-thiadiazol-2-yl, and —O—M, M being H or a pharmaceutically acceptable cation;

provided that when $L^1$ is —C(O)NH—, Y is —$(CH_2)_n$—, n being 1, 2, or 3, and Z is —O—M, then Cy is not aminophenyl, dimethylaminophenyl, or hydroxyphenyl.

In a second embodiment according to this aspect of the invention, the inhibitor of histone deacetylase is represented by formula (2):

$$Cy—L^2—Ar—Y^2—C(O)NH—Z \quad (2)$$

wherein

Cy is cycloalkyl, aryl, heteroaryl, or heterocyclyl, any of which may be optionally substituted;

$L^2$ is $C_1$–$C_6$ saturated alkylene or $C_2$–$C_6$ alkenylene, either of which may be optionally substituted;

Ar is arylene, wherein said arylene optionally may be additionally substituted and optionally may be fused to an aryl or heteroaryl ring, or to a saturated or partially unsaturated cycloalkyl or heterocyclic ring, any of which may be optionally substituted; and $Y^2$ is a chemical bond or a straight- or branched-chain saturated alkylene, which may be optionally substituted, provided that the alkylene is not substituted with a substituent of the formula —C(O)R wherein R comprises an α-amino acyl moiety; and Z is selected from the group consisting of anilinyl, pyridyl, 2-thioxo-1,3,4-thiadiazol-2-yl, and —O—M, M being H or a pharmaceutically acceptable cation.

In a third embodiment according to this aspect of the invention, the inhibitor of histone deacetylase is represented by the formula (3):

$$Cy—L^3—Ar—Y^3—C(O)NH—Z \quad (3)$$

wherein

Cy is cycloalkyl, aryl, heteroaryl, or heterocyclyl, any of which may be optionally substituted, provided that Cy is not a (spirocycloalkyl)heterocyclyl;

$L^3$ is selected from the group consisting of (a) —$(CH_2)_n$—W—, where m is 0, 1, 2, 3, or 4, and W is selected from the group consisting of —C(O)NH—, —$S(O)_2$NH—, —NHC(O)—, —NHS$(O)_2$—, and —NH—C(O)—NH—; and (b) $C_1$–$C_6$ alkylene or $C_2$–$C_6$ alkenylene, wherein the alkylene or alkenylene optionally may be substituted, provided that $L^3$ is not —C(O)—, and wherein one of the carbon atoms of the alkylene optionally may be replaced by O; NR', R' being alkyl, acyl, or hydrogen; S; S(O); or $S(O)_2$;

Ar is arylene, wherein said arylene optionally may be additionally substituted and optionally may be fused to an aryl or heteroaryl ring, or to a saturated or partially unsaturated cycloalkyl or heterocyclic ring, any of which may be optionally substituted; and $Y^3$ is $C_2$ alkenylene or $C_2$ alkynylene, wherein one or both carbon atoms of the alkenylene optionally may be substituted with alkyl, aryl, alkaryl, or aralkyl; and Z is selected from the group consisting of anilinyl, pyridyl, thiadiazolyl, and —O—M, M being H or a pharmaceutically acceptable cation;

provided that when Cy is unsubstituted phenyl, Ar is not phenyl wherein $L^3$ and $Y^3$ are oriented ortho or meta to each other.

In a fourth embodiment according to this aspect of the invention, the novel histone deacetylase inhibitor is selected from the group represented by formulae (4)–(6):

(4)

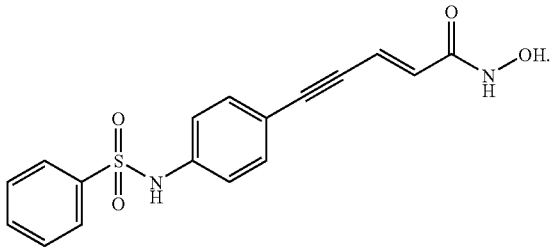

(5)

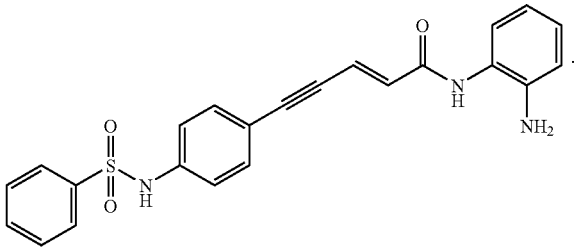

(6)

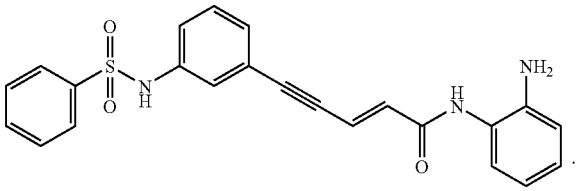

Measurement of the enzymatic activity of a histone deacetylase can be achieved using known methodologies. For example, Yoshida et al., J. Biol. Chem., 265: 17174–17179 (1990), describes the assessment of histone deacetylase enzymatic activity by the detection of acetylated histones in trichostatin. A treated cells. Taunton et al., Science, 272: 408–411 (1996), similarly describes methods to measure histone deacetylase enzymatic activity using endogenous and recombinant HDAC-1. Both of these references are hereby incorporated by reference in their entirety.

In some preferred embodiments, the histone deacetylase inhibitor interacts with and reduces the activity of all histone deacetylases in the cell. In some other preferred embodiments according to this aspect of the invention, the histone deacetylase inhibitor interacts with and reduces the activity of fewer than all histone deacetylases in the cell. In certain preferred embodiments, the inhibitor interacts with and reduces the activity of one histone deacetylase (e.g., HDAC-1), but does not interact with or reduce the activities of other histone deacetylases (e.g., HDAC-2, HDAC-3, HDAC-4, HDAC-5, HDAC-6, HDAC-7, and HDAC-8). As discussed below, certain particularly preferred histone deacetylase inhibitors are those that interact with and reduce the enzymatic activity of a histone deacetylase that is involved in tumorigenesis. Certain other preferred histone deacetylase inhibitors interact with and reduce the enzymatic activity of a fungal histone deacetylase.

Preferably, the method according to the third aspect of the invention causes an inhibition of cell proliferation of the contacted cells. The phrase "inhibiting cell proliferation" is used to denote an ability of an inhibitor of histone deacetylase to retard the growth of cells contacted with the inhibitor as compared to cells not contacted. An assessment of cell proliferation can be made by counting contacted and non-contacted cells using a Coulter Cell Counter (Coulter, Miami, Fla.) or a hemacytometer. Where the cells are in a solid growth (e.g., a solid tumor or organ), such as assessment of cell proliferation can be made by measuring the growth with calipers and comparing the size of the growth of contacted cells with non-contacted cells.

Preferably, growth of cells contacted with the inhibitor is retarded by at least 50% as compared to growth of non-contacted cells. More preferably, cell proliferation is inhibited by 100% (i.e., the contacted cells do not increase in number). Most preferably, the phrase "inhibiting cell proliferation" includes a reduction in the number or size of contacted cells, as compared to non-contacted cells. Thus, an inhibitor of histone deacetylase according to the invention that inhibits cell proliferation in a contacted cell may induce the contacted cell to undergo growth retardation, to undergo growth arrest, to undergo programmed cell death (i.e., to apoptose), or to undergo necrotic cell death.

The cell proliferation inhibiting ability of the histone deacetylase inhibitors according to the invention allows the synchronization of a population of asynchronously growing cells. For example, the histone deacetylase inhibitors of the invention may be used to arrest a population of non-neoplastic cells grown in vitro in the G1 or G2 phase of the cell cycle. Such synchronization allows, for example, the identification of gene and/or gene products expressed during the G1 or G2 phase of the cell cycle. Such a synchronization of cultured cells may also be useful for testing the efficacy of a new transfection protocol, where transfection efficiency varies and is dependent upon the particular cell cycle phase of the cell to be transfected. Use of the histone deacetylase inhibitors of the invention allows the synchronization of a population of cells, thereby aiding detection of enhanced transfection efficiency.

In some preferred embodiments, the contacted cell is a neoplastic cell. The term "neoplastic cell" is used to denote a cell that shows aberrant cell growth. Preferably, the aberrant cell growth of a neoplastic cell is increased cell growth. A neoplastic cell may be a hyperplastic cell, a cell that shows a lack of contact inhibition of growth in vitro, a benign tumor cell that is incapable of metastasis in vivo, or a cancer cell that is capable of metastasis in vivo and that may recur after attempted removal. The term "tumorigenesis" is used to denote the induction of cell proliferation that leads to the development of a neoplastic growth. In some embodiments, the histone deacetylase inhibitor induces cell differentiation in the contacted cell. Thus, a neoplastic cell, when contacted with an inhibitor of histone deacetylase may be induced to differentiate, resulting in the production of a daughter cell that is phylogenetically more advanced than the contacted cell.

In some preferred embodiments, the contacted cell is in an animal. Thus, the invention provides a method for treating a cell proliferative disease or condition in an animal, comprising administering to an animal in need of such treatment a therapeutically effective amount of a histone deacetylase inhibitor of the invention. Preferably, the animal is a mammal, more preferably a domesticated mammal. Most preferably, the animal is a human.

The term "cell proliferative disease or condition" is meant to refer to any condition characterized by aberrant cell growth, preferably abnormally increased cellular proliferation. Examples of such cell proliferative diseases or conditions include, but are not limited to, cancer, restenosis, and psoriasis. In particularly preferred embodiments, the invention provides a method for inhibiting neoplastic cell proliferation in an animal comprising administering to an animal having at least one neoplastic cell present in its body a therapeutically effective amount of a histone deacetylase inhibitor of the invention.

It is contemplated that some compounds of the invention have inhibitory activity against a histone deacetylase from a protozoal source. Thus, the invention also provides a method for treating or preventing a protozoal disease or infection, comprising administering to an animal in need of such treatment a therapeutically effective amount of a histone deacetylase inhibitor of the invention. Preferably the animal is a mammal, more preferably a human. Preferably, the histone deacetylase inhibitor used according to this embodiment of the invention inhibits a protozoal histone deacetylase to a greater extent than it inhibits mammalian histone deacetylases, particularly human histone deacetylases.

The present invention further provides a method for treating a fungal disease or infection comprising administering to an animal in need of such treatment a therapeutically effective amount of a histone deacetylase inhibitor of the invention. Preferably the animal is a mammal, more preferably a human. Preferably, the histone deacetylase inhibitor used according to this embodiment of the invention inhibits a fungal histone deacetylase to a greater extent than it inhibits mammalian histone deacetylases, particularly human histone deacetylases.

The term "therapeutically effective amount" is meant to denote a dosage sufficient to cause inhibition of histone deacetylase activity in the cells of the subject, or a dosage sufficient to inhibit cell proliferation or to induce cell differentiation in the subject. Administration may be by any route, including, without limitation, parenteral, oral, sublingual, transdermal, topical, intranasal, intratracheal, or intrarectal. In certain particularly preferred embodiments, compounds of the invention are administered intravenously in a hospital setting. In certain other preferred embodiments, administration may preferably be by the oral route.

When administered systemically, the histone deacetylase inhibitor is preferably administered at a sufficient dosage to attain a blood level of the inhibitor from about 0.01 M to about 100 M, more preferably from about 0.05 M to about 50 M, still more preferably from about 0.1 M to about 25 M, and still yet more preferably from about 0.5 M to about 25 M. For localized administration, much lower concentrations than this may be effective, and much higher concentrations may be tolerated. One of skill in the art will appreciate that the dosage of histone deacetylase inhibitor necessary to produce a therapeutic effect may vary considerably depending on the tissue, organ, or the particular animal or patient to be treated.

In certain preferred embodiments of the fifth and sixth aspects of the invention, the method further comprises contacting the cell with an antisense oligonucleotide that inhibits the expression of a histone deacetylase. The combined use of a nucleic acid level inhibitor (i.e., antisense oligonucleotide) and a protein level inhibitor (i.e., inhibitor of histone deacetylase enzyme activity) results in an improved inhibitory effect, thereby reducing the a mounts of the inhibitors required to obtain a given inhibitory effect as compared to the amounts necessary when either is used individually. The antisense oligonucleotides according to this aspect of the invention are complementary to regions of RNA or double-stranded DNA that encode HDAC-1, HDAC-2, HDAC-3, HDAC-4, HDAC-5, HDAC-6, HDAC7, and/or HDAC-8.

For purposes of the invention, the term "oligonucleotide" includes polymers of two or more deoxyribonucleosides, ribonucleosides, or 2'-O-substituted ribonucleoside residues, or any combination thereof. Preferably, such oligonucleotides have from about 6 to about 100 nucleoside residues, more preferably from about 8 to about 50 nucleoside residues, and most preferably from about 12 to about 30 nucleoside residues. The nucleoside residues may be coupled to each other by any of the numerous known internucleoside linkages. Such internucleoside linkages include without limitation phosphorothioate, phosphorodithioate, alkylphosphonate, alkylphosphonothioate, phosphotriester, phosphoramidate, siloxane, carbonate, carboxymethylester, acetamidate, carbamate, thioether, bridged phosphoramidate, bridged methylene phosphonate, bridged phosphorothioate and sulfone internucleoside linkages. In certain preferred embodiments, these internucleoside linkages may be phosphodiester, phosphotriester, phosphorothioate, or phosphoramidate linkages, or combinations thereof. The term oligonucleotide also encompasses such polymers having chemically modified bases or sugars and/or having additional substituents, including without limitation lipophilic groups, intercalating agents, diamines and adamantane. For purposes of the invention the term "2'-O-substituted" means substitution of the 2' position of the pentose moiety with an —O-lower alkyl group containing 1–6 saturated or unsaturated carbon atoms, or with an —O-aryl or allyl group having 2–6 carbon atoms, wherein such alkyl, aryl or allyl group may be unsubstituted or may be substituted, e.g., with halo, hydroxy, trifluoromethyl, cyano, nitro, acyl, acyloxy, alkoxy, carboxyl, carbalkoxyl, or amino groups; or such 2' substitution may be with a hydroxy group (to produce a ribonucleoside), an amino or a halo group, but not with a 2'-H group. The term "oligonucleotide" also encompasses linked nucleic acid and peptide nucleic acid.

Particularly preferred antisense oligonucleotides utilized in this aspect of the invention include chimeric oligonucleotides and hybrid oligonucleotides.

For purposes of the invention, a "chimeric oligonucleotide" refers to an oligonucleotide having more than one type of internucleoside linkage. One preferred example of such a chimeric oligonucleotide is a chimeric oligonucleotide comprising a phosphorothioate, phosphodiester or phosphorodithioate region, preferably comprising from about 2 to about 12 nucleotides, and an alkylphosphonate or alkylphosphonothioate region (see e.g., Pederson et al. U.S. Pat. Nos. 5,635,377 and 5,366,878). Preferably, such chimeric oligonucleotides contain at least three consecutive internucleoside linkages selected from phosphodiester and phosphorothioate linkages, or combinations thereof. For purposes of the invention, a "hybrid oligonucleotide" refers to an oligonucleotide having more than one type of nucleoside. One preferred example of such a hybrid oligonucleotide comprises a ribonucleotide or 2'-O-substituted ribonucleotide region, preferably comprising from about 2 to about 12 2'-O-substituted nucleotides, and a deoxyribonucleotide region. Preferably, such a hybrid oligonucleotide will contain at least three consecutive deoxyribonucleosides and will also contain ribonucleosides, 2'-O-substituted ribonucleosides, or combinations thereof (see e.g., Metelev and Agrawal, U.S. Pat. No. 5,652,355).

The exact nucleotide sequence and chemical structure of an antisense oligonucleotide utilized in the invention can be varied, so long as the oligonucleotide retains its ability to inhibit expression of the gene of interest. This is readily determined by testing whether the particular antisense oligonucleotide is active by quantitating the mRNA encoding a product of the gene, or in a Western blotting analysis assay for the product of the gene, or in an activity assay for an enzymatically active gene product, or in a soft agar growth assay, or in a reporter gene construct assay, or an in vivo tumor growth assay, all of which are described in detail in this specification or in Ramchandani et al. (1997) Proc. Natl. Acad. Sci. USA 94: 684–689.

Antisense oligonucleotides utilized in the invention may conveniently be synthesized on a suitable solid support using well known chemical approaches, including H-phosphonate chemistry, phosphoramidite chemistry, or a combination of H-phosphonate chemistry and phosphoramidite chemistry (i.e., H-phosphonate chemistry for some cycles and phosphoramidite chemistry for other cycles). Suitable solid supports include any of the standard solid supports used for solid phase oligonucleotide synthesis, such as controlled-pore glass (CPG) (see, e.g., Pon, R. T. (1993) Methods in Molec. Biol. 20: 465–496).

Particularly, preferred oligonucleotides have nucleotide sequences of from about 13 to about 35 nucleotides which include the nucleotide sequences shown in Tables 1–3. Yet additional particularly preferred oligonucleotides have nucleotide sequences of from about 15 to about 26 nucleotides of the nucleotide sequences shown in Tables 1–3.

TABLE 1

| SEQ ID NO. | SEQUENCE | TARGET(**) |
|---|---|---|
| 1 | 5'-GAG ACA GCA GCA CCA GCG GG-3' | 17–36 |
| 2 | 5'-ATG ACC GAG TGG GAG ACA GC-3' | 21–49 |
| 3 | 5'-GGA TGA CCG AGT GGG AGA CA-3' | 31–50 |
| 4 | 5'-CAG GAT GAC CGA GTG GGA GA-3' | 33–52 |
| 5 | 5'-TGT GTT CTC AGG ATG ACC GA-3' | 41–60 |
| 6 | 5'-GAG TGA CAG AGA CGC TCA GG-3' | 62–81 |
| 7 | 5'-TTC TGG CTT CTC CTC CTT GG-3' | 1504–1523 |
| 8 | 5'-CTT GAC CTC CTC CTT GAC CC-3' | 1531–1550 |
| 9 | 5'-GGA AGC CAG AGC TGG AGA GG-3' | 1565–1584 |
| 10 | 5'-GAA ACG TGA GGG ACT CAG CA-3' | 1585–1604 |
| 11 | 5'-CCG TCG TAG TAG TAA CAG ACT TT-3' | 138–160 |
| 12 | 5'-TGT CCA TAA TAG TAA TTT CCA A-3' | 166–187 |
| 13 | 5'-CAG CAA ATT ATG AGT CAT GCG GAT TC-3' | 211–236 |

(**)target reference numbering is in accordance with HDAC-1, GenBank Accession Number U50079.

TABLE 2

| SEQ ID NO. | SEQUENCE | TARGET(***) |
|---|---|---|
| 14 | 5'-CTC CTT GAC TGT ACG CCA TG-3' | 1–20 |
| 15 | 5'-TGC TGC TGC TGC TGC TGC CG-3' | 121–141 |
| 16 | 5'-CCT CCT GCT GCT GCT GCT GC-3' | 132–152 |
| 17 | 5'-CCG TCG TAG TAG TAG CAG ACT TT-3' | 138–160 |
| 18 | 5'-TGT CCA TAA TAA TAA TTT CCA A-3' | 166–187 |
| 19 | 5'-CAG CAA GTT ATG GGT CAT GCG GAT TC-3' | 211–236 |
| 20 | 5'-GGT TCC TTT GGT ATC TGT TT-3' | 1605–1625 |

(***)target reference numbering is in accordance with HDAC-2, GenBank Accession Number U31814.

TABLE 3

| SEQ ID NO. | SEQUENCE | TARGET(***) |
|---|---|---|
| 21 | 5'-GCT GCC TGC CGT GCC CAC CC-3' | 514–533 |

(***)target reference numbering is in accordance with HDAC-4

The following examples are intended to further illustrate certain preferred embodiments of the invention, and are not intended to limit the scope of the invention.

EXAMPLES

Preparation of Amines

Methyl-3-aminophenylacetate (1)

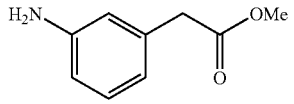

To a solution of 3-aminophenylacetic acid (3 g, 19.85 mmol) in methanol (50 mL) at room temperature was added HCl conc. (37%, 7.5 mL). The mixture was stirred 6 h at room temperature then treated with a saturated aqueous solution of $NaHCO_3$. The solvent was removed under reduced pressure then the aqueous phase was extracted several times with $CH_2Cl_2$. The combined organic extracts were dried over ($MgSO_4$) and evaporated. The crude mixture was purified by flash chromatography using hexane/AcOEt (1:1) yielding 1 as a yellow oil (3.06 g, 79%).

$^1$H NMR: (300 MHz, $CDCl_3$): 7.10 (t, J=8 Hz, 1H), 6.68–6.58 (m, 3H), 3.69–3.65 (m, 5H), 3.53 (s, 2H).

Methyl-4-aminophenyl Benzoate (2)

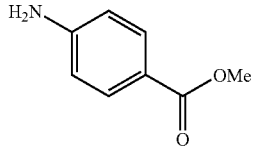

To a solution of 4-aminobenzoic acid (10 g, 72.92 mmol) in methanol (200 mL) at room temperature was added HCl conc. (37%, 25 mL). The solution mixture was heated overnight at 70° C. Once the solution was clear (completed) the reaction was treated with a saturated aqueous solution of $NaHCO_3$ and $Na_2CO_3$ powder until pH 9. The solvent was then evaporated under reduced pressure and the aqueous phase was extracted several times with AcOEt. The combined organic extracts were dried over ($MgSO_4$) and evaporated. The crude product 2 (9.30 g 85%) was obtained as a beige solid and was clean enough to use without further purification.

$^1$H NMR: (300 MHz, $CDCl_3$): 7.85 (d, J=8 Hz, 2H), 6.63 (d, J=8 Hz, 2H), 4.04 (broad s, 2H), 3.85 (s, 3H).

Methyl-4-aminophenylacetate (3)

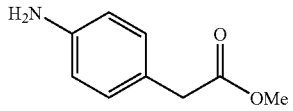

To a solution of 4-aminophenylacetic acid (10 g, 66.2 mmol) in methanol (150 mL) at room temperature was added HCl conc. (37% 25 mL). The mixture became yellow and was stirred overnight. The reaction mixture was then quenched with a saturated aqueous solution of $NaHCO_3$. The methanol was evaporated under reduced pressure and the aqueous layer was extracted several times with AcOEt. The combined organic extracts were dried over ($MgSO_4$) and evaporated. The crude residue was purified by flash chromatography using hexane/AcOEt (4:1) as solvent mixture yielding 3 as a yellow oil (9.44 g, 74%).

$^1$H NMR: (300 MHz, $CDCl_3$): 7.05 (d, J=10 Hz, 2H), 6.65 (d, J=10 Hz, 2H), 3.65 (s, 3H), 3.63 (broad s, 2H), 3.51 (s, 2H).

Example 1

2-[4-Benzo[b]thiophene-2-sulfonylamino)-phenyl]-N-hydroxy-acetamide (4)

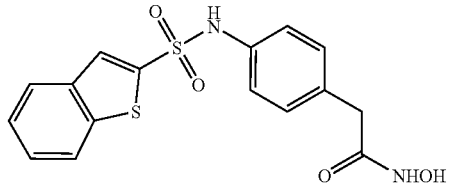

Step 1: Methyl-2-[4-benzo[b]thiophene-2-sulfonylamino)-phenyl]-acetate (5)

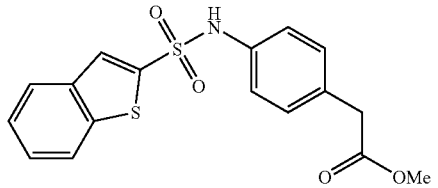

To a solution of 3 (500 mg, 2.56 mmol), in $CH_2Cl_2$ (8 mL) at room temperature were added $Et_3N$ (712 μL, 5.12 mmol) followed by 2-benzothiophenesulfonyl chloride (712 mg, 3.07 mmol). The mixture was stirred overnight at room temperature then quenched with a saturated aqueous solution of $NaHCO_3$. The phases were separated and the aqueous layer was extracted several times with $CH_2Cl_2$. The combined organic extracts were dried over ($MgSO_4$) and evaporated. The mixture of the mono and bis alkylated products were dissolved in methanol (~8 mL) and NaOMe was added (691 mg, 12.8 mmol). The resulting mixture was heated at 60° C. for 30 min the HCl 1N was added until pH 2. Then a saturated aqueous solution of $NaHCO_3$ was added until pH 7–8. The solvent was evaporated under reduced pressure then the aqueous layer was extracted several times with $CH_2Cl_2$. The combined organic extracts were dried over ($MgSO_4$) and evaporated. The residue was purified by flash chromatography using toluene/AcOEt 7:3 as solvent mixture and a second flash chromatography using $CH_2Cl_2$/acetone 98:2 as solvent yielding the title compound 5 as yellowish powder (487 mg, 53%).

$^1$H NMR: (300 MHz, $CDCl_3$): 7.80 (d, J=8 Hz, 2H), 7.75 (s, 1H), 7.44 (m, 2H), 7.14 (m, 4H), 6.79 (broad s, 1H) 3.67 (s, 3H), 3.56 (s, 2H)

Step 2: 2-[4-Benzo[b]thiophene-2-sulfonylamino)-phenyl]-acetic Acid (6)

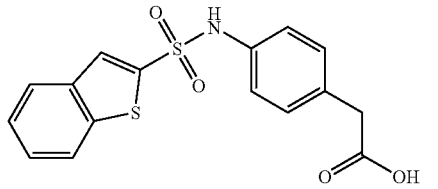

To a solution of 5 from step 1 (451 mg, 1.25 mmol) in a solvent mixture of THF (20 mL) and $H_2O$ (20 mL) at room temperature was added LiOH (524 mg, 12.5 mmol). The mixture was stirred for 2 h at room temperature and then was treated with a saturated aqueous solution of $NH_4Cl$. The resulting solution was extracted several times with AcOEt. The combined organic extracts were dried over ($MgSO_4$). The crude residue was then purified by flash chromatography using $CH_2Cl_2$/MeOH (9:1) as solvent mixture yielding the title compound 6 as white solid (404 mg, 93%).

$^1$H NMR: (300 MHz, DMSO-$d_6$): 8.03 (d, J=8 Hz, 1H), 7.97 (d, J=7 Hz, 1H), 7.92 (s, 1H), 7.50–7.45 (m, 2H), 7.13–7.06 (m, 4H), 3.44 (s, 2H).

Step 3: 2-[4-Benzo[b]thiophene-2-sulfonylamino)-phenyl]-N-hydroxy-acetamide (4)

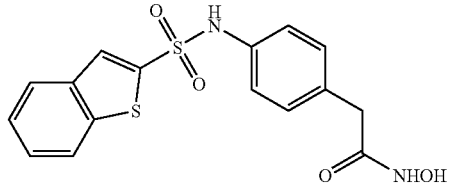

Method A:

To a solution of 6 (150 mg, 0.432 mmol) in a solvent mixture of $CH_2Cl_2$ (10 mL) and THF (5 mL) was added at room temperature 1,3-dicyclohexylcarbodiimide (DCC, 116 mg, 0.563 mmol). The reaction mixture was stirred 30 min at room temperature then $NH_2OTHP$ (76 mg, 0.650 mmol) and dimethylaminopyridine (DMAP, 5 mg) were added. The solution was stirred over night at room temperature and the solvents were evaporated under reduced pressure. The crude material was purified by flash chromatography using $CH_2Cl_2$/MeOH (9:1) as solvent. The residue was dissolved in MeOH (10 mL) and 10-camphorsulfonic acid (CSA, 100 mg, 0.432 mmol) was added. The mixture was stirred at room temperature overnight then treated with a saturated aqueous solution of $NaHCO_3$. The solvent was evaporated under reduced pressure and the aqueous phase was extracted several times with $CH_2Cl_2$ (3×) and AcOEt (3×). The combined organic extracts were dried over ($MgSO_4$) and evaporated. The crude product was purified by preparative high pressure liquid chromatography on reversed phase silica gel using a gradient of water/$CH_3CN$ (10–65%) yielding the title compound 4 as yellowish solid (70 mg, 45%).

$^1$H NMR (300 MHz, $CD_3OD$): 7.92–7.88 (m, 2H), 7.80 (s, 1H), 7.50–7.45 (m, 2H), 7.23–7.16 (m, 4H) 3.35 (s, 2H).

Except where otherwise indicated, the following compounds were prepared by procedures analogous to those described in Example 1, but substituting the sulfonyl chloride indicated for 2-benzothiophenesulfonyl chloride in step 1.

Example 2

2-[4-(2-Nitrobenzenesulfonylamino)-phenyl]-N-hydroxy-acetamide (7)

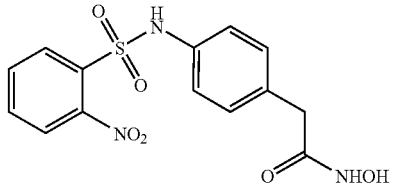

Sulfonyl chloride: 2-nitrobenzenesulfonyl chloride

Yield: Step 1: 82%

Yield: Step 2: 99%

Yield: Step 3: 19%

$^1$H NMR (300 MHz, DMSO-$_6$); δ 10.59 (s, 1H); 8.78 (s, 1H); 7.94 (s, 2H), 7.81 (s, 2H), 7.20–7.02 (m, 4H); 3.13 (s, 2H).

Example 3

2-[4-(2.5-Dichlorobenzenesulfonylamino)-phenyl]-N-hydroxy-acetamide (8)

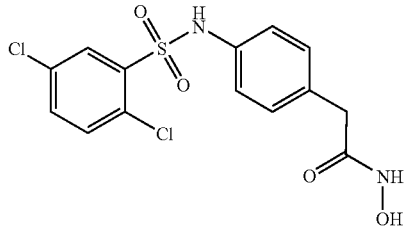

Sulfonyl chloride: 2.5-Dichlorobenzenesulfonyl chloride

Yield: Step 1: 66%

Yield: Step 2: 96%

Yield: Step 3: 66%

$^1$H NMR (300 MHz, DMSO-$d_6$); δ 10.68 (s, 1H), 8.88 (s, 1H), 7.95 (s, 1H), 7.67 (s, 2H); 7.13 (d, 2H, J=8 Hz), 7.02 (d, 2H, J=8 Hz), 3.16 (s, 2H).

Example 4

2-[4-(4-Methylbenzenesulfonylamino)-phenyl]-N-hydroxy-acetamide (9)

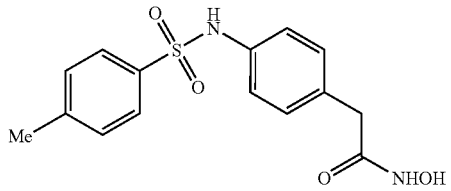

Sulfonyl chloride: 4-methylbenzenesulfonyl chloride

Step 1: Yield 100%

Step 2: 2-[4-(4-Methylbenzenesulfonylamino)-phenyl]-N-hydroxy-acetamide (9)

Method B:

To a solution of methyl-2-[4-(4-methylbenzenesulfonylamino)]phenylacetate (459 mg, 1.44 mmol) in methanol (10 mL), at room temperature were added hydroxylamine hydrochloride (200 mg, 2.88 mmol) followed by sodium methoxide (389 mg, 7.19 mmol). The resulting mixture was heated overnight at 60° C. then treated with HCl (1N) until pH 2. The solvent was evaporated under reduced pressure then the aqueous phase was extracted several times with $CH_2Cl_2$. The combined organic extracts were dried over ($MgSO_4$) then evaporated. The crude mixture was purified by flash chromatography using $CH_2Cl_2$/MeOH (9:1) as solvent mixture yielding the title compound 9 (244 mg, 53%) as a white powder.

$^1$H NMR (300 MHz, acetone-$d_6$); δ 7.68(d, J=8 Hz, 2H); 7.29 (d, J=8 Hz, 2H), 7.15 (br. s, 4H), 3.33 (s, 2H, $CH_2$), 2.33 (s, 3H, $CH_3$).

The following compounds were prepared following procedures analogous to those described in Example 1, step 1, and Example 4, step 2 (Method B), but substituting the sulfonyl chloride indicated for 2-benzothiophenesulfonyl chloride in step 1.

Example 5

2-[4-(3-Trifluromethylbenzenesulfonylamino)-phenyl]-N-hydroxy Acetamide (10)

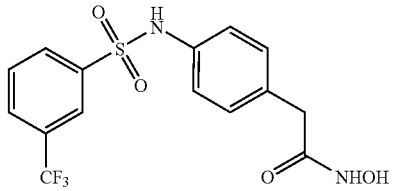

Sulfonyl chloride: 3-trifluromethylbenzenesulfonyl chloride

Yield: Step 1: 70%

Yield: Step 2: 49%

$^1$H NMR (300 MHz, acetone-$d_6$); δ 8.09 (s, 1H), 8.05 (d, 1H, J=8 Hz), 7.95 (d, 1H, J=8 Hz); 7.77 (t, 1H, J=8 Hz); 7.21 (d, 2H, J=8 Hz), 7.13 (d, 2H, J=8 Hz); 3.35 (s, 2H, $CH_2$)

Example 6

2-[4-(tert-Butylsulfonylamino)-phenyl]-N-hydroxy-acetamide (11)

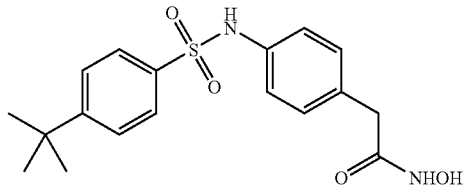

Sulfonyl chloride: 4-tert-butylsulfonyl chloride

Yield: Step 1: 76%

Yield: Step 2: 40%

$^1$H NMR (300 MHz, acetone-$d_6$); δ 7.75 (d, 2H, J=9 Hz), 7.56 (d, 2H, J=9 Hz); 7.17 (s, 4H); 3.34 (s, 2H), 1.29 (s, 9H).

The following compound was prepared following procedures analogous to those described in Example 1, steps 1–2, substituting the sulfonyl chloride indicated for 2-benzothiophenesulfonyl chloride in step 1, followed by hydroxamic acid formation using Method C.

Example 7

2-[2-(Naphthylsulfonylamino)-phenyl]-N-hydroxy-acetamide (12)

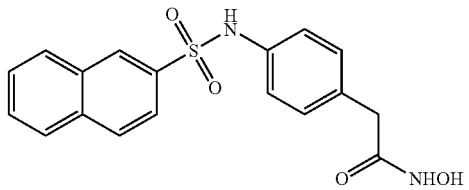

Sulfonyl chloride: 2-naphthylsulfonyl chloride

Yield: Step 1:100%

Yield: Step 2: 100%

Step 3: 2-[2-(Naphthylsulfonylamino)-phenyl]-N-hydroxy-acetamide (12)

Method C:

To a solution of 2-[2-(naphthylsulfonylamino)]-phenylacetic acid (191 mg, 0.563 mmol) in $CH_2Cl_2$ (20 mL) at room temperature were added DMF (1 drop) followed by $(COCl)_2$ (250 μL, 2.81 mmol). The mixture became yellow and solidification appeared. The reaction was stirred 90 min at room temperature then $(COCl)_2$ was added until no bubbling (~1 mL). Then the solvents were evaporated under reduced pressure. The crude material was dissolved in $CH_2Cl_2$ and $TMSONH_2$ (3 mL) was added to the solution. The reaction was exothermic and the resulting mixture was stirred 2 h at room temperature then treated with HCl (1N) until pH 2. The phases were separated and the aqueous layer was extracted several times with $CH_2Cl_2$. The combined organic extracts were dried over ($MgSO_4$) then evaporated. The crude compound was purified 3 times by flash chromatography using $CH_2Cl$/MeOH (9:1) as solvent mixture then another purification using preparative high pressure liquid chromatography using reversed phase chromatography with a gradient of water/$CH_3CN$ (10–70%) yielding the title compound 12 as a white powder (29 mg, 15%).

$^1$H NMR (300 MHz, acetone-$d_6$); δ 9.13 (s, 1H), 8.42 (s, 1H), 8.08–7.97 (m, 3H), 7.82 (dd, 1H, J=9 Hz, 1.5 Hz), 7.70–7.63 (m, 2H), 7.21–7.14 (m, 4H), 3.50 (s, 2H).

The following compound was prepared following procedures analogous to those described in Example 1, steps 1–2, substituting the indicated sulfonyl chloride and amine indicated for 2-benzothiophenesulfonyl chloride and 3 in step 1, followed by hydroxamic acid formation using Method D.

Example 8

N-Hydroxy-[4-benzo[b]thiophene-2-sulfonylamino)-phenyl]-benzamide (13)

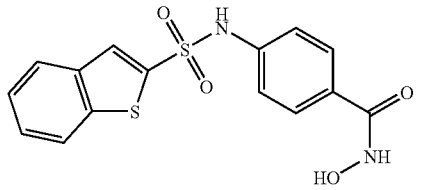

Sulfonyl chloride: 2-Benzothiophenesulfonyl chloride

Amine: Methyl-4-aminobenzoate (2)

Yield: Step 1: 80%

Yield: Step 2: 69%

Step 3: N-Hydroxy-[4-benzo[b]thiophene-2-sulfonylamino)-phenyl]-benzamide (13)

Method D:

To a solution of 2-[4-benzo[b]thiophene-2-sulfonylamino]benzoic acid (300 mg, 0.90 mmol) in DMF (20 mL) at room temperature were added 1-(3-dimethylaminopropyl)-3-ethylcarbodiimide hydrochloride (EDC, 207 mg, 1.08 mmol), and 1-Hydroxybenzotriazole hydrate (HOBT, 182 mg, 1.35 mmol). The mixture was stirred 20 min. at room temperature then $NH_2OTHP$ (1.58 mg, 1.35 mmol) was added. The resulting mixture was heated at 50° C. for 24 h then stirred at room temperature for 24 h. The DMF solvent was evaporated under reduced pressure and the residue was dissolved in $CH_2Cl_2$ and washed with brine or a saturated aqueous solution of $NaHCO_3$. The combined organic extracts were dried over ($MgSO_4$) then condensed. The crude compound was purified by flash chromatography using $CH_2Cl_2$/MeOH (9:1) as solvent mixture. The residue was then dissolved in methanol (20 mL) then 10-camphorsulfonic acid (CSA, 100 mg, 0.45 mmol) was added. The mixture was stirred 2 h at room temperature then the solvents were evaporated under reduced pressure at room temperature to avoid thermal decomposition. The crude was purified by flash chromatography using $CH_2Cl_2$/MeOH (9:1) as solvent mixture. A second purification was performed using a preparative high pressure liquid chromatography using a gradient of water/$CH_3CN$ (10–85%) as solvent giving the title compound 13 as a red solid (212 mg, 68%).

$^1$H NMR (300 MHz, acetone-$d_6$); δ 10.69 (s, 1H), 9.70 (s, 1H); 8.01–7.97 (m, 3H), 7.77 (d, 2H, J=9 Hz); 7.55–7.39 (m, 4H).

Example 9

2-[3-Benzo[b]thiopene-2-sulfonylamino)-phenyl]N-hydroxy-acetamide (14)

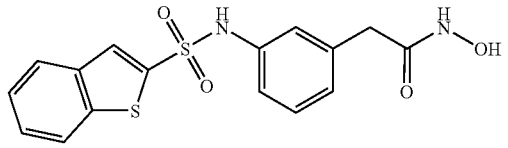

Sulfonyl chloride: 2-Benzothiophenesulfonyl chloride

Amine: Methyl-3-aminophenyl acetate (1)

Yield: Step 1: 88%

Yield: Step 2: 89%

Yield: Step 3: 32%

$^1$H NMR (300 MHz, Acetoned$_6$); δ 10.20 (s, 1H), 8.33 (s, 1H), 7.99–7.95 (m, 3H), 7.53–7.43 (m, 2H), 7.35 (s, 1H), 7.21–7.17 (m, 2H), 7.067.03 (m, 1H), 3.38 (s, 2H).

Example 10

2-[4-(3,4-Dichlorobenzenesulfonylamino)-phenyl]-N-hydroxy-acetamide (15)

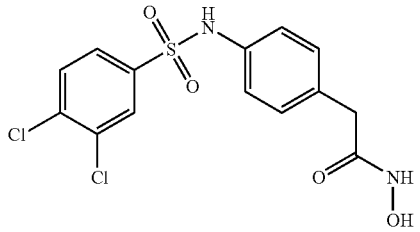

Sulfonyl chloride: 3.4-Dichlorobenzenesulfonyl chloride

Yield: Step 1: 80%

Yield: Step 2: 67%

Yield: Step 3: 81%

$^1$H NMR (300 MHz, acetone-$d_6$); δ 10.12 (s, 1H), 9.15 (s, 1H), 7.92 (s, 1H), 7.74–7.71 (m, 2H), 7.23 (d, 2H, J=9 Hz), 7.14 (d, 2H, J=9 Hz), 3.36 (s, 2H).

Example 11

2-[4-(2-Thiophenesulfonylamino)-phenyl]-N-hydroxy-acetamide (16)

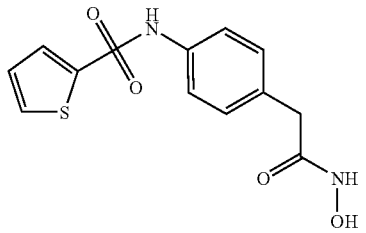

Sulfonyl chloride: 2-Thiophenesulfonyl chloride

Yield: Step 1: 84%

Yield: Step 2: 83%

Yield: Step 3: 9%

$^1$H NMR (300 MHz, acetone-$d_6$); δ 7.78 (s, 1H), 7.53 (s, 1H), 7.21 (s, 4H), 7.09 (s, 1H), 3.37 (s, 2H).

Example 12

2-[4-(3-Nitrobenzenesulfonylamino)-phenyl]-N-hydroxy-acetamide (17)

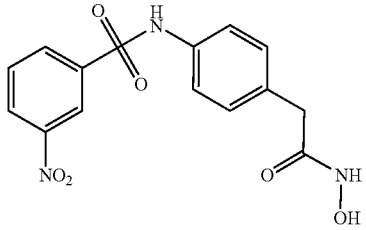

Sulfonyl chloride: 3-Nitrobenzenesulfonyl chloride

Yield: Step 1: 47%

Yield: Step 2: 34%

Yield: Step 3: 16%

$^1$H NMR (300 MHz, acetone-$d_6$); δ 9.31 (s, 1H), 8.59 (s, 1H), 8.45 (d, 1H, J=8 Hz), 8.16 (d, 1H, J=8 Hz), 7.85 (t, 1H, J=8 Hz), 7.20–7.14 (m, 4H), 3.35 (s, 2H).

Example 13

2-[4-(8-Quinolinesulfonylamino)-phenyl]-N-hydroxy-acetamide (18)

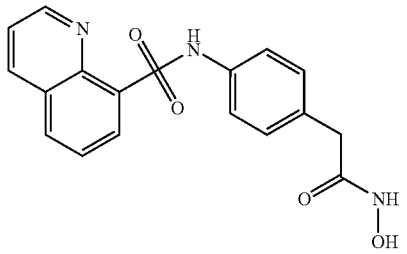

Sulfonyl chloride: 8-quinolinesulfonyl chloride

Yield: Step 1: 83%

Yield: Step 2: 78%

Yield: Step 3: 42%

$^1$H NMR (300 MHz, acetone-$d_6$); δ 9.17 (s, 1H), 8.50 (d, 1H, J=8 Hz), 8.33 (d, 1H, J=8 Hz), 8.21 (d, 1H, J=8 Hz), 7.71–7.68 (m, 3H), 7.05 (broad s., 4H), 3.22 (s, 2H).

Example 14

2-[4-(4-Bromobenzenesulfonylamino)-phenyl]-N-hydroxy-acetamide (19)

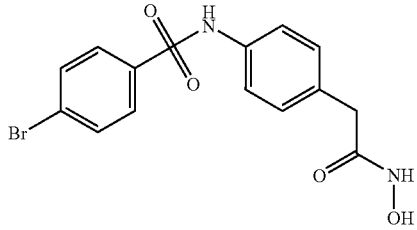

Sulfonyl chloride: 4-Bromobenzenesulfonyl chloride

Yield: Step 1: 80%

Yield: Step 2: 81%

Yield: Step 3: 48%

$^1$H NMR (300 MHz, acetone-$d_6$); δ 9.17 (s, 1H), 7.72 (s, 4H), 7.19–7.14 (m, 4H), 3.35 (s, 2H).

Example 15

N-Hydroxy-5-[3-benzenesulfonylamino)-phenyl]-pentanamide (26)

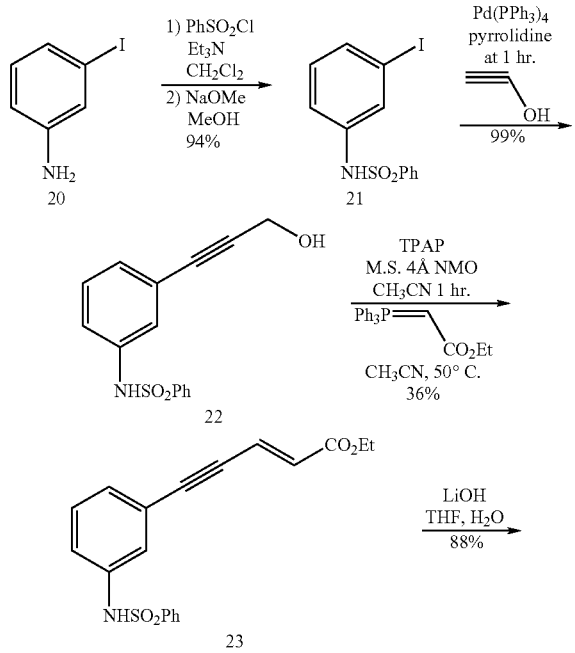

-continued

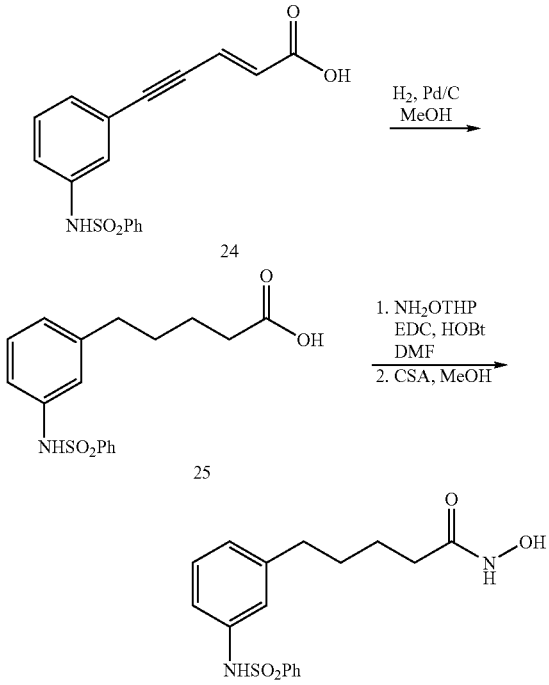

Example 15

Step 1: 3-(Benzenesulfonylamino)-phenyl Iodide (21)

To a solution of 3iodoaniline (5 g, 22.8 mmol), in $CH_2Cl_2$ (100 mL), were added at room temperature $Et_3N$ (6.97 mL) followed by benzenesulfonyl chloride (5.84 mL). The mixture was stirred 4 h then a white precipitate was formed. A saturated aqueous solution of $NaHCO_3$ was added and the phases were separated. The aqueous layer was extracted several times with $CH_2Cl_2$ and the combined extracts were dried over ($MgSO_4$) then evaporated. The crude mixture was dissolved in MeOH (100 mL) and NaOMe (6 g), was added and the mixture was heated 1 h at 60° C. The solution became clear with time and HCl (1N) was added. The solvent was evaporated under reduced pressure then the aqueous phase was extracted several times with $CH_2Cl_2$. The combined organic extracts were dried over ($MgSO_4$) and evaporated. The crude material was purified by flash chromatography using (100% $CH_2Cl_2$) as solvent yielding the title compound 21 (7.68g, 94%) as yellow solid.

$^1$H NMR: (300 MHz, $CDCl_3$): 7.82–7.78 (m, 2H), 7.60–7.55 (m, 1H), 7.50–7.42 (m, 4H), 7.10–7.06 (m, 1H), 6.96 (t, J=8 Hz, 1H), 6.87 (broad s, 1H).

Step 2: 3-(Benzenesulfonylamino)-phenyl-propargylic Alcohol (22)

To a solution of 21 (500 mg, 1.39 mmol) in pyrrolidine (5 mL) at room temperature was added $Pd(PPh_3)_4$ (80 mg, 0.069 mmol), followed by CuI (26 mg, 0.139 mmol). The mixture was stirred until complete dissolution. Propargylic alcohol (162 L, 2.78 mmol) was added and stirred 6 h at room temperature. Then the solution was treated with a saturated aqueous solution of $NH_4Cl$ and extracted several times with AcOEt. The combined organic extracts were dried over ($MgSO_4$) then evaporated. The residue was purified by flash chromatography using hexane/AcOEt (1:1) as solvent mixture yielding 22 (395 mg, 99%) as yellow solid.

$^1$H NMR: (300 MHz, $CDCl_3$): 7.79–7.76 (m, 2H), 7.55–7.52 (m, 1H), 7.45 (t, J=8 Hz, 2H), 7.19–7.15 (m, 3H), 7.07–7.03 (m, 1H), 4.47 (s, 2H).

Step 3: 5-[3-(Benzenesulfonylamino)-phenyl]-4-yn-2-pentenoate (23)

To a solution of 22 (2.75 g, 9.58 mmol) in $CH_3CN$ (150 mL) at room temperature were added 4-methylmorpholine N-oxide (NMO, 1.68 g, 14.37 mmol) followed by tetrapropylammonium perruthenate (TPAP, 336 mg, 0.958 mmol). The mixture was stirred at room temperature 3 h, and then filtrated through a Celite pad with a fritted glass funnel. To the filtrate carbethoxymethylenetriphenylphosphorane (6.66 g, 19.16 mmol) was added and the resulting solution was stirred 3 h at room temperature. The solvent was evaporated and the residue was dissolved in $CH_2Cl_2$ and washed with a saturated aqueous solution of $NH_4Cl$. The aqueous layer was extracted several times with $CH_2Cl_2$ then the combined organic extract were dried over ($MgSO_4$) and evaporated. The crude material was purified by flash chromatography using hexane/AcOEt (1:1) as solvent mixture giving 23 (1.21 g, 36%) as yellow oil.

$^1$H NMR: (300 MHz, $CDCl_2$): 7.81 (d, J=8 Hz, 2H), 7.56–7.43 (m, 3H), 7.26–7.21 (m, 3H), 7.13–7.11 (m, 1H), 6.93 (d, J=16 Hz, 1H), 6.29 (d, J=16 Hz, 1H), 4.24 (q, J=7 Hz, 2H), 1.31 (t, J=7 Hz, 3H).

Step 4: 5-[3-(Benzenesulfonylamino)-phenyl]-4-yn-2-pentenic Acid (24)

To a solution of 23 (888 mg, 2.50 mmol) in a solvent mixture of THF (10 mL) and water (10 mL) at room temperature was added LiOH (1.04 g, 25.01 mmol). The resulting mixture was heated 2 h at 60° C. and treated with HCl (1N) until pH 2. The phases were separated and the aqueous layer was extracted several times with AcOEt. The combined organic extracts were dried over ($MgSO_4$) then evaporated. The crude residue was purified by flash chromatography using $CH_2Cl_2$/MeOH (9:1) as solvent mixture yielding 24 (712 mg, 88%), as white solid.

$^1$H NMR: (300 MHz, DMSO-$d_6$): 7.78–7.76 (m, 2H), 7.75–7.53 (m, 3H), 7.33–7.27 (m, 1H), 7.19–7.16 (m, 3H), 6.89 (d, J=16 Hz, 1H), 6.33 (d, J=16 Hz, 1H).

Step 5: 5-[3-(Benzenesulfonylamino)-phenyl]-pentanoic Acid (25)

To a solution 24 (100 mg, 0.306 mmol), in MeOH (6 mL) at room temperature was added a solution of Pd/C (10%, 20 mg, 1 mL MeOH). The reaction mixture was degassed and purged several times with $H_2$ gas with a final pressure of 60 psi. The mixture was stirred 2 h at room temperature then the resulting solution was filtrated over a silica gel pad with a fritted glass funnel. The solvent was evaporated yielding 25 (68 mg, 96%) and it was used directly for the next step without further purification.

$^1$H NMR: (300 MHz, acetone-$d_6$): 7.81–7.78 (m, 2H), 7.56–7.46 (m, 3H), 7.11–7.01 (m, 3H), 6.87 (d, J=8 Hz, 1H), 2.49 (broad s, 2H), 2.25 (broad s, 2H), 1.52 (broad s, 4H).

Step 6: N-Hydroxy-5-[3-benzenesulfonylamino)-phenyl]-pentanamide (26)

To a solution of 25 (100 mg, 300 mmol) in DMF (10 mL) at room temperature were added 1-(3-dimethylaminopropyl)-3-ethyl-carbodiimide hydrochloride (EDC, 69 mg, 0.320 mmol), and 1-hydroxybenzotriazole hydrate (HOBT, 61 mg, 0.45 mmol). The mixture was stirred 20 min. at room temperature then $NH_2OTHP$ (53 mg, 0.45 mmol) was added. The resulting mixture was heated overnight at 50° C. The DMF solvent was evaporated under reduced pressure and the residue was dissolved in $CH_2Cl_2$ and washed with brine or a saturated aqueous solution of $NaHCO_3$. The combined organic extracts were dried over ($MgSO_4$) then evaporated. The crude compound was purified by flash chromatography using hexane/acetone (7:3) as solvent mixture. The residue was then dissolved in MeOH (20 mL) then 10-camphorsulfonic acid (CSA, 35 mg, 150 mmol) was added. The mixture was stirred 2 h at room temperature then the solvents were evaporated under reduced pressure at room temperature to avoid thermal decomposition. The crude mixture was purified by flash chromatography using $CH_2Cl_2$/MeOH (9:1) as solvent mixture giving 26 as a yellowish solid (62 mg, 60%).

$^1$H NMR: (300 MHz, acetone-$d_6$): =7.80–7.78 (m, 2H), 7.56–7.52 (m, 3H), 7.13–6.89 (m, 4H), 2.52 (broad s, 2H), 2.10 (broad s, 2H), 1.53 (broad s, 4H).

Example 16

N-Hydroxy-5-[4-(benzenesulfonylamino)-phenyl]-4-yn-2-pentanamide (32)

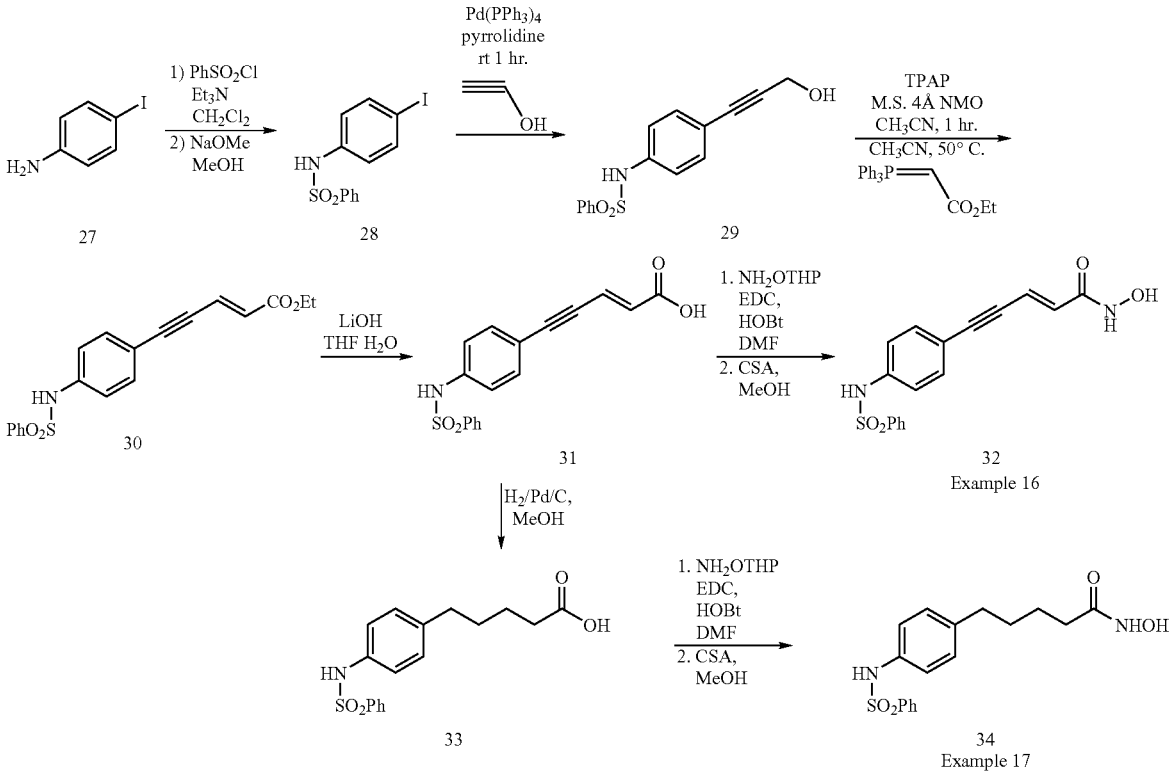

Step 1: 4-(Benzenesulfonylamino)-phenyl Iodide (28)

Compound 28 was prepared using the procedure described in Example 15, step 1, but substituting 4-iodoaniline for 3-iodoaniline.

Yield: 97%

$^1$H NMR: (300 MHz, $CDCl_2$): 9.15 (broad s, 1H), 7.82 (d, J=8 Hz, 2H), 7.68–7.51 (m, 5H), 7.05 (d, J=8 Hz, 2H).

Step 2: 4-(Benzenesulfonylamino)-phenyl-propargylic Alcohol (29)

Compound 29 was prepared using the procedure described in Example 15, step 2 but substituting compound 21 for compound 28.

Yield: 61%

$^1$H NMR: (300 MHz, acetone-$d_6$): 7.83–7.80 (m, 2H), 7.62–7.51 (m, 3H), 7.30 (d, J=8 Hz, 2H), 7.21 (d, J=8 Hz, 2H), 4.36 (s, 2H), 2.80 (broad s, 2H).

Step 3: 5-[4-(Benzenesulfonylamino)-phenyl]-4-yn-2-pentenoate (30)

Compound 30 was prepared using the procedure described in Example 15, step 3 but substituting compound 22 for compound 29.

Yield: 16%

$^1$H NMR: (300 MHz, $CDCl_2$): 7.81–7.78 (m, 2H), 7.59–7.43 (m, 3H), 7.34 (d, J=8 Hz, 2H), 7.05 (d, J=8 Hz, 2H), 6.93 (d, J=16 Hz, 1H), 6.26 (d, J=16 Hz, 1H), 4.23 (q, J=7 Hz, 2H), 1.30 (t, J=7 Hz, 3H).

Step 4: 5-[4-(Benzenesulfonylamino)-phenyl]-4-yn-2-pentenic Acid (31)

Compound 31 was prepared using the procedure described in Example 15 step 4 but substituting compound 23 for compound 30.

Yield: 92%

$^1$H NMR: (300 MHz, acetone-$d_6$): 7.87–7.84 (m, 2H), 7.62 (m, 3H), 7.42 (d, J=8 Hz, 2H), 7.28 (d, J=8 Hz, 2H), 6.94 (d, J=16 Hz, 1H), 6.29 (d, J=16 Hz, 1H).

Step 5: N-Hydroxy-5-[4-(benzenesulfonylamino)-phenyl]-4-yn-2-pentanamide (32)

Compound 32 was prepared using the procedure described in Example 15 step 6 but substituting compound 25 for compound 31.

Yield: 78%

$^1$H NMR: (300 MHz, acetone-$d_6$): 7.84 (broad s, 2H), 7.60–7.55 (m, 3H), 7.38–7.30 (m, 4H), 6.84 (d, J=16 Hz, 1H), 6.40 (d, J=16 Hz, 1H).

Example 17

N-Hydroxy-5-[4-benzenesulfonylamino)-phenyl]-pentanamide (34)

Step 1: 5-[4-(Benzenesulfonylamino)-phenyl]-pentanoic Acid (33)

Compound 33 was prepared using the procedure described in Example 15 step 5 but substituting compound 24 for compound 31.

Yield: 100%

$^1$H NMR: (300 MHz, acetone-$d_6$):=7.78–7.75 (m, 2H), 7.56–7.46 (m, 3H), 7.16–7.05 (m, 4H), 2.52 (broad s, 2H), 2.29–2.25 (m, 2H), 1.56 (broad s, 4H).

Step 2: N-Hydroxy-5-[4-benzenesulfonylamino)-phenyl]-pentanamide (34)

Compound 34 was prepared using the procedure described in Example 15 step 6 but substituting compound 25 for compound 33.

Yield: 62%

$^1$H NMR: (300 MHz, acetone-$d_6$): 7.78–7.75 (m, 2H), 7.59–7.51 (m, 3H), 7.09 (broad s, 4H), 2.85 (broad s, 1H), 2.53 (broad s, 2H), 2.05 (broad s, 2H), 1.56 (broad s, 4H).

Example 18

N-Hydroxy-3-[4-(Benzenesulfonylamino)-phenyl]-2-propenamide (36)

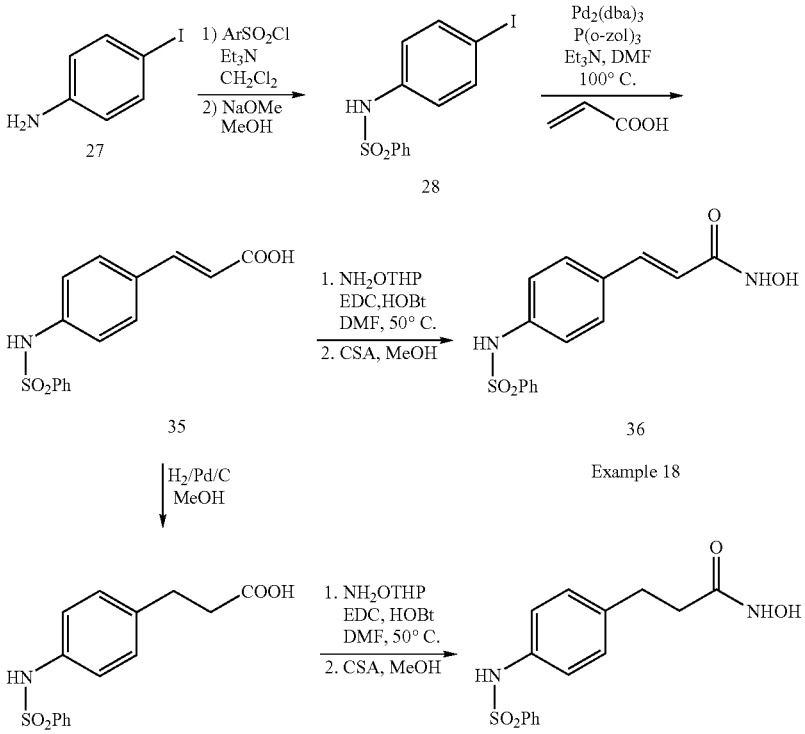

Example 18

Example 19

Step 1: 3-[4-(Benzenesulfonylamino)-phenyl]-2-propenoic Acid (35)

To a solution of 28 (500 mg, 1.39 mmol), in DMF (10 mL) at room temperature were added tris(dibenzylideneacetone) dipalladium(0) ($Pd_2(dba)_3$; 38 mg, 1.67 mmol), tri-o-tolylphosphine ($P(o\text{-}tol)_3$, 25 mg, 0.83 mmol), $Et_3N$ (483 μL, 3.48 mmol) and finally acrylic acid (84 μL, 1.67 mmol). The resulting solution was degassed and purged several times with $N_2$ then heated overnight at 100° C. The solution was filtrated through a Celite pad with a fritted glass funnel then the filtrate was evaporated. The residue was purified by flash chromatography using $CH_2Cl_2$/MeOH (95:5) as solvent mixture yielding the title compound 35 (415 mg, 99%) as yellowish solid.

$^1$H NMR: (300 MHz, acetone-$d_6$): 7.88–7.85 (m, 2H), 7.62–7.55 (m, 6H), 7.29 (d, J=9 Hz, 2H), 6.41 (d, J=16 Hz, 1H), 2.95 (s, 1H), 2.79 (s, 1H).

Step 2: N-Hydroxy-3-[4-(benzenesulfonylamino)-phenyl]-2-propanamide (36)

To a solution of 35 (200 mg, 0.660 mmol) in DMF (10 mL) at room temperature were added 1-(3-Dimethylaminopropyl)-3-ethyl-carbodiimide hydrochloride (EDCI, 151 mg, 0.79 mmol), and 1-Hydroxybenzotriazole hydrate (HOBT, 134 mg, 0.99 mmol). The mixture was stirred 20 min. at room temperature then $NH_2OTHP$ (116 mg, 0.99 mmol) was added. The resulting mixture was heated at 50° C. for 24 h then the DMF solvent was evaporated under reduced pressure and the residue was dissolved in $CH_2Cl_2$, washed with a saturated aqueous solution of $NaHCO_3$. The combined organic extracts were dried over ($MgSO_4$) then condensed. The crude compound was purified by flash chromatography using Hexane/acetone (7:3) as solvent mixture. The residue was then dissolved in MeOH (10 mL) then 10-camphorsulfonic acid (CSA, 77 mg, 0.33 mmol) was added. The mixture was stirred 2 h at room temperature then the solvents were evaporated under reduced pressure at room temperature to avoid thermal decomposition. The crude product was purified by flash chromatography using $CH_2Cl_2$/MeOH (9:1) as solvent mixture giving compound 36 (116 mg, 55%) as a orange solid.

$^1$H NMR: (300 MHz, acetone-$d_6$): 7.85–7.83 (m, 2H), 7.64–7.47 (m, 6H), 7.26 (d, J=8 Hz, 2H), 6.48 (m, 1H), 2.82 (s, 1H), 2.79 (s, 1H).

Example 19

N-Hydroxy-3-[4-(benzenesulfonylamino)-phenyl]-2-propanamide (38)

Step 1: 3-[4-(Benzenesulfonylamino)-phenyl]-2-propionic Acid (37)

To a solution of 35 (350 mg, 1.16 mmol) in MeOH (15 mL) at room temperature was added a solution of Pd/C 10%

(50 mg, in MeOH 3 mL). Then the resulting solution was purged several times with $H_2$ with a final pressure of 60 psi. The solution was stirred 4 h then filtrated through a Celite pad with a fritted glass funnel. The filtrate was evaporated and the residue compound 37 was pure enough to use for the next step without further purification.

$^1$H NMR: (300 MHz, acetone-$d_6$): 8.92 (broad s, 1H), 7.79–7.76 (m, 2H), 7.60–7.47 (m, 3H), 7.12 (s, 4H), 3.32 (s, 1H), 2.81 (t, J=8 Hz, 2H), 2.53 (t, J=8 Hz, 2H).

Step 2: N-Hydroxy-3-[4-(benzenesulfonylamino)-phenyl]-2-propanamide (38)

To a solution of 37 (1.16 mmol) in DMF (10 mL) at room temperature were added 1-(3-Dimethylaminopropyl)-3-ethyl-carbodiimide hydrochloride (EDC, 266 mg, 1.39 mmol), and 1-Hydroxybenzotriazole hydrate (HOBT, 235 mg, 1.74 mmol). The mixture was stirred 20 min. at room temperature then $NH_2OTHP$ (204 mg, 1.74 mmol) was added. The resulting mixture was heated at 50° C. for 24 h then the DMF solvent was condensed under reduced pressure and the residue was dissolved in $CH_2Cl_2$, washed with a saturated aqueous solution of $NaHCO_3$. The combined organic extracts were dried over ($MgSO_4$) then evaporated. The crude compound was purified by flash chromatography using Hexane/acetone (7:3) as solvent mixture. The residue was then dissolved in MeOH (10 mL) then 10-camphorsulfonic acid (CSA, 135 mg, 0.58 mmol) was added. The mixture was stirred 2 h at room temperature then the solvents were evaporated under reduced pressure at room temperature to avoid thermal decomposition. The crude was purified by flash chromatography using $CH_2Cl_2$/MeOH (9:1) as solvent mixture giving the title compound 38 (237 mg, 64%, for the last 3 steps) as a yellow solid.

$^1$H NMR: (300 MHz, acetone-$d_6$): 8.91 (broad s, 1H), 7.78–7.76 (m, 2H), 7.57–7.51 (m, 3H), 7.10 (broad s, 4H), 2.82 (broad s, 2H), 2.34 (broad s, 2H), 1.07 (s, 1H), 0.85 (s, 1H).

Example 20

N-Hydroxy-4-[4-(benzenesulfonylamino)-phenyl]-butanamide (42)

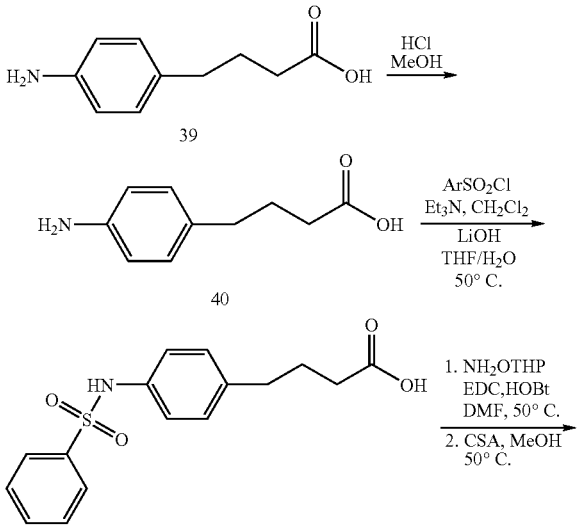

-continued

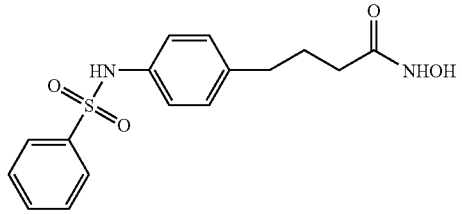

Example 20

Step 1: Methyl-4-(4-aminophenyl)-butanoate (40)

To a solution of 4-(4-aminophenyl)-butyric acid (5 g, 27.90 mmol) in MeOH (100 mL) at room temperature was added HCl conc. (37% 15 mL). The resulting mixture was stirred overnight at 50° C. then treated with a saturated aqueous solution $NaHCO_3$ and $Na_2CO_3$ solid until pH 9. The solvent was evaporated under reduced pressure then the aqueous phase was extracted several times with $CH_2Cl_2$. The crude material was purified by flash chromatography using $CH_2Cl_2$/MeOH as solvent mixture yielding 40 (4.93 g, 91%) as orange solid.

$^1$H NMR: (300 MHz, acetone-$d_6$): 6.89 (d, J=8 Hz, 2H), 6.59 (d, J=8 Hz, 2H), 4.40 (broad s, 1H), 3.60 (s, 3H), 2.48 (t, J=7 Hz, 2H), 2.28 (t, J=7 Hz, 2H), 1.82 (qt, J=7 Hz, 2H).

Step 2: 4-[4-(Benzenesulfonylamino)-phenyl]-butyric Acid (41)

To a solution of 40 (500 mg, 2.59 mmol) in $CH_2Cl_2$ at room temperature were added $Et_3N$ (901 μL, 6.48 mmol) followed by benzenesulfonyl chloride (661 μL, 5.18 mmol). The mixture was stirred overnight at room temperature then treated with a saturated aqueous solution of $NH_4Cl$. The phases were separated and the organic layer was extracted several times with $CH_2Cl_2$. The combined organic extracts were dried over ($MgSO_4$) then evaporated under reduced pressure. The residue was dissolved in a solvent mixture of THF (25 mL) and water (25 mL) then LiOH (1.08 g, 25.9 mmol) was added. The mixture was heated at 50° C. for 1 h then treated with HCl (1N) until pH2. The phases were separated and the aqueous layer was extracted several times with AcOEt. The combined organic extracts were dried over ($MgSO_4$) then evaporated. The crude was purified by flash chromatography using $CH_2Cl_2$/MeOH (95:5) as solvent mixture yielding 41 (800 mg, 96%) as a white solid $^1$H NMR: (300 MHz, $CDCl_3$): 8.82 (1H, s broad), 7.77–7.74 (2H, m), 7.55–50 (1H, m), 7.44–7.39 (2H, m), 7.05–6.97 (4H, m), 2.58 (2H, t, J=7 Hz), 2.31 (2H, t, J=7 Hz), 2.17 (1H, s), 1.94–1.84 (2H, m).

Step 3: N-Hydroxy-4-[4-(benzenesulfonylamino)-phenyl]-butanamide (42)

To a solution 41 (800 mg, 2.59 mmol) in DMF (20 mL) at room temperature were added 1-(3-Dimethylaminopropyl)-3-ethyl-carbodiimide hydrochloride (EDC, 593 mg, 3.12 mmol), and 1-Hydroxybenzotriazole hydrate (HOBT, 524 mg, 3.89 mmol). The mixture was stirred 20 min. at room temperature then $NH_2OTHP$ (455 mg, 3.89 mmol) was added. The resulting mixture was heated at 50° C. for 24 h then the DMF solvent was evaporated under reduced pressure and the residue was dissolved in $CH_2Cl_2$, washed with a saturated aqueous solution of $NaHCO_3$. The combined organic extracts were dried over ($MgSO_4$) then evaporated. The crude compound was purified by flash chromatography using Hexane/acetone (7:3) as solvent mixture. The residue was then dissolved in MeOH (30 mL) then 10-camphorsulfonic acid (CSA, 300 mg, 1.30 mmol) was added. The mixture was stirred 2 h at 50° C. then the solvents were condensed under reduced pressure at room temperature to avoid thermal decomposition. The crude was purified by flash chromatography using $CH_2Cl^2$/MeOH (9:1) as solvent mixture giving the title compound 42 (115 mg, 13%) as a yellowish solid.

$^1$H NMR: (300 MHz, $CDCl_3$): 7.79–7.76 (m, 2H), 7.61–7.48 (m, 3H), 7.13–7.05 (m, 4H), 2.83 (broad s, 1H), 2.53 (t, J=7 Hz, 2H), 2.14–2.04 (m, 2H), 1.83 (t, J=7 Hz, 2H).

Example 21

N-Hydroxy-4-(3-oxo-3-phenylpropenyl)-benzamide (45)

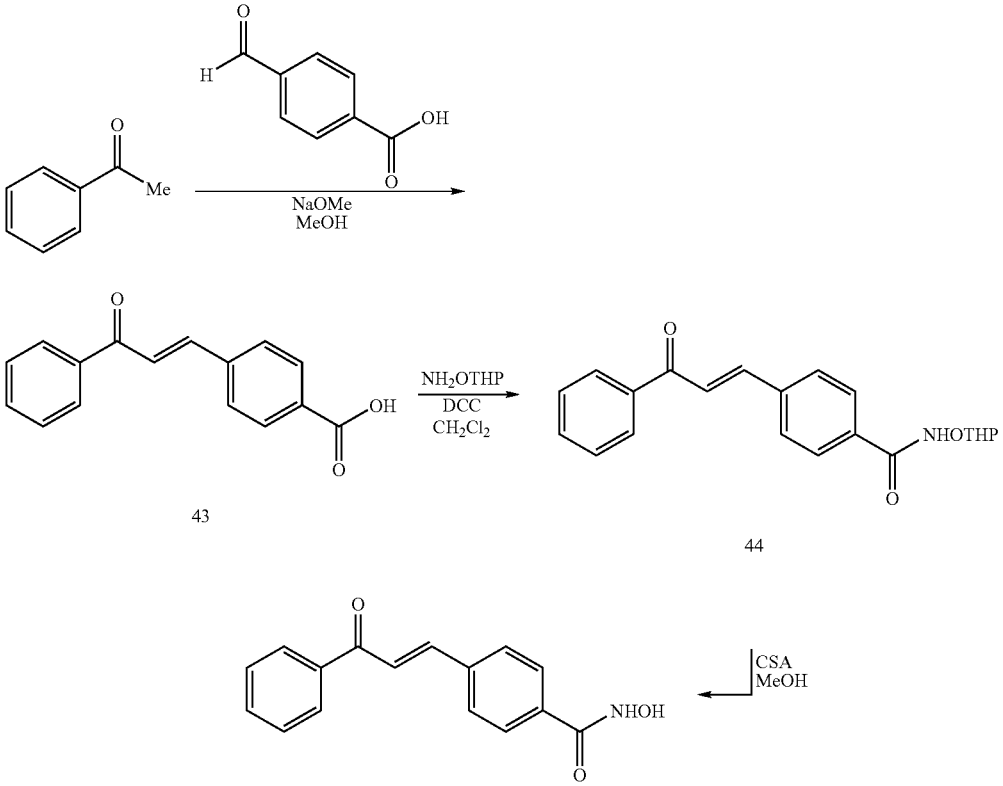

Example 21

Step 1: 4-(3-oxo-3-Phenylpropenyl)-benzoic Acid (43)

Sodium methoxide (1.8 g, 33.3 mmol) was added to a stirred suspension of 4-carboxybenzaldehyde (2.5 g, 16.6 mmol) and acetophenone (2.0 g uL, 16.6 mmol) in methanol (50 mL) at room temperature. The mixture was stirred at room temperature for 16 hours, and half of the volume of methanol was removed under reduced pressure. The mixture was poured into HCl 1M (50 mL) (until pH=2) and ethyl acetate was added. The separated aqueous layer was extracted with ethyl acetate (3×30 mL) dried ($MgSO_4$ anh.), filtered and evaporated. The residue was triturated with dichloromethane-hexanes (1:1) to afford 3 g of 43 (72% yield).

$^1$H NMR (300 MHz, $CDCl_3$); δ 7.50–7.87 (m, 7H), 8.04 (d, 2H, J=8 Hz), 8.16 (d, 2H, J=8 Hz).

Step 2: 4-(3-oxo-3-Phenylpropenyl)-N-(O-tetrahydropyranyl)-benzamide (44)

The carboxylic acid 43 (260 mg, 1.0 mmol) was dissolved in anhydrous $CH_2Cl_2$ (10 mL) and DCC (256 mg, 1.2 mmol) followed by $NH_2OTHP$ (145 mg, 1.2 mmol) were added. The mixture was allowed to stir at room temperature for 2 h. Added $NH_4Cl$ sat. and extracted with EtOAc. The organic layer was dried over $MgSO_4$, filtered and the solvent was evaporated under vacuum. (Purification by column chromatography using 1% MeOH/$CH_2Cl$ give the title compound which was used directly in the next step.

Step 3: N-Hydroxy-4-(3-oxo-3-phenylpropenyl)-benzamide (45)

The protected hydroxamic acid 44 (234 mg, 0.67 mmol) was dissolved in MeOH (7mL) then CSA (31 mg, 0.13 mmol) was added. The mixture was allowed to stir at reflux for 2 hours or until the reaction was complete by TLC. Added HCl 1N, extracted with EtOAc, dried the organic layer over anhydrous $MgSO_4$ and filtered. The solvent was evaporated under vacuum. Purification by column chromatography using 5% MeOH/$CH_2Cl_2$, gave the title compound.

$^1$H NMR (300 MHz, DMSO-$d_6$), δ 7.53–8.20 (m, 11H); 9.12 (br. s, 1H); 11.35 (br. s, 1H).

Example 22

N-Hydroxy-4-(3-oxo-3-phenylpropyl)-benzamide (50)

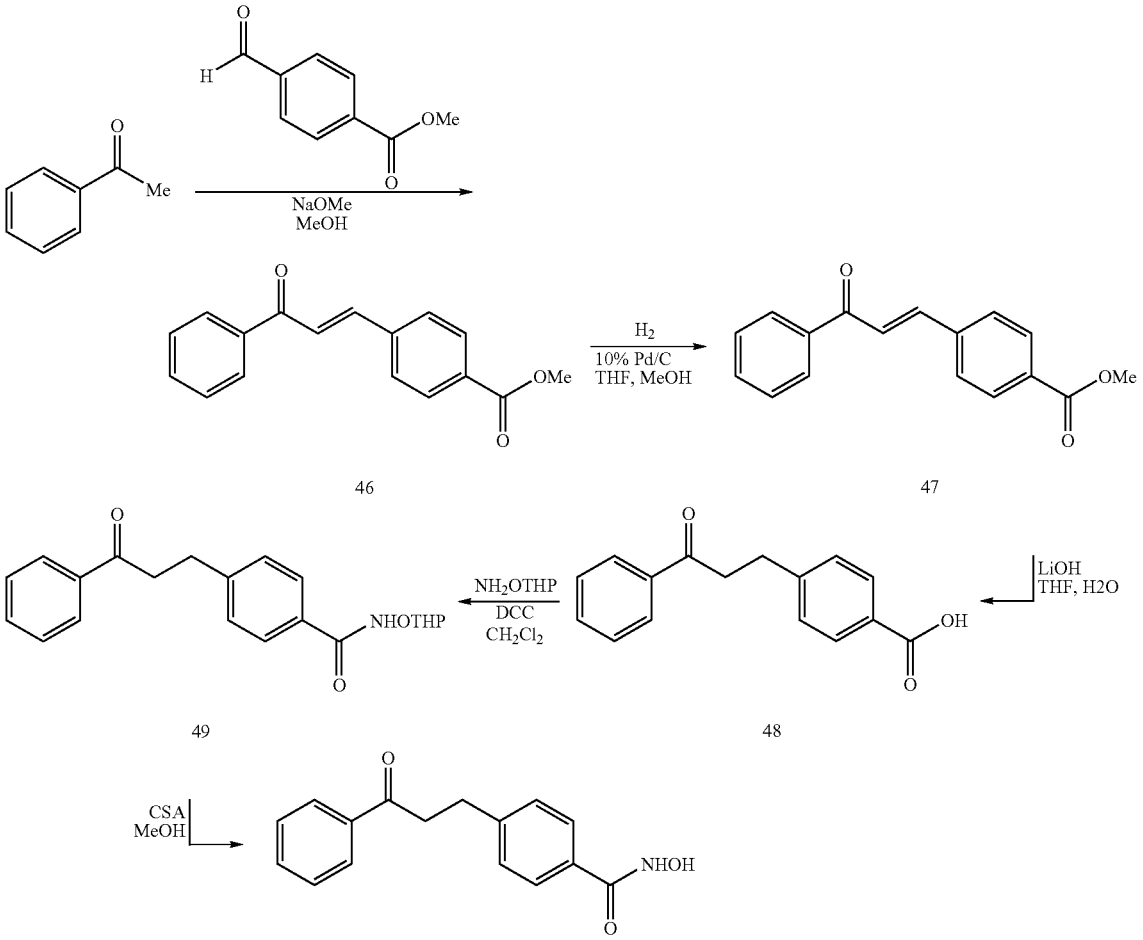

Example 22

Step 1: Methyl-4-(3-oxo-3-phenylpropenyl)-benzoate (46)

To 4-carbomethoxybenzaldehyde (79 mg, 0.48 mmol) and acetophenone (56 μL, 0.48 mmol) in anhydrous methanol (1.6 mL), was added neat sodium methoxide (26 mg, 0.48 mmol). The mixture was stirred at room temperature overnight then heated to reflux for 1 hour, cooled down to room temperature and added HCl 1N and EtOAc. The layers were separated and the organic layer dried over anhydrous $MgSO_4$ and filtered. The solvent was evaporated under vacuum to afford a yellow solid, which was recrystallized from acetonitrile/water to give a pale yellow crystalline solid.

$^1$H NMR (300 MHz, $CDCl_3$); δ 3.95 (s, 3H), 7.50–8.12 (m, 11H).

Step 2: Methyl-4-(3-oxo-3-phenylpropyl)-benzoate (47)

The aromatic enone 46 (321 mg, 1.20 mmol) was dissolved in anhydrous THF (6 mL) and anhydrous MeOH (6 ml). Added 2 small scoops of Pd 10% on activated C, placed under an atmosphere of hydrogen and allowed to stir for 2 hours at room temperature. Purged with nitrogen, filtered through Celite and removed solvent by evaporation under vacuum. The benzylic alcohol is reoxidized to the ketone by the following procedure. The crude was taken back in anhydrous $CH_2Cl_2$ (10 mL), with 3 Å molecular sieves, TPAP (1 scoop) was added followed by NMO (212 mg, 1.8 mmol). Stirred at room temperature for 30 minutes and filtered through a plug of silica gel. Solvent was evaporated under vacuum and purified by column chromatography using 10% EtOAc/Hexane.

$^1$H NMR (300 MHz, $CDCl_3$); δ 3.14 (t, 2H), 3.34 (t, 2H), 3.90 (s, 3H), 7.30–7.60 (m, 6H), 7.92–7.99 (m, 4H).

Step 3: 4-(3-oxo-3-Phenylpropyl)-benzoic Acid (48)

To a solution of methyl ester 47 (195 mg, 0.73 mmol) in water/THF (1:1, 0.07M) was added LiOH (46 mg, 1.1 mmol). The resulting solution was stirred overnight at room temperature or until no starting material was detected by TLC. HCl 1N was added and the solution was extracted with EtOAc and the organic layer was dried over anhydrous $MgSO_4$. Filtration and evaporation of the solvent under vacuum followed by purification by column chromatography using 10% MeOH/$CH_2Cl_2$, gave the title compound.

$^1$H NMR (300 MHz, $CDCl_3$); δ 3.16 (t, 2H), 3.36 (t, 2H), 7.33–7.60 (m, 5H), 7.93–8.06 (m, 4H).

Step 4: N-Hydroxy-4-(3-oxo-3-phenylpropyl)-benzamide (50)

Following the procedure described in Example 21, Steps 2–3, but substituting compound 48 for carboxylic acid 4, the title compound was obtained.

$^1$H NMR (300 MHz, DMSO-$d_6$); δ 2.97 (t, 2H), 3.38 (t, 2H), 7.34 (d, 2H, J=8 Hz), 7.45–7.70 (m, 5H), 7.96 (dd, 2H, J=8 Hz, 1 Hz), 11.14 (br. s, 1H).

Example 23

N-Hydroxy-4-(3-oxo-3-phenyl-1-hydroxypropyl)-benzamide (53)

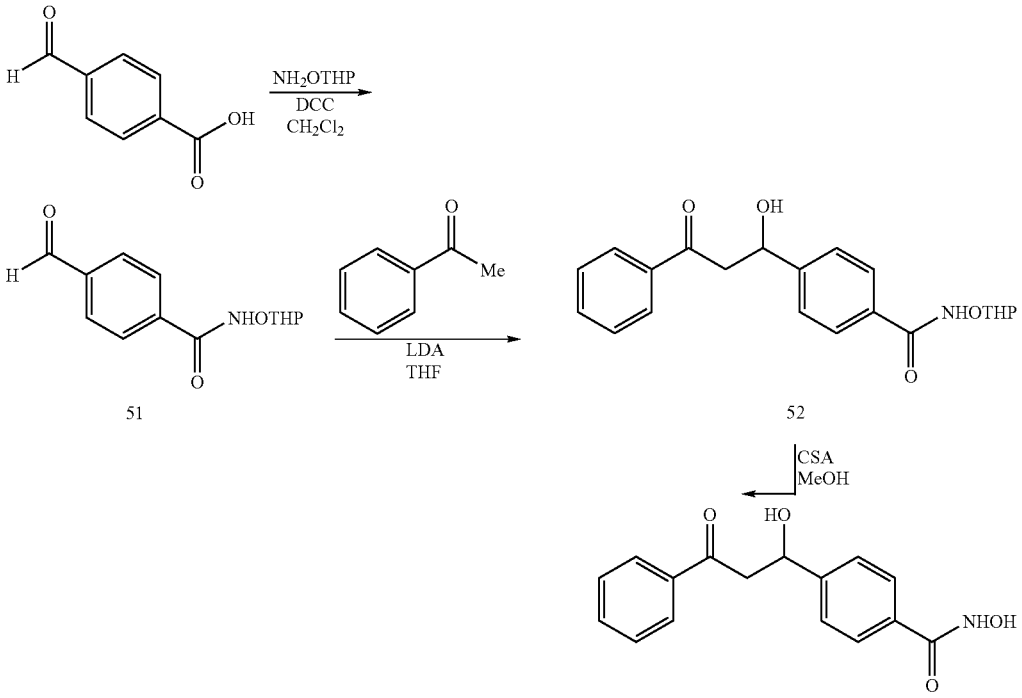

Example 23

Step 1: 4-Carboxy-N-(O-tetrahydropyranyl)-benzamide (51)

Hydroxylamine-O-THP (3.9 g, 33.2 mmol) was added to a suspension of 4-formylbenzoic acid (4.2 g, 27.7 mmol) and DCC (6.8 g, 33.2 mmol) in dichloromethane (200 mL). The mixture was stirred at room temperature overnight and quenched with saturated ammonium chloride. The separated aqueous layer was extracted with ethyl acetate (3×100ml) and the combined organic layers were washed with brine, dried ($MgSO_4$ anh), filtered and evaporated. Flash chromatography of the residue (10% methanol in $CH_2Cl_2$), afforded (51).

$^1$H NMR (300 MHz, $CDCl_3$); δ ppm. 10.04 (s, 1H), 8.95 (s, 1H), 7.99 (d, 2H, J=7.0 Hz), 7.93 (d, 2H, J=7.0 Hz), 5.1 (s, 1H), 3.60 (m, 2H), 1.60 (m, 6H).

Step 2: 4-(3-oxo-3-Phenyl-1-hydroxypropyl)-N-(O-tetrahydropyranyl)-benzamide (52)

n-BuLi (1.4M/hexane, 1.6 mL, 2.2 mmol) was added to a 0° C. solution of diisopropylamine (337 μL, 2.4 mmol) in anhydrous THF (15 mL). Stirred at 0° C. 10 minutes, then cooled to −78° C. Added acetophenone, then stirred 30 minutes at −78° C. Cannulated into a −78° C. solution of the aldehyde 9 (50 mg, 2.0 mmol) in anhydrous THF (10 mL). Stirred 3 hours at −78° C., then added $NH_4Cl$. Warmed to room temperature, extracted with EtOAc, dried over $MgSO_4$, filtered and evaporated solvent under vacuum. Purification by HPLC $CH_3CN$: $H_2O$: TFA 0.1%; 10–95% gave the title compound 52.

Step 3: N-Hydroxy-4-(3-oxo-3-phenyl-1-hydroxypropyl)-benzamide (53)

Following the same procedure as described in Example 21, Step 3, but substituting compound 52 for compound 44, the title compound was obtained.

$^1$H NMR (300 MHz, DMSO-$d_6$); δ 3.20 (dd, 1H, J=4 Hz, J=16 Hz), 3.42 (dd, 1H=16 Hz, 8 Hz), 5.20 (m, 1H), 7.44–8.18 (m, 9H), 11.15 (br. s, 1H), 11.32 (br. s, 1H).

Example 24

N-Hydroxy-4-(3-phenylpropyl)-benzamide (56)

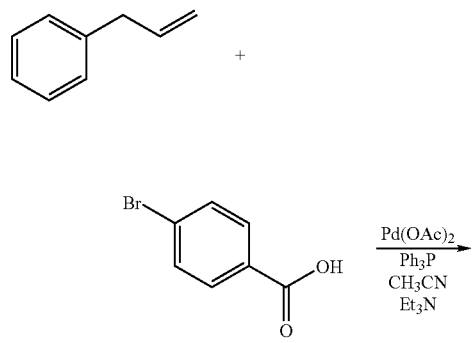

-continued

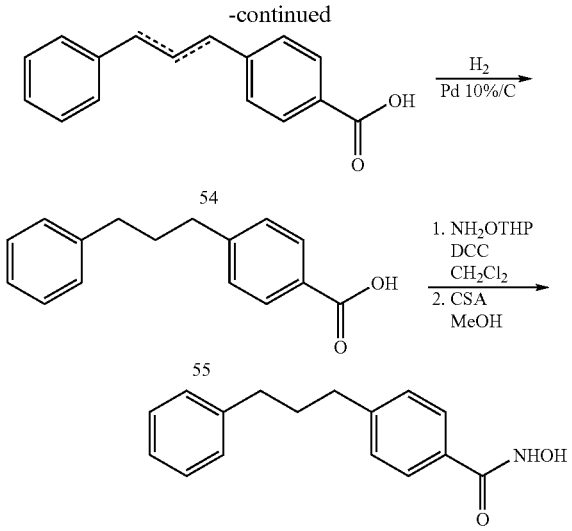

Example 24

Step 1: 4(3-Phenylpropenyl)-benzoic Acid/4-(3-Phenyl-2-propenyl)-benzoic Acid (54)

Allylbenzene (255 μL, 1.9 mmol), 4-bromobenzoic acid (523 mg, 2.6 mmol), $Et_3N$ (0.91 mL, 6.5 mmol), Palladium (II) Acetate (16 mg, 0.052 mmol), triphenylphosphine (60 mg, 0.21 mmol) and acetonitrile (5 mL) were stirred at reflux overnight in a round bottom flask. Added HCl 1N, extracted with EtOAc, dried the organic layer on anhydrous $MgSO_4$, filtered, evaporated solvent under vacuum. Purified by column chromatography using 10% MeOH/$CH_2Cl_2$ yielded 90 mg (14%) of mixture of two regioisomers 54. The mixture was then submitted for hydrogenation without further characterization.

Step 2: 4-(3-Phenylpropyl)-benzoic Acid (55)

A mixture of regioisomeric olefins 54 (100 mg, 0.42 mmol) and Pd 10% on C (10 mg) in methanol (4 mL) was vigorously stirred under $H_2$ atmosphere (14 psi). The mixture was stirred for 2 hours at room temperature, filtered through Celite and evaporated to afford 55 as an oil. Flash chromatography of the residue gave 55 (88 mg, 88%).

$^1$H NMR (300 MHz, $CDCl_3$); δ ppm 8.10 (d, 2H, J=8.0 Hz), 7.35 (m, 7H), 2.73 (m, 4H), 2.00 (m, 2H).

Step 3: N-Hydroxy-4-(phenylpropyl)-benzamide (56)

Following the same procedure as described in Example 21, Steps 2–3, but substituting compound 55 for compound 43, the title compound was obtained as a beige solid. (24 mg, 26% yield).

$^1$H NMR (300 Mz, $CD_3OD$); δ (ppm) 7.63 (d, 2H, J=8.0 Hz); 7.38–7.05 (m, 7H), 2.63 (m, 4H), 1.91 (m, 2H).

Example 25

N-Hydroxy-4-(4-phenylbutyl)-benzamide (61)

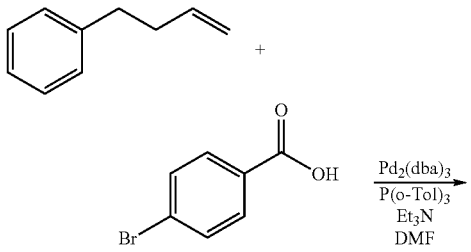

-continued

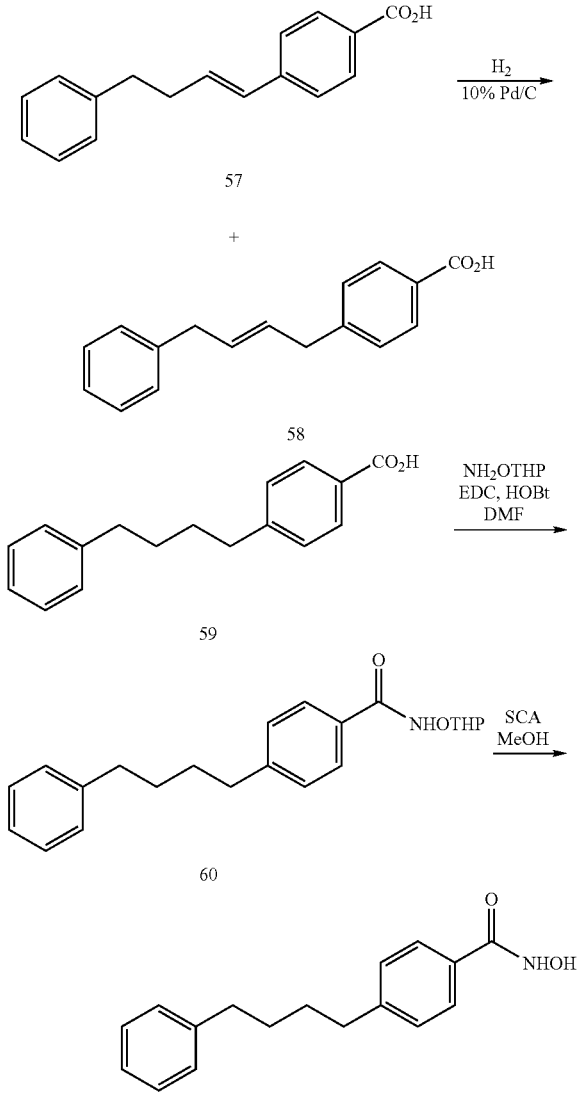

Example 25

Step 1:4-(1-Butenyl-4-phenyl)-benzoic Acid/4-(2-Butenyl-4-phenyl)-benzoic Acid (57/58)

Under nitrogen atmosphere in a 25 mL round bottomed flask were mixed: 4-phenyl-1-butene (568 μL, 3.8 mmol), 4-bromobenzoic acid (634 mg, 3.2 mmol), tris (dibenzylideneacetone)dipalladium(0) (87 mg, 0.1 mmol), tri-o-tolylphosphine (58 mg, 0.2 mmol), triethylamine (1.1 mL, 7.9 mmol) in N,N-dimethylformamide (7 mL, 0.5 M solution). The mixture was stirred for 22 hours at 100° C. Then, the resulting suspension was cooled to room temperature, filtered through Celite and rinsed with ethyl acetate. The filtrate was acidified with 1N HCl, the phases were separated and the aqueous layer was extracted with ethyl acetate. The combined organic layers were washed with water, brine, dried over $MgSO_4$, filtered and concentrated. The resulting solid was triturated with hexane:dichloromethane (9:1) to give 367 mg (46%) of beige solid 57/58.

$^1$H NMR (300 MHz, $(CD_3)_2CO$): δ (ppm) 2.50–2.60 (m, 2H), 2.80 (t, 2H, J=9.0 Hz), 6.40–6.50 (m, 2H), 7.12–7.35 (m, 5H), 7.41 (d, 2H, J=9.0 Hz), 7.92 (d, 2H, J=9.0 Hz).

Step 2: 4-(4-Phenylbutyl)-benzoic Acid (59)

Following the procedure described in Example 24, Step 2, but substituting compound 57/58 for compounds 54, the title compound was obtained as a white solid in 92% yield.

$^1$H NMR (300 MHz, $CD_3OD$); δ (ppm) 1.60–1.75 (m, 4H), 2.65 (t, 2H, J=9.0 Hz), 2.72 (t, 2H, J=9.0 Hz), 7.12–7.30 (m, 5H), 7.33 (d, 2H, J=9.0 Hz), 7.96 (d, 2H, J=9.0 Hz).

Step 3: 4-(4-Phenylbutyl)-N-(O-tetrahydropyranyl)-benzamide (60)

Under nitrogen atmosphere in a 25 mL round bottomed flask, to 4-(4-phenylbutyl)benzoic acid 59 (341 mg, 1.3 mmol) in 5 mL of N,N-dimethylformamide (0.3 M solution) was added the 1-(3-dimethylaminopropyl)-3-ethylcarbodiimide hydrochloride (308 mg, 1.6 mmol) and the 1-hydroxybenzotriazole hydrate (272 mg, 2.0 mmol) at room temperature. The mixture was stirred for 30 minutes then, the 2-(tetrahydropyranyl)hydroxylamine (235 mg, 2.0 mmol) was added and the mixture was stirred for 4 days. The N,N-dimethylformamide was removed under vacuum, the resulting oil was dissolved in ethyl acetate, washed with water and brine, dried over $MgSO_4$, filtered and concentrated to give 95% yield of crude title compound 60.

$^1$H NMR (300 MHz, $CD_3OD$); δ (ppm) 1.50–1.75 (m, 10H), 2.65 (t, 2H, J=9.0 Hz), 2.72 (t, 2H, J=9.0 Hz), 3.51 (d, 1H, J=15 Hz), 4.05 (t, 1H, J=15 Hz), 5.05 (s, 1H), 7.10–7.35 (m, 7H), 7.75 (d, 2H, J=9.0 Hz), 10.60 (s, 1H).

Step 4: N-Hydroxy-4-(4-phenylbutyl)-benzamide (61)

Under nitrogen atmosphere, to the crude oil in a 25 mL round bottomed flask, were added 5 mL of methyl alcohol (0.3 M solution) and camphorsulfonic acid (333 mg, 1.4 mmol). The mixture was stirred for 2 hours at room temperature. The methyl alcohol was removed under vacuum without heating and the resulting oil was purified by flash chromatography eluting methyl alcohol and dichloromethane (1:19). The solid was with hexane:dichloromethane (9:1) to give 212 mg (59%) of beige solid 61.

$^1$H NMR (300 MHz, $(CD_3)_2CO$): δ 1.66 (m, 4H), 2.65 (t, 2H, J=7.2 Hz), 2.70 (t, 2H, J=7.1 Hz), 7.15–7.31 (m, 7H), 7.75 (d, 2H, J=7.8 Hz), 8.18 (broad s, 1H), 10.68 (broad s, 1H).

$^{13}$C NMR (75.46 MHz, $(CD_3)_2CO$): δ 31.6 (t), 31.8 (t), 36.1 (t), 36.2 (t), 2×126.4 (d), 127.8 (d), 2×129.1 (d), 2×129.2 (d), 2+129.3 (d), 130.6 (s), 143.3 (s), 147.3 (s), 165.9 (s).

Example 26

N-Hydroxy-3-(3-phenylpropyl)-benzamide (64)

Step 1: 3-(3-Phenylpropenyl)-benzoic Acid (62)

Following the same procedure as described in Example 24, step 1, but substituting 4-bromobenzoic acid for 3-bromobenzoic acid, the title compound was obtained as mixture of olefins. The mixture was submitted to the next step without purification.

$^1$H NMR (300 MHz, $CDCl_3$); δ (ppm); 3.6 (dd, 2H, $CH_2$); 6.4 (dd, 2H, vinylic); 7.0–7.5 (m, 8H, CHAr); 8.0 (s, 1H, CHAr).

Step 2: 3-(3-Phenylpropyl)-benzoic Acid (63)

Following the same procedure as described in Example 24, Step 2, but substituting compound 62 for compound 54, the title compound was obtained in 52% yield and submitted to the next step without further purification.

$^1$H NMR (300 MHz, $CDCl_3$); δ (ppm); 2.0 (m, 2H, $CH_2$); 2.7 (m, 4H, $2CH_2$); 7.0–7.4 (m, 8H, CHAr); 8.0 (s, 1H, CHAr).

Step 3: N-Hydroxy-3-(3-phenylpropyl)-benzamide (64)

Following the procedure described in Example 25, Step 3–4, but substituting compound 63 for compound 59, the title compound was obtained. Purification by flash chromatography using $CH_2C_2$:MeOH (9.5:0.5) gave compound 64 in 20% yield.

$^1$H NMR (300 MHz, DMSO-$d_6$); δ 1.8 (m, 2H, $CH_2$); 2.8 (m, 4H, $CH_2$); 7.0–7.4 (m, 7H, CHAr); 7.6 (s, CHAr); 9.0 (s, NH); 11.2 (s, OH).

Example 27

N-Hydroxy-3-(2-phenylethyl)-benzamide (68)

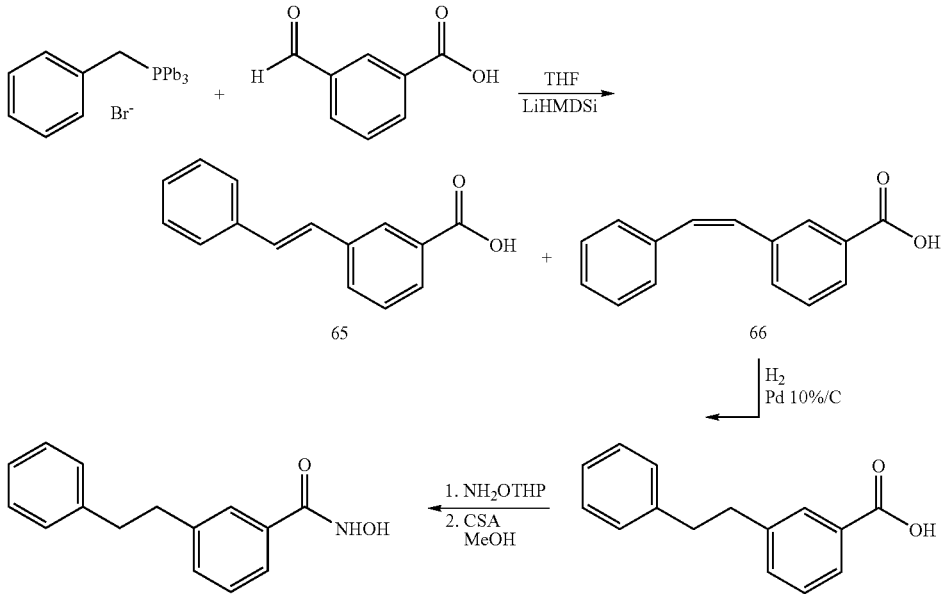

Example 27

Step 1: 3-(2-Phenylethenyl)-benzoic Acid (65/66)

A 1.0 M solution of lithium bis(trimethylsilyl) amide (3.3 mL, 3.3 mmol) in THF was added to a stirred suspension of benzyltriphenylphosphonium bromide (1.44 g, 3.6 mmol) in THF (35 mL) at 0° C. The resulting orange solution was added via cannula to a mixture of 3-carboxybenzaldehyde (500 mg, 3.3 mmol) and lithium bis(trimethylsilyl)amide (3.3 mL, 3.3 mmol) in THF (10 mL). The mixture was stirred overnight at room temperature. A 1N solution of HCl (75 mL) and ethyl acetate (75 mL) were added and the separated aqueous layer was extracted with ethyl acetate (3×50 mL), dried ($MgSO_4$ anh.) filtered and evaporated. The residue was purified by HPLC (10:95 $CH_3CN:H_2O$, TFA 0.1%) to afford 130 mg of the title compound (17%).

$^1$H NMR (300 MHz, $CDCl_3$); δ (ppm) (1:1) E:Z mixture 8.22 (s, 1H), 7.98 (s, 1H), 7.90–7.10 (m, 16H), 6.70 (d, 1H, J=15.0 Hz), 6.62 (d, 1H, J=15.0 Hz).

Step 2: 3-(2-Phenylethyl)-benzoic Acid (67)

Following the same procedure as described in Example 24, Step 2, but substituting compounds 65/66 for compound 54, the title compound was obtained quantitatively.

$^1$H NMR (300 MHz, $CDCl_3$); δ (ppm) 2.98 (m, 4H); 7.30 (m, 7H); 7.99 (m, 2H).

Step 3: N-Hydroxy-3-(2-phenylethyl)-benzamide (68)

Following the same procedure as described in Example 25, Step 3 and 4, but substituting compound 67 for compound 59, the title compound was obtained in 22% yield.

$^1$H NMR (300 MHz, DMSO-$d_6$); δ (ppm) 2.82 (s, 4H); 7.03–7.08 (m, 8H); 7.62 (s, 1H); 8.98 (br. s, 1H); 11.15 (br. s, 1H).

Example 28

N-Hydroxy-4-(2-thiophenyl)-ethyl Benzamide (70)

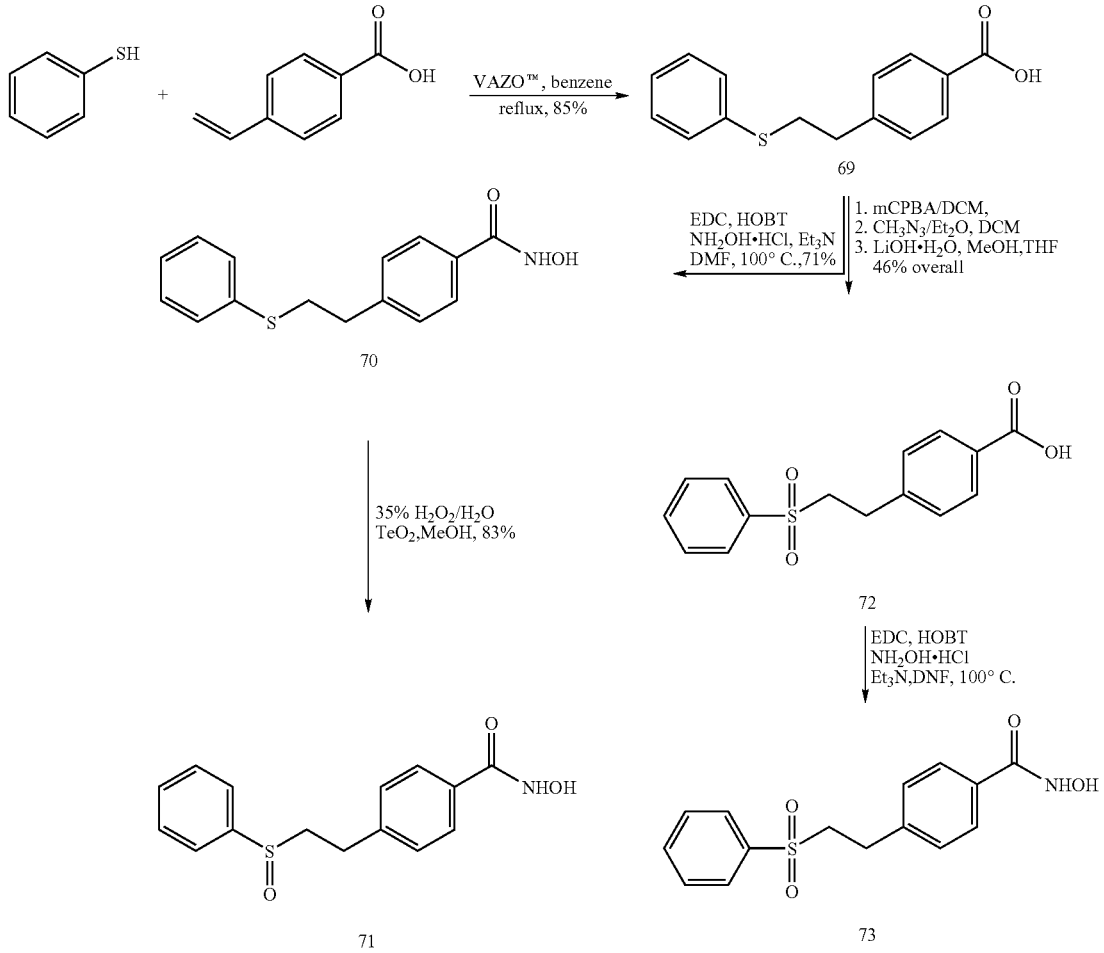

Step 1: 4-(2-Thiophenyl)-ethyl Benzoic Acid (69)

According to the published procedure (Gareau et al., Tet. Lett., 1994, 1837), under nitrogen atmosphere in a 50 mL round bottomed flask containing 4-vinyl-benzoic acid (1.0 g, 6.75 mmoles) in 10 mL of benzene (0.7 M) was added benzenethiol (797 μL, 7.76 mmoles) followed by VAZO™ (Aldrich Chemical Company, 495 mg, 2.02 mmoles). The mixture was stirred for 12 hours at reflux. The resulting solution was cooled at room temperature and the solvent was evaporated under vacuo. The solid was purified by trituration using hexane and dichloromethane to afford 1.94 g (85%) of white solid.

$^1$H NMR (300 MHz, $CDCl_3$): δ 3.01 (t, 2H, J=8.4 Hz), 3.28 (d, 2H, J=7.2, 7.8 Hz), 7.21 (tt, 1H, J=1.2, 7.2 Hz), 7.34 (t, 2H, J=8.1 Hz), 7.38–7.43 (m, 1H), 7.41 (d, 2H, J=8.4 Hz), 7.97 (d, 2H, J=8.1 Hz).

Step 2: N-Hydroxy-4-(2-thiophenyl)-ethyl Benzamide (70)

Under nitrogen atmosphere in a 50 mL round bottomed flask containing 4-(2-thiophenyl)-ethyl benzoic acid (600 mg, 2.32 mmoles) in 12 mL of N,N-dimethylformamide (0.2 M) was added 1-(3-dimethylaminopropyl)-3-ethylcarbodiimide hydrochloride (579 mg, 3.02 mmoles) and 1-hydroxy-benzotriazole hydrate (377 mg, 2.79 mmoles) at room temperature. The mixture was stirred 30 minutes then, hydroxylamine hydrochloride (242 mg, 3.48 mmoles) and triethylamine (971 μL, 6.97 mmoles) was added and the mixture was stirred for 12 hours at 50° C. The N,N-dimethylformamide was removed under vacuo and the resulting oil was dissolved in ethyl acetate, washed with water, saturated sodium hydrogen carbonate solution, water and brine. The organic layer was dried over anhydrous magnesium sulfate, filtered and concentrated under vacuo. The crude solid was purified by trituration using hexane and dichloromethane to afford 450 mg (71%) of a beige solid.

RP-HPLC (Hewlett-Packard 1100, column C18 HP 4.6× 250 mm, flow 1 mL/min, 10–95% $CH_3CN/H_2O$ in 42 min with 0.1% TFA); Purity: 95.8% (220 nm), 93.2% (254 nm).

$^1$H NMR (300.072 MHz, $(CD_3)_2CO$): δ 2.98 (t, 2H, J=7.2 Hz), 3.26 (dd, 2H, J=6.6, 8.4 Hz), 7.21 (tt, 1H, J=1.5, 6.9 Hz), 7.31–7.42 (m, 6H), 7.77 (d, 2H, J=9.3 Hz), 8.08 (broad s, 1H), 10.69 (broad s, 1H).

$^{13}$C NMR (75.46 MHz, $(CD_3)_2CO$): δ 34.8 (t), 35.9 (t), 126.7 (d), 127.9 (d), 2×129.6 (d), 2×129.7 (d), 2×129.9 (d), 131.3 (s), 137.3 (s), 145.0 (s).

Elemental Analysis: Calc for $C_{15}H_{15}O_2NS$×0.1 $H_2O$: % C=75.31, % H=7.14, % N=5.17. Found: % C=75.2±0.1, % H=7.41±0.07, % N=5.17±0.01.

N-Hydroxy-4-(2-benzenesulfonyl)-ethyl Benzamide (73)

Step 1: 4-(2-Benzenesulfonyl)-ethyl Benzoic Acid (72)

Under nitrogen atmosphere in a 100 mL round bottomed flask containing 4-(2-thiophenyl)-ethyl benzoic acid (69) (600 mg, 2.32 mmoles) in 20 mL of dichloromethane (0.1 M) at 0° C. was added portionwise 3-chloroperbenzoic acid (Aldrich Chemical Co., 57–86% pure solid by, 2 g, 6.97 mmoles), as described by Nicolaou et al., J. Am. Chem. Soc., 114: 8897 (1992). The mixture was allowed to reach room temperature and was stirred for 1 hour. Dimethyl sulfide (5 mL) was added, the mixture was diluted in dichloromethane and washed 3 times with water. The organic layer was dried over anhydrous magnesium sulfate, filtered and the solvent were evaporated in vacuo to afford 3 g of white solid. This mixture of 3-chloro-benzoic acid and the desired 4-(2-benzenesulfonyl)-ethyl benzoic acid was placed in a 125 mL Erlenmeyer flask, dissolved in 30 mL of dichloromethane and treated with an excess of freshly prepared diazomethane solution in diethyl ether (0.35 M). Nitrogen was bubbled to removed the excess of diazomethane and solvents were evaporated under vacuum. The resulting solid was purified by flash chromatography, eluting with 20% ethyl acetate:80% hexane to afford 341.6 mg (48%) of the corresponding ester. Saponification of this ester was done using the same procedure was described in Example 1, step 2, to afford 312.4 mg (96%) of 4(2-benzenesulfonyl)-ethyl benzoic acid (72).

$^1$H NMR (300 MHz, $CDCl_3$): δ 3.06–3.11 (m, 2H), 3.56–3.61 (m, 2H), 7.37 (d, 2H, J=8.4 Hz), 7.67 (tt, 2H, J=1.5, 7.2 Hz), 7.76 (tt, 1H, J=1.2, 7.5 Hz), 7.93 (d, 2H, J=8.7 Hz), 7.97 (dd, 2H, J=1.8, 6.9 Hz).

Step 2: N-Hydroxy-4-(2-benzenesulfonyl)-ethyl Benzamide (73)

Following the procedure described for N-hydroxy-4-(2-thiophenyl)-ethyl benzamide, but substituting 4-(2-benzenesulfonyl)-ethyl benzoic acid for 4-(2-thiophenyl)-ethyl benzoic acid, the title compound was obtained as a beige solid.

RP-HPLC (Hewlett-Packard 1100, column C18 HP 4.6× 250 mm, flow 1 mL/min, 10–95% $CH_3CN/H_2O$ in 42 min with 0.1% TFA); Purity: 98.8% (220 nm), 97.6% (254 nm).

$^1$H NMR (300.072 MHz, $(CD_3)_2CO$): δ 2.98 (t, 2H, J=7.2 Hz), 3.26 (dd, 2H, J=6.6, 8.4 Hz), 7.21 (tt, 1H, J=1.5, 6.9 Hz), 7.31–7.42 (m, 6H), 7.77 (d, 2H, J=9.3 Hz), 8.08 (broad s, 1H), 10.69 (broad s, 1H).

$^{13}$C NMR (75.46 MHz, $(CD_3)_2CO$): δ 25.2 (t), 34.3 (t), 55.6 (t), 128.0 (d), 2×128.8 (d), 129.4 (d), 2×130.2 (d), 131.1 (s), 134.5 (d), 140.7 (s), 145.5 (s), 165.8 (s).

N-Hydroxy-4-(2-benzenesulfoxide)-ethyl Benzamide (71)

According to the procedure described by Van Der Borght et al., J. Org. Chem., 65: 288 (2000), under nitrogen atmosphere in a 10 mL round bottomed flask containing N-hydroxy-4-(2-thiophenyl)-ethyl benzamide (70) (50 mg, 0.18 mmol) in 2 mL of methanol (0.1 M) was added tellurium dioxide (3 mg, 0.018 mmol) followed by solution 35% in water of hydrogen peroxide (32 μL, 0.36 mmol). The mixture was stirred for five days and then brine was added. The aqueous layer was extracted 3 times with ethyl acetate and the combined organic layers were dried over anhydrous magnesium sulfate, filtered and the solvent were evaporated under vacuo. The resulting solid (43.3 mg) was purified by trituration using acetonitrile to afford 10 mg (20%) of beige solid.

RP-HPLC (Hewlett-Packard 1100, column C18 HP 4.6× 250 mm, flow 1 mL/min, 10–95% $CH_3CN/H_2O$ in 42 min with 0.1% TFA); Purity: 98.8% (220 nm), 97.9% (254 nm).

$^1$H NMR (300.072 MHz, $(CD_3)_2CO$): δ 2.76–2.91 (m, 1H), 3.00–3.29 (m, 3H), 7.34 (d, 2H, J=8.4 Hz), 7.55–7.62 (m, 3H), 7.70 (dd, 2H, J=1.5, 8.1 Hz), 7.76 (d, 2H, J=8.1 Hz), 8.08 (broad s, 1H), 10.70 (broad s, 1H).

$^{13}$C NMR (75.46 MHz, $(CD_3)_2CO$): δ 28.3 (t), 57.8 (t), 2×124.8 (d), 128.0 (d), 2×129.6 (d), 2×130.0 (d), 131.5 (d), 144.1 (s), 145.7 (s).

Example 29

N-Hydroxy-3-[4-(3-phenylpropyl)-phenyl]-propanamide (77)

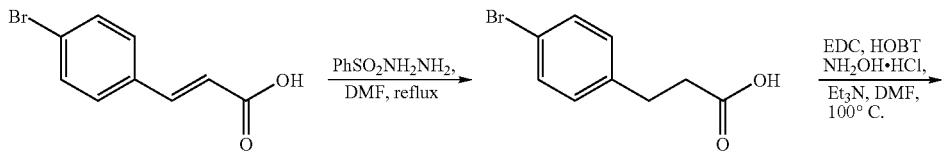

-continued

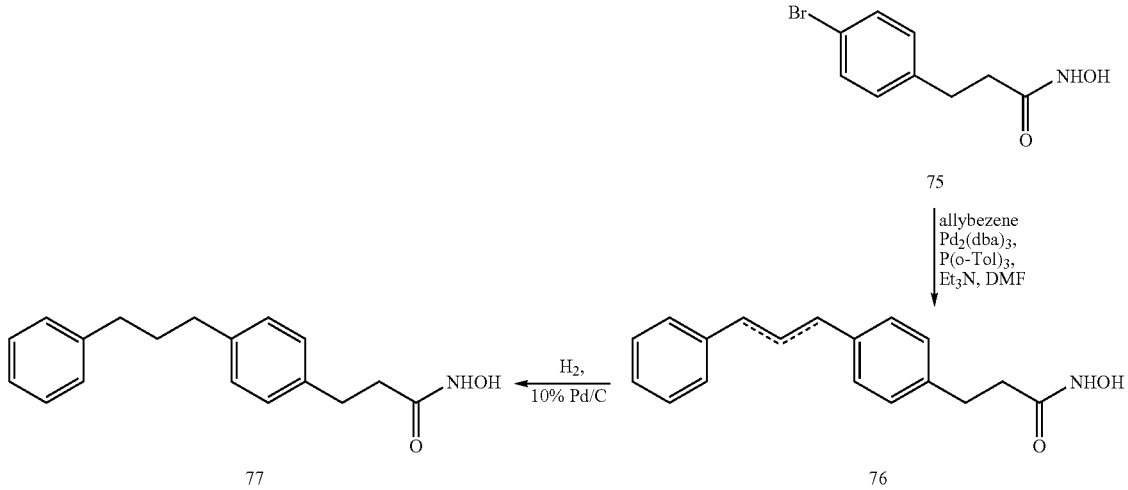

Step 1: 3-(4-Bromophenyl)-propanoic Acid (74)

Under nitrogen atmosphere in a 250 mL round bottomed flask containing 4-bromocinnamic acid (5.0 g, 22 mmoles) in 45 mL of N,N-dimethylformamide (0.5 M) was added benzenesulfonylhydrazide (7.6 g, 44 mmoles). The mixture was stirred at reflux for 12 hours. The solution was cooled at room temperature, aqueous saturated ammonium chloride was added and the aqueous layer was extracted with ethyl acetate 3 times. Combined organic layers were washed with water and brine, dried over anhydrous magnesium sulfate, filtered and concentrated under vacuo. The resulting solid was purified by flash chromatography eluting with 5% methanol:95% dichloromethane to afford 3.66 g (73%) of beige solid.

$^1$H NMR (300 MHz, $CDCl_3$): δ 2.66 (t, 2H, J=7.5 Hz), 2.91 (d, 2H, J=7.5 Hz), 7.08 (d, 2H, J=8.4 Hz), 7.41 (d, 2H, J=8.4 Hz).

Step 2: N-Hydroxy-3-(4-bromophenyl)-propanamide (75)

Following a procedure analogous to that described for the preparation of 70, 1.54 g (39%) of the title compound was obtained.

$^1$H NMR (300 MHz, $CDCl_3$): δ 2.39 (t, 2H, J=7.8 Hz), 2.89 (d, 2H, J=7.2 Hz), 7.18 (d, 2H, J=8.1 Hz), 7.42 (d, 2H, J=8.7 Hz), 8.18 (broad s, 1H), 9.98 (broad s, 1H).

Step 3: N-Hydroxy-3-[4-(3-phenyl-1-propenyl)-phenyl]-propanamide and N-Hydroxy-3-[4-(3-phenyl-2-propenyl)-phenyl]-propanamide (76)

Following a procedure analogous to that described in Example 25, step 1, but substituting N-hydroxy-3-(4-bromophenyl)-propanamide (75) (250 mg, 1.02 mmol) for 4-bromobenzoic acid and allyl benzene (163 μL, 1.2 mmol) for 4-phenyl-1-butene, to yield 155.4 mg (54%) of the mixed title compounds.

$^1$H NMR (300 MHz, $CDCl_3$): δ 2.39 (m, 2H), 2.88 (t, 2H, J=8.4 Hz), 3.51 (t, 2H, J=8.1 Hz), 6.32–6.53 (m, 2H), 7.14–7.44 (m, 9H), 8.60 (broad s, 1H), 10.04 (broad s, 1H).

Step 4: N-Hydroxy-3[4-(3-phenylpropyl)-phenyl]-propanamide (77)

Following a procedure analogous to that described in Example 24, step 2, but substituting the mixture of N-hydroxy-3-[4-(3-phenyl-1-propenyl)-phenyl]-propanamide and N-hydroxy-3-[4-(3-phenyl-2-propenyl)-phenyl]-propanamide (155 mg, 0.55 mmol) for olefins 54, 155.4 mg (99%) of the title compound was obtained.

RP-HPLC: (Hewlett-Packard 1100, column C18 HP 4.6×250 mm, flow 1 mL/min, 10–95% $CH_3CN/H_2O$ in 42 min with 0.1% TFA); Purity: 99.9% (220 nm) (2 peaks but same compound proven by LCMS, 99.9% (254 nm). $^1$H NMR (300.072 MHz, $(CD_3)_2CO$): δ 1.91 (quintuplet, 2H, J=8.1 Hz), 2.38 (t, 2H, J=7.8 Hz), 2.61 (q, 4H, J=9.6 Hz), 2.87 (t, 2H, J=7.2 Hz), 7.12–7.29 (m, 9H), 8.42 (broad s, 1H), 10.01 (broad s, 1H).

$^{13}$C NMR (75.46 MHz, $(CD_3)_2CO$): δ 26.3 (t), 28.7 (t), 29.8 (t), 30.3 (t), 30.7 (t), 121.1 (d), 3×123.7 (d), 3×123.8 (d), 133.9 (s), 133.4 (s), 137.8 (s), 164.9 (s).

Elemental Analysis: Calc for $C_{18}H_{21}O_2NX0.1\ H_2O$: % C=75.81, % H=7.49, % N=4.91. Found: % C=75.7±0.3; % H=7.54±0.02, % N=4.85±0.03.

Example 30

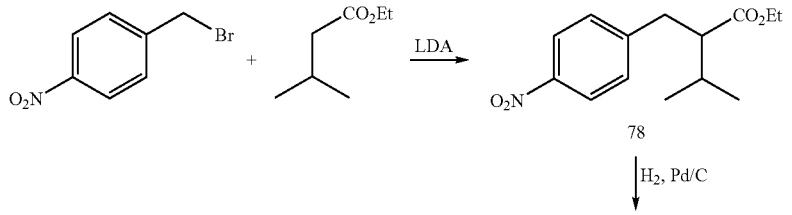

-continued

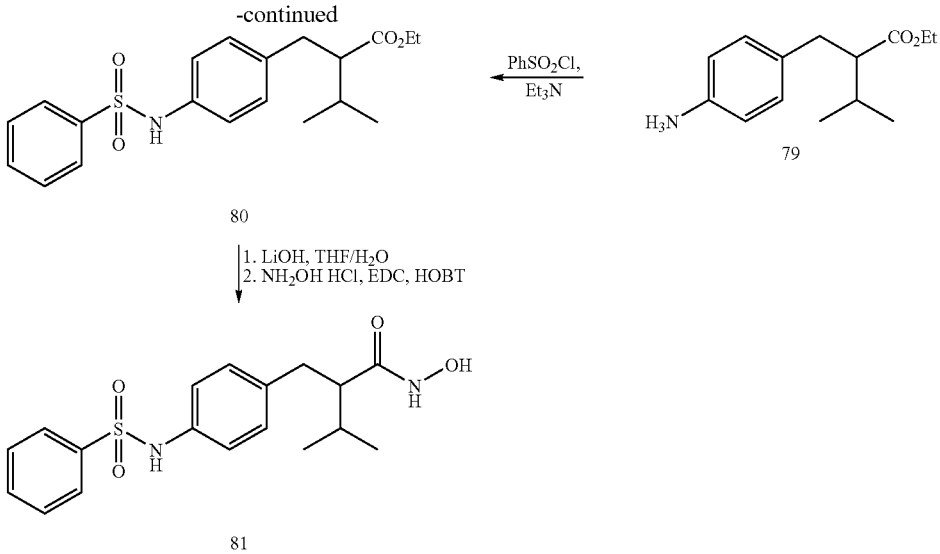

Step 1: Ethyl 3-(4-Nitrophenyl),2-isopropyl Propanoate (78)

To a precooled solution of diisopropylamine (34.7 mmol) in THF (30 mL) under nitrogen was added dropwise a 1.0 M solution of n-butyllithium (33.3 mmol). The resulting light yellow solution was stirred at −78° C. over 30 minutes and transferred via canula to a precooled (−78° C.) solution of ethyl isovalerate (34.7 mmol) in THF (50 mL). The mixture was stirred at −78° C. over 1 hour and a 4-nitrobenzyl bromide (13.9 mmol) solution in THF (20 mL) at room temperature was transferred dropwise via canula to the enolate solution which turned deep red. The mixture was stirred over 15 minutes and the reaction was quenched with aqueous saturated ammonium chloride solution ($NH_4Cl$). The mixture was allowed to warm to room temperature over 1 hour and turned brown upon warming. It was poured into a large volume of saturated $NH_4Cl$ solution and the layers were separated. The aqueous layer was extracted twice with diethyl ether and the combined organic layers were washed with brine, dried over magnesium sulfate and concentrated in vacuo. The residue was purified by flash chromatography on silica gel using ethyl acetate and hexanes (10:90) as the eluent, yielding 73% of the pure title compound 78 as a light yellow oil.

Step 2: Ethyl 3-(4-Aminophenyl),2-isopropyl Propanoate (79):

To a hydrogen flushed (vacuum/$H_2$, 3 times) solution of 1 (1.88 mmol) in methanol (10 mL) was added 10% palladium on charcoal (0.018 mmol) previously quenched with methanol in a separate flask. The black heterogeneous resulting mixture was stirred at room temperature under hydrogen atmosphere (1 atm) over 20 hours. The hydrogen was then evacuated by vacuum and replaced with air. Then, the mixture was filtered through celite, rinsing with methanol while making sure the pad never gets dry. The filtrate was concentrated to a red oil. The residue was purified by flash chromatography on silica gel using ethyl acetate and hexanes (30:70) as the eluent, yielding 73% of the pure title compound 79 as a light red oil.

Steps 3–5: (81)

Compound 79 was coupled with benezenesulfonyl chloride in the presence of triethylamine according to the procedure described in Example 1, step 1, to afford the sulfonamide 80. Ester hydrolysis and coupling with hydroxylamine were then accomplished as described in Example 28 to afford the hydroxamic acid 81.

$^1$H NMR: (Acetone-$d_6$) δ (ppm): 9.76 (bs, 1H), 8.83 (bs, 1H), 7.74 (d, J=8.2 Hz, 2H), 7.59–7.49 (m, 3H), 7.04 (s, 4H), 2.83–2.73 (m, 3H), 1.83 (sext, J=6.9 Hz, 1H), 1.00 (d, J=6.9 Hz, 3H), 0.83 (d, J=6.9 Hz, 3H).

HRMS: 344.1195 ($M^+$—$H_2O$) (calc.); 344.1200±0.0010 (found).

Example 31

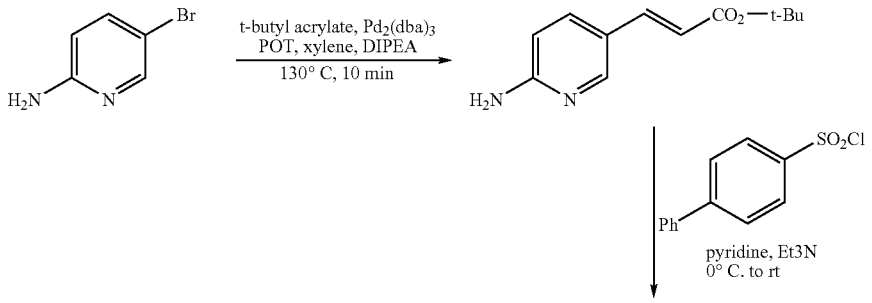

-continued

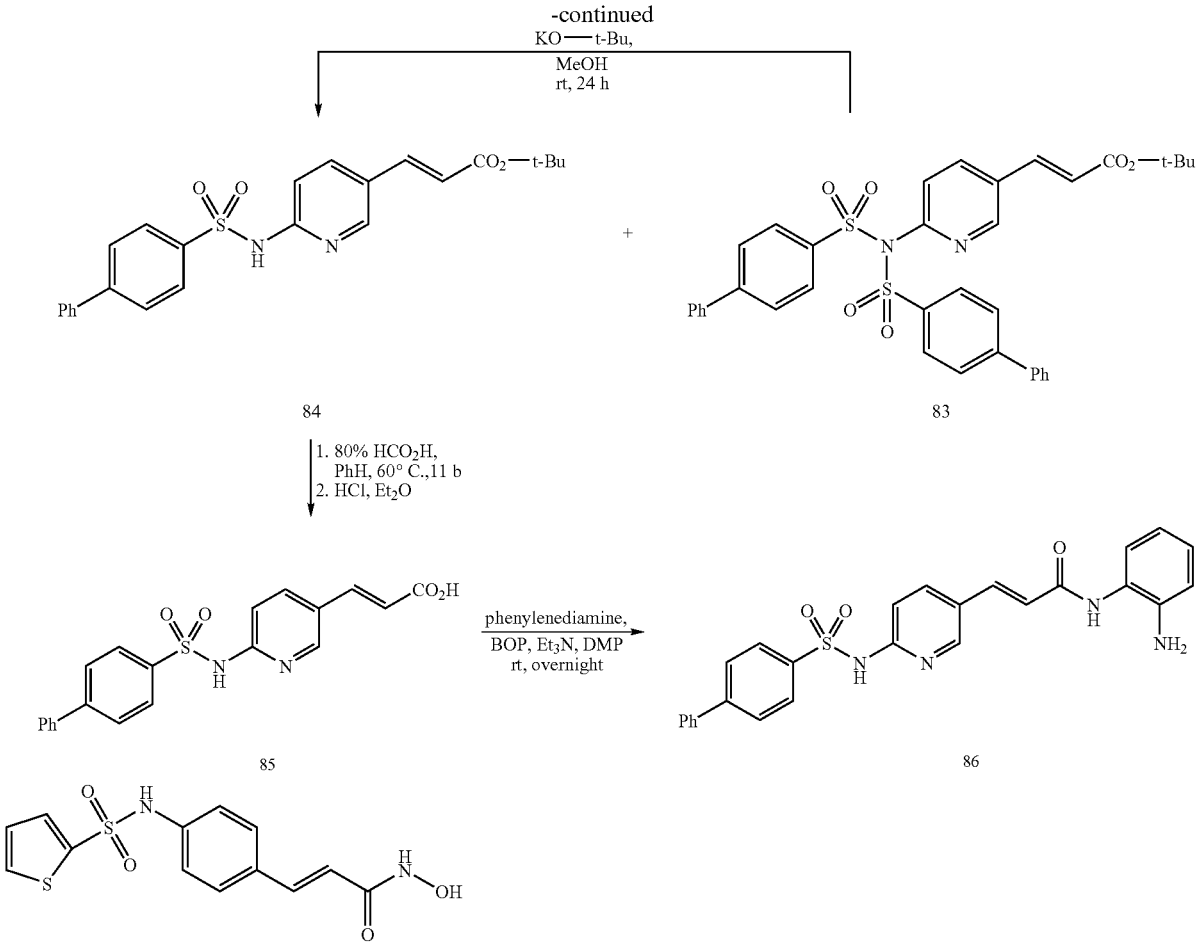

Compound 82 was obtained in good yield from commercially available bromoaminopyridine through a palladium catalyzed coupling with tert-butyl acrylate. Treatment of 82 with 4-phenylbenzenesulfonyl chloride afforded a mixture of sulfonamide 84 and bis-sulfonamide 83, which was converted to 84 upon chromatographic isolation followed by basic methanolysis. Acidic cleavage of the t-butyl ester was effected by treatment of 84 with aqueous formic acid and a tert-butyl cation scavenger to afford the acrylic acid 85 in quantitative yield. Finally, coupling of 85 with o-phenylenediamine in the presence of benzotriazol-1-yloxytris(dimethylamino)phosphonium hexafluorophosphate (BOP) afforded the anilide 86.

Data for 86:

$^1$H NMR: (300.07 MHz; $CD_3OD$): δ (ppm): 8.23 (d, J=1.9 1H); 8.03 (bd, J=8.5; 2H); 7.96 (dd, J=1.9, 9.1; 1H); 7.76 (bd, J=8.5, 2H); 7.63 (dd, J=1.4, 8.2); 7.53 (J=15.5; 1H), 7.48–7.36 (m, 3H); 7.29 (d, J9.1, 1H) 7.18 (dd, J=1.4, 8.0, 1H); 7.03 (dt, J=1.4, 7.8, 1H); 6.86 (d, J=1.4, 7.9, 1H) 6.76 (d, J=15.6, 1H) 6.75–6.69 (m, 1H); 4.85 (bs, 4H).

$^{13}$C NMR: (75.5 MHz; $CD_3OD$) (ppm): 166.4; 154.7; 146.9; 146.2; 143.1; 141.1; 140.6; 138.6; 137.9; 130.1; 129.5; 128.8; 128.5; 128.3; 126.7; 125.6; 125.0; 122.1; 120.8; 119.5; 118.6; 114.9.

MS: calc for $C_{26}H_{22}O_3N_4S$: 470.556; found: 471.5 for [M+H] (low resolution MS).

By procedures analogous to those described in Examples 1–31 above, the following compounds were synthesized:

$^1$H NMR: (300 MHz, $CD_3OD$): d=7.76–7.74 (1H, m), 7.58–7.48 (4H, m), 7.22 (2H, d, J=7.5 Hz), 7.10 (1H, t, J=5.1 Hz), 6.41 (1H, d broad, J=14.7 Hz).

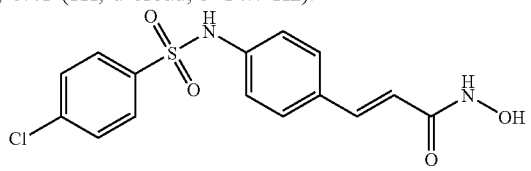

$^1$H NMR: (300 MHz, $CD_3OD$): d=7.79 (2H, d, J=8.1 Hz), 7.56–7.46 (5H, m), 7.17 (2H, d, J=8.1 Hz), 6.39 (1H, d, J=15.9 Hz).

Analysis: $C_{15}H_{13}N_2O_4SClX0.1\ H_2O$, X0.3 TFA Found: C=48.26%, H=3.58%, N=6.97%, S=7.86%. Calc.: C=48.19%, H=3.50%, N=7.20%, S=8.25%.

89

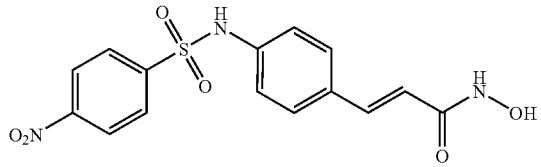

$^1$H NMR: (300 MHz, DMSO $d_6$): d=10.85 (1H, s br), 10.70 (1H, s br), 8.99 (1H, s), 8.37 (2H, d, J=9 Hz), 8.01 (2H, d, J=9 Hz), 7.44 (2H, d, J=8.7 Hz), 7.33 (1H, d, J=15.3 Hz), 7.12 (2H, d, J=8.4 Hz), 6.31 (1H, d, J=15.9 Hz).

Analysis: $C_{15}H_{13}N_3O_6SX0.4\ H_2O$, X0.3 TFA Found: C=46.39%, H=3.49%, N=10.44%, S=7.92%. Calc.: C=46.29%, H=3.51%, N=10.38%, S=7.92%.

90

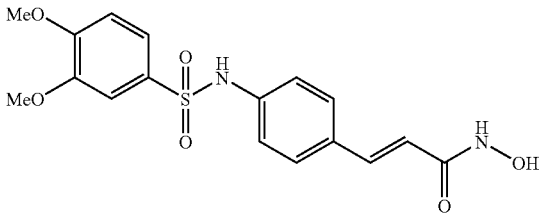

$^1$H NMR: (300 MHz, DMSO $d_6$): d=10.70 (1H, s br), 10.33 (1H, s br), 8.99 (1H, s br), 7.44–7.26 (5H, m), 7.12 (2H, d, J=8.7 Hz), 7.06 (1H, d, J=8.4 Hz), 6.30 (1H, d, J=16.2 Hz), 3.78 (3H, s), 3.75 (3H, s).

Analysis: $C_{17}H_{18}N_2O_6SX0.2\ H_2O$ Found: C=53.56%, H=5.03%, N=7.71%, S=8.01%. Calc.: C=53.45%, H=4.86%, N=7.33%, S=8.39%.

91

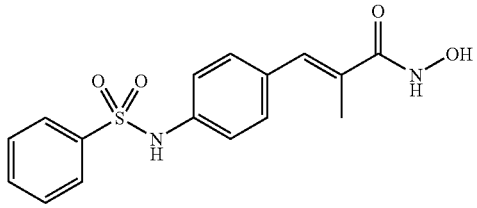

$^1$H NMR: ($CD_3OD$) δ (ppm): 7.78 (d, J=7.1 Hz, 1H), 7.56–7.45 (m, 3H), 7.24 (d, J=8.5 Hz, 2H), 7.12 (d, J=8.8 Hz, 2H), 7.06 (s, 1H), 2.00 (d, J=1.4 Hz, 3H).

$^{13}$C NMR: ($CD_3OD$) δ (ppm): 135.2, 132.9, 128.1, 127.7, 125.5, 124.6, 124.1, 122.3, 116.8, 115.6, 8.4.

92

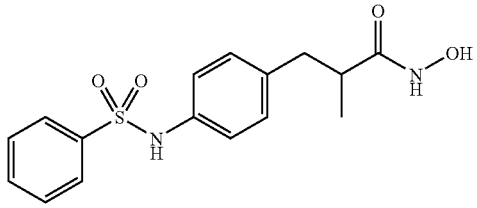

$^1$H NMR: (Acetone-$d_6$) δ (ppm): 9.86 (bs, 1H), 8.86 (bs, 1H), 7.83 (bs, 1H), 7.76 (d, J=6.7 Hz, 1H), 7.62–7.48 (m, 3H), 7.10–7.03 (m, 4H), 2.87–2.79 (m, 3H), 2.56–2.39 (m, 2H), 1.05 (d, J=6.6 Hz, 3H).

HRMS: 334.0987 (calc.); 334.0991±0.0010 (found)

93

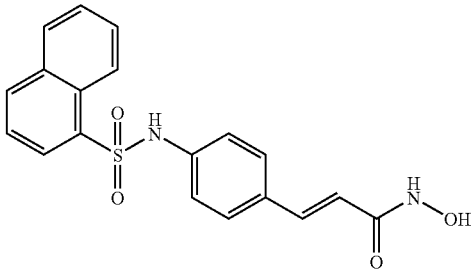

$^1$H NMR: (300 MHz, DMSO $d_6$): d=10.94 (1H, s broad), 10.65 (1H, s broad), 8.95 (1H, s Broad), 8.73–8.71 (1H, m), 8.24–8.21 (2H, m), 8.05 (1H, m), 7.74–7.63 (3H, m), 7.33–7.23 (2H, m), 7.067.04 (2H, m), 6.24 (1H, d, J=15.3).

Analysis: $C_{19}H_{16}N_2O_4SX0.5\ H_2O$ Found: C=60.31%, H=4.58%, N=7.43%. Calc.: C=60.46%, H=4.54%, N=7.42%.

94

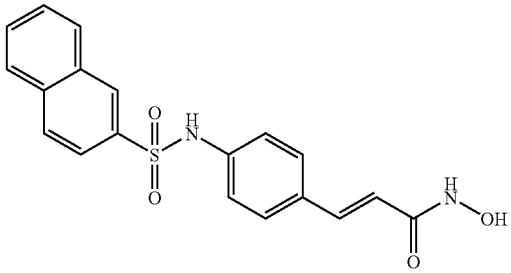

$^1$H NMR: (300 MHz, DMSO $d_6$): δ=10.65 (2H, s broad), 8.48 (1H, s), 8.15–8.08 (2H, m), 8.00 (1H, d, J=7.5 Hz), 7.77 (1H, d, J=9 Hz), 7.70–7.62 (2H, m), 7.39 (2H, d, J=8.4 Hz), 7.28 (1H, d, J=15.6 Hz), 7.15 (2H, d, J=8.4 Hz), 6.26 (1H, d, J=15.6 Hz).

Analysis: $C_{19}H_{16}N_2O_4SX0.2\ H_2O$, X0.5 TFA Found: C=56.01%, H=3.94%, N=6.60%, S=7.41%. Calc.: C=55.99%, H=3.97%, N=6.53%, S=7.47%.

95

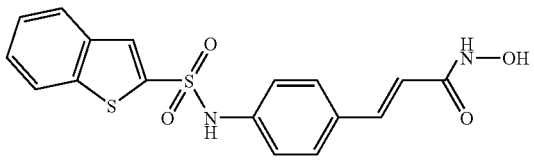

$^1$H NMR: (300 MHz, DMSO $d_6$): δ=10.91 (1H, s), 10.69 (1H, s br), 8.06–7.98 (3H, m), 7.57–7.46 (4H, m), 7.34 (1H, d, J=15.9 Hz), 7.21 (2H, d, J=8.4 Hz), 6.33 (1H, d, J=15.9 Hz).

96

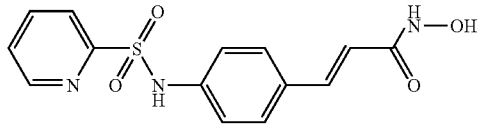

$^1$H NMR: (300 Mz, DMSO $d_6$): δ=8.69–8.8 (1H, m), 8.02–8.01 (2H, m), 7.61–7.59 (1H, m), 7.52–7.43 (3H, m), 7.25 (2H, d, J=7.5 Hz), 6.37 (1H, d, J=15.9 Hz).

Analysis: $C_{14}H_{13}N_3O_4SX0.9$ TFA Found: C=45.36%, H=3.51%, N=9.77%, S=7.09%. Calc.: C=44.97%, H=3.32%, N=9.96%, S=7.60%.

97

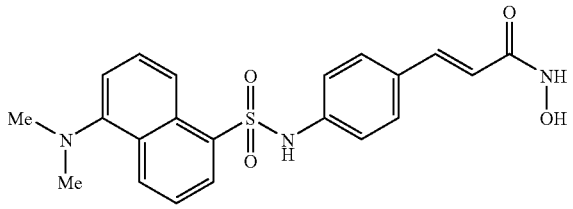

$^1$H NMR: (300 MHz, DMSO $d_6$): δ=10.91 (1H, s), 10.62 (1H, s br), 8.45 (1H, 8.1 Hz), 8.36 (1H, d, J=8.7 Hz), 8.25 (1H, d, J=6.9 Hz), 7.65–7.59 (2H, m), 7.37–7.34 (2H, m), 7.29–7.23 (2H, m), 7.06 (2H, d, J=8.7 Hz), 6.25 (1H, d, J=15.9 Hz), 2.80 (6H, s).

98

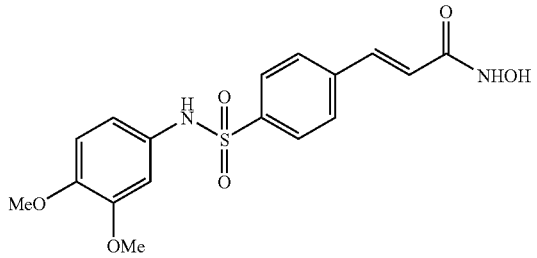

$^1$H NMR: (300 MHz, DMSO $d_6$): δ=10.82 (1H, s br), 9.95 (1H, s br), 9.12 (1H, s br), 7.70 (4H, s), 7.46 (1H, d, J=15.9 Hz), 6.79 (1H, d, J=8.7 Hz), 6.68 (1H, s), 6.56–6.51 (2H, m), 3.65 (3H, s), 3.62 (3H, s).

99

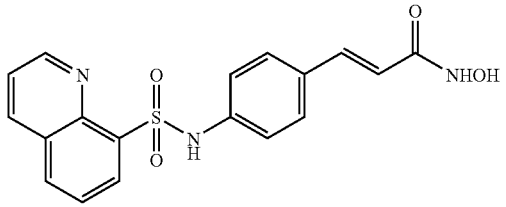

$^1$H NMR: (300 MHz, DMSO $d_6$): δ=10.63 (1H, s), 10.36 (1H, s br), 9.13–9.12 (1H, m), 8.93 (1H, s br), 8.51 (1H, d, J=8.1 Hz), 8.40 (1H, d, J=7.2 Hz), 8.28 (1H, d, J=8.4 Hz), 7.75–7.70 (2H, m), 7.30–720 (3H, m), 7.09 (2H, d, J=8.4 Hz) 6.21 (1H, d, J=15.9 Hz).

Analysis: $C_{18}H_{15}N_3O_4SX1.1$ $H_2O$ Found: C=55.72%, H=4.45%, N=10.64%, S=6.93%. Calc.: C=55.55%, H=4.45%, N=10.80%, S=8.24%.

100

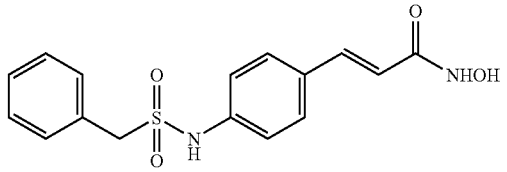

$^1$H NMR: (300 MHz, DMSO $d_6$): δ=10.72 (1H, s br), 10.07 (1H, s), 7.53–7.51 (2H, m), 7.437.34 (4H, m), 7.26–7.19 (4H, m), 6.38 (1H, d, J=15.6 Hz), 4.51 (2H, s).

Analysis: $C_{16}H_{16}N_2O_4SX0.4$ TFA Found: C=53.60%, H=4.46%, N=7.36%, S=7.81%. Calc.: C=53.38%, H=4.37%, N=7.41%, O=20.32%, S=8.48%, F=6.03%.

101

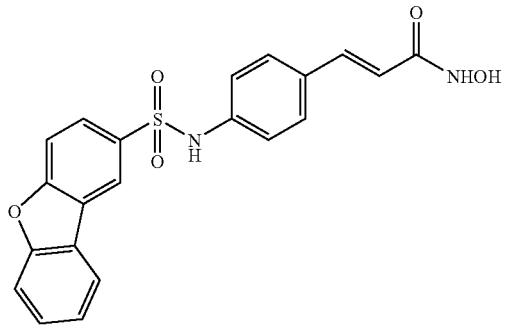

$^1$H NMR: (300 MHz, DMSO $d_6$): δ=10.63 (1H, s br), 10.56 (1H, s), 8.67 (1H, s), 8.29 (1H, d, J=6.9 Hz), 7.89–7.85 (2H, m), 7.75 (1H, d, J=8.4 Hz), 7.59 (1H, t, J=7.2 Hz), 7.47–7.38 (3H, m), 7.27 (1H, d, J=15.6 Hz), 7.15 (2H, d, J=8.7 Hz), 6.25 (1H, d, J=15.9 Hz).

102

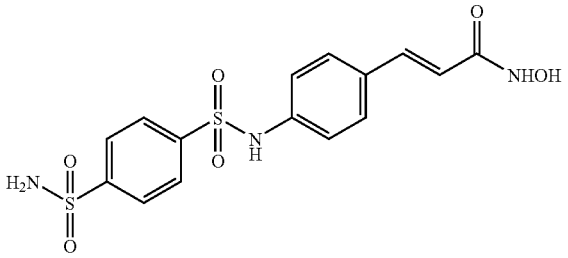

$^1$H NMR: (300 MHz, DMSO $d_6$): δ=10.72 (2H, s), 8.98 (1H, s br), 7.97 (4H, s), 7.55 (2H, s), 7.45 (2H, d, J=8.7 Hz), 7.33 (1H, d, J=15.9 Hz), 7.13 (2H, d, J=8.7 Hz), 6.32 (1H, d, J=15.9 Hz).

103

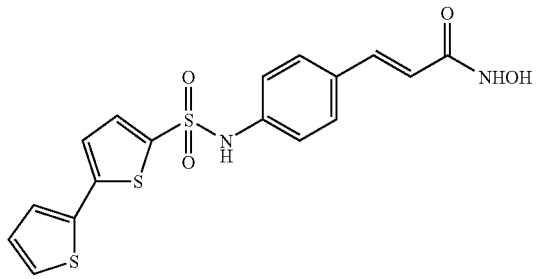

1H NMR: (300 MHz, DMSO $d_6$): δ=10.75 (2H, m), 7.65–7.64 (1H, m), 7.53–7.45 (4H, m), 7.35 (1H, d, J=16.2 Hz), 7.29 (1H, d, J=3.9 Hz), 7.20 (2H, d, J=8.7 Hz), 7.12 (1H, t, J=3.6 Hz), 6.34 (1H, d, J=15.6 Hz).

Analysis: $C_{17}H_{14}N_2O_4S_3X0.1\ H_2O$, X1.0 TFA Found: C=43.83%, H=3.26%, N=5.73%, S=18.15%. Calc.: C=43.69%, H=2.93%, N=5.36%, S=18.42%.

104

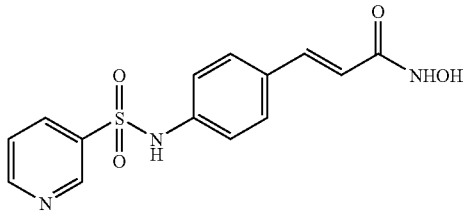

$^1$H NMR: (300 MHz, DMSO $d_6$): δ=10.72 (1H, s), 8.91 (1H, d, J=1.8 Hz), 8.80–8.78 (1H, m), 8.13 (1H, d, J=7.8 Hz), 7.63–7.59 (1H, m), 7.46 (2H, d, J=8.7 Hz), 7.33 (1H, d, J=15.6 Hz), 7.14 (2H, d, J=8.7 Hz), 6.32 (1H, d, J=15.9 Hz).

105

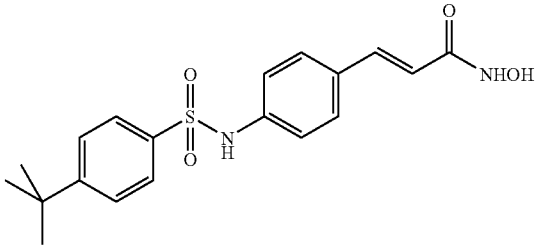

$^1$H NMR: (300 MHz, DMSO $d_6$): δ=10.54 (1H, s), 7.73 (2H, d, J=8.4 Hz), 7.58 (2H, d, 8.4 Hz), 7.43 (2H, d, J=8.4 Hz), 7.32 (1H, d, J=15.6 Hz), 7.15 (2H, d, J=8.4 Hz), 6.30 (1H, d, J=15.9 Hz), 1.25 (9H, s).

Analysis: $C_{19}H_{22}N_2O_4SX0.3\ H_2O$, 0.6 TFA Found: C=54.17%, H=5.25%, N=6.32%, S=6.85%. Calc.: C=54.12%, H=5.22%, N=6.25%, S=7.15%.

106

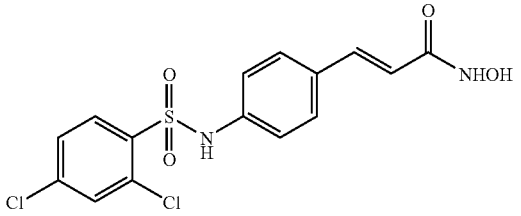

$^1$H NMR: (300 MHz, DMSO $d_6$): δ=11.02 (1H, s), 10.70 (1H, s), 8.99 (1H, s br), 8.03 (1H, d, J=1.8 Hz), 7.76–7.67 (2H, m), 7.45 (2H, d, J=8.1 Hz), 7.33 (1H, d, J=15.6 Hz), 7.13 (2H, d, J=8.4 Hz), 6.31 (1H, d, J=16.2 Hz).

Analysis: $C_{15}H_{12}N_2O_4SCl_2X0.3\ H_2O$ Found: C=45.96%, H=3.11%, N=7.21%, S=8.06%. Calc.: C=45.89%, H=3.23%, N=7.13%, S=8.17%.

107

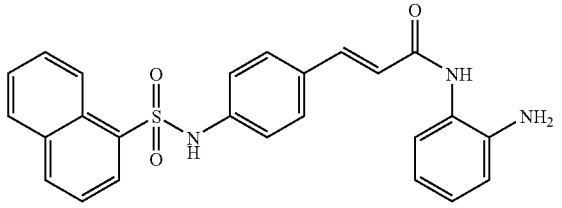

$^1$H NMR: (300 MHz, Acetone $d_6$): δ=8.81 (1H, d, J=8.4 Hz), 8.34 (2H, d, J=7.2 Hz), 8.20 (1H, d, J=8.1 Hz), 8.05 (1H, d, J=7.5 Hz), 7.75–7.59 (4H, m), 7.53–7.41 (4H, m), 7.23–7.07 (4H, m), 6.89–6.86 (2H, m), 6.75 (1H, d, J=15.3 Hz).

Analysis: $C_{25}H_{21}N_3O_3SX0.4\ H_2O$, 0.6 TFA Found: C=60.68%, H=4.36%, N=8.11%, S=6.15%. Calc.: C=60.62%, H=4.35%, N=8.09%, S=6.18%.

108

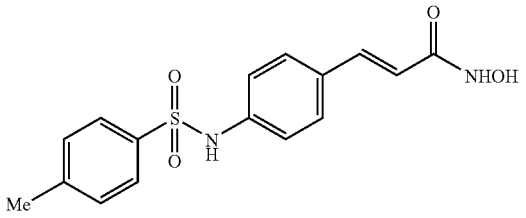

$^1$H NMR: (300 MHz, DMSO $d_6$): δ=10.7 (1H, s br), 10.45 (1H, s br), 8.96 (1H, s br), 7.64 (2H, d, J=8.1 Hz), 7.38 (2H, d, J=8.4 Hz), 7.32–7.29 (3H, m), 7.09 (2H, d, J=8.4 Hz), 6.29 (1H, d, J=16.2 Hz), 2.30 (3H, s).

Analysis: $C_{16}H_{16}N_2O_4SX1.6\ H_2O$, X1.6 TFA Found: C=42.26%, H=3.62%, N=5.45%, S=6.09%. Calc.: C=42.42%, H=3.86%, N=5.15%, S=5.9%.

109

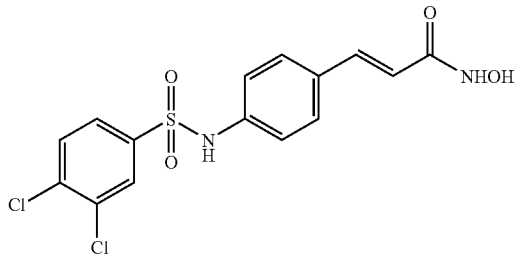

$^1$H NMR: (300 MHz, DMSO $d_6$): δ=10.71 (1H, s), 10.67 (1H, s), 9.00 (1H, s br), 7.96 (1H, d, J=2.4 Hz), 7.85 (1H, d, J=8.4 Hz), 7.69 (1H, dd, J=8.4 Hz and 2.1 Hz), 7.47 (2H, d, J=8.4 Hz), 7.35 (1H, d, J=15.9 Hz), 7.13 (2H, d, J=8.7 Hz), 6.33 (1H, d, J=15.9 Hz).

Analysis: $C_{15}H_{12}N_2O_4SCl_2$X0.3 $H_2O$, X0.3 AcOEt Found: C=46.30%, H=3.27%, N=6.56%, S=7.57%. Calc.: C=46.43%, H=3.61%, N=6.68%, S=7.65%.

110

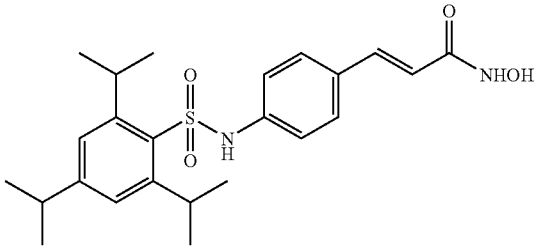

$^1$H NMR: (300 MHz, DMSO $d_6$): δ=10.65 (1H, s br), 10.45 (1H, s br), 8.96 (1H, s br), 7.42 (2H, d, J=8.1 Hz), 7.31 (1H, d, J=15.6 Hz), 7.22 (2H, s), 7.01 (2H, d, J=8.1 Hz), 6.30 (1H, d, J=15.9 Hz), 4.24–4.16 (2H, m), 2.93–2.84 (1H, m), 1.18–1.14 (18H, m).

Analysis: $C_{24}H_{32}N_2O_4SX1.10$ $H_2O$ Found: C=62.14%, H=7.17%, N=6.20%, S=6.71%. Calc.: C=62.07%, H=7.42%, N=6.03%, S=6.9%.

111

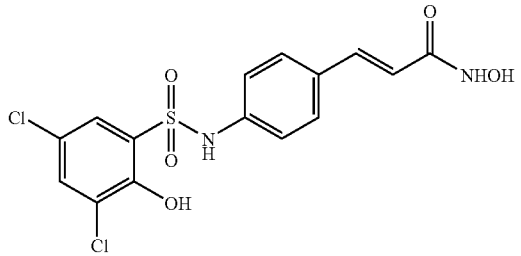

$^1$H NMR: (300 MHz, DMSO $d_6$): δ=11.18 (1H, s br), 10.69 (2H, m), 7.83–7.82 (1H, m), 7.68 (1H, m), 7.43 (2H, d, J=8.1 Hz), 7.32 (1H, d, J=15.3 Hz), 7.13 (2H, d, J=8.1 Hz), 6.31 (1H, d, J=15.9 Hz).

Analysis: $C_{15}H_{12}N_2O_5SCl_2$X0.2 $H_2O$, X0.2 TFA Found: C=43.14%, H=3.04%, N=6.54%, S=7.19%. Calc.: C=43.05%, H=2.96%, N=6.52%, S=7.46%.

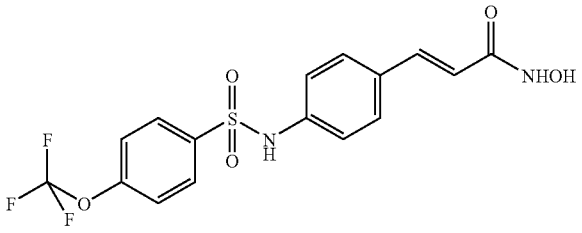

$^1$H NMR: (300 MHz, DMSO $d_6$): δ=10.70 (1H, s), 10.65 (1H, s), 9.01 (1H, s br), 7.91 (2H, d, J=8.4 Hz), 7.56 (2H, d, J=8.4 Hz), 7.45 (2H, d, J=8.1 Hz), 7.33 (1H, d, J=15.6 Hz), 7.13 (2H, d, J=8.1 Hz), 6.31 (1H, d, J=15.6 Hz).

Analysis: $C_{16}H_{13}N_2O_5SF_3$X0.2 TFA Found: C=46.43%, H=3.33%, N=6.22%, S=7.25%. Calc.: C=46.33%, H=3.13%, N=6.59%, S=7.54%.

113

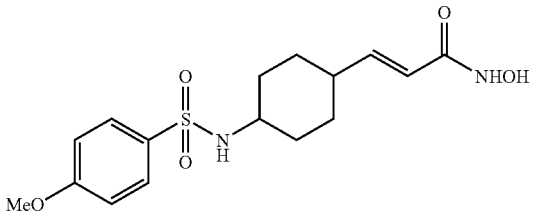

$^1$H NMR: (300 MHz, DMSO $d_6$):=10.66 (1H, s br), 10.37 (1H, s br), 8.56 (1H, s br), 7.69 (2H, d, J=8.7 Hz), 7.39 (2H, d, J=8.1 Hz), 7.30 (1H, d, J=16.2 Hz), 7.10–7.03 (4H, m), 6.27 (1H, d, J=15.9 Hz), 3.77 (3H, s).

Analysis: $C_{16}H_{16}N_2O_5SX0.7$ $H_2O$ Found: C=53.32%, H=5.05%, N=7.98%, S=7.78%. Calc.: C=53.24%, H=4.86%, N=7.76%, S=8.88%.

114

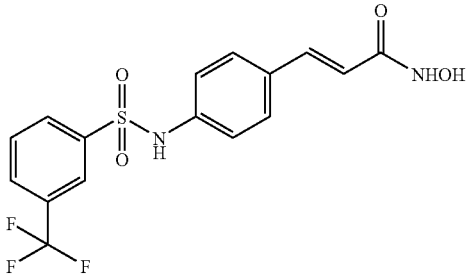

$^1$H NMR: (300 MHz, DMSO $d_6$): δ=10.70 (1H, s), 10.66 (1H, s), 8.99 (1H, s), 8.06–7.98 (3H, m), 7.84–7.79 (1H, m), 7.45 (2H, d, J=8.4 Hz), 7.33 (1H, d, J=15.6 Hz), 7.12 (2H, d, J=8.7 Hz), 6.32 (1H, d, J=15.9 Hz).

Analysis: $C_{16}H_{13}F_3N_2O_4S$ Found: C=49.64%, H=3.30%, N=7.18%. Calc.: C=49.74%, H=3.39%, N=7.25%.

115

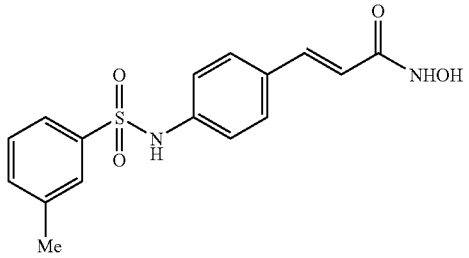

$^1$H NMR: (300 MHz, DMSO $d_6$): δ=10.69 (1H, s br), 10.47 (1H, s br), 8.98 (1H, s br), 7.62 (1H, s), 7.58–7.56 (1H, m), 7.44–7.41 (4H, m), 7.32 (1H, d, J=16.2 Hz), 7.11 (2H, d, J=8.1 Hz), 6.30 (1H, d, J=15.6 Hz), 2.34 (3H, s).

Analysis: $C_{16}H_{16}N_2O_4SX0.3$ TFA Found: C=54.64%, H=4.75%, N=7.92%. Calc.: C=54.66%, H=4.59%, N=7.82%.

116

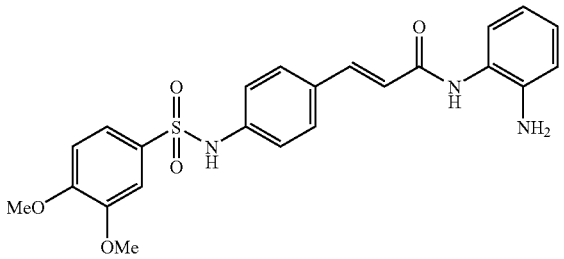

$^1$H NMR: (300 MHz, MeOD $d_4$): 7.62–6.61 (m, 13H); 3.81 (broad s, 3H, OC$\underline{H}_3$), 3.80 (broad s, 3H, OC$\underline{H}_3$), 3.26 (broad s, 4H, N$\underline{H}$).

$^{13}$C NMR: (75 MHz, MeOD $d_4$): 167.0 (C═O); 154.4; 150.5; 143.1; 141.9; 141.0; 132.5; 132.3; 129.9; 128.2; 126.7; 125.2; 122.4; 121.8; 120.8; 119.6; 118.7; 111.9; 110.9; 56.6 (2C, $OCH_3$). Combustion analysis: Calc: 60.91%, C, 5.11% H, 9.27%, N, 7.07% S Found: 60.40% C, 5.21% H, 9.16% N, 6.47% S HRMS: Calc: 453.1358; Found: 453.1351

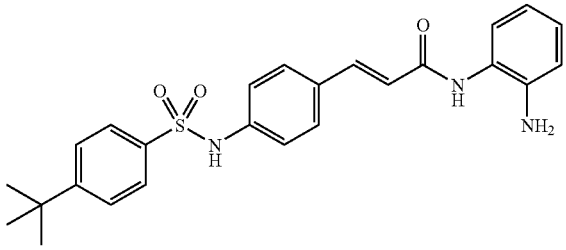

$^1$H NMR: (Acetone-$d_6$): δ (ppm): 9.25 (bs, 1H), 8.77(bs, 1H), 7.79 (d, J=8.5 Hz, 2H), 7.61–7.51 (m, 5H), 7.36–7.28 (m, 3H), 6.99–6.93 (m, 1H), 6.86–6.82 (m, 2H), 6.68–6.62 (m, 1H), 4.63 (bs, 2H).

HRMS: 449.1773 (calc.):449.1767±0.0013 (found)

118

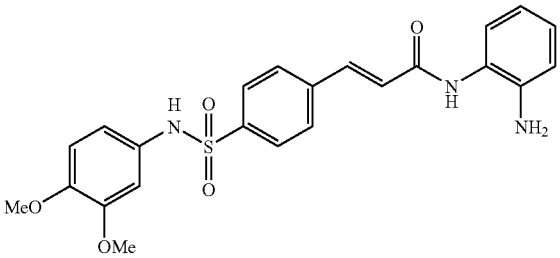

$^1$H NMR: (300 MHz, MeOD $d_4$): 8.00–6.56 (m, 13H); 3.77 (broad s, 3H, OC$\underline{H}_3$), 3.74 (broad s, 3H, OC$\underline{H}_3$), 3.33 (broad s, 2H, N$\underline{H}$), 3.00 (broad s, 1H, N$\underline{H}$), 2.88 (broad s, 1H, N$\underline{H}$).

$^{13}$C NMR: (75 MHz, MeOD $d_4$): 166.2 ($\underline{C}$═O); 150.7; 148.5; 143.2; 141.7; 140.6; 140.5; 131.9; 129.2; 128.9; 128.4; 126.7; 124.9; 119.5; 118.6; 116.4; 113.2; 108.9; 56.6 ($OCH_3$); 56.4 ($OCH_3$).

MS: Calc: 453.1358: Found: 453.1351

119

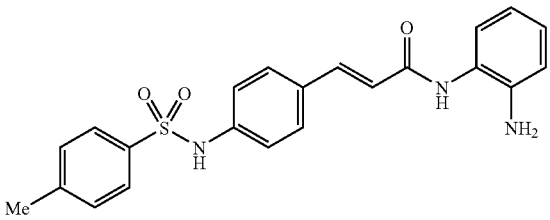

$^1$H NMR: ($CD_3OD$) δ (ppm): 7.68 (d, J=8.2 Hz, 2H), 7.55 (d, J=15.9 Hz, 1H), 7.47 (d, J=8.5 Hz, 2H), 7.30 (d, J=8.0 Hz, 2H), 7.19–7.12 (m, 3H), 7.03 (t, J=7.1 Hz, 1H), 6.86 (d, J=8.0 Hz, 1H), 6.75–6.69 (m, 2H), 2.37 (s, 3H).

HRMS: 407.1304 (calc.): 407.1293±0.0012 (found)

120

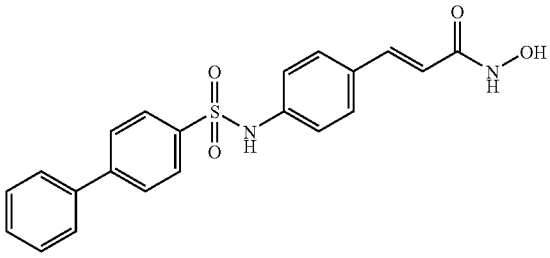

$^1$H NMR: (300 MHz, DMSO-$d_6$) δ 10.6 (s, OH); 9 (s, NH); 7.1–7.8 (m, 14H, CH Ar); 6.2 (d, 1H, J=15 Hz)

121
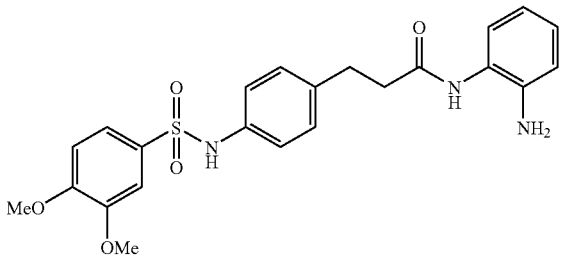
$^1$H NMR: (300 MHz, MeODd$_4$): 7.31–6.62 (m, 11H); 3.72 (broad s, 3H); 3.70 (broad s, 3H); 2.91 (t, 2H, J=7.1 Hz); 2.65 (broad t, 2H, J=7.4 Hz).
$^{13}$C NMR: (75 MHz, MeODd$_4$): 173.9; 154.0; 150.3; 143.4; 138.6; 137.4; 132.6; 130.2; 128.4; 127.4; 124.6; 123.1; 122.3; 119.3; 118.1; 111.7; 110.9; 56.5 (2C); 38.8; 32.2.
HRMS: calc: 455.1515: Found: 455.1521
122
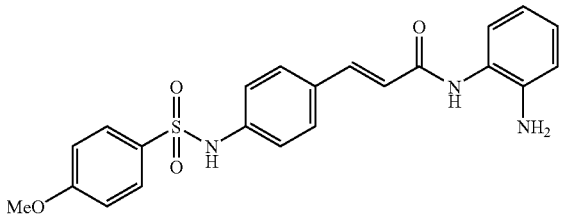
$^1$H NMR: (300 MHz, DMSO d$_6$): 7.77 (d, 2H, J=8.8 Hz); 7.51 (d, 2H, J=8.5 Hz); 7.34 (d, 2H, J=8.8 Hz); 7.18 (d, 2H, J=8.5 Hz); 7.11 (d, 2H, 8.8 Hz); 6.94 (t, 1H, J=7.4 Hz); 6.77 (broad d, 2H, J=7.9 Hz); 6.6 (t, 1H, J=7.4 Hz), 4.95 (broad s, 1H), 3.83 (s, 3H).
$^{13}$C NMR: (75 MHz, DMSO d$_6$): 162.5; 141.5; 139.2; 138.8; 130.9; 130.2; 128.9; 128.6; 125.7; 124.7; 119.4; 116.2; 115.99.3;4.5; 55.6.
HRMS: Calc: 423.1253: Found: 423.1235
123
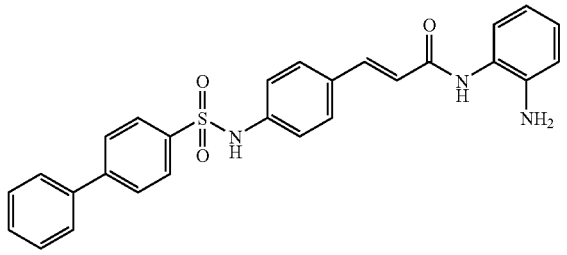
$^1$H NMR: (300 MHz, DMSO-d$_6$) 7.1–7.8 (m, 14H, CH Ar); 6.8–6.9 (m, 4H, CH Ar); 6.3 (d, 1H, J=15 Hz).
Example 32
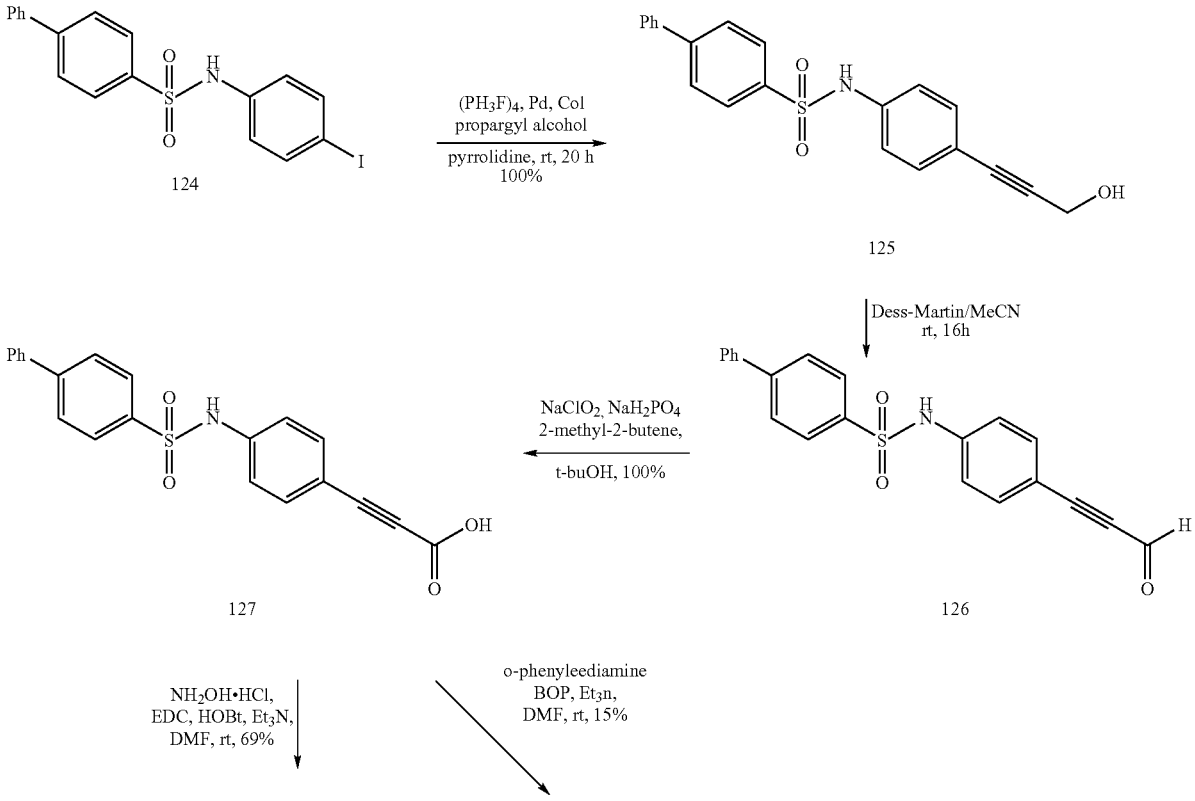

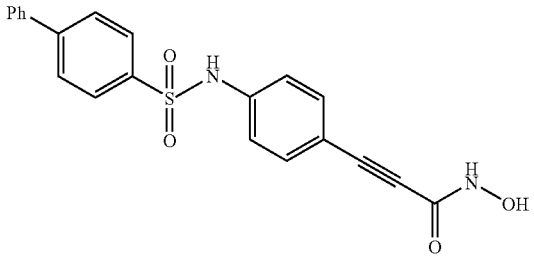

128

-continued

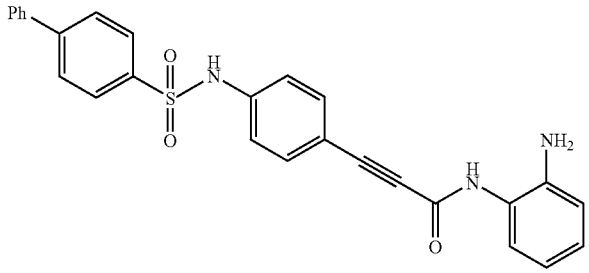

129

Sulfonamide 124 was prepared by condensation of 4-iodoaniline with benzenesulfonyl chloride. Compound 125 was quantitatively furnished by a Pd—Cu catalyzed coupling reaction of 124 with propargyl alcohol in basic solvent. Primary alcohol 125 was oxidized to the corresponding carboxylic acid 127 in two steps, including Dess-Martin periodinane oxidation to afford aldehyde 126, followed by treatment with sodium chlorite in buffered aqueous media in the presence of a chlorine scavenger. Acid 127 was derivatized to the hydroxamic acid 128 by treatment with hydroxylamine hydrochloride and the coupling reagent EDC in the presence of N-hydroxybenzotriazole in basic, aprotic media. Compound 129 was prepared by coupling acid 130 with o-phenylenediamine as described in Example 31 for compound 86.

Data for 128:

$^1$H NMR: (300.07 MHz; acetone-$d_6$) δ (ppm): 9.4 (bs, 2H); 7.93 (dd, J=1.9, 6.6; 2H); 7.82 (dd, J=1.9, 6.6; 2H); 7.68 (dd, J=1.4, 8.2; 2H); 7.48–741 (m, 5H); 7.35–7.32 (m, 2H); 2.90 (bs, 1H).

$^{13}$C NMR: (75.5 MHz; acetone-$d_6$) (ppm): 153.5; 147.2; 141.3; 140.3; 139.5; 134.6; 130.1; 129.5; 128.8; 128.6; 128.3; 120.8; 116.5; 87.7; 81.0.

MS: calc for $C_{21}H_{16}O_4N_2S$: 392.438; found: 393.4 for [M+H] (low resolution MS).

Data for 129:

$^1$H NMR: (300.07 MHz; acetone-$d_6$) δ (ppm): 9.43 (bs, 1H); 8.02 (d, J=8.5 Hz; 2H); 7.93 (d, J=8.5 Hz, 2H); 7.90 (d, J=8.5 Hz; 2H); 7.65 (d, J=8.5 Hz; 2H); 7.47–7.34 (m, 7H); 7.21–7.17 (m, 2H); 2.80 (bs, 3H).

$^{13}$C NMR: (75.5 MHz; acetone-$d_6$) δ (ppm): 167.2; 158.6; 146.3; 141.3; 140.9; 139.8; 139.5; 134.2; 131.0; 129.9; 129.8; 129.3; 128.7; 128.6; 128.4; 128.0; 126.8; 125.1; 122.7; 122.6; 120.1.

MS: calc for $C_{27}H_{12}O_3N_3S$: 467.552; found: 468.5 for [M+H] (low resolution MS).

Example 33

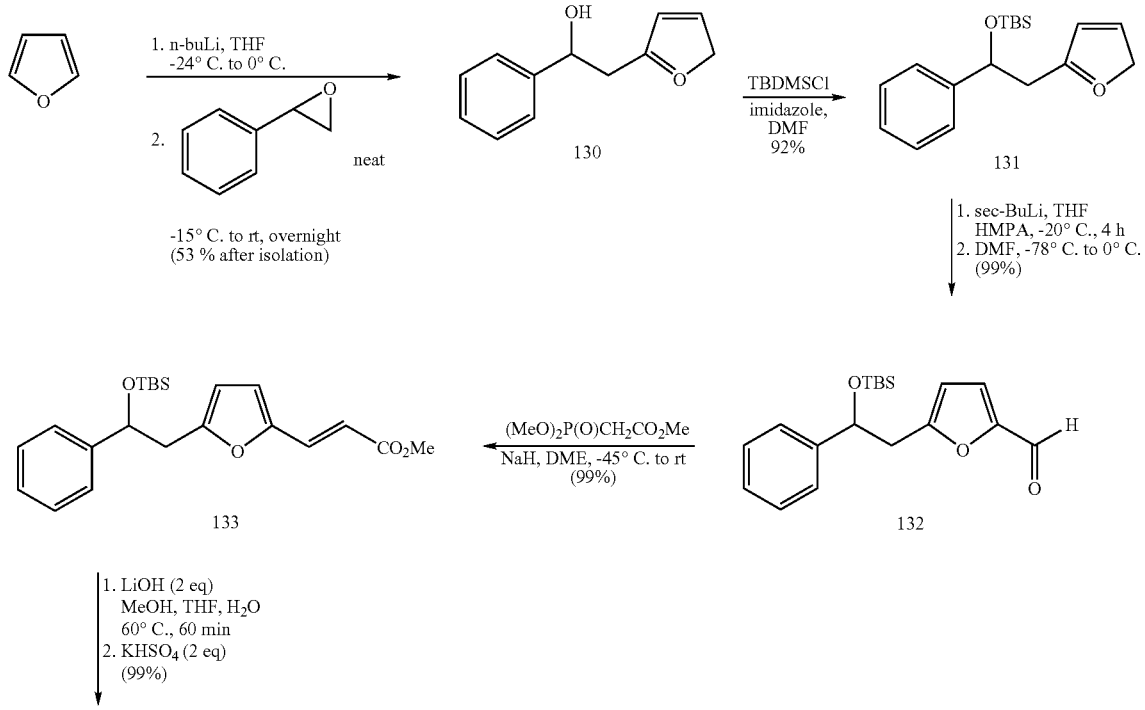

-continued

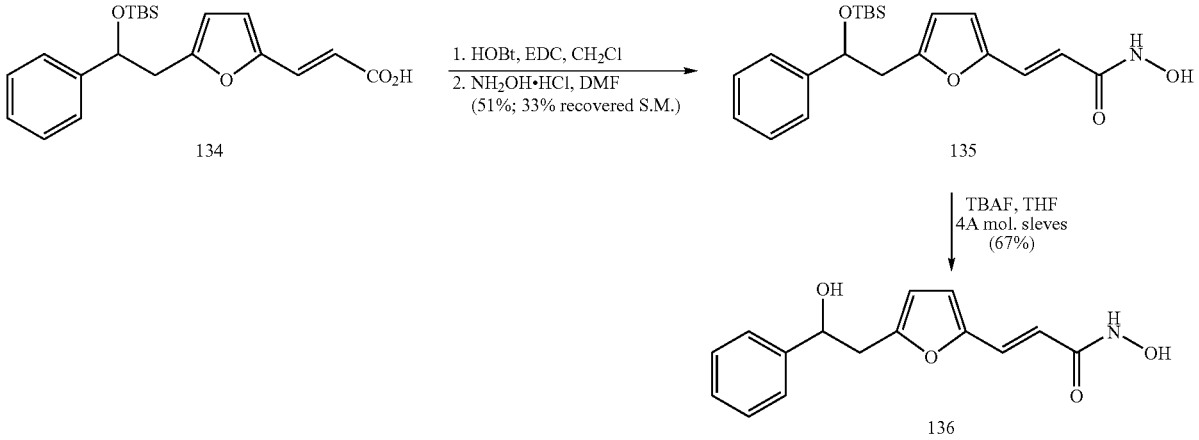

Benzylic alcohol 130 was prepared in 53% yield by addition of 2-lithiofuran to styrene oxide. After protection of the resulting hydroxyl group with tert-butyldimethylsilyl chloride, the lithiated species of compound 131 was treated with DMF to afford the formyl derivative 132. Wadsworth-Horner-Emmons olefination was effected by treatment of 132 with the sodium enolate of trimethylphosphono-acetate to afford the key intermediate 133 in 90% overall yield for the last three steps. Saponification of the methyl ester with LiOH yielded the acid 134, which in turn was converted into its hydroxamic acid form 135 by conventional activation with HOBt/EDC, followed by reaction with hydroxylamine. Fluoride-promoted cleavage of silylated ether gave alcohol 136 in 67% yield.

Data for 136:

$^{1}$H NMR: (300.07 MHz; acetone-d6) δ (ppm): 9.35 (bs, 1H); 7.40–7.15 (m; 6H); 6.56 (d, J=2.9 Hz, 1H); 6.24 (d, J=15.3 Hz, 1H); 4.96 (t, J=6.2 Hz, 1H); 3.00 (d, J=6.2 Hz, 2H).

$^{13}$C NMR: (75.5 MHz; $CD_3OD$) δ (ppm): 166.6; 156.6; 151.3; 145.2; 129.3; 128.5; 126.9; 116.2; 114.5; 111.0; 73.6; 39.1

Example 34

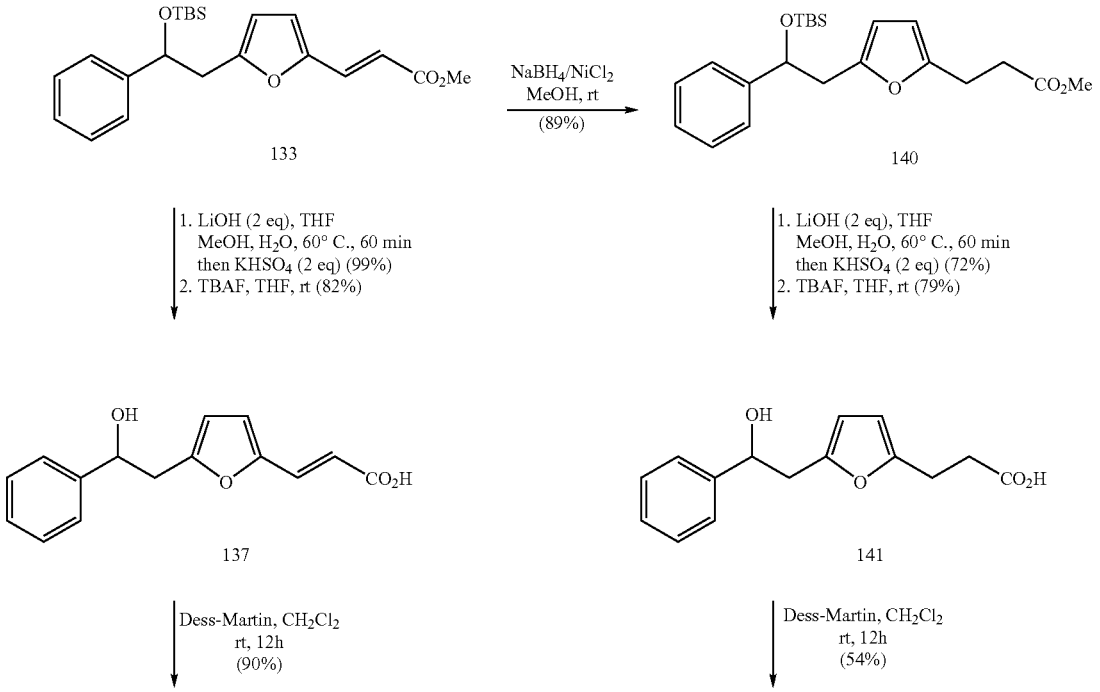

-continued

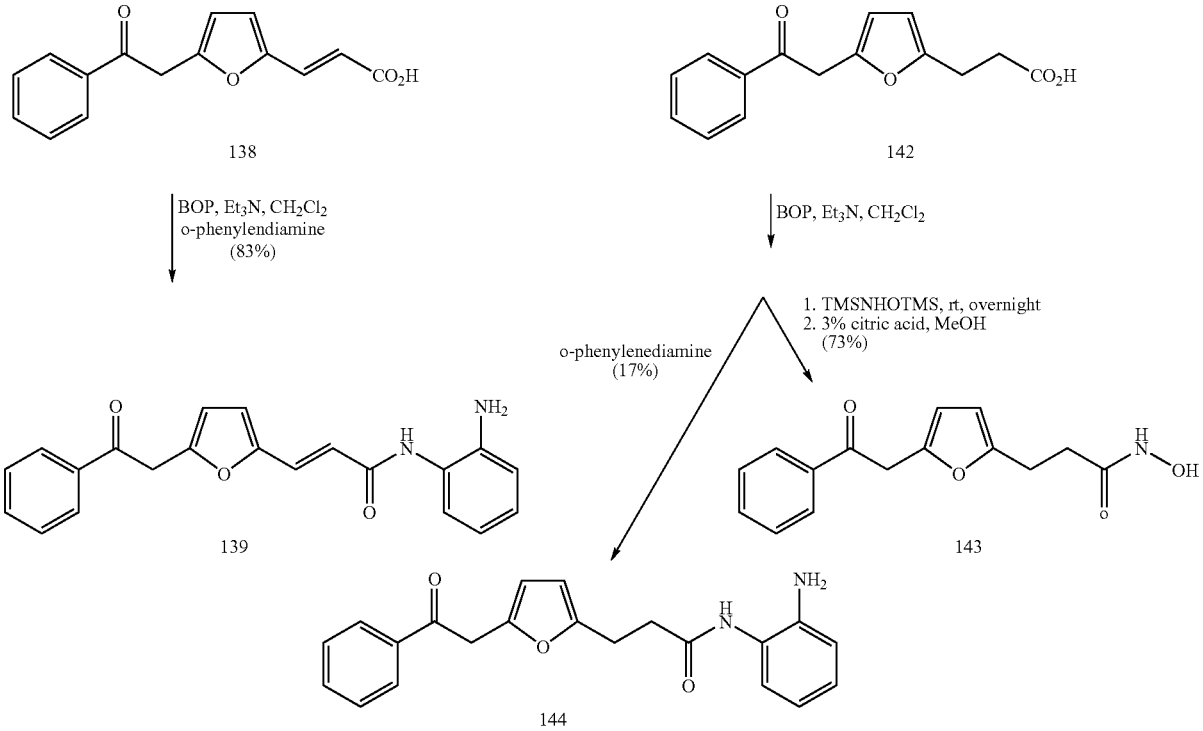

Unsaturated ketoacid 138 was obtained from ester 133 in 73% overall yield after three consecutive steps, including saponification ($LiOH/H_2O/MeOH/THF$), desilylation (TBAF/THF), and oxidation of benzylic alcohol 137 using Dess-Martin periodinane. Anilide 139 was obtained by BOP-mediated condensation of compound 138 with o-phenylenediamine in 83% yield.

Regioselective hydrogenation of the acrylate moiety in 133 was accomplished by treatment with $NaBH_4$ in the presence of $NiCl_2$, to afford the propionate 140 in high yield. Ketoacid 142 was then obtained in 31% overall yield from 140 by an identical procedure to that followed in the synthesis of 138 from 133. With compound 142 in hand, anilide 144 was obtained as described above (BOP/o-phenylenediamine). The low yield was due to a difficult purification process. To avoid oxime formation, hydroxamic acid 143 was synthesized from 142 in 73% overall yield over two steps, including BOP-mediated coupling with N,O-bistrimethylsilylhydroxylamine, followed by cleavage of silylated groups under acidic conditions (citric acid/MeOH).

Data for 139:

$^1$H NMR: (300.07 MHz; $CDCl_3$) δ (ppm): 8.02–7.42 (series of multiplets, 7H); 7.34 (bs, 1H); 7.06 (m, 1H); 6.80 (d, J=7.8; 1H); 6.79 (d, J=8.1; 1H); 6.54 (d, J=3.0 Hz, 1H); 6.38 (m, 1H); 6.34 (d, J=3.0 Hz, 1H); 4.37 (s, 2H); 3.90 (bs, 2H).

$^{13}$C NMR: (75.5 MHz; $CDCl_3$) δ (ppm): 194.5; 164.4; 150.9; 150.8; 150.5; 140.5; 135.9; 133.7; 128.7; 128.5; 126.9; 125.0; 124.4; 119.4; 118.0; 117.5; 115.7; 111.3; 38.5.

Data for 143:

$^1$H NMR: (300.07 MHz; $CDCl_3$) δ (ppm): 8.99 (bs, 1H); 8.09–7.42 (series of multiplets, 5H); 6.09 (d, J=3.0 Hz, 1H); 6.00 (d, J=3.0 Hz; 1H); 4.35 (s, 2H); 2.95 (t, J=6.60 Hz, 2H); 2.50 (t, J=3.0 Hz, 1H).

$^{13}$C NMR: (75.5 MHz; $CDCl_3$) δ (ppm): 196.2; 162.8; 153.2; 146.8; 134.9; 133.7; 128.7; 128.5; 109.3; 107.1; 38.2; 31.7; 24.2.

Data for 144:

$^1$H NMR: (300.07 MHz; $CDCl_3$) δ (ppm): 7.99–7.42 (series of multiplets, 5H); 7.36 (bs, 1H); 7.02 (d, J=7.8, 2H); 6.73 (d, J=7.8 Hz, 2H); 6.13 (d, J=3.0 Hz, 1H); 6.04 (d, J=3.0 Hz, 1H); 4.30 (s, 2H); 3.70 (bs, 2H); 3.03 (t, J=6.9 Hz, 2H); 2.69 (t, J=6.9 Hz, 2H).

$^{13}$C NMR: (75.5 MHz; $CDCl_3$) δ (ppm): 195.4; 170.7; 153.6; 147.1; 140.9; 136.1; 133.5; 128.7; 128.5; 127.1; 125.7; 124.0; 119.2; 117.8; 109.1; 107.2; 38.4; 35.7; 24.7

Example 35

General Procedure for Synthesis of Urea Compounds

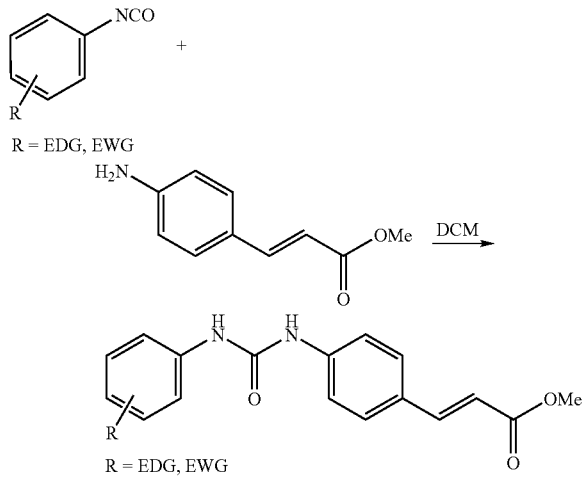

To a solution of isocyanate (1.5 mmol) in 15 mL of anhydrous dichloromethane, was added a solution of 4-anilinylmethylacrylate (1.5 mmol) in dichloromethane (10 mL). The mixture was stirred at room temperature for 15 hours. After addition of ammonium chloride solution the new mixture was extracted from dichloromethane. The organic layers were combined and washed with ammonium chloride solution, water, brine and dried over magnesium sulfate. The crude was then flashed over silica gel using $CH_2Cl_2$:MeOH (9.5:0.5) as eluent.

The following compounds were synthesized according to the general procedure:

145

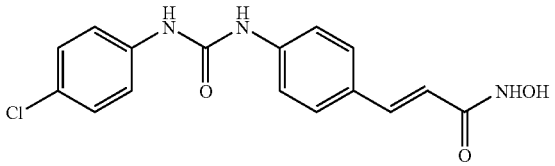

$^1$H NMR: (300 MHz, DMSO-$d_6$) δ 7.5–7.7 (m, 4H, CH Ar); 7.5 (d, 2H, J=6.6 Hz); 7.3 (d, 2H, J=6.6 Hz); 6.3 (d, 1H, J=15 Hz).

146

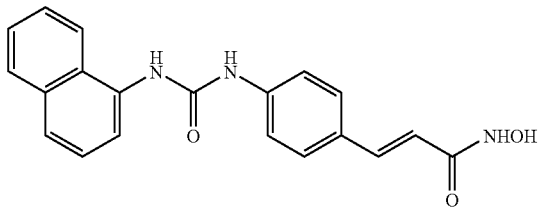

$^1$H NMR: (300 MHz, DMSO-$d_6$) δ 7.5–8.2 (m, 7H, CH Ar); 7.5 (d, 2H, J=6.6 Hz); 7.3 (d, 2H, J=6.6 Hz); 6.3 (d, 1H, J=15 Hz).

147

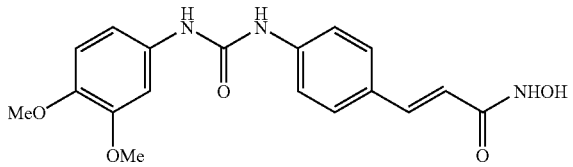

$^1$H NMR: (300 MHz, DMSO-$d_6$) δ 7.5–7.7 (m, 3H, CH Ar); 7.5 (d, 2H, J=6.6 Hz); 7.3 (d, 2H, J=6.6 Hz); 6.3 (d, 1H, J=15 Hz).

Example 36

The following additional compounds were prepared by procedures analogous to those described in the foregoing Examples:

148

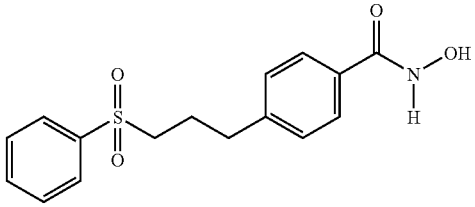

$^1$H NMR (300.072 MHz, $(CD_3)_2CO$): δ 1.99 (m, 2H), 2.79 (t, 2H, J=7.2 Hz), 3.21 (dd, 2H, J=6.8, 7.8 Hz), 7.27 (d, 2H, J=8.1 Hz), 7.65 (t, 2H, J=7.8 Hz), 7.72–7.77 (m, 3H), 7.90 (d, 2H, J=7.2 Hz), 10.77 (broad s, 1H).

$^{13}$C NMR (75.46 MHz, $(CD_3)_2CO$): δ 25.2 (t), 34.3 (t), 55.6 (t), 128.0 (d), 2×128.8 (d), 129.4 (d), 2×130.2 (d), 131.1 (s), 134.5 (d), 140.7 (s), 145.5 (s), 165.8 (s).

149

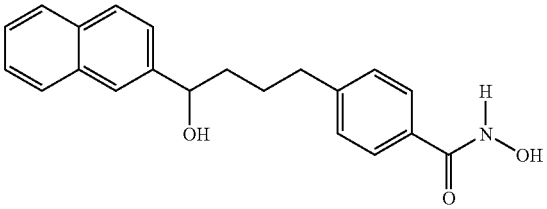

$^1$H NMR (300.072 MHz, $(CD_3)_2CO$): δ 1.66–1.88 (m, 4H), 2.71 (t, 2H, J=6.3 Hz), 4.34 (d, 1H, J=303 Hz), 4.87 (m, 1H), 7.27 (d, 2H, J=7.8 Hz), 7.44–7.48 (m, 2H), 7.52 (dd, 1H, J=1.5, 9.4 Hz), 7.73 (d, 2H, J=7.8 Hz), 7.83 (s, 1H), 7.83–7.88 (m, 3H), 8.16 (broad s, 1H), 10.67 (broad s, 1H).

$^{13}$C NMR (75.46 MHz, $(CD_3)_2CO$): δ 28.3 (t), 36.2 (t), 39.8 (t), 74.0 (d), 125.0 (d), 125.3 (d), 126.2 (d), 126.7 (d), 2×127.8 (d), 128.4 (d), 128.5 (d), 128.6 (d), 2×129.3 (d), 130.6 (s), 133.7 (s), 134.3 (s), 144.7 (s), 147.4 (s), 165.9 (s).

150

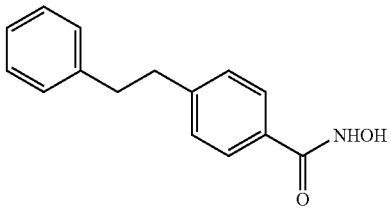

$^1$H NMR: (300 MHz, DMSO-$d_6$) δ 11.2 (s, OH); 9 (s, NH); 7.6–7.8 (m, 4H, CH Ar); 7–7.4 (m, 5H, CH Ar); 2.8 (m, 4H, $CH_2$).

151

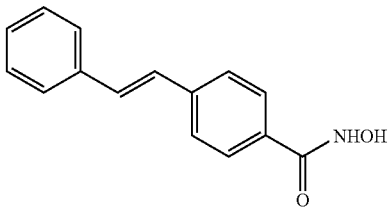

$^1$H NMR: (300 MHz, DMSO-$d_6$) δ 11.2 (s, 1H); 9.0 (s, 1H); 7.7 (m, 6H); 7.34 (m, 5H).

152

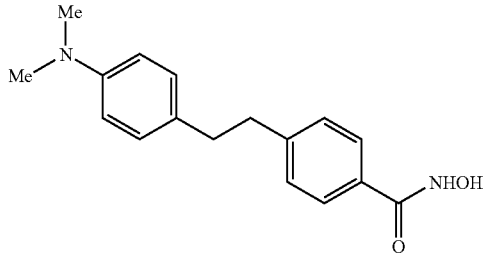

$^1$H NMR: (300 MHz, DMSO-$d_6$) δ 11.2 (s, OH); 9 (s, NH); 7.6–7.8 (m, 4H, CH Ar); 7–6.8 (m, 4H, CH Ar); 2.9 (s, 6H, 2CH3); 2.8 (m, 4H, $CH_2$).

153

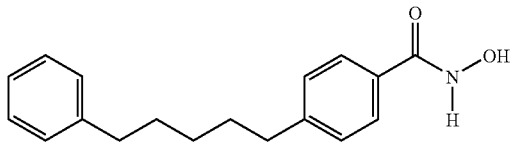

$^1$H NMR (300.072 MHz, $(CD_3)_2CO$): δ 1.38 (quintuplet, 2H, J=7.5 Hz), 1.60–1.72 (m, 4H), 2.60 (t, 2H, J=7.8 Hz), 2.67 (t, 2H, J=7.5 Hz), 7.15–7.31 (m, 7H), 7.75 (d, 2H, J=8.1 Hz), 8.11 (broad s, 1H), 10.68 (broad s, 1H).

$^{13}$C NMR (75.46 MHz, $(CD_3)_2CO$): δ 31.8 (t), 32.1 (t), 36.2 (t), 36.4 (t), 126.4 (d), 127.8 (d), 2×129.0 (d), 2×129.2 (d), 2×129.3 (d), 143.3 (s).

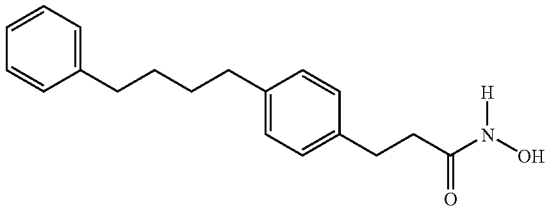

$^1$H NMR (300.072 MHz, $(CD_3)_2CO$): δ 1.63 (m, 4H, J=4.5 Hz), 2.37 (t, 2H, J=7.8 Hz), 2.57–2.66 (m, 4H), 2.86 (t, 2H, J=7.5 Hz), 7.10–7.28 (m, 9H), 8.01 (broad s, 1H), 9.98 (broad s, 1H).

$^{13}$C NMR (75.46 MHz, $(CD_3)_2CO$): δ 31.0 (t), 2×31.9 (t), 35.1 (t), 35.8 (t), 36.2 (t), 126.4 (d), 2×129.0 (d), 2×129.1 (d), 2×129.1 (d), 129.2 (d), 138.8 (s), 141.2 (s), 143.4 (s), 164.1 (s).

155

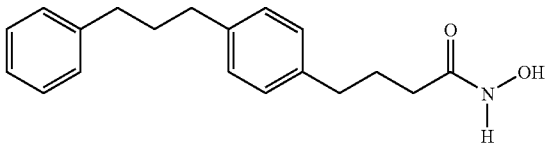

$^1$H NMR (300.072 MHz, $(CD_3)_2CO$): δ 1.83–1.98 (m, 4H), 2.08–2.14 (m, 2H), 2.56–2.67 (m, 6H), 7.12–7.30 (m, 9H), 9.98 (broad s, 1H).

156

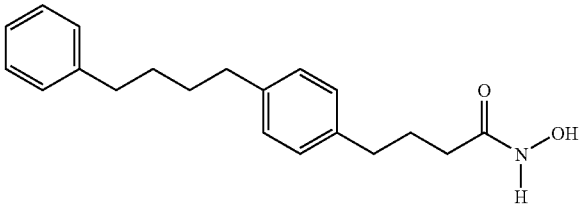

$^1$H NMR (300.072 MHz, $(CD_3)_2CO$): δ 1.60–1.68 (m, 4H), 1.87 (quintuplet, 2H, J=7.5 Hz), 2.03–2.14 (m, 2H), 2.55–2.67 (m, 6H), 7.09–7.28 (m, 9H).

157

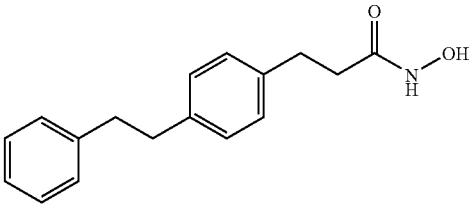

$^1$H NMR (300.072 MHz, $(CD_3)_2CO$): δ 2.37 (t, 2H, J=7.2 Hz), 2.78–2.89 (m, 6H), 7.13–7.29 (m, 9H), 7.84 (broad s, 1H), 9.90 (broad s, 1H).

$^{13}$C NMR (75.46 MHz, $(CD_3)_2CO$): δ 31.6 (t), 35.1 (t), 38.2 (t), 38.6 (t), 2×126.6 (d), 2×129.1 (d), 2×129.2 (d), 2×129.3 (d), 139.4 (s), 140.4 (s), 142.8 (s), 170.1 (s).

158

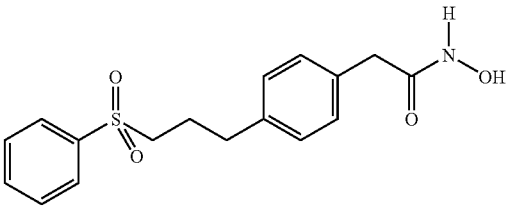

$^1$H NMR (300.072 MHz, $(CD_3)_2CO$): δ 1.96 (quintuplet, 2H, J=6.0 Hz), 2.69(t, 2H, J=8.0 Hz), 3.19 (dd, 2H, J=6.0, 9.0 Hz), 3.38 (s, 2H), 7.09 (d, 2H, J=7.5 Hz), 7.21 (d, 2H, J=7.5 Hz), 7.66 (t, 2H, J=8.1 Hz), 7.747 (t, 1H, J=6.9 Hz), 7.90 (d, 2H, J=6.6 Hz), 10.08 (broad s, 1H).

$^{13}$C NMR (75.46 MHz, $(CD_3)_2CO$): δ 25.5 (t), 34.1 (t), 39.9 (t), 55.7 (t), 2×128.8 (d), 130.0 (d), 2×130.2 (d), 134.4 (s), 139.9 (s), 140.7 (s), 168.5 (s).

159

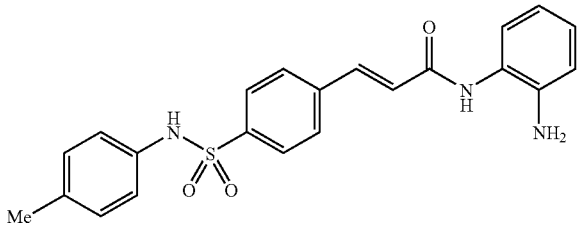

$^1$H NMR: (300 MHz, DMSO $d_6$): δ 7.77 (broad s, 4H); 7.57 (d, 1H, J=15.7 Hz); 7.35 (d, 1H, J=6.9 Hz); 7.03–6.94

(m, 6H); 6.76 (d, 1H, J=7.1 Hz); 6.59 (d, 1H, J=6.9 Hz); 4.98 (broad s, 2H); 2.19 (s, 3H).

$^{13}$C NMR: (75 MHz, DMSO $d_6$): δ 162.9; 141.6; 139.8; 139.0; 137.6; 134.8; 133.6; 129.6; 128.1; 127.3; 125.9; 125.4; 124.7; 123.2; 120.7; 116.2; 115.9; 20.3.

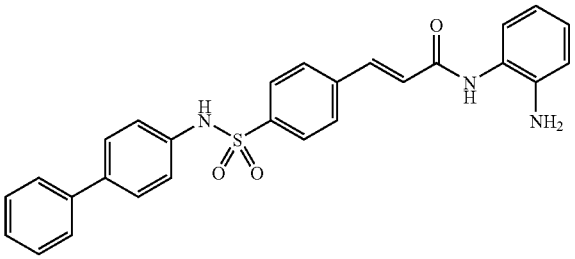

$^1$H NMR: (300 MHz, DMSO $d_6$): δ 7.91–7.81 (m, 4H); 7.63–7.58 (m, 5H); 7.48–7.43 (m, 2H); 7.39–7.33 (m, 2H); 7.24 (d, 2H, J=8.5 Hz); 6.97 (d 2H, J=9.9, 7.1 Hz); 6.79 (d, 1H, J=7.7 Hz) 6.61 (dd, 1H, J=7.7, 7.1 Hz); 5.01 (broad s, 2H).

$^{13}$C NMR: (75 MHz, DMSO $d_6$): δ 162.9; 141.9; 141.6; 139.8; 139.2; 137.6; 136.9; 135.8; 128.9; 128.3; 127.4; 127.3; 127.2; 126.3; 126.0; 125.5; 124.8; 123.2; 120.4; 116.2; 115.9.

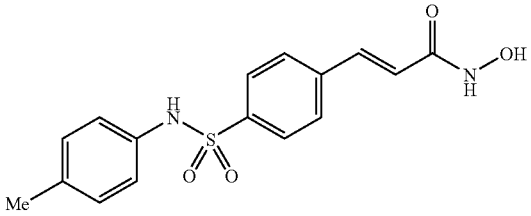

$^1$H NMR: (300 MHz, MeOD$d_4$): δ 7.74–7.54 (m, 5H); 7.07–6.96 (m, 4H); 6.55 (d, 1H, J=15.7); 2.25 (s, 3H).

$^{13}$C NMR: (75 MHz, MeOD$d_4$): δ 163.5; 141.6; 140.4; 139.5; 136.1; 135.9; 130.6; 129.0; 128.8; 123.1; 121.7; 20.8

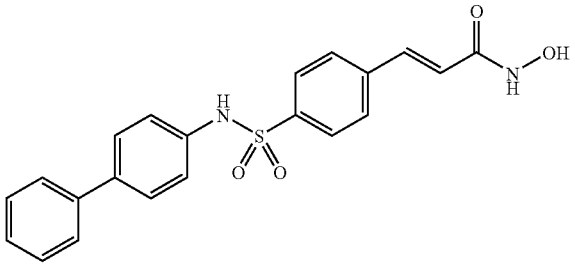

$^1$H NMR: (300 MHz, MeOD$d_4$): δ 7.83–7.19 (m, 14H); 6.56 (d, 1H, J=15.7 Hz).

$^{13}$C NMR: (75 MHz, MeOD$d_4$): δ 165.4; 141.6; 141.4; 140.5; 139.5; 139.0; 137.9; 129.8; 129.2; 128.7; 128.6; 128.2; 127.6; 122.7; 121.7.

Example 37

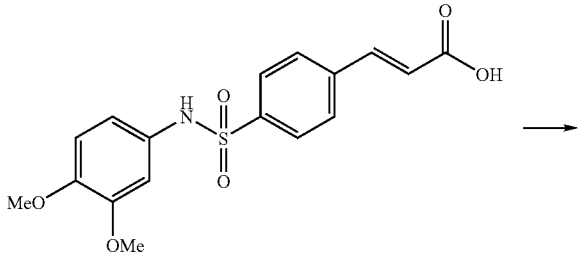

163

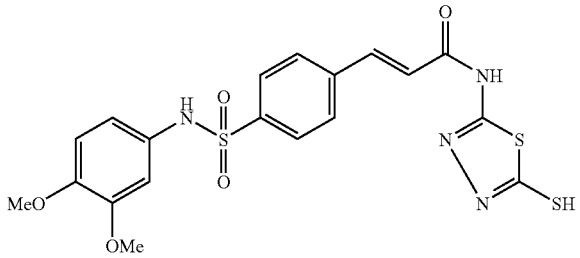

164

To a solution of carboxylic acid 163 (131 mg, 0.36 mmol), prepared according to procedures described above, in 6 mL of dry DMF was added $Et_3N$ (190 μl, 1.37 mmol), followed by the addition of solid BOP (259 mg; 0.59 mmol). The reaction mixture was stirred for 10 min. at room temperature and then solid 5-amino-1,3,4-thiadiazole-2-thiol (58 mg, 0.43 mmol) was added. After being stirred for 12 h, the mixture was diluted with methanol and concentrated under vacuum. Upon dilution with $CH_2Cl_2$/MeOH, crystallization of 164 (150 mg, 87%) from the crude oil took place.

$^1$H NMR: (300 MHz, DMSO $d_6$): δ 7.85 (broad s, 5H); 7.04–6.58 (m, 4H); 3.69 (s, 3H); 3.67 (s, 3H); 3.38 (broad s, 3H).

$^{13}$C NMR: (75 MHz, DMSO $d_6$): δ 163.3; 161.7; 158.7; 148.7; 146.2; 142.0; 140.7; 137.9; 130.1; 128.7; 127.5; 121.4; 113.7; 112.0; 106.6; 55.5; 55.4.

Following this general procedure, the following thiadiazole derivatives were prepared from the corresponding carboxylic acids:

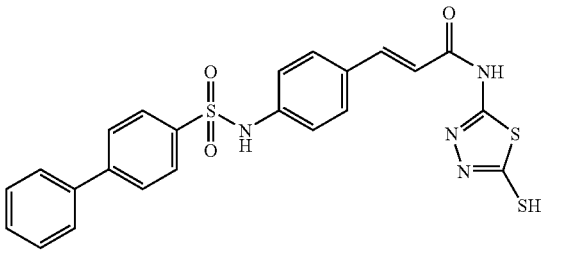

$^1$H NMR: (300 MHz, DMSO-$d_6$); δ (ppm): 7.89–7.72 (series of multiplets, 7H); 7.50–7.05 (series of multiplets, 6H); 3.32 (broad singlet, 3H).

$^{13}C$ NMR: (75 MHz, DMSO-$d_6$); d (ppm): 162.6; 162.3; 144.5; 138.3; 138.3; 138.2; 132.5; 130.1; 129.7; 129.1; 128.6; 127.6; 127.3; 127.1; 120.9; 118.7; 116.8.

MS: calc. for M+H: 493.6. obs. for M+H: 496.3.

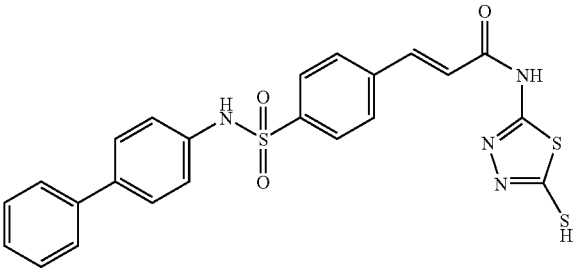

$^1H$ NMR: (300 MHz, DMSO $d_6$): 7.87–7.72 (m, 5H), 7.57–7.53 (m, 4H), 7.39 (dd, 2H, J=6.9, 7.7 Hz), 7.30 (d, 1H, J=7.1 Hz), 7.17 (d, 2H, J=8.5 Hz), 6.85 (d, 1H, J=15.9 Hz).

MS: cal: 495.61; found: 496.6.

Following an analogous procedure, but substituting 2-amino-5-trifluoro-methyl-1,3,4-thiadiazole for 5-amino-1,3,4-thiadiazol-2-thiol, the following compound was prepared:

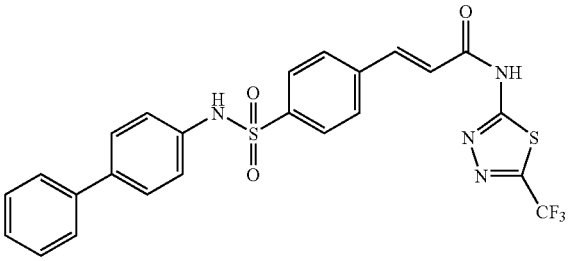

$^1H$ NMR: (300 MHz, DMSO $d_6$): δ 7.96–7.81 (m, 5H); 7.71–7.48 (m, 4H); 7.38 (dd, 2H, J=7.1, 7.41 Hz); 7.28 (d, 1H, J=7.1 Hz); 7.19 (d, 2H, J=8.5 Hz); 6.98 (d, 1H, J=15.7 Hz).

$^{13}C$ NMR: (75 MHz, DMSO $d_6$): 192.3; 163.6; 161.6; 142.4; 140.9; 139.2; 138.0; 136.8; 135.9; 129.0; 128.8; 127.4; 127.2; 126.2; 121.2; 120.4.

MS: cal: 530.55 found: 531.5.

Example 38

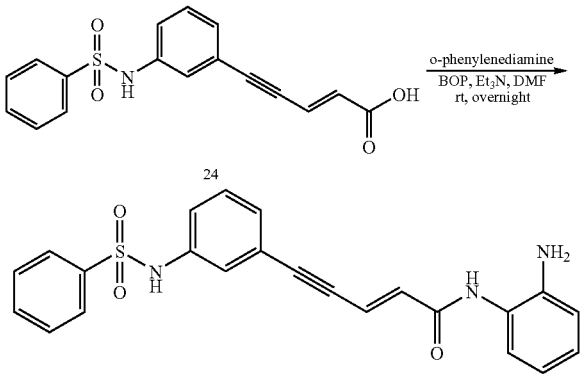

Coupling of 24 (from Example 15) with o-phenylenediamine in the presence of benzotriazol-1-yloxytris(dimethylamino)phosphonium hexafluorophosphate (BOP) afforded the anilide 168.

By an analogous procedure, the corresponding para-substituted compound is prepared from 32 (from Example 16).

Example 39

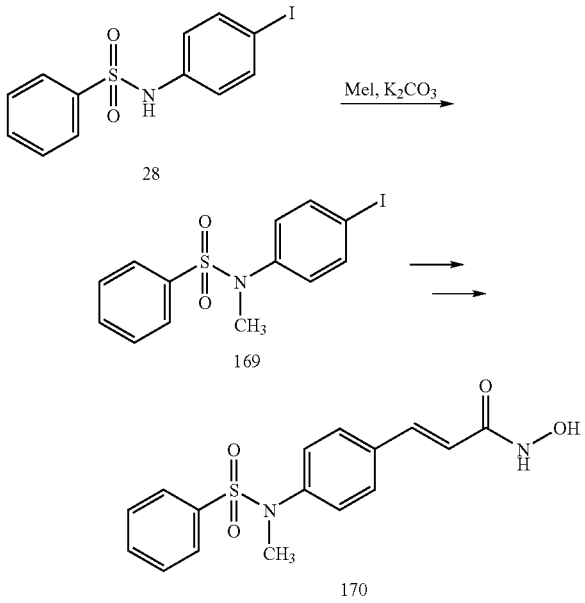

Step 1: N-Methyl-4-iodophenylbenzenesulfonamide (169)

To compound 28 (from Example 18) (500 mg, 1.39 mmol) in DMF (10 mL) were added at room temperature $K_2CO_3$ (962 mg, 6.96 mmol), followed by methyl iodide (395 mg, 2.78 mmol). The resulting reaction mixture was stirred at room temperature for 16 hours. The solvent is then removed and water was added. The resulting mixture was extracted with ethyl acetate, and the combined organic phases were dried and concentrated. Purification by flash chromatography using hexane:ethyl acetate (8:2) afforded 510 mg (98%) of the title compound as a white solid.

Compound 169 was converted to the hydroxamic acid 170 according to the procedures described in Example 18 for the preparation of compound 36.

Data for 170:

$^1H$ NMR: (300 MHz, DMSO $d_6$): δ=10.76 (1H, s), 9.04 (1H, s), 7.73–7.68 (1H, m), 7.61–7.51 (6H, m), 7.43 (1H, d, J=15.9 Hz), 7.15 (2H, d, J=8.7 Hz), 6.43 (1H, d, J=16.2 Hz), 3.15 (3H, s).

Analysis: $C_{16}H_{16}N_2O_4SX0.5\ H_2\ O$ Found: C=56.36%, H=5.09%, N=8.69%, S=8.33%. Calc.: C=56.29%, H=5.02%, N=8.21%, S=9.39%.

Example 40

Inhibition of Histone Deacetylase Enzymatic Activity

HDAC inhibitors were screened against histone deacetylase enzyme in nuclear extracts prepared from the human small cell lung cancer cell line H446 (ATTC HTB-171) and against a cloned recombinant human HDAC-1 enzyme expressed and purified from a Baculovirus insect cell expression system.

For deacetylase assays, 20,000 cpm of the [$^3H$]-metabolically labeled acetylated histone substrate (M.

Yoshida et al., J. Biol. Chem. 265(28): 17174–17179 (1990)) was incubated with 30 μg of H446 nuclear extract or an equivalent amount of the cloned recombinant hHDAC-1 for 10 minutes at 37° C. The reaction was stopped by adding acetic acid (0.04 M, final concentration) and HCl (250 mM, final concentration). The mixture was extracted with ethyl acetate and the released [$^3$H]-acetic acid was quantified by scintillation counting. For inhibition studies, the enzyme was preincubated with compounds at 4° C. for 30 minutes prior to initiation of the enzymatic assay. $IC_{50}$ values for HDAC enzyme inhibitors were determined by performing dose response curves with individual compounds and determining the concentration of inhibitor producing fifty percent of the maximal inhibition.

Representative data are presented in Table 4. In the first column are reported $IC_{50}$ values determined against histone deacetylase in nuclear extracts from H446 cells (pooled HDACs). In the second column are reported $IC_{50}$ values determined against recombinant human HDAC-1 enzyme (rHDAC-1). For less active compounds, the data are expressed as the percent inhibition at the specified concentration.

TABLE 4

Inhibition of Histone Deacetylase

| Example | Cpd. | Structure | pooled HDACs $IC_{50}$ (μM) | rHDAC-1 $IC_{50}$ (μM) |
|---|---|---|---|---|
| Ex. 31 | 118 | 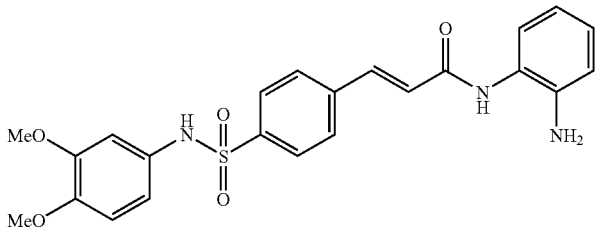 | 0% @ 20 μM | 2.3 |
| Ex. 31 | 119 | 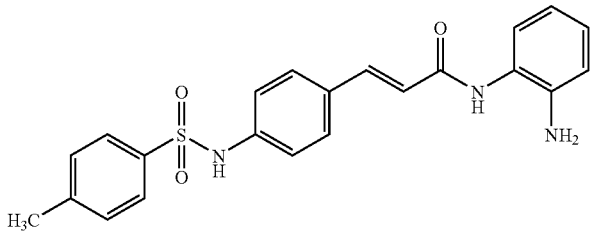 | | 3 |
| Ex. 31 | 120 | 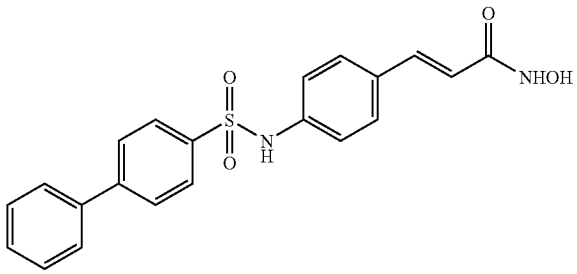 | 0.12 | 0.01 |
| Ex. 31 | 121 | 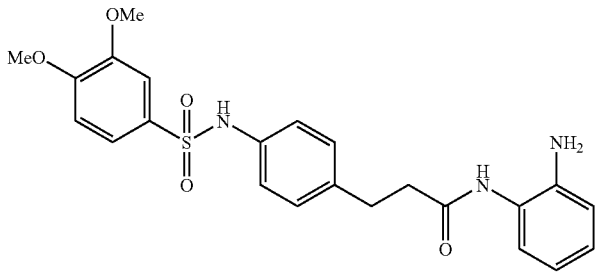 | | 23 |

TABLE 4-continued
Inhibition of Histone Deacetylase
| Example | Cpd. | Structure | pooled HDACs $IC_{50}$ (μM) | rHDAC-1 $IC_{50}$ (μM) |
|---|---|---|---|---|
| Ex. 31 | 122 | 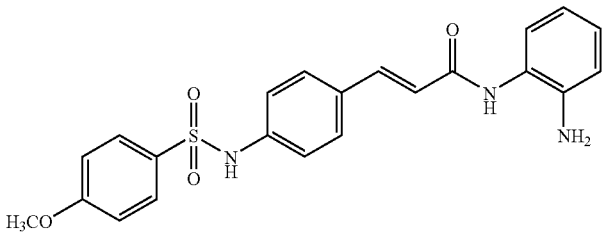 | | 2.3 |
| Ex. 31 | 123 | 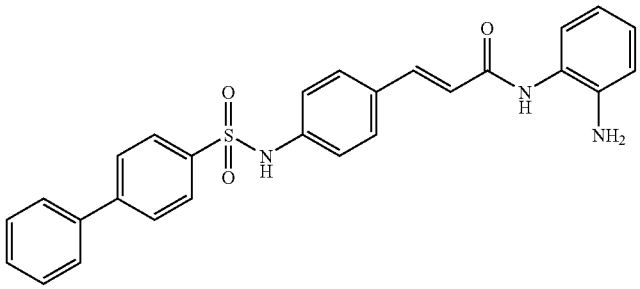 | | 1 |
| Ex. 32 | 128 | 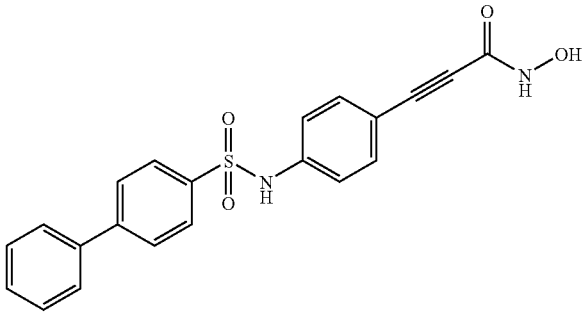 | | 0.3 |
| Ex. 32 | 129 | 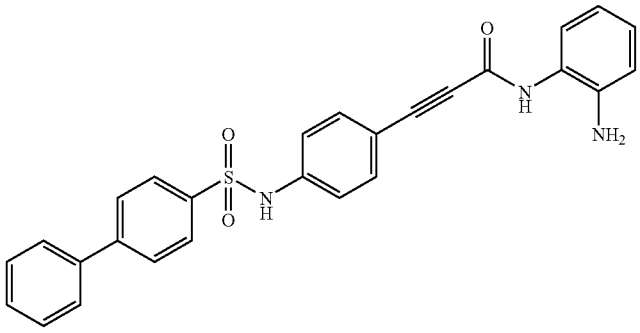 | | 3.0 |
| Ex. 33 | 136 | 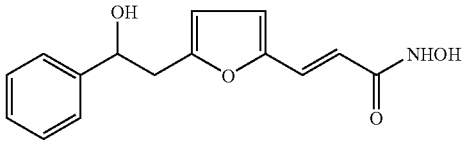 | 9 | 0.5 |

TABLE 4-continued
Inhibition of Histone Deacetylase
| Example | Cpd. | Structure | pooled HDACs $IC_{50}$ (μM) | rHDAC-1 $IC_{50}$ (μM) |
|---|---|---|---|---|
| Ex. 34 | 139 | 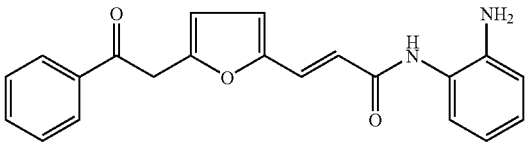 | 44% @ 20 μM | |
| Ex. 34 | 143 | 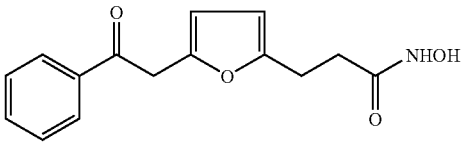 | 55% @ 20 μM | 2.4 |
| Ex. 34 | 144 | 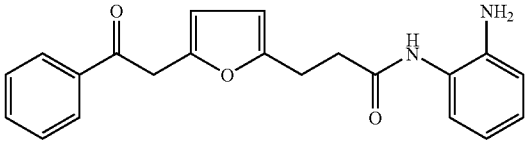 | 6% @ 20 μM | 6.9 |
| Ex. 35 | 145 | 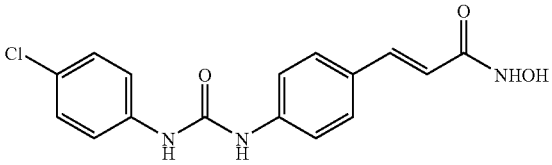 | 3.8 | 0.84 |
| Ex. 35 | 146 | 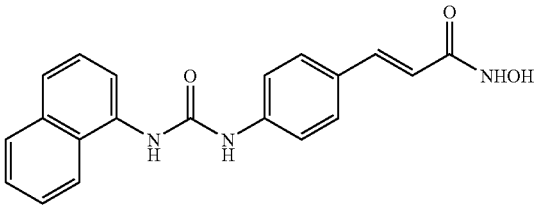 | 2.9 | 0.91 |
| Ex. 35 | 147 | 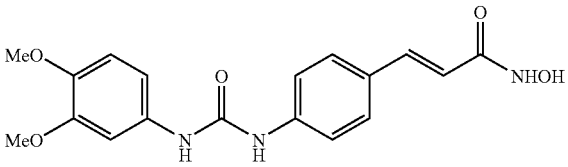 | 1.9 | 0.48 |
| Ex. 36 | 148 | 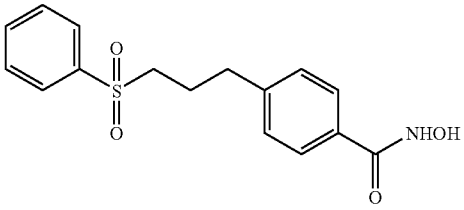 | 5 | 2.0 |
| Ex. 36 | 149 | 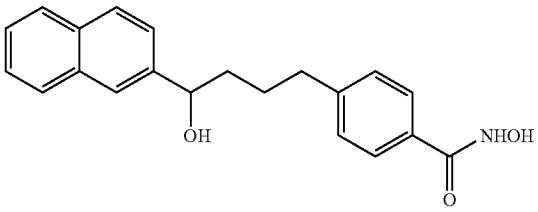 | 8% @ 20 μM | 0.1 |

TABLE 4-continued
Inhibition of Histone Deacetylase
| Example | Cpd. | Structure | pooled HDACs $IC_{50}$ (μM) | rHDAC-1 $IC_{50}$ (μM) |
|---|---|---|---|---|
| Ex. 36 | 150 | 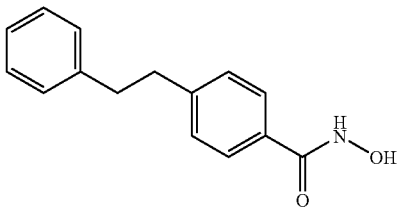 | 10 | 1.0 |
| Ex. 36 | 151 | 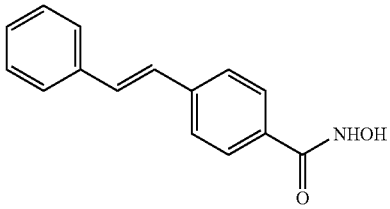 | 7.5 | 2.3 |
| Ex. 36 | 152 | 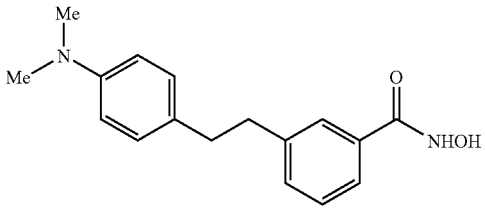 | 35% @ 20 μM | |
| Ex. 36 | 153 | 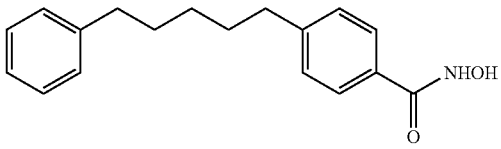 | 5 | 4.8 |
| Ex. 36 | 154 | 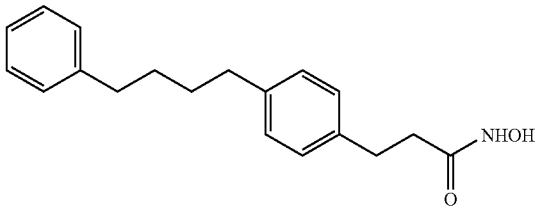 | 2 | 0.9 |
| Ex. 36 | 155 | 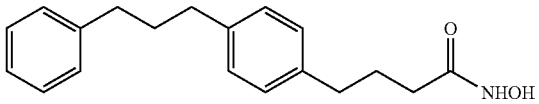 | 39% @ 20 μM | |
| Ex. 36 | 156 | 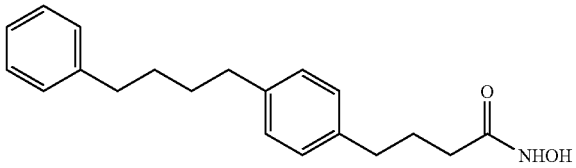 | 5 | 0.75 |

TABLE 4-continued
Inhibition of Histone Deacetylase
| Example | Cpd. | Structure | pooled HDACs $IC_{50}$ (μM) | rHDAC-1 $IC_{50}$ (μM) |
|---|---|---|---|---|
| Ex. 36 | 157 | 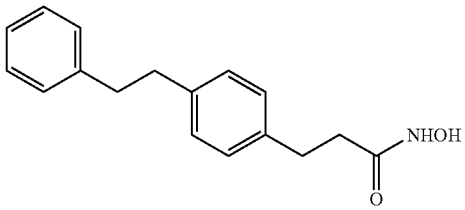 | 6 | 2.4 |
| Ex. 36 | 158 | 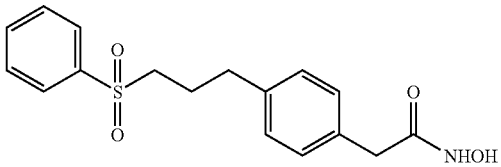 | >20 | |
| Ex. 36 | 159 | 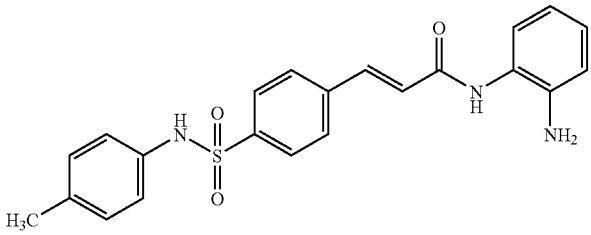 | | 1.5 |
| Ex. 36 | 160 | 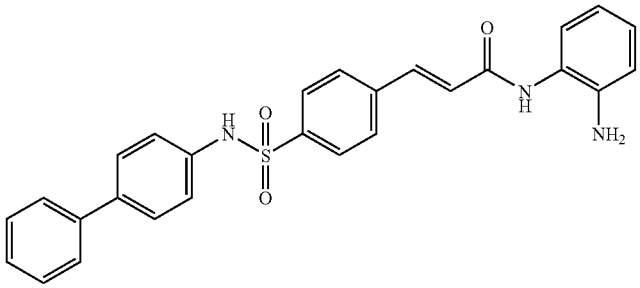 | | 1.2 |
| Ex. 36 | 161 | 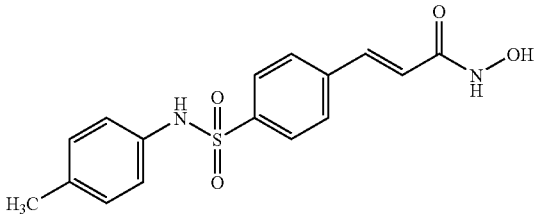 | | 0.05 |
| Ex. 36 | 162 | 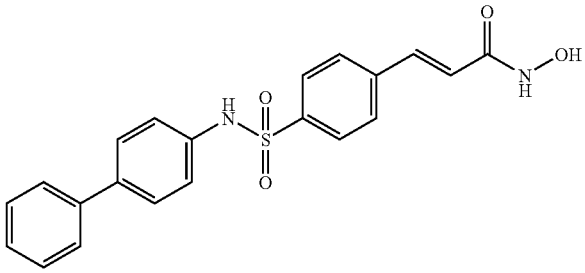 | | 0.04 |

TABLE 4-continued
Inhibition of Histone Deacetylase
| Example | Cpd. | Structure | pooled HDACs $IC_{50}$ (μM) | rHDAC-1 $IC_{50}$ (μM) |
|---|---|---|---|---|
| Ex. 37 | 164 | 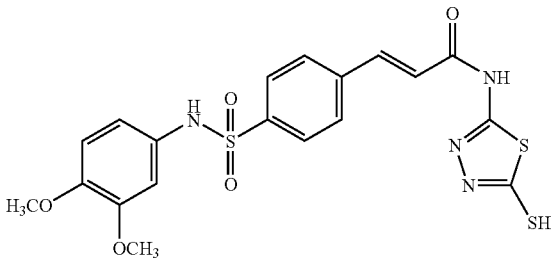 | | 5.0 |
| Ex. 37 | 165 | 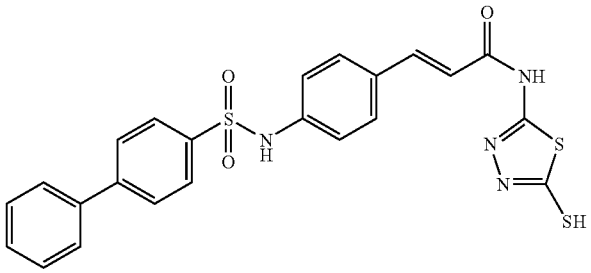 | | 2.0 |
| Ex. 37 | 166 | 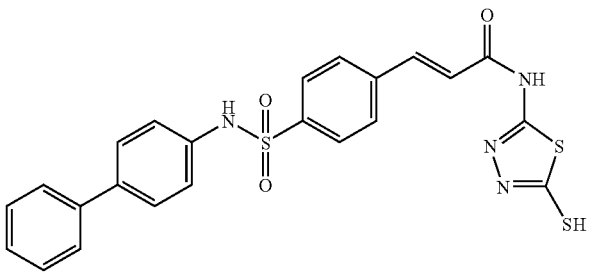 | | |
| Ex. 37 | 167 | 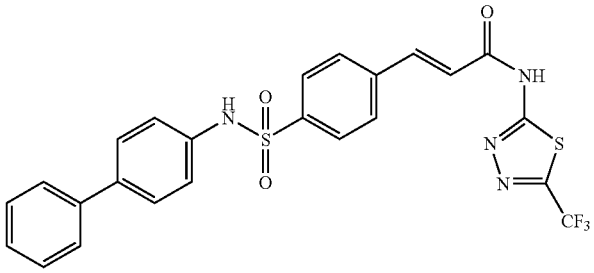 | | |
| Ex. 38 | 168 | 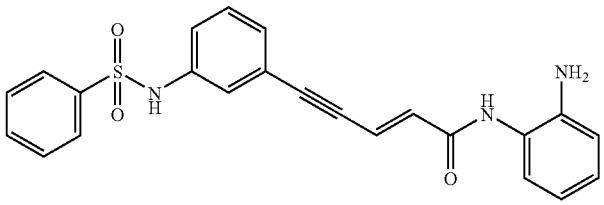 | 0% @ 20 μM | 3 |

TABLE 4-continued
Inhibition of Histone Deacetylase
| Example | Cpd. | Structure | pooled HDACs $IC_{50}$ (μM) | rHDAC-1 $IC_{50}$ (μM) |
|---|---|---|---|---|
| Ex. 39 | 170 | 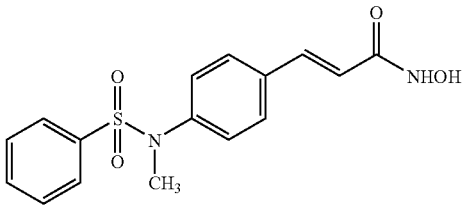 | 48% @ 2 μM | 0.57 |
| | 171 | 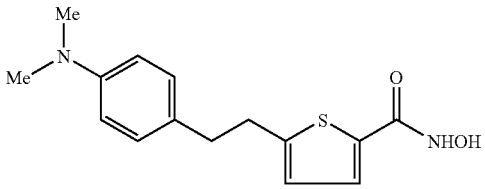 | 20 | |
| | 172 | 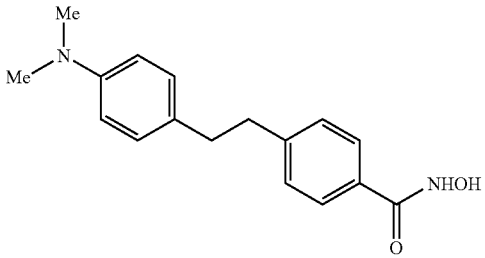 | 10 | |
| | 173 | 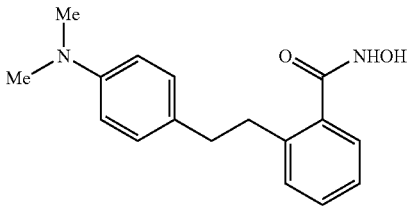 | 35% @ 20 μM | |
| | 174 | 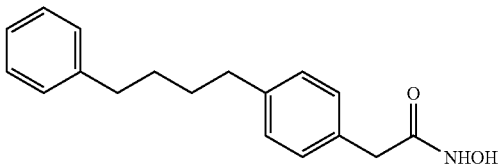 | >20 | |
| | 175 | 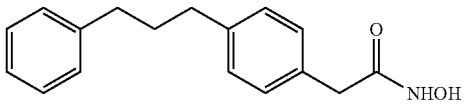 | >20 | |
| | 176 | 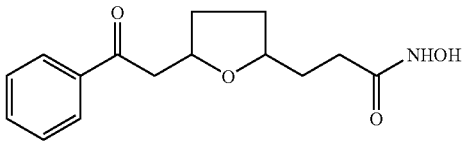 | 20% @ 20 μM | |

TABLE 4-continued

Inhibition of Histone Deacetylase

| Example | Cpd. | Structure | pooled HDACs $IC_{50}$ (μM) | rHDAC-1 $IC_{50}$ (μM) |
|---|---|---|---|---|
| | 177 | 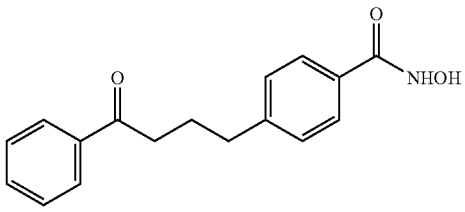 | 10% @ 20 μM | |
| | 178 | 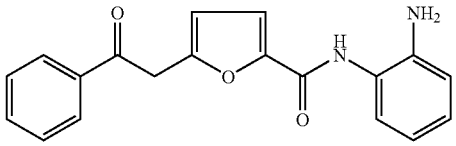 | 2% @ 20 μM | >20 |

Example 41

Inhibition of Histone Deacetylase in Whole Cells

1. Histone H4 Acetylation in Whole Cells by Immunoblots

T24 human bladder cancer cells growing in culture were incubated with HDAC inhibitors for 16 hours. Histones were extracted from the cells after the culture period as described by M. Yoshida et al. (J. Biol. Chem. 265(28): 17174–17179 (1990)). 20 μg of total histone protein was loaded onto SDS/PAGE and transferred to nitrocellulose membranes. Membranes were probed with polyclonal antibodies specific for acetylated histone H-4 (Upstate Biotech Inc.), followed by horse radish peroxidase conjugated secondary antibodies (Sigma). Enhanced Chemiluminescence (ECL) (Amersham) detection was performed using Kodak films (Eastman Kodak). Acetylated H-4 signal was quantified by densitometry.

Data for selected compounds are presented in Table 5. Data are presented as the concentration effective for reducing the acetylated H-4 signal by 50% ($EC_{50}$).

TABLE 5

Inhibition of Histone Acetylation in Cells

| Cpd. | Structure | $EC_{50}$ (μM) |
|---|---|---|
| 36 | 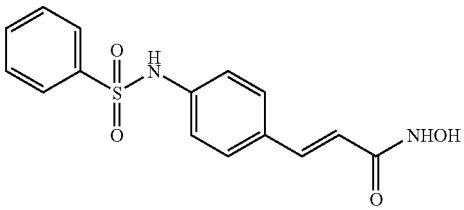 | 5 |
| 90 | 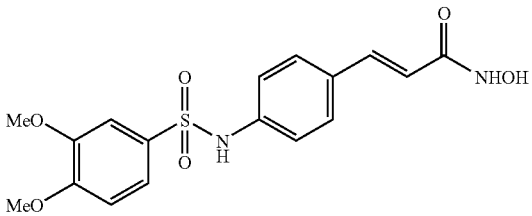 | 1 |
| 98 | 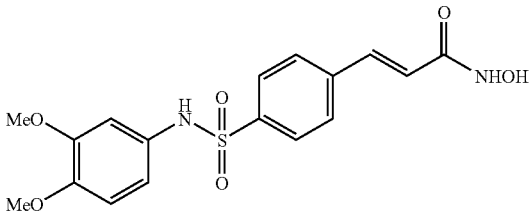 | 1 |

TABLE 5-continued

| Inhibition of Histone Acetylation in Cells | | |
|---|---|---|
| Cpd. | Structure | $EC_{50}$ (μM) |
| 107 | 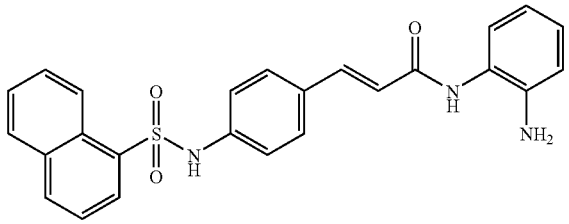 | 5 |
| 118 | 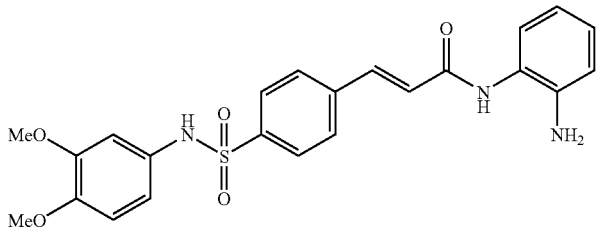 | 3 |
| 120 | 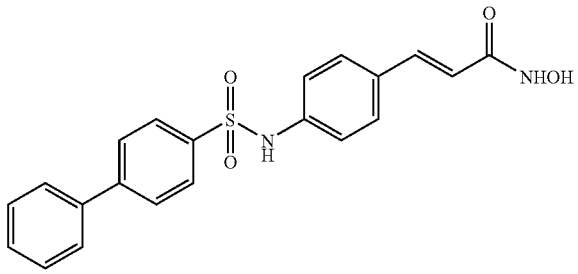 | 1 |
| 122 | 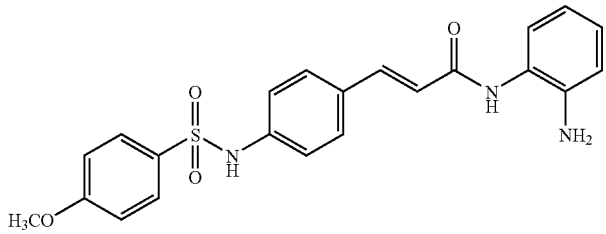 | 2 |

2. Acid Urea Triton (AUT) Gel Analysis of Histone Acetylation.

Human cancer cells (T24, 293T or Jurkat cells) growing in culture are incubated with HDAC inhibitors for 24 h. Histones are extracted from the cells as described by M. Yoshida et al. (J. Biol. Chem. 265(28): 17174–17179 (1990)). Acid urea triton (AUT) gel electrophoresis is used for detection of acetylated histone molecules. Histones (150 μg of total protein) are electrophoresed at 80 V for 16 h at room temperature as described by M. Yoshida et al., supra. Gels are stained with Coomassie brillant blue to visualize histones, dried and scanned by densitometry to quantified acetylation of histones.

Example 42

Antineoplastic Effect of Histone Deacetylase Inhibitors on Tumor Cells In Vivo Eight to ten week old female BALB/c nude mice (Taconic Labs, Great Barrington, N.Y.) are injected subcutaneously in the flank area with $2\times10^6$ preconditioned A549 human lung carcinoma cells. Preconditioning of these cells is done by a minimum of three consecutive tumor transplantations in the same strain of nude mice. Subsequently, tumor, fragments of approximately 30 mgs are excised and implanted subcutaneously in mice, in the left flank area, under Forene anesthesia (Abbott Labs, Geneve, Switzerland). When the tumors reach a mean volume of 100 $mm^3$, the mice are treated intravenously, subcutaneously, or intraperitoneally by daily injection, with a solution of the histone deacetylase inhibitor in an appropriate vehicle, such as PBS, DMSO/water, or Tween 80/water, at a starting dose of 10 mg/kg. The optimal dose of the HDAC inhibitor is established by dose response experiments according to standard protocols. Tumor volume is calculated every second day post infusion according to standard methods (e.g., Meyer et al., Int. J. Cancer 43: 851–856 (1989)). Treatment with the HDAC inhibitors according to the invention causes a significant reduction in tumor weight and volume relative to controls treated with saline only (i.e., no HDAC inhibitor). In addition, the activity of histone deacetylase when measured is expected to be significantly reduced relative to saline treated controls.

Example 43

Synergistic Antineoplastic Effect on Histone Deacetylase Inhibitors and Histone Deacetylase Antisense Oligonucleotides on Tumor Cells In Vivo The purpose of this example is to illustrate the ability of the histone deacetylase inhibitor of the invention and a histone deacetylase antisense oligonucleotide to synergistically inhibit tumor growth in a mammal. Preferably, the antisense oligonucleotide and the HDAC inhibitor inhibit the expression and activity of the same histone deacetylase.

As described in Example 10, mice bearing implanted A549 tumors (mean volume 100 $mm^3$) are treated daily with saline preparations containing from about 0.1 mg to about 30 mg per kg body weight of histone deacetylase antisense oligonucleotide. A second group of mice is treated daily with pharmaceutically acceptable preparations containing from about 0.01 mg to about 5 mg per kg body weight of HDAC inhibitor.

Some mice receive both the antisense oligonucleotide and the HDAC inhibitor. Of these mice, one group may receive the antisense oligonucleotide and the HDAC inhibitor simultaneously intravenously via the tail vein. Another group may receive the antisense oligonucleotide via the tail vein, and the HDAC inhibitor subcutaneously. Yet another group may receive both the antisense oligonucleotide and the HDAC inhibitor subcutaneously. Control groups of mice are similarly established which receive no treatment (e.g., saline only), a mismatch antisense oligonucleotide only, a control compound that does not inhibit histone deacetylase activity, and a mismatch antisense oligonucleotide with a control compound.

Tumor volume is measured with calipers. Treatment with the antisense oligonucleotide plus the histone deacetylase protein inhibitor according to the invention causes a significant reduction in tumor weight and volume relative to controls.

What is claimed is:

1. An inhibitor of histone deacetylase represented by the formula $$Cy—L^1—Ar—Y^1—C(O)—NH—Z$$

wherein

Cy is cycloalkyl, aryl, heteroaryl, or heterocyclyl, any of which may be optionally substituted;

$L^1$ is $—(CH_2)_m—W—$, where m is 0, 1, 2, 3, or 4, and W is selected from the group consisting of —C(O)NH—, $—S(O)_2NH—$, —*NHC(O)*—, $—NHS(O)_2—$, and —NH—C(O)—NH—;

Ar is arylene *or heteroarylene*, wherein said arylene optionally may be additionally substituted and optionally may be fused to an aryl or heteroaryl ring, or to a saturated or partially unsaturated cycloalkyl or heterocyclic ring, any of which may be optionally substituted;

$Y^1$ is a [chemical bond or a] straight- or branched-chain saturated alkylene, wherein said alkylene may be optionally substituted; and Z is selected from the group consisting of anilinyl, pyridyl, thiadiazolyl, and —O—M, M being H or a pharmaceutically acceptable cation, *wherein said thiadiazolyl may be optionally substituted with a substituent selected from the group consisting of thiol, trifluoromethyl, amino and sulfonamido*;

provided that when $L^1$ is —C(O)NH—, $Y^1$ is an [alklene] *alkylene* of *the* formula $—(CH_2)_n—$, n being 1, 2 or 3, and Z is —O—M, then Cy is not aminophenyl, dimethylaminophenyl, or hydroxyphenyl; and further provided that when $L^1$ is —C(O)NH— and Z is pyridyl, then Cy is not substituted indolinyl.

2. The inhibitor of claim 1, wherein Z is selected from the group consisting of 2-anilinyl, 2-pyridyl, 1,3,4-thiadiazol-2-yl, and —O—M, M being H or a pharmaceutically acceptable cation.

3. The inhibitor of [claim 2]*claim 1*, wherein Z is 1,3,4-thiadiazol-2-yl which is substituted at the 5-position with a substituent selected from the group consisting of thiol, trifluoromethyl, amino, and sulfonamido.

4. The inhibitor of claim 1, wherein $Y^1$ is $C_1$–$C_6$ alkylene.

5. The inhibitor of claim 1, wherein $Y^1$ is $C_1$–$C_3$ alkylene.

6. The inhibitor of claim 1, wherein Ar is substituted or unsubstituted phenylene, which optionally may be fused to an aryl or heteroaryl ring, or to a saturated or partially unsaturated cycloalkyl or heterocyclic ring, any of which may be optionally substituted.

7. The inhibitor of claim 6, wherein the phenylene is 4-phenylene.

[8. The inhibitor of claim 1, wherein Cy is selected from the group consisting of phenyl, naphthyl, thienyl, benzothienyl, and quinolyl, any of which may be optionally substituted.]

[9. The inhibitor of claim 8, herein the phenyl, naphthyl, thienyl, benzothienyl, or quinolyl is unsubstituted or is substituted by one or two substituents independently selected from the group consisting of $C_1$–$C_4$ alkyl, $C_1$–$C_4$ haloalkyl, $C_6$–$C_{10}$ aryl, ($C_6$–$C_{10}$)ar($C_1$–$C_6$)alkyl, halo, nitro, hydroxy, $C_1$–$C_6$ alkoxy, $C_1$–$C_6$ alkoxycarbonyl, carboxy, and amino.]

10. The inhibitor of claim 1, wherein m is zero.

11. An inhibitor of histone deacetylase represented by the formula $$Cy—L^2—Ar—Y^2—C(O)NH—Z$$

wherein

Cy is cycloalkyl, aryl, heteroaryl, or heterocyclyl, any of which may be optionally substituted, provided that Cy is not a (spirocycloalkyl)heterocyclyl;

$L^2$ is [$C_1$–$C_6$]$C_2$-$C_8$ saturated alkylene or [$C_2$–$C_6$]$C_2$-$C_8$ alkenylene, wherein the alkylene or alkenylene optionally may be substituted, provided that $L^2$ is not —C(O)—, and wherein one of the carbon atoms of the alkylene optionally may be replaced by a heteroatom moiety selected from the group consisting of [O;] NR'; R' being alkyl, acyl, or hydrogen; S; S(O); or $S(O)_2$;

Ar is arylene *or heteroarylene*, wherein said arylene optionally may be additionally substituted and optionally may be fused to an aryl or heteroaryl ring, or to a saturated or partially unsaturated cycloalkyl or heterocyclic ring, any of which may be optionally substituted; and $Y^2$ is a [chemical bond or a] straight- or branched-chain saturated alkylene, which may be optionally substituted, provided that the alkylene is not substituted with a substituent of the formula —C(O)R wherein R comprises an α-amino acyl moiety; and Z is selected from the group consisting of anilinyl, pyridyl, thiadiazolyl, and —O—M, M being H or a pharmaceutically acceptable cation, *wherein said thiadiazolyl may be optionally substituted with a substituent selected from the group consisting of thiol, trifluoromethyl, amino and sulfonamido*;

provided that when the carbon atom to which Cy is attached is oxo substituted, then Cy and Z are not both pyridyl.

12. The inhibitor of claim 11, wherein Z is selected from the group consisting of 2-anilinyl, 2-pyridyl, 1,3,4-thiadiazol-2-yl, and —O—M, M being H or a pharmaceutically acceptable cation.

13. The inhibitor of claim 12, wherein Z is 1,3,4-thiadiazol-2-yl which is substituted at the 5-position with a substituent selected from the group consisting of thiol, trifluoromethyl, amino, and sulfonamido.

[14. The inhibitor of claim 11, wherein $Y^2$ is a chemical bond.]

15. The inhibitor of claim 11, wherein $Y^2$ is $C_1$–$C_3$ alkylene.

16. The inhibitor of claim 11, wherein $Y^2$ is $C_1$–$C_2$ alkylene.

17. The inhibitor of claim 11, wherein Ar is substituted or unsubstituted phenylene, which optionally may be fused to an aryl or heteroaryl ring, or to a saturated or partially unsaturated cycloalkyl or heterocyclic ring, any of which may be optionally substituted.

18. The inhibitor of claim 17, wherein the phenylene is 4-phenylene.

19. The inhibitor of claim 11, wherein Cy is selected from the group consisting of phenyl, naphthyl, thienyl, benzothienyl, and quinolyl, any of which may be optionally substituted.

20. The inhibitor of claim 19, wherein the phenyl, naphthyl, thienyl, benzothienyl, or quinolyl is unsubstituted or is substituted by one or two substituents independently selected from the group consisting of $C_1$–$C_4$ alkyl, $C_1$–$C_4$ haloalkyl, $C_6$–$C_{10}$ aryl, $(C_6$–$C_{10})$ar$(C_1$–$C_6)$alkyl, halo, nitro, hydroxy, $C_1$–$C_6$ alkoxy, $C_1$–$C_6$ alkoxycarbonyl, carboxy, and amino.

21. The inhibitor of claim 11, wherein one or two saturated carbons in $L^2$ are substituted with a substituent independently selected from the group consisting of $C_1$–$C_6$ alkyl, $C_6$–$C_{10}$ aryl, amino, oxo, hydroxy, $C_1$–$C_4$ alkoxy, and $C_6$–$C_{10}$ aryloxy.

22. The inhibitor of claim 21, wherein the substituent is oxo or hydroxy.

23. The inhibitor of claim 11, wherein $L^2$ is [$C_1$–$C_6$]$C_2$-$C_8$ saturated alkylene, and no carbon atom of the alkylene is replaced by a heteroatom moiety.

24. The inhibitor of claim 11, wherein one carbon atom of the $Y^2$ alkylene is replaced by a heteroatom moiety selected from the group consisting of O; NR', R' being alkyl, acyl, or hydrogen; S; S(O); or $S(O)_2$.

25. The inhibitor of claim [24] *11*, wherein $L^2$ is selected from the group consisting of —S—$(CH_2)_n$, —S(O)—$(CH_2)_n$—, and —$S(O)_2$—$(CH_2)_n$—, wherein n is 0, 1, 2, 3, or 4.

26. An inhibitor of histone deacetylase represented by the formula $$Cy—L^3—Ar—Y^3—C(O)NH—Z$$

wherein

Cy is cycloalkyl, [aryl, heteroaryl,] or heterocyclyl, any of which may be optionally substituted, provided that Cy is not a (spirocycloalkyl)heterocyclyl;

$L^3$ is selected from the group consisting of (a) —$(CH_2)_m$—W—, where m is 0, 1, 2, 3, or 4, and W is selected from the group consisting of —C(O)NH—, —$S(O)_2$NH—, —NHC(O)—, —NHS$(O)_2$—, and —NH—C(O)—NH—; and (b) [$C_1$–$C_6$]$C_2$-$C_8$ alkylene or [$C_2$–$C_6$]$C_2$-$C_8$ alkenylene, wherein the alkylene or alkenylene optionally may be substituted, provided that $L^3$ is not —C(O)—, and wherein one of the carbon atoms of the alkylene optionally may be replaced by [O;] NR'; R' being alkyl, acyl, or hydrogen; S; S(O); or $S(O)_2$;

Ar is arylene *or heteroarylene*, wherein said arylene optionally may be additionally substituted and optionally may be fused to an aryl or heteroaryl ring, or to a saturated or partially unsaturated cycloalkyl or heterocyclic ring, any of which may be optionally substituted; and $Y^3$ is $C_2$ alkenylene or $C_2$ alkynylene, wherein one or both carbon atoms of the alkenylene optionally may be substituted with alkyl, aryl, alkaryl, or aralkyl; and Z is selected from the group consisting of anilinyl, pyridyl, thiadiazolyl, and —O—M, M being H or a pharmaceutically acceptable cation, *wherein said thiadiazolyl may be optionally substituted with a substituent selected from the group consisting of thiol, trifluoromethyl, amino and sulfonamido*;

provided that when Cy is unsubstituted phenyl, Ar is not phenyl wherein $L^3$ and $Y^3$ are oriented ortho or meta to each other.

27. The inhibitor of claim 26, wherein Z is selected from the group consisting of 2-anilinyl, 2-pyridyl, 1,3,4-thiadiazol-2-yl, and —O—M, M being H or a pharmaceutically acceptable cation.

28. The inhibitor of claim 27, wherein Z is 1,3,4-thiadiazol-2-yl which is substituted at the 5-position with a substituent selected from the group consisting of thiol, trifluoromethyl, amino, and sulfonamido.

29. The inhibitor of claim 26, wherein $Y^3$ is selected from the group consisting of —CH═CH—, —$C(CH_3)$═CH—, and —CH═$C(CH_3)$—.

30. The inhibitor of claim 26, wherein Ar is substituted or unsubstituted phenylene, which optionally may be fused to an aryl or heteroaryl ring, or to a saturated or partially unsaturated cycloalkyl or heterocyclic ring, any of which may be optionally substituted.

31. The inhibitor of claim 30, wherein the phenylene is 4-phenylene.

[32. The inhibitor of claim 26, wherein Cy is selected from the group consisting of phenyl, naphthyl, thienyl, benzothienyl, and quinolyl, any of which may be optionally substituted.]

[33. The inhibitor of claim 32, wherein the phenyl, naphthyl, thienyl, benzothienyl, or quinolyl is unsubstituted or is substituted by one or two substituents independently selected from the group consisting of $C_1$–$C_4$ alkyl, $C_1$–$C_4$ haloalkyl, $C_6$–$C_{10}$ aryl, $(C_6$–$C_{10})$ar$(C_1$–$C_6)$alkyl, halo, nitro, hydroxy, $C_1$–$C_6$ alkoxy, $C_1$–$C_6$ alkoxycarbonyl, carboxy, and amino.]

34. An inhibitor of histone deacetylase selected from the group consisting of

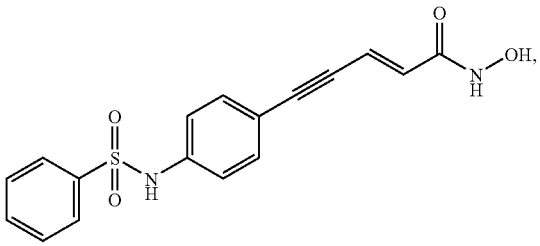

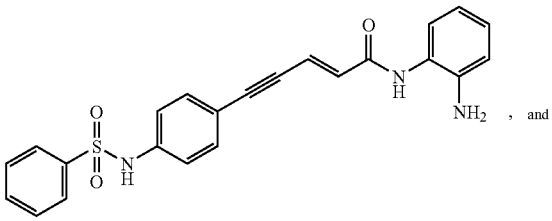

, and

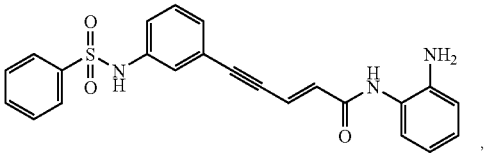

,

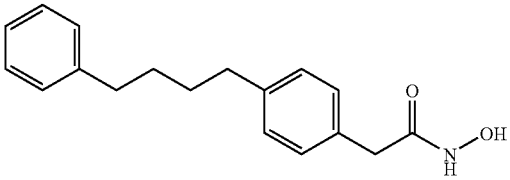

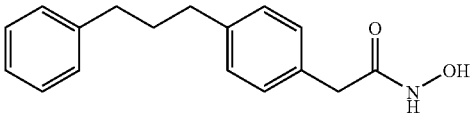

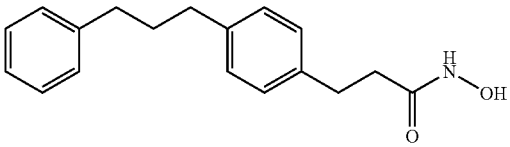

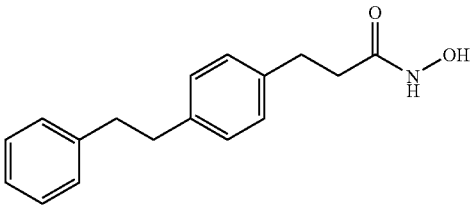

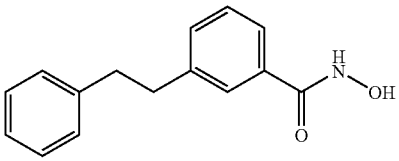

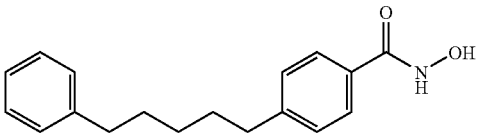

and

-continued

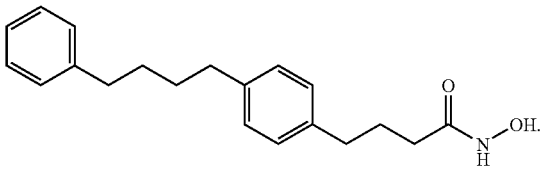

*35. The inhibitor according to claim 11 selected from the group consisting of*

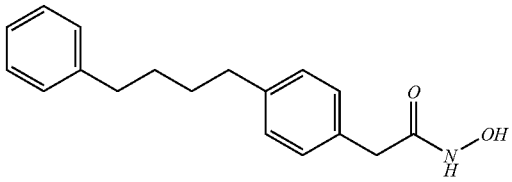

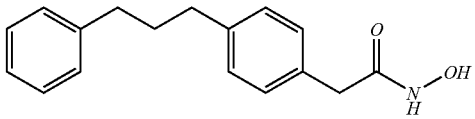

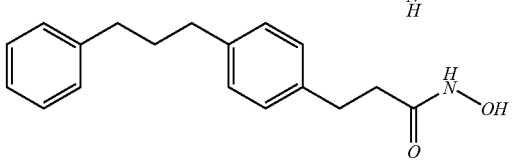

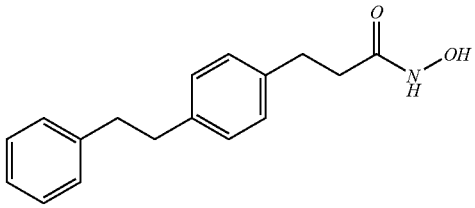

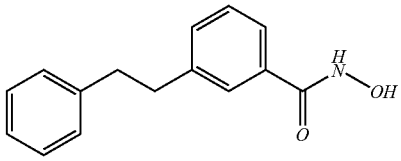

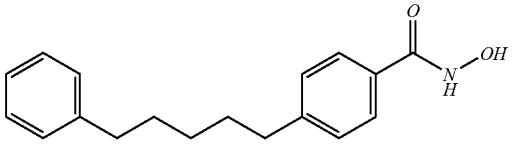

*and*

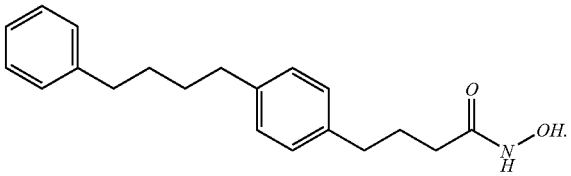

*36. An inhibitor of histone deacetylase represented by the formula*

$$Cy—L^2—Ar—Y^2—C(O)NH—Z$$

*Wherein*

*Cy is cycloalkyl, aryl, heteroaryl, or heterocyclyl, any of which may be optionally substituted, provided that Cy is not a (spirocycloalkyl)heterocyclyl;*

*$L^2$ is $C_1$-$C_8$ saturated alkylene or $C_2$-$C_8$ alkenylene, wherein the alkylene or alkenylene optionally may be*

*substituted, provided that $L_2$ is not —C(O)—, and wherein one of the carbon atoms of the alkylene optionally may be replaced by a heteroatom moiety selected from the group consisting of NR', R' being alkyl, acyl, or hydrogen; S; or S(O); or $L^2$ is —S(O)$_2$-(CH$_2$)$_n$, wherein n is 1, 2, 3 or 4,*

*Ar is arylene or heteroarylene, wherein said arylene optionally may be additionally substituted and optionally may be fused to an aryl or heteroaryl ring, or to a saturated or partially unsaturated cycloalkyl or heterocyclic ring, any of which may be optionally substituted; and*

*$Y^2$ is a straight- or branched-chain saturated alkylene, which may be optionally substituted, provided that the alkylene is not substituted with a substituent of the formula —C(O)R wherein R comprises an α-amino acyl moiety; and*

*Z is selected from the group consisting of anilinyl, pyridyl, thiadiazolyl, and —O—M, M being H or a pharmaceutically acceptable cation, wherein said thiadiazolyl may be optionally substituted with a substituent selected from the group consisting of thiol, trifluoromethyl, amino and sulfonamido;*

*provided that when the carbon atom to which Cy is attached is oxo substituted, then Cy and Z are not both pyridyl.*

*37. The inhibitor of claim 36, wherein Z is selected from the group consisting of 2-anilinyl, 2-pyridyl, 1,3,4-thiadiazol-2-yl, and —O—M, M being H or a pharmaceutically acceptable cation.*

*38. The inhibitor of claim 36 wherein Z is 1,3,4-thiadiazol-2-yl which is substituted at the 5-position with a substituent selected from the group consisting of thiol, trifluoromethyl, amino, and sulfonamido.*

*39. The inhibitor of claim 36, wherein $Y^2$ is $C_1$-$C_3$ alkylene.*

*40. The inhibitor of claim 36, wherein $Y^2$ is $C_1$-$C_2$ alkylene.*

*41. The inhibitor of claim 36, wherein Ar is substituted or unsubstituted phenylene, which optionally may be fused to an aryl or heteroaryl ring, or to a saturated or partially unsaturated cycloalkyl or heterocyclic ring, any of which may be optionally substituted.*

*42. The inhibitor of claim 41, wherein the phenylene is 4-phenylene.*

*43. The inhibitor of claim 36, wherein Cy is selected from the group consisting of phenyl, naphthyl, thienyl, benzothienyl, and quinolyl, any of which may be optionally substituted.*

*44. The inhibitor of claim 43, wherein the phenyl, naphthyl, thienyl, benzothienyl, or quinolyl is unsubstituted or is substituted by one or two substituents independently selected from the group consisting of $C_1$-$C_4$ alkyl, $C_1$-$C_4$ haloalkyl, $C_6$-$C_{10}$ aryl, ($C_6$-$C_{10}$)ar($C_1$-$C_6$)alkyl, halo, nitro, hydroxy, $C_1$-$C_6$ alkoxy, $C_1$-$C_6$ alkoxycarbonyl, carboxy, and amino.*

*45. The inhibitor of claim 36, wherein one or two saturated carbons in $L^2$ are substituted with a substituent independently selected from the group consisting of $C_1$-$C_6$ alkyl, $C_6$-$C_{10}$ aryl, amino, oxo, hydroxy, $C_1$-$C_4$ alkoxy, and $C_6$-$C_{10}$ aryloxy.*

*46. The inhibitor of claim 45, wherein the substituent is oxo or hydroxy.*

*47. The inhibitor of claim 36, wherein $L^2$ is $C_2$-$C_8$ saturated alkylene, and no carbon atom of the alkylene is replaced by a heteroatom moiety.*

*48. The inhibitor of claim 36, wherein one carbon atom of the $Y^2$ alkylene is replaced by a heteroatom moiety selected from the group consisting of O; NR', R' being alkyl, acyl, or hydrogen; S; or S(O); or S(O)$_2$.*

*49. The inhibitor of claim 36, wherein $L^2$ is selected from the group consisting of —S—(CH$_2$)$_n$, —S(O)—(CH$_2$)$_n$, —S(O)$_2$—(CH$_2$)$_n$ and wherein n is 1, 2, 3, or 4.*

*50. An inhibitor of histone deacetylase represented by the formula*

$$Cy—L^3—Ar—Y^3—C(O)NH—Z$$

*wherein*

*Cy is cycloalkyl,* [aryl, heteroaryl,] *or heterocyclyl, any of which may be optionally substituted, provided that Cy is not a (spirocycloalkyl)heterocyclyl;*

*$L^3$ is selected from the group consisting of*

*(a) —(CH$_2$)$_m$—W, where m is 0, 1, 2, 3, or 4, and W is selected from the group consisting of —C(O)NH—, —S(O)$_2$NH—, —NHC(O)—, —NHS(O)$_2$—, and —NH—C(O)—NH—; and*

*(b) $C_1$-$C_8$ alkylene or $C_2$-$C_8$ alkenylene, wherein the alkylene or alkenylene optionally may be substituted, provided that $L_3$ is not —C(O)—, and wherein one of the carbon atoms of the alkylene optionally may be replaced by NR', R' being alkyl, acyl, or hydrogen; S; or S(O);*

*Ar is arylene or heteroarylene, wherein said arylene optionally may be additionally substituted and optionally may be fused to an aryl or heteroaryl ring, or to a saturated or partially unsaturated cycloalkyl or heterocyclic ring, any of which may be optionally substituted; and*

*$Y^3$ is $C_2$ alkenylene or $C_2$ alkynylene, wherein one or both carbon atoms of the alkenylene optionally may be substituted with alkyl, aryl, alkaryl, or aralkyl; and*

*Z is selected from the group consisting of anilinyl, pyridyl, thiadiazolyl, and —O—M, M being H or a pharmaceutically acceptable cation, wherein said thiadiazolyl may be optionally substituted with a substituent selected from the group consisting of thiol, trifluoromethyl, amino and sulfonamido;*

*provided that when Cy is unsubstituted phenyl, Ar is not phenyl wherein $L^3$ and $Y^3$ are oriented ortho or meta to each other.*

*51. The inhibitor of claim 50, wherein Z is selected from the group consisting of 2-anilinyl, 2-pyridyl, 1,3,4-thiadiazol-2-yl, and —O—M, M being H or a pharmaceutically acceptable cation.*

*52. The inhibitor of claim 51, wherein Z is 1,3,4-thiadiazol-2-yl which is substituted at the 5-position with a substituent selected from the group consisting of thiol, trifluoromethyl, amino, and sulfonamido.*

*53. The inhibitor of claim 50, wherein $Y^3$ is selected from the group consisting of —CH=CH—, —C(CH$_3$)=CH—, and —CH=C(CH$_3$)—.*

*54. The inhibitor of claim 50, wherein Ar is substituted or unsubstituted phenylene, which optionally may be fused to an aryl or heteroaryl ring, or to a saturated or partially unsaturated cycloalkyl or heterocyclic ring, any of which may be optionally substituted.*

*55. The inhibitor of claim 54, wherein the phenylene is 4-phenylene.*

*56. An inhibitor of histone deacetylase represented by the formula*

$$Cy—L^1—Ar—Y^1—C(O)—NH—Z$$

wherein

Cy is aryl or heteroaryl, either of which may be optionally substituted;

$L^1$ is —$(CH_2)m$ —W—, where m is 0, 1, 2, 3, or 4, and W is selected from the group consisting of —C(O)NH—, —NHC(O)— and —NH—C(O)—NH—;

Ar is arylene or heteroarylene, wherein said arylene optionally may be additionally substituted and optionally may be fused to an aryl or heteroaryl ring, or to a saturated or partially unsaturated cycloalkyl or heterocyclic ring, any of which may be optionally substituted;

$Y^1$ is a straight- or branched-chain saturated alkylene, wherein said alkylene may be optionally substituted; and Z is selected from the group consisting of anilinyl, pyridyl, thiadiazolyl, and —O—M, M being H or a pharmaceutically acceptable cation, wherein said thiadiazolyl may be optionally substituted with a substituent selected from the group consisting of thiol, trifluoromethyl, amino and sulfonamido;

provided that when $L^1$ is —C(O)NH—, $Y^1$ is an alkylene of the formula —$(CH_2)_n$—, being 1, 2, or 3, and Z is —O—M, then Cy is not aminophenyl, dimethylaminophenyl, or hydroxyphenyl; and further provided that when $L^1$ is —C(O)NH— and Z is pyridyl, then Cy is not substituted indolinyl.

57. The inhibitor of claim 56, wherein Z is selected from the group consisting of 2-anilinyl, 2-pyridyl, 1,3,4-thiadiazol-2-yl, and —O—M, M being H or a pharmaceutically acceptable cation.

58. The inhibitor of claim 56, wherein Z is 1,3,4-thiadiazol-2-yl which is substituted at the 5-position with a substituent selected from the group consisting of thiol, trifluoromethyl, amino, and sulfonamido.

59. The inhibitor of claim 56, wherein $Y^1$ is $C_1$-$C_6$ alkylene.

60. The inhibitor of claim 56, wherein $Y^1$ is $C_1$-$C_3$ alkylene.

61. The inhibitor of claim 56, wherein Ar is substituted or unsubstituted phenylene, which optionally may be fused to an aryl or heteroaryl ring, or to a saturated or partially unsaturated cycloalkyl or heterocyclic ring, any of which may be optionally substituted.

62. The inhibitor of claim 61, wherein the phenylene is 4-phenylene.

63. The inhibitor of claim 56, wherein Cy is selected from the group consisting of phenyl, naphthyl, thienyl, benzothienyl, and quinolyl, any of which may be optionally substituted.

64. The inhibitor of claim 63, wherein the phenyl, naphthyl, thienyl, benzothienyl, or quinolyl is unsubstituted or is substituted by one or two substituents independently selected from the group consisting of $C_1$-$C_4$ alkyl, $C_1$-$C_4$ haloalkyl, $C_6$-$C_{10}$ aryl, $(C_6$-$C_{10})ar(C_1$-$C_6)alkyl$, halo, nitro, hydroxy, $C_1$-$C_6$ alkoxy, $C_1$-$C_6$ alkoxycarbonyl, carboxy, and amino.

65. The inhibitor of claim 56, wherein m is zero.

66. An inhibitor of histone deacetylase represented by the formula $$Cy—L^1—Ar—Y^1—C(O)—NH—Z$$

wherein

Cy is aryl or heteroaryl, any of which may be optionally substituted;

$L^1$ is —$S(O)_2NH$—

Ar is arylene or heteroarylene, wherein said arylene optionally may be additionally substituted and optionally may be fused to an aryl or heteroaryl ring, or to a saturated or partially unsaturated cycloalkyl or heterocyclic ring, any of which may be optionally substituted;

$Y^1$ is a straight- or branched-chain saturated alkylene, wherein said alkylene may be optionally substituted; and Z is selected from the group consisting of anilinyl, pyridyl, thiadiazolyl, and —O—M, M being H or a pharmaceutically acceptable cation, wherein said thiadiazolyl may be optionally substituted with a substituent selected from the group consisting of thiol, trifluoromethyl, amino and sulfonamide.

67. The inhibitor of claim 66, wherein Z is selected from the group consisting of 2-anilinyl, 2-pyridyl, 1,3,4-thiadiazol-2-yl, and —O—M, M being H or a pharmaceutically acceptable cation.

68. The inhibitor of claim 66, wherein Z is 1,3,4-thiadiazol-2-yl which is substituted at the 5-position with a substituent selected from the group consisting of thiol, trifluoromethyl, amino, and sulfonamido.

69. The inhibitor of claim 66, wherein $Y^1$ is $C_1$-$C_6$ alkylene.

70. The inhibitor of claim 66, wherein $Y^1$ is $C_1$-$C_3$ alkylene.

71. The inhibitor of claim 66, wherein Ar is substituted or unsubstituted phenylene, which optionally may be fused to an aryl or heteroaryl ring, or to a saturated or partially unsaturated cycloalkyl or heterocyclic ring, any of which may be optionally substituted.

72. The inhibitor of claim 71, wherein the phenylene is 4-phenylene.

73. The inhibitor of claim 66, wherein Cy is selected from the group consisting of phenyl, naphthyl, thienyl, benzothienyl, and quinolyl, any of which may be optionally substituted.

74. The inhibitor of claim 73, wherein the phenyl, naphthyl, thienyl, benzothienyl, or quinolyl is unsubstituted or is substituted by one or two substituents independently selected from the group consisting of $C_1$-$C_4$ alkyl, $C_1$-$C_4$ haloalkyl, $C_6$-$C_{10}$ aryl, $(C_6$-$C_{10})ar(C_1$-$C_6)alkyl$, halo, nitro, hydroxy, $C_1$-$C_6$ alkoxy, $C_1$-$C_6$ alkoxycarbonyl, carboxy, and amino.

75. An inhibitor of histone deacetylase represented by the formula $$Cy—L^1—Ar—Y^1—C(O)—NH—Z$$

wherein

Cy is aryl or heteroaryl, any of which may be optionally substituted;

$L^1$ is —$(CH_2)m$ —$S(O)_2NH$—, where m is 1,2,3, or 4,

Ar is arylene or heteroarylene, wherein said arylene optionally may be additionally substituted and optionally may be fused to an aryl or heteroaryl ring, or to a saturated or partially unsaturated cycloalkyl or heterocyclic ring, any of which may be optionally substituted;

$Y^1$ is a straight- or branched-chain saturated alkylene, wherein said alkylene may be optionally substituted; and Z is selected from the group consisting of anilinyl, pyridyl, thiadiazolyl, and —O—M, M being a pharmaceutically acceptable cation, wherein said thiadiazolyl may be optionally substituted with a substituent selected from the group consisting of thiol, trifluoromethyl, amino and sulfonamide.

76. The inhibitor of claim 75, wherein Z is selected from the group consisting of 2-anilinyl, 2-pyridyl, 1,3,4-thiadiazol-2-yl, and —O—M, M being a pharmaceutically acceptable cation.

77. The inhibitor of claim 75, wherein Z is 1,3,4-thiadiazol-2-yl which is substituted at the 5-position with a substituent selected from the group consisting of thiol, trifluoromethyl, amino, and sulfonarnido.

78. The inhibitor of claim 75, wherein $Y^1$ is $C_1$-$C_6$ alkylene.

79. The inhibitor of claim 75, wherein $Y^1$ is $C_1$-$C_3$ alkylene.

80. The inhibitor of claim 75, wherein Ar is substituted or unsubstituted phenylene, which optionally may be fused to an aryl or heteroaryl ring, or to a saturated or partially unsaturated cycloalkyl or heterocyclic ring, any of which may be optionally substituted.

81. The inhibitor of claim 80, wherein the phenylene is 4-phenylene.

82. The inhibitor of claim 75, wherein Cy is selected from the group consisting of phenyl, naphthyl, thienyl, benzothienyl, and quinolyl, any of which may be optionally substituted.

83. The inhibitor of claim 82, wherein the phenyl, naphthyl, thienyl, benzothienyl, or quinolyl is unsubstituted or is substituted by one or two substituents independently selected from the group consisting of $C_1$-$C_4$ alkyl, $C_1$-$C_4$ haloalkyl, $C_6$-$C_{10}$ aryl, $(C_6$-$C_{10})ar(C_1$-$C_6)$alkyl, halo, nitro, hydroxy, $C_1$-$C_6$ alkoxy, $C_1$-$C_6$ alkoxycarbonyl, carboxy, and amino.

84. An inhibitor of histone deacetylase represented by the formula $$Cy—L^1—Ar—Y^1—C(O)—NH—Z$$

wherein

Cy is aryl or heteroaryl, either of which may be optionally substituted;

$L^1$ is $—(CH_2)_m—NHS(O)_2—$, where m is 0,1,2,3, or 4;

Ar is arylene or heteroarylene, wherein said arylene optionally may be additionally substituted and optionally may be fused to an aryl or heteroaryl ring, or to a saturated or partially unsaturated cycloalkyl or heterocyclic ring, any of which may be optionally substituted;

$Y^1$ is a straight- or branched-chain saturated alkylene, wherein said alkylene may be optionally substituted; and Z is selected from the group consisting of anilinyl, pyridyl, thiadiazolyl, and —O—M, M being a pharmaceutically acceptable cation, wherein said thiadiazolyl may be optionally substituted with a substituent selected from the group consisting of thiol, trifluoromethyl, amino and sulfonamide.

85. The inhibitor of claim 84, wherein Z is selected from the group consisting of 2-anilinyl, 2-pyridyl, 1,3,4-thiadiazol-2-yl, and —O—M, M being a pharmaceutically acceptable cation.

86. The inhibitor of claim 84, wherein Z is 1,3,4-thiadiazol-2-yl which is substituted at the 5-position with a substituent selected from the group consisting of thiol, trifluoromethyl, amino, and sulfonamido.

87. The inhibitor of claim 84, wherein $Y^1$ is $C_1$-$C_6$ alkylene.

88. The inhibitor of claim 84, wherein $Y^1$ is $C_1$-$C_3$ alkylene.

89. The inhibitor of claim 84, wherein Ar is substituted or unsubstituted phenylene, which optionally may be fused to an aryl or heteroaryl ring, or to a saturated or partially unsaturated cycloalkyl or heterocyclic ring, any of which may be optionally substituted.

90. The inhibitor of claim 89, wherein the phenylene is 4-phenylene.

91. The inhibitor of claim 84, wherein Cy is selected from the group consisting of phenyl, naphthyl, thienyl, benzothienyl, and quinolyl, any of which may be optionally substituted.

92. The inhibitor of claim 91, wherein the phenyl, naphthyl, thienyl, benzothienyl, or quinolyl is unsubstituted or is substituted by one or two substituents independently selected from the group consisting of $C_1$-$C_4$ alkyl, $C_1$-$C_4$ haloalkyl, $C_6$-$C_{10}$ aryl, $(C_6$-$C_{10})ar(C_1$-$C_6)$alkyl, halo, nitro, hydroxy, $C_1$-$C_6$ alkoxy, $C_1$-$C_6$ alkoxycarbonyl, carboxy, and amino.

93. The inhibitor of claim 84, wherein m is zero.

94. An inhibitor of histone deacetylase represented by the formula $$Cy—L^3—Ar—Y^3—C(O)NH—Z$$

wherein

Cy is aryl or heteroaryl, either of which may be optionally substituted;

$L^3$ is selected from the group consisting of (a) $—(CH_2)_m—W$, where m is 0,1,2,3, or 4, and W is selected from the group consisting of —C(O)NH—,—NHC(O)—, and —NH—C(O)—NH—; and (b) $C_2$-$C_8$ alkylene or $C_2$-$C_8$ alkenylene, wherein the alkylene or alkenylene optionally may be substituted, provided that $L^3$ is not —C(O)—, and wherein one of the carbon atoms of the alkylene optionally may be replaced by NR', R' being alkyl, acyl, or hydrogen; S; S(O); or $S(O)_2$;

Ar is arylene or heteroarylene, wherein said arylene optionally may be additionally substituted and optionally may be fused to an aryl or heteroaryl ring, or to a saturated or partially unsaturated cycloalkyl or heterocyclic ring, any of which may be optionally substituted; and $Y^3$ is $C_2$ alkenylene or $C_2$ alkynylene, wherein one or both carbon atoms of the alkenylene optionally may be substituted with alkyl, aryl, alkaryl, or aralkyl; and Z is selected from the group consisting of anilinyl, pyridyl, thiadiazolyl, and —O—M, M being H or a pharmaceutically acceptable cation, wherein said thiadiazolyl may be optionally substituted with a substituent selected from the group consisting of thiol, trifluoromethyl, amino and sulfonamido;

provided that when Cy is unsubstituted phenyl, Ar is not phenyl wherein $L^3$ and $Y^3$ are oriented ortho or meta to each other.

95. The inhibitor of claim 94, wherein Z is selected from the group consisting of 2-anilinyl, 2-pyridyl, 1,3,4-thiadiazol-2-yl, and —O—M, M being H or a pharmaceutically acceptable cation.

96. The inhibitor of claim 95, wherein Z is 1,3,4-thiadiazol-2-yl which is substituted at the 5-position with a substituent selected from the group consisting of thiol, trifluoromethyl, amino, and sulfonaniido.

97. The inhibitor of claim 94, wherein $Y^3$ is selected from the group consisting of CH=CH—, —C($CH_3$)=CH—, and —CH=C($CH_3$)—.

98. The inhibitor of claim 94, wherein Ar is substituted or unsubstituted phenylene, which optionally may be fused to an aryl or heteroaryl ring, or to a saturated or partially unsaturated cycloalkyl or heterocyclic ring, any of which may be optionally substituted.

99. The inhibitor of claim 98, wherein the phenylene is 4-phenylene.

100. The inhibitor of claim 94, wherein Cy is selected from the group consisting of phenyl, naphthyl, thienyl, benzothienyl, and quinolyl, any of which may be optionally substituted.

101. The inhibitor of claim 100, wherein the phenyl, naphthyl, thienyl, benzothienyl, or quinolyl is unsubstituted or is substituted by one or two substituents independently selected from the group consisting of $C_1$-$C_4$ alkyl, $C_1$-$C_4$ haloalkyl, $C_6$-$C_{10}$ aryl, ($C_6$-$C_{10}$)ar($C_1$-$C_6$)alkyl, halo, nitro, hydroxy, $C_1$-$C_6$ alkoxy, $C_1$-$C_6$ alkoxycarbonyl, carboxy, and amino.

102. An inhibitor of histone deacetylase represented by the formula $$Cy—L^3—Ar—Y^3—C(O)NH—Z$$

wherein

Cy is aryl or heteroaryl, either of which may be optionally substituted;

$L^3$ is selected from the group consisting of (a) —$S(O)_2NH$—; and (b) $C_2$-$C_8$ alkylene or $C_2$-$C_8$ alkenylene, wherein the alkylene or alkenylene optionally may be substituted, provided that $L^3$ is not —C(O)—, and wherein one of the carbon atoms of the alkylene optionally may be replaced by NR', R' being alkyl, acyl, or hydrogen; S; S(O); or $S(O)_2$;

Ar is arylene or heteroarylene wherein said arylene optionally may be additionally substituted and optionally may be fused to an aryl or heteroaryl ring, or to a saturated or partially unsaturated cycloalkyl or heterocyclic ring, any of which may be optionally substituted; and $Y^3$ is $C_2$ alkenylene or $C_2$ alkynylene, wherein one or both carbon atoms of the alkenylene optionally may be substituted with alkyl, aryl, alkaryl, or aralkyl; and Z is selected from the group consisting of anilinyl, pyridyl, thiadiazolyl, and —O—M, M being H or a pharmaceutically acceptable cation, wherein said thiadiazolyl may be optionally substituted with a substituent selected from the group consisting of thiol, trifluoromethyl, amino and sulfonamido;

provided that when Cy is unsubstituted phenyl, Ar is not phenyl wherein $L^3$ and $Y^3$ are oriented ortho or meta to each other.

103. The inhibitor of claim 102, wherein Z is selected from the group consisting of 2-anilinyl, 2-pyridyl, 1,3,4-thiadiazol-2-yl, and —O—M, M being H or a pharmaceutically acceptable cation.

104. The inhibitor of claim 103, wherein Z is 1,3,4-thiadiazol-2-yl which is substituted at the 5-position with a substituent selected from the group consisting of thiol, trifluoromethyl, amino, and sulfonamido.

105. The inhibitor of claim 102, wherein $Y^3$ is selected from the group consisting of —CH=CH—, —C($CH_3$)=CH—, and —CH=C($CH_3$)—.

106. The inhibitor of claim 102, wherein Ar is substituted or unsubstituted phenylene, which optionally may be fused to an aryl or heteroaryl ring, or to a saturated or partially unsaturated cycloalkyl or heterocyclic ring, any of which may be optionally substituted.

107. The inhibitor of claim 106, wherein the phenylene is 4-phenylene.

108. The inhibitor of claim 102, wherein Cy is selected from the group consisting of phenyl, naphthyl, thienyl, benzothienyl, and quinolyl, any of which may be optionally substituted.

109. The inhibitor of claim 108, wherein the phenyl, naphthyl, thienyl, benzothienyl, or quinolyl is unsubstituted or is substituted by one or two substituents independently selected from the group consisting of $C_1$-$C_4$ alkyl, $C_1$-$C_4$ haloalkyl, $C_6$-$C_{10}$ aryl, ($C_6$-$C_{10}$)ar($C_1$-$C_6$)alkyl, halo, nitro, hydroxy, $C_1$-$C_6$ alkoxy, $C_1$-$C_6$ alkoxycarbonyl, carboxy, and amino.

110. An inhibitor of histone deacetylase represented by the formula $$Cy—L^3—Ar—Y^3—C(O)NH—Z$$

wherein

Cy is aryl or heteroaryl, either of which may be optionally substituted, $L^3$ is selected from the group consisting of (a) —$(CH_2)_m$—$S(O)_2NH$—, where m is 1,2,3, or 4; and (b) $C_2$-$C_8$ alkylene or $C_2$-$C_8$ alkenylene, wherein the alkylene or alkenylene optionally may be substituted, provided that $L^3$ is not —C(O)—, and wherein one of the carbon atoms of the alkylene optionally may be replaced by NR', R' being alkyl, acyl, or hydrogen; S; S(O); or $S(O)_2$;

Ar is arylene or heteroarylene, wherein said arylene optionally may be additionally substituted and optionally may be fused to an aryl or heteroaryl ring, or to a saturated or partially unsaturated cycloalkyl or heterocyclic ring, any of which may be optionally substituted; and $Y^3$ is $C_2$ alkenylene or $C_2$ alkynylene, wherein one or both carbon atoms of the alkenylene optionally may be substituted with alkyl, aryl, alkaryl, or aralkyl; and Z is selected from the group consisting of anilinyl, pyridyl, thiadiazolyl, and —O—M, M being a pharmaceutically acceptable cation, wherein said thiadiazolyl may be optionally substituted with a substituent selected from the group consisting of thiol, trifluoromethyl, amino and sulfonamido;

provided that when Cy is unsubstituted phenyl, Ar is not phenyl wherein $L^3$ and $Y^3$ are oriented ortho or meta to each other.

111. The inhibitor of claim 110, wherein Z is selected from the group, consisting of 2-anilinyl, 2-pyridyl, 1,3,4-thiadiazol-2-yl, and —O—M, M being a pharmaceutically acceptable cation.

112. The inhibitor of claim 111, wherein Z is 1,3,4-thiadiazol-2-yl which is substituted at the 5-position with a substituent selected from the group consisting of thiol, trifluoromethyl, amino, and sulfonamido.

113. The inhibitor of claim 110, wherein $Y^3$ is selected from the group consisting of— CH=CH—, —C($CH_3$)=CH—, and —CH=C($CH_3$)—.

114. The inhibitor of claim 110, wherein Ar is substituted or unsubstituted phenylene, which optionally may be fused to an aryl or heteroaryl ring, or to a saturated or partially unsaturated cycloalkyl or heterocyclic ring, any of which may be optionally substituted.

115. The inhibitor of claim 114, wherein the phenylene is 4-phenylene.

116. The inhibitor of claim 110, wherein Cy is selected from the group consisting of phenyl, naphthyl, thienyl, benzothienyl, and quinolyl, any of which may be optionally substituted.

117. The inhibitor of claim 116, wherein the phenyl, naphthyl, thienyl, benzothienyl, or quinolyl is unsubstituted or is substituted by one or two substituents independently selected from the group consisting of $C_1$-$C_4$ alkyl, $C_1$-$C_4$ haloalkyl, $C_6$-$C_{10}$ aryl, $(C_6$-$C_{10})ar(C_1$-$C_6)$alkyl, halo, nitro, hydroxy, $C_1$-$C_6$ alkoxy, $C_1$-$C_6$ alkoxycarbonyl, carboxy, and amino.

118. An inhibitor of histone deacetylase represented by the formula $$Cy—L^3—Ar—Y^3—C(O)NH—Z$$

wherein

Cy is aryl or heteroaryl, either of which may be optionally substituted;

$L^3$ is selected from the group consisting of (a) $—(CH_2)_m—NHS(O)_2—$, where m is 0,1,2,3, or 4; and (b) $C_2$-$C_8$ alkylene or $C_2$-$C_8$ alkenylene, wherein the alkylene or alkenylene optionally may be substituted, provided that $L^3$ is not —C(O)—, and wherein one of the carbon atoms of the alkylene optionally may be replaced by NR', R' being alkyl, acyl, or hydrogen; S; S(O); or $S(O)_2$;

Ar is arylene or heteroarylene, wherein said arylene optionally may be additionally substituted and optionally may be fused to an aryl or heteroaryl ring, or to a saturated or partially unsaturated cycloalkyl or heterocyclic ring, any of which may be optionally substituted; and $Y^3$ is $C_2$ alkenylene or $C_2$ alkynylene, wherein one or both carbon atoms of the alkenylene optionally may be substituted with alkyl, aryl, alkaryl, or aralkyl; and Z is selected from the group consisting of anilinyl, pyridyl, thiadiazolyl, and —O—M, M being a pharmaceutically acceptable cation, wherein said thiadiazolyl may be optionally substituted with a substituent selected from the group consisting of thiol, trifluoromethyl, amino and sulfonamido:

provided that when Cy is unsubstituted phenyl, Ar is not phenyl wherein $L^3$ and $Y^3$ are oriented ortho or meta to each other.

119. The inhibitor of claim 118, wherein Z is selected from the group consisting of 2-anilinyl, 2-pyridyl, 1,3,4-thiadiazol-2-yl, and —O—M, M being a pharmaceutically acceptable cation.

120. The inhibitor of claim 119, wherein Z is 1,3,4-thiadiazol-2-yl which is substituted at the 5-position with a substituent selected from the group consisting of thiol, trifluoromethyl, amino, and sulfonamido.

121. The inhibitor of claim 118, wherein $Y^3$ is selected from the group consisting of— CH═CH—, —$C(CH_3)$═CH—, and —CH═$C(CH_3)$—.

122. The inhibitor of claim 118, wherein Ar is substituted or unsubstituted phenylene, which optionally may be fused to an aryl or heteroaryl ring, or to a saturated or partially unsaturated cycloalkyl or heterocyclic ring, any of which may be optionally substituted.

123. The inhibitor of claim 122, wherein the phenylene is 4-phenylene.

124. The inhibitor of claim 118, wherein Cy is selected from the group consisting of phenyl, naphthyl, thienyl, benzothienyl, and quinolyl, any of which may be optionally substituted.

125. The inhibitor of claim 124, wherein the phenyl, naphthyl, thienyl, benzothienyl, or quinolyl is unsubstituted or is substituted by one or two substituents independently selected from the group consisting of $C_1$-$C_4$ alkyl, $C_1$-$C_4$ haloalkyl, $C_6$-$C_{10}$ aryl, $(C_6$-$C_{10})ar(C_1$-$C_6)$alkyl, halo, nitro, hydroxy, $C_1$-$C_6$ alkoxy, $C_1$-$C_6$ alkoxycarbonyl, carboxy, and amino.

126. An inhibitor of histone deacetylase represented by the formula $$Cy—L^3—Ar—Y^3—C(O)NH—Z$$

wherein

Cy is aryl or heteroaryl, either of which may be optionally substituted;

$L^3$ is selected from the group consisting of (a) $—(CH_2)_m—W$, where m is 0,1,2,3, or 4, and W is selected from the group consisting of —C(O)NH—, —NHC(O)—, and —NH—C(O)—NH—; and (b) $C_1$-$C_8$ alkylene or $C_2$-$C_8$ alkenylene, wherein the alkylene or alkenylene ontionally may be substituted, provided that $L_3$ is not —C(O)—, and wherein one of the carbon atoms of the alkylene optionally may be replaced by NR', R' being alkyl, acyl, or hydrogen; S; or S(O);

Ar is arylene or heteroarylene, wherein said arylene optionally may be additionally substituted and optionally may be fused to an arvl or heteroaryl ring, or to a saturated or partially unsaturated cycloalkyl or heterocyclic ring, any of which may be optionally substituted; and $Y^3$ is $C_2$ alkenylene or $C_2$ alkynylene, wherein one or both carbon atoms of the alkenylene optionally may be substituted with alkyl, aryl, alkaryl, or aralkyl; and Z is selected from the group consisting of anilinyl, pyridyl, thiadiazolyl, and —O—M, M being H or a pharmaceutically acceptable cation, wherein said thiadiazolyl may be optionally substituted with a substituent selected from the group consisting of thiol, trifluoromethyl, amino and sulfonarnido;

provided that when Cy is unsubstituted phenyl, Ar is not phenyl wherein $L^3$ and $Y^3$ are oriented ortho or meta to each other.

127. The inhibitor of claim 126, wherein Z is selected from the group consisting of 2-anilinyl, 2-pyridyl, 1,3,4-thiadiazol-2-yl, and —O—M, M being H or a pharmaceutically acceptable cation.

128. The inhibitor of claim 127, wherein Z is 1,3,4-thiadiazol-2-yl which is substituted at the 5-position with a substituent selected from the group consisting of thiol, trifluoromethyl, amino, and sulfonamido.

129. The inhibitor of claim 126, wherein $Y^3$ is selected from the group consisting of— CH═CH—, —$C(CH_3)$═CH—, and —CH═$C(CH_3)$—.

130. The inhibitor of claim 126, wherein Ar is substituted or unsubstituted phenylene, which optionally may be fused

*to an aryl or heteroaryl ring, or to a saturated or partially unsaturated cycloalkyl or heterocyclic ring, any of which may be optionally substituted.*

*131. The inhibitor of claim 130, wherein the phenylene is 4-phenylene.*

*132. The inhibitor of claim 126, wherein Cy is selected from the group consisting of phenyl, naphthyl, thienyl, benzothienyl, and quinolyl, any of which may be optionally substituted.*

*133. The inhibitor of claim 132, wherein the phenyl, naphthyl, thienyl, benzothienyl, or quinolyl is unsubstituted or is substituted by one or two substituents independently selected from the group consisting of $C_1$-$C_4$ alkyl, $C_1$-$C_4$ haloalkyl, $C_6$-$C_{10}$ aryl, ($C_6$-$C_{10}$)ar($C_1$-$C_6$)alkyl, halo, nitro, hydroxy, $C_1$-$C_6$ alkoxy, $C_1$-$C_6$ alkoxycarbonyl, carboxy, and amino.*

*134. An inhibitor of histone deacetylase represented by the formula*

$$Cy—L^3—Ar—Y^3—C(O)NH—Z$$

*wherein*

*Cy is aryl or heteroaryl, either of which may be optionally substituted;*

*$L^3$ is selected from the group consisting of*

*(a) —$S(O)_2NH$—; and*

*(b) $C_1$-$C_8$ alkylene or $C_2$-$C_8$ alkenylene, wherein the alkylene or alkenylene optionally may be substituted, provided that $L_3$ is not —C(O)—, and wherein one of the carbon atoms of the alkylene optionally may be replaced by NR', R' being alkyl, acyl, or hydrogen; S; or S(O);*

*Ar is arylene or heteroarylene, wherein said arylene optionally may be additionally substituted and optionally may be fused to an aryl or heteroaryl ring, or to a saturated or partially unsaturated cycloalkyl or heterocyclic ring, any of which may be optionally substituted; and*

*$Y^3$ is $C_2$ alkenylene or $C_2$ alkynylene, wherein one or both carbon atoms of the alkenylene optionally may be substituted with alkyl, aryl, alkaryl, or aralkyl; and*

*Z is selected from the group consisting of anilinyl, pyridyl, thiadiazolyl, and —O—M, M being H or a pharmaceutically acceptable cation, wherein said thiadiazolyl may be optionally substituted with a substituent selected from the group consisting of thiol, trifluoromethyl, amino and sulfonamido;*

*provided that when Cy is unsubstituted phenyl, Ar is not phenyl wherein $L^3$ and $Y^3$ are oriented ortho or meta to each other.*

*135. The inhibitor of claim 134, wherein Z is selected from the group consisting of 2-anilinyl, 2-pyridyl, 1,3,4-*thiadiazol-*2-yl, and —O—M, M being H or a pharmaceutically acceptable cation.*

*136. The inhibitor of claim 135, wherein Z is 1,3,4-thiadiazol-2-yl which is substituted at the 5-position with a substituent selected from the group consisting of thiol, trifluoromethyl, amino, and sulfonamido.*

*137. The inhibitor of claim 134, wherein $Y^3$ is selected from the group consisting of —CH═CH—, —C($CH_3$)═CH—, and —CH═C($CH_3$)—.*

*138. The inhibitor of claim 134, wherein Ar is substituted or unsubstituted phenylene, which optionally may be fused to an aryl or heteroaryl ring, or to a saturated or partially unsaturated cycloalkyl or heterocyclic ring, any of which may be optionally substituted.*

*139. The inhibitor of claim 138, wherein the phenylene is 4-phenylene.*

*140. The inhibitor of claim 134, wherein Cy is selected from the group consisting of phenyl, naphthyl, thienyl, benzothienyl, and quinolyl, any of which may be optionally substituted.*

*141. The inhibitor of claim 140, wherein the phenyl, naphthyl, thienyl, benzothienyl, or quinolyl is unsubstituted or is substituted by one or two substituents independently selected from the group consisting of $C_1$-$C_4$ alkyl, $C_1$-$C_4$ haloalkyl, $C_6$-$C_{10}$ aryl, ($C_6$-$C_{10}$)ar($C_1$-$C_6$)alkyl, halo, nitro, hydroxy, $C_1$-$C_6$ alkoxy, $C_1$-$C_6$ alkoxycarbonyl, carboxy, and amino.*

*142. An inhibitor of histone deacetylase represented by the formula*

$$Cy—L^3—Ar—Y^3—C(O)NH—Z$$

*wherein*

*Cy is aryl or heteroaryl, either of which may be optionally substituted;*

*$L^3$ is selected from the group consisting of*

*(a) —$(CH_2)_m$—$S(O)_2NH$—, where m is 1,2,3, or 4; and*

*(b) $C_1$-$C_8$ alkylene or $C_2$-$C_8$ alkenylene, wherein the alkylene or alkenylene optionally may be substituted, provided that $L_3$ is not —C(O)—, and wherein one of the carbon atoms of the alkylene optionally may be replaced by NR', R' being alkyl, acyl, or hydrogen; S; or S(O);*

*Ar is arylene or heteroarylene wherein said arylene optionally may be additionally substituted and optionally may be fused to an aryl or heteroaryl ring, or to a saturated or partially unsaturated cycloalkyl or heterocyclic ring, any of which may be optionally substituted; and*

*$Y^3$ is $C_2$ alkenylene or $C_2$ alkynylene, wherein one or both carbon atoms of the alkenylene optionally may be substituted with alkyl, aryl, alkaryl, or aralkyl; and*

*Z is selected from the group consisting of anilinyl, pyridyl, thiadiazolyl, and —O—M, M being a pharmaceutically acceptable cation, wherein said thiadiazolyl may be optionally substituted with a substituent selected from the group consisting of thiol, trifluoromethyl, amino and sulfonamido;*

*provided that when Cy is unsubstituted phenyl, Ar is not phenyl wherein $L^3$ and $Y^3$ are oriented ortho or meta to each other.*

*143. The inhibitor of claim 142, wherein Z is selected from the group consisting of 2-anilinyl, 2-pyridyl, 1,3,4-thiadiazol-2-yl, and —O—M, M being a pharmaceutically acceptable cation.*

*144. The inhibitor of claim 143, wherein Z is 1,3,4-*thiadiazol-*2-yl which is substituted at the 5-position with a substituent selected from the group consisting of thiol, trifluoromethyl amino, and sulfonamido.*

*145. The inhibitor of claim 142, wherein $Y^3$ is selected from the group consisting of —CH═CH—, —C($CH_3$)═CH—, and —CH═C($CH_3$)—.*

*146. The inhibitor of claim 142, wherein Ar is substituted or unsubstituted phenylene, which optionally may be fused to an aryl or heteroaryl ring, or to a saturated or partially unsaturated cycloalkyl or heterocyclic ring, any of which may be optionally substituted.*

*147. The inhibitor of claim 146, wherein the phenylene is 4-phenylene.*

148. The inhibitor of claim 142, wherein Cy is selected from the group consisting of phenyl, naphthyl, thienyl, benzothienyl, and quinolyl, any of which may be optionally substituted.

149. The inhibitor of claim 148, wherein the phenyl, naphthyl, thienyl, benzothienyl, or quinolyl is unsubstituted or is substituted by one or two substituents independently selected from the group consisting of $C_1$-$C_4$ alkyl, $C_1$-$C_4$ haloalkyl, $C_6$-$C_{10}$ aryl, $(C_6$-$C_{10})ar(C_1$-$C_6)alkyl$, halo, nitro, hydroxy, $C_1$-$C_6$ alkoxy, $C_1$-$C_6$ alkoxycarbonyl, carboxy, and amino.

150. An inhibitor of histone deacetylase represented by the formula $$Cy—L^3—Ar—Y^3—C(O)NH—Z$$

wherein

Cy is aryl or heteroaryl, either of which may be optionally substituted;

$L^3$ is selected from the group consisting of (a) $—(CH_2)_m—NHS(O)_2—$, where m is 0,1,2,3, or 4; and (b) $C_1$-$C_8$ alkylene or $C_2$-$C_8$ alkenylene, wherein the alkylene or alkenylene optionally may be substituted, provided that $L_3$ is not —C(O)—, and wherein one of the carbon atoms of the alkylene optionally may be replaced by NR', R' being alkyl, acyl, or hydrogen; S; or S(O);

Ar is arylene or heteroarylene, wherein said arylene optionally may be additionally substituted and optionally may be fused to an aryl or heteroaryl ring, or to a saturated or partially unsaturated cycloalkyl or heterocyclic ring, any of which may be optionally substituted; and $Y^3$ is $C_2$ alkenylene or $C_2$ alkynylene, wherein one or both carbon atoms of the alkenylene optionally may be substituted with alkyl, aryl, alkaryl, or aralkyl; and Z is selected from the group consisting of anilinyl, pyridyl, thiadiazolyl, and —O—M, M being a pharmaceutically acceptable cation, wherein said thiadiazolyl may be optionally substituted with a substituent selected from the group consisting of thiol, trifluoromethyl, amino and sulfonamido;

provided that when Cy is unsubstituted phenyl, Ar is not phenyl wherein $L^3$ and $Y^3$ are oriented ortho or meta to each other.

151. The inhibitor of claim 150, wherein Z is selected from the group consisting of 2-anilinyl, 2-pyridyl, 1,3,4-thiadiazol-2-yl, and —O—M, M being a pharmaceutically acceptable cation.

152. The inhibitor of claim 151, wherein Z is 1,3,4-thiadiazol-2-yl which is substituted at the 5-position with a substituent selected from the group consisting of thiol, trifluoromethyl, amino, and sulfonamido.

153. The inhibitor of claim 150, wherein $Y^3$ is selected from the group consisting of —CH═CH—, $—C(CH_3)═CH—$, and $—CH═C(CH_3)—$.

154. The inhibitor of claim 150, wherein Ar is substituted or unsubstituted phenylene, which optionally may be fused to an aryl or heteroaryl ring, or to a saturated or partially unsaturated cycloalkyl or heterocyclic ring, any of which may be optionally substituted.

155. The inhibitor of claim 154, wherein the phenylene is 4-phenylene.

156. The inhibitor of claim 150, wherein Cy is selected from the group consisting of phenyl, naphthyl, thienyl, benzothienyl, and quinolyl, any of which may be optionally substituted.

157. The inhibitor of claim 156, wherein the phenvl, naphthyl, thienyl, benzothienyl, or quinolyl is unsubstituted or is substituted by one or two substituents independently selected from the group consisting of $C_1$-$C_4$ alkyl, $C_1$-$C_4$ haloalkyl, $C_6$-$C_{10}$ aryl, $(C_6$-$C_{10})ar(C_1$-$C_6)alkyl$, halo, nitro, hydroxy, $C_1$-$C_6$ alkoxy, $C_1$-$C_6$ alkoxycarbonyl, carboxy, and amino.

158. The inhibitor according to claim 66 selected from the group consisting of

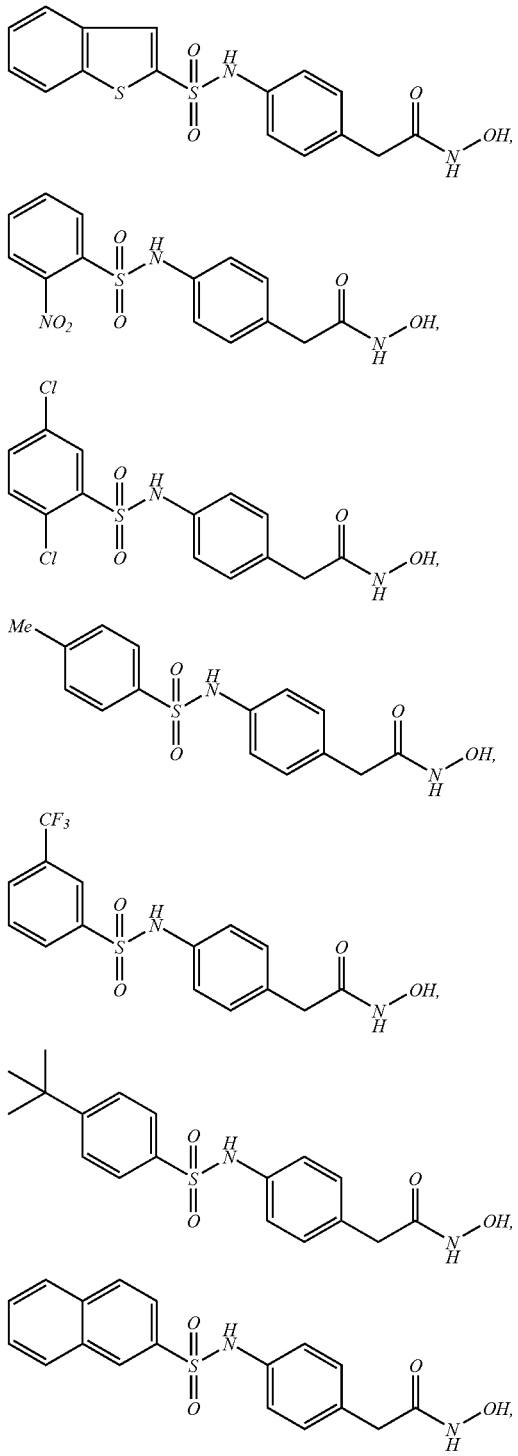

-continued
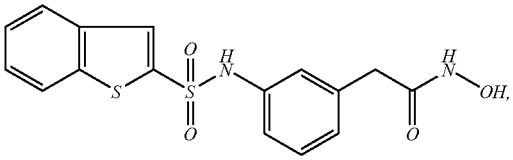
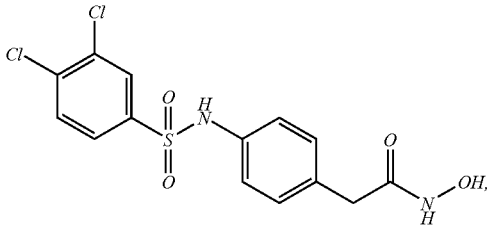
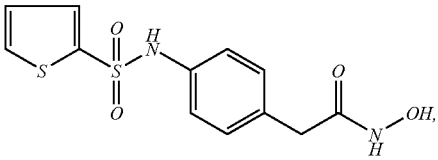
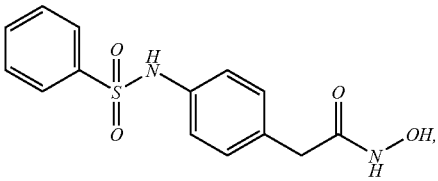
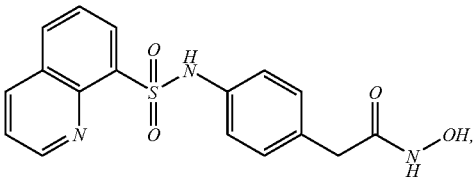
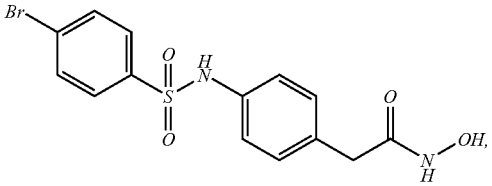
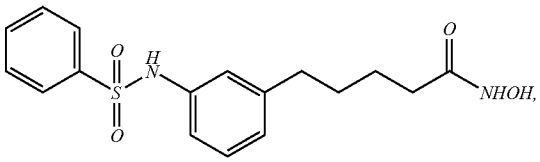
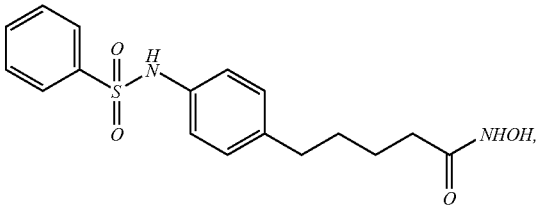
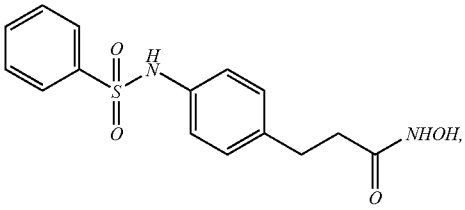
-continued
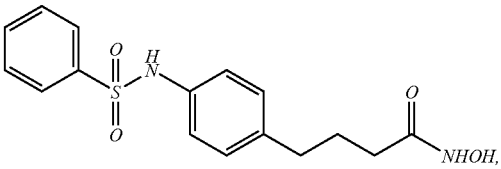
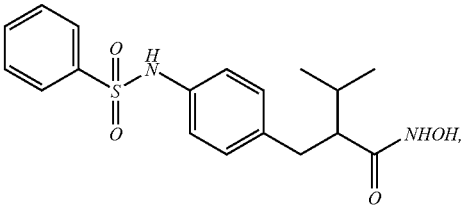
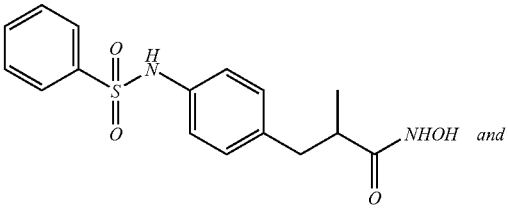
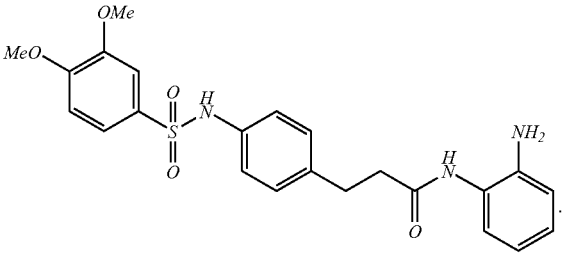
*159. The inhibitor according to claim 11 selected from the group consisting of*
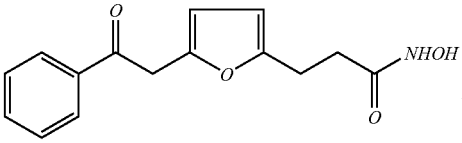
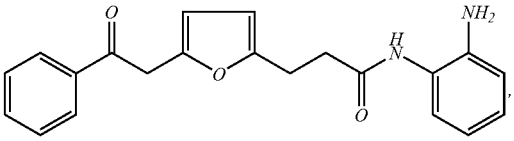
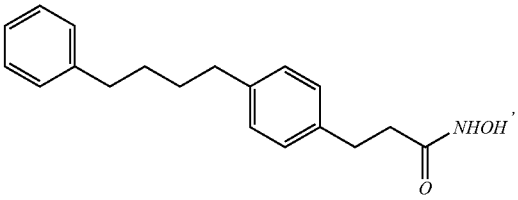
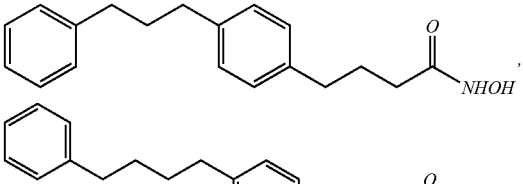
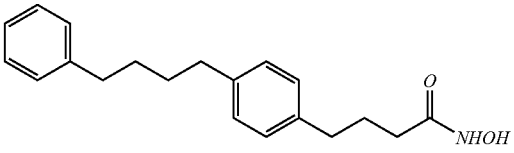
*and*

-continued
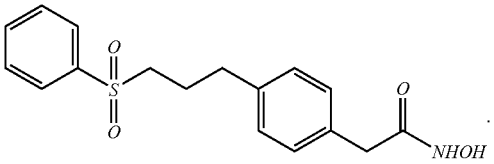
*160. The inhibitor according to claim 102 selected from the group consisting of*
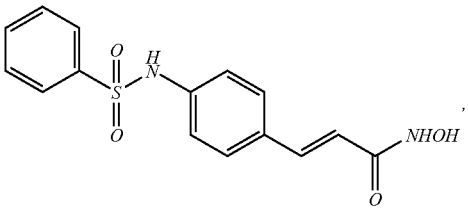
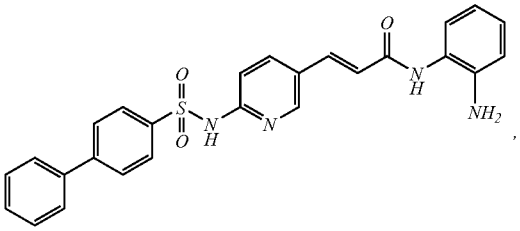
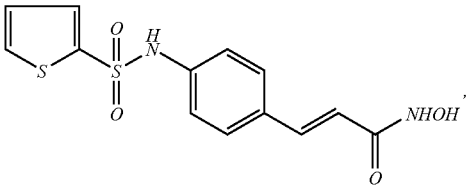
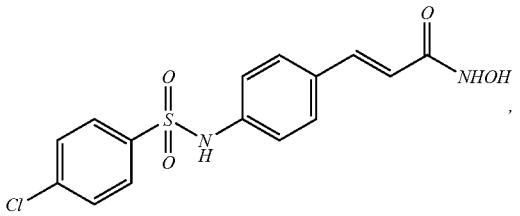
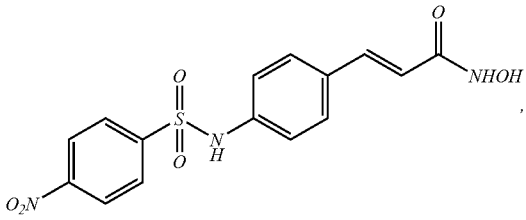
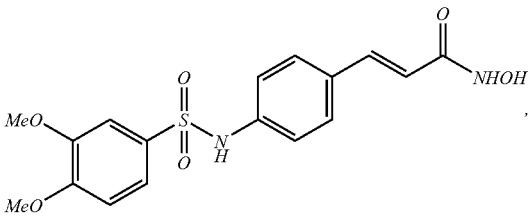
-continued
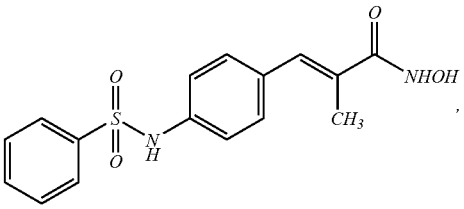
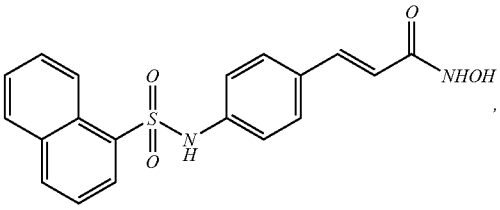
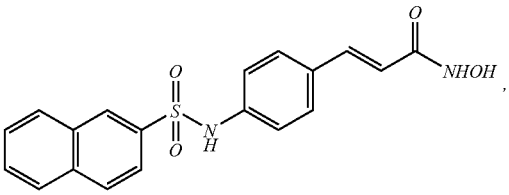
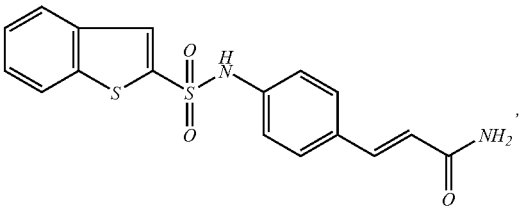
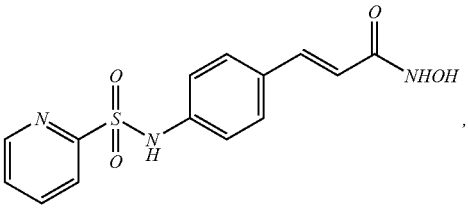
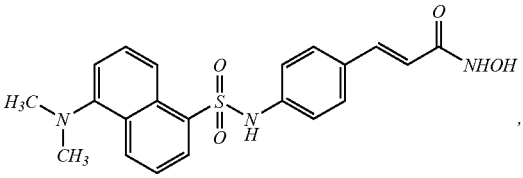
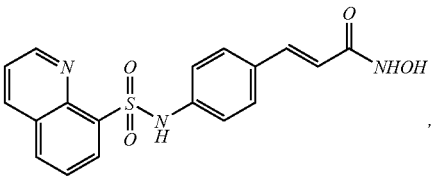
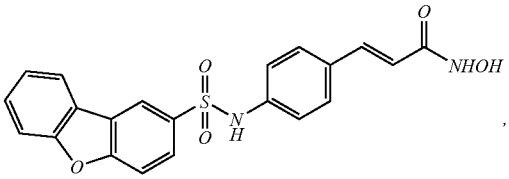

-continued
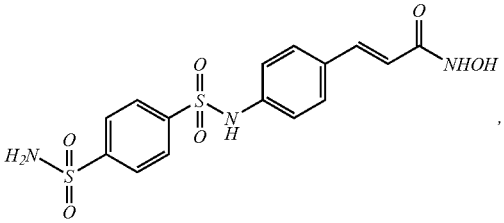
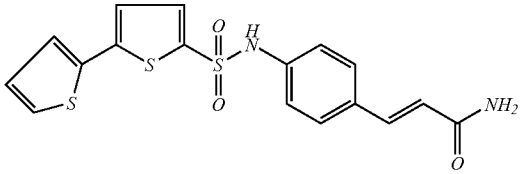
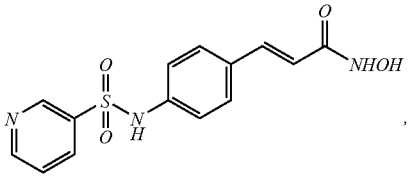
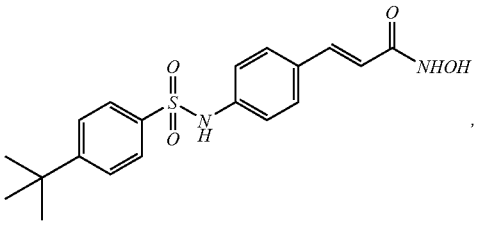
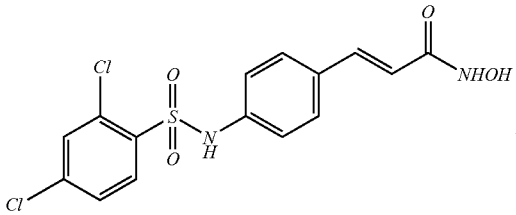
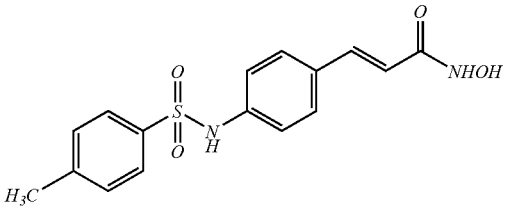
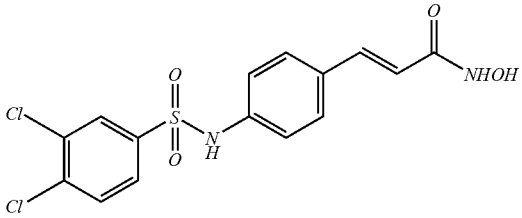
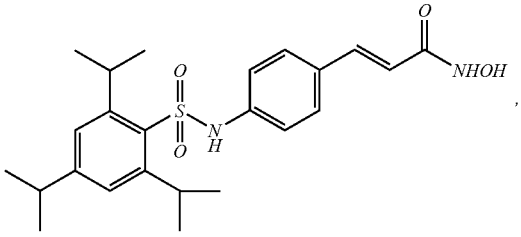
-continued
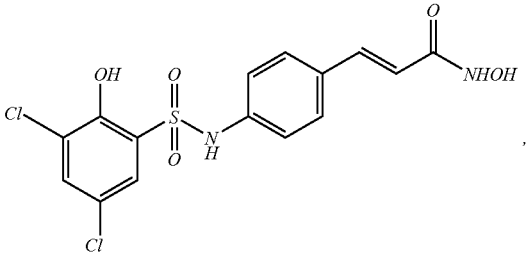
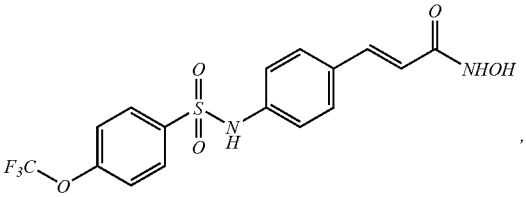
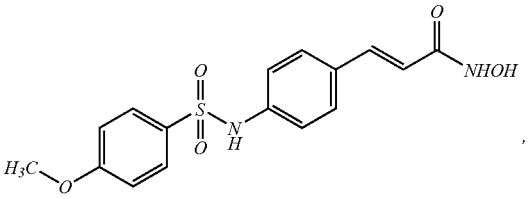
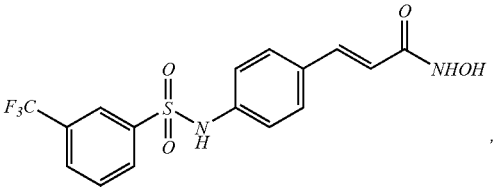
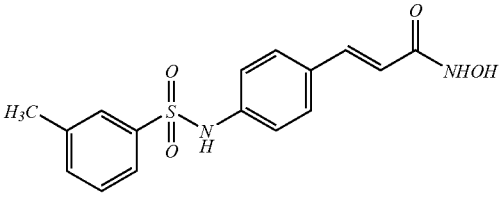
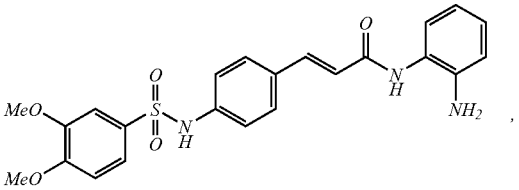
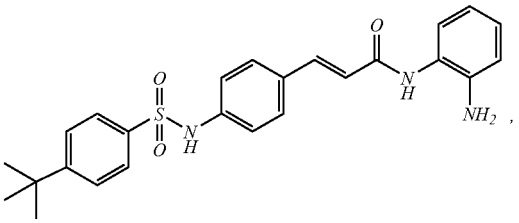
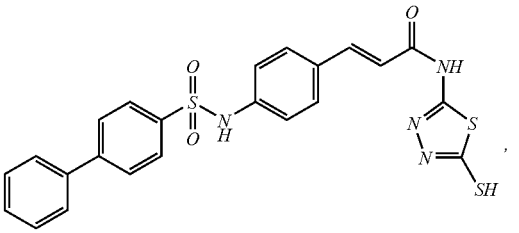

-continued
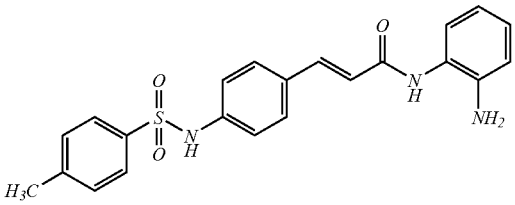
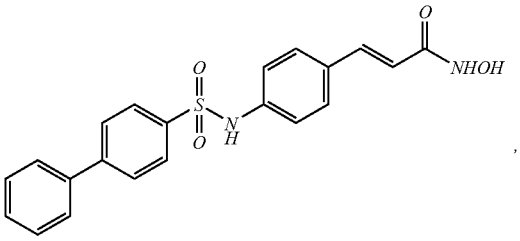
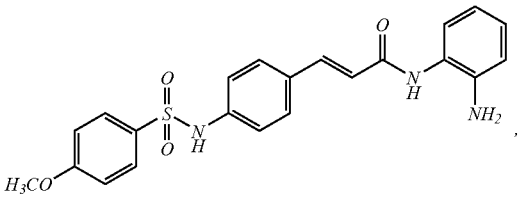
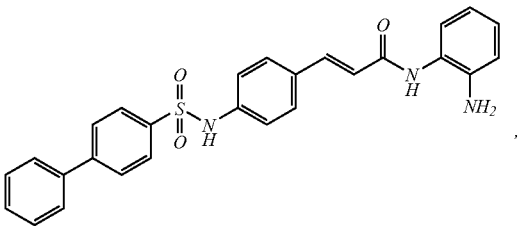
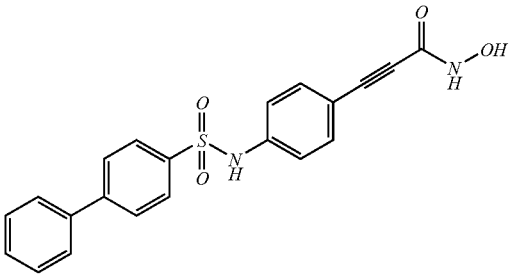
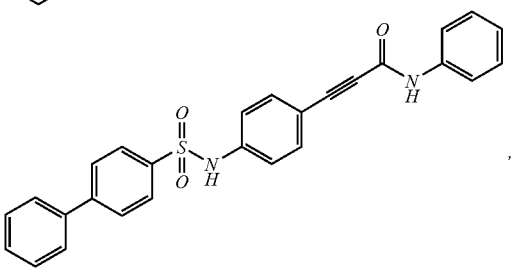
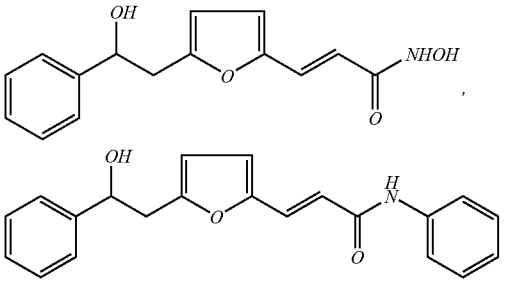
*and*
-continued
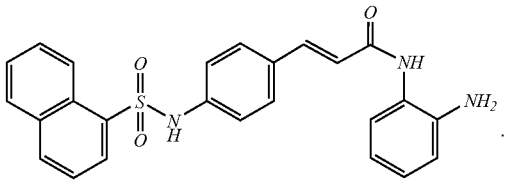
*161. The inhibitor according to claim 118 selected from the group consisting of*
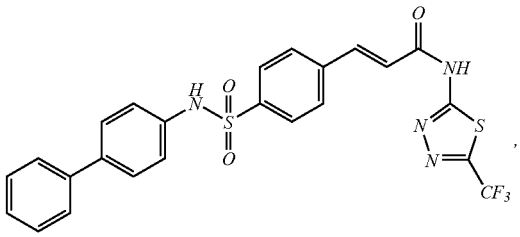
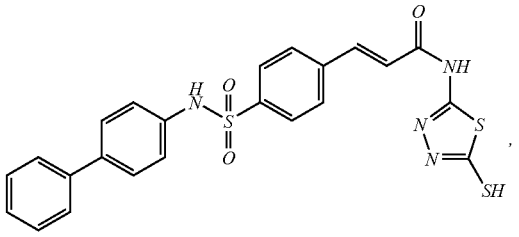
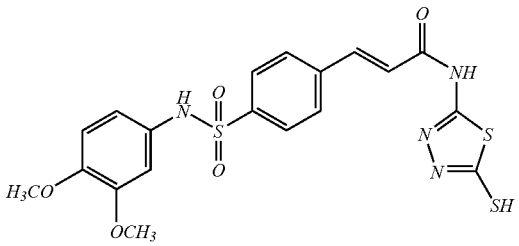
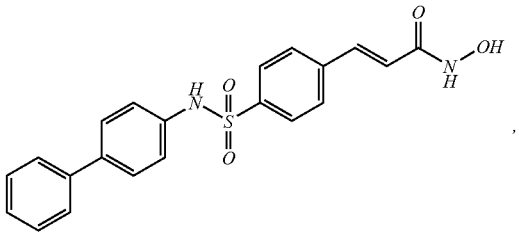
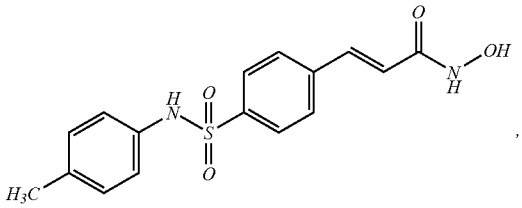
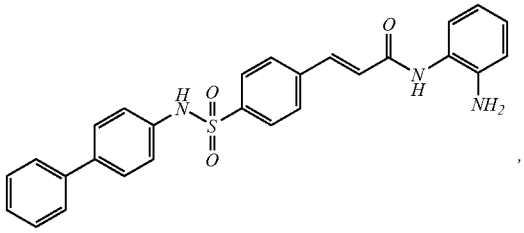

-continued
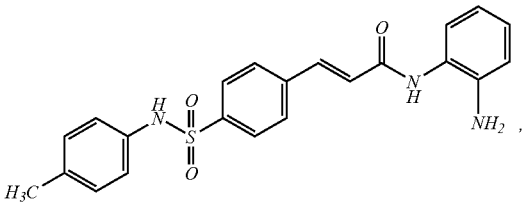
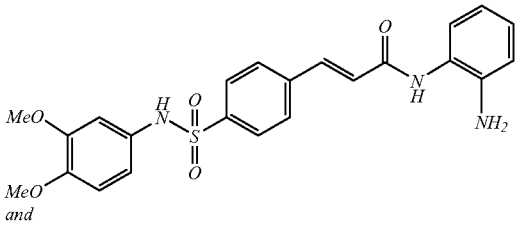
and
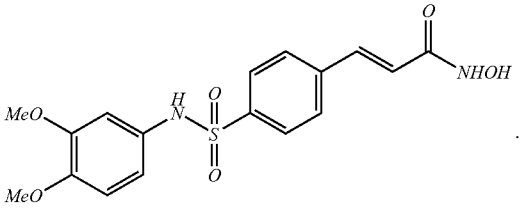
*162. The inhibitor according to claim 94 selected from the group consisting of*
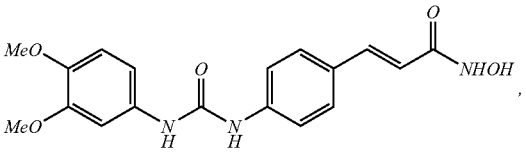
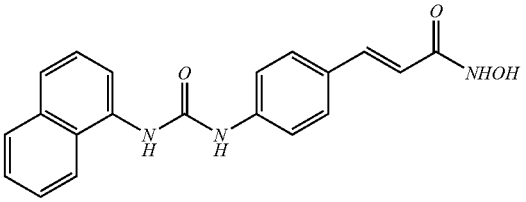
*and*
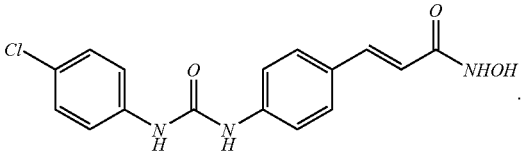
* * * * *

UNITED STATES PATENT AND TRADEMARK OFFICE

CERTIFICATE OF CORRECTION

PATENT NO. : RE 39,850 E
APPLICATION NO. : 10/880444
DATED : September 18, 2007
INVENTOR(S) : Daniel Delorme et al.

It is certified that error appears in the above-identified patent and that said Letters Patent is hereby corrected as shown below:

On the Front Page, in the Related U.S. Patent Documents section, please cancel the text "Issued: Apr. 1, 2005" and insert the following text: --Issued: Apr. 1, 2003--

In Claim 1, Column 115, line 50, please cancel the text "Cy is cycloalkyl, aryl, heteroaryl, or heterocyclyl, any of" and insert the following text: --Cy is cycloalkyl, [aryl, heteroaryl,] or heterocyclyl, any of--

Column 119, line 1 to Column 120, line 8, please cancel the text of claim 34 and insert the following claim:
--34. An inhibitor of histone deacetylase selected from the group consisting of

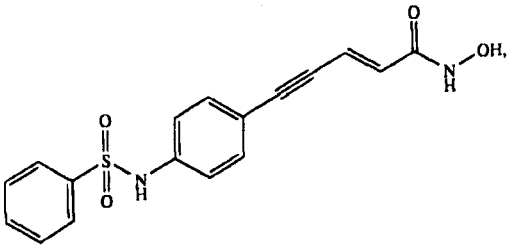

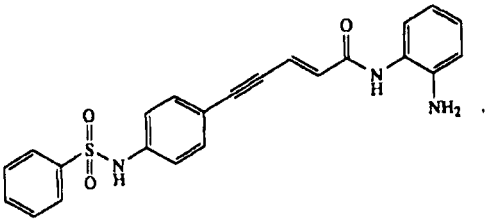

and

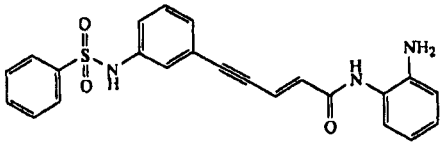

--

Signed and Sealed this

Eleventh Day of May, 2010

David J. Kappos

David J. Kappos
*Director of the United States Patent and Trademark Office*

In Claim 51, Column 122, line 46 to line 47, please cancel the text "l,3,4-thiadiazol-2-yl," and insert the following text: --1,3,4-thiadiazol-2-yl--

In Claim 77, Column 125, line 12, please cancel the text "sulfonarnido" and insert the following text: --sulfonamido--

In Claim 96, Column 127, line 2, please cancel the text "sulfonaniido" and insert the following text: --sulfonamido--

In Claim 126, Column 130, line 31, please cancel the text "ontionally" and insert the following text: --optionally--

In Claim 126, Column 130, line 50, please cancel the text "sulfonarnido" and insert the following text: --sulfonamido--

In Claim 144, Column 132, line 57, please cancel the text "trifluoromethyl amino, and sulfonamido" and insert the following text: --trifluoromethyl, amino, and sulfonamido--

In Claim 158, Column 135, line 25 to line 30, please cancel the fourth chemical formula and insert the following chemical formula:

--

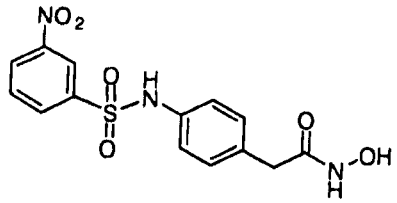

--

In Claim 160, Column 141, line 45 to line 65, please cancel the sixth, seventh and eighth chemical formulas and insert the following chemical formulas:

--

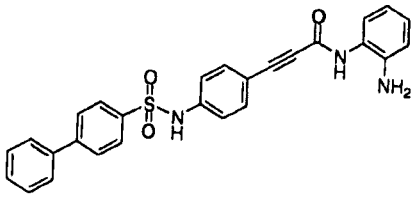

,

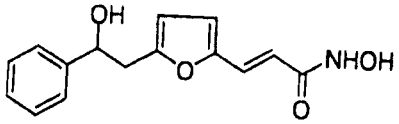

,

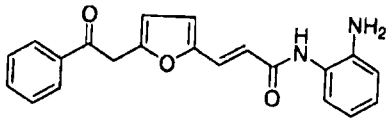

*and*--